US011491133B2

(12) United States Patent
Bowen et al.

(10) Patent No.: US 11,491,133 B2
(45) Date of Patent: Nov. 8, 2022

(54) HETEROARYL-ISOCHROMAN COMPOUNDS AND USES THEREOF

(71) Applicants: Sunovion Pharmaceuticals Inc., Marlborough, MA (US); PGI Drug Discovery LLC, Paramus, NJ (US)

(72) Inventors: Carrie A. Bowen, Uxbridge, MA (US); Douglas F. Burdi, Arlington, MA (US); Michele L. R. Heffernan, Holliston, MA (US); Lee W. Herman, Natick, MA (US); Linghong Xie, Southborough, MA (US)

(73) Assignees: Sunovion Pharmaceuticals Inc., Marlborough, MA (US); PGI Drug Discovery LLC, Paramus, NJ (US)

( * ) Notice: Subject to any disclaimer, the term of this patent is extended or adjusted under 35 U.S.C. 154(b) by 0 days.

(21) Appl. No.: 16/991,771

(22) Filed: Aug. 12, 2020

(65) Prior Publication Data

US 2021/0093606 A1    Apr. 1, 2021

Related U.S. Application Data

(62) Division of application No. 16/051,863, filed on Aug. 1, 2018, now Pat. No. 10,780,074.

(60) Provisional application No. 62/540,249, filed on Aug. 2, 2017.

(51) Int. Cl.

| | | |
|---|---|---|
| *A61K 31/352* | (2006.01) |
| *A61P 25/28* | (2006.01) |
| *A61P 25/24* | (2006.01) |
| *A61P 25/08* | (2006.01) |
| *A61P 25/16* | (2006.01) |
| *C07D 413/04* | (2006.01) |
| *C07D 417/04* | (2006.01) |
| *C07D 405/04* | (2006.01) |
| *A61K 31/4155* | (2006.01) |
| *A61K 31/4178* | (2006.01) |
| *A61K 31/42* | (2006.01) |
| *A61K 31/427* | (2006.01) |
| *A61K 31/443* | (2006.01) |
| *A61K 31/4433* | (2006.01) |
| *A61K 31/497* | (2006.01) |
| *A61K 31/506* | (2006.01) |

(52) U.S. Cl.
CPC ........ *A61K 31/352* (2013.01); *A61K 31/4155* (2013.01); *A61K 31/4178* (2013.01); *A61K 31/42* (2013.01); *A61K 31/427* (2013.01); *A61K 31/443* (2013.01); *A61K 31/4433* (2013.01); *A61K 31/497* (2013.01); *A61K 31/506* (2013.01); *A61P 25/08* (2018.01); *A61P 25/16* (2018.01); *A61P 25/24* (2018.01); *A61P 25/28* (2018.01); *C07D 405/04* (2013.01); *C07D 413/04* (2013.01); *C07D 417/04* (2013.01)

(58) Field of Classification Search
CPC .................................................. C07D 311/76
See application file for complete search history.

(56) References Cited

U.S. PATENT DOCUMENTS

| | | | |
|---|---|---|---|
| 3,438,995 | A | 4/1969 | Faust et al. |
| 3,470,179 | A | 9/1969 | Ott |
| 3,536,809 | A | 10/1970 | Applezweig |
| 3,549,624 | A | 12/1970 | Conover et al. |
| 3,551,427 | A | 12/1970 | Ott |
| 3,598,123 | A | 8/1971 | Zaffaroni |
| 3,845,770 | A | 11/1974 | Theeuwes et al. |
| 3,916,899 | A | 11/1975 | Theeuwes et al. |
| 3,995,052 | A | 11/1976 | Jirkovsky et al. |
| 4,008,719 | A | 2/1977 | Theeuwes et al. |
| 4,021,451 | A | 5/1977 | Dobson et al. |
| 4,021,452 | A | 5/1977 | Floyd |
| 4,036,842 | A | 7/1977 | Dobson et al. |
| 4,041,169 | A | 9/1977 | Demerson et al. |
| 4,066,648 | A | 1/1978 | Oka et al. |

(Continued)

FOREIGN PATENT DOCUMENTS

| | | |
|---|---|---|
| AU | 2010325925 | 6/2011 |
| AU | 2016200448 | 2/2016 |

(Continued)

OTHER PUBLICATIONS

Adaa.org [online] "Treatment: Anxiety and Depression Association of America," Jan. 29, 2006, [Retrieved on Dec. 28, 2018]Retrieved from URL <https://adaa.org/understanding-anxiety/depression/treatment>, 4 pages.

(Continued)

*Primary Examiner* — Susanna Moore
(74) *Attorney, Agent, or Firm* — Fish & Richardson P.C.

(57) ABSTRACT

Compounds of Formula I are described as are pharmaceutical compositions containing such compounds. Methods of treating neurological or psychiatric diseases and disorders in a subject in need are also disclosed.

57 Claims, No Drawings

(56) References Cited

U.S. PATENT DOCUMENTS

| | | | |
|---|---|---|---|
| 4,127,665 A | 11/1978 | Sarges et al. |
| 4,337,343 A | 6/1982 | Maillard et al. |
| 4,500,543 A | 2/1985 | Debernardis et al. |
| 4,556,656 A | 12/1985 | Mcall |
| 4,904,300 A | 2/1990 | Lutz |
| 4,963,568 A | 10/1990 | Schoenleber et al. |
| 4,994,486 A | 2/1991 | Schoenleber et al. |
| 4,999,359 A | 3/1991 | Vecchietti et al. |
| 5,032,598 A | 7/1991 | Baldwin et al. |
| 5,041,451 A | 8/1991 | Colle et al. |
| 5,059,595 A | 10/1991 | Le Grazie |
| 5,073,543 A | 12/1991 | Marshall et al. |
| 5,109,008 A | 4/1992 | Scopes et al. |
| 5,120,548 A | 6/1992 | McClelland et al. |
| 5,134,127 A | 7/1992 | Stella et al. |
| 5,288,749 A | 2/1994 | Meyer et al. |
| 5,304,657 A | 4/1994 | Toki et al. |
| 5,354,556 A | 10/1994 | Sparks et al. |
| 5,391,556 A | 2/1995 | Heckel et al. |
| 5,393,759 A | 2/1995 | Combourieu et al. |
| 5,464,834 A | 11/1995 | Peligion et al. |
| 5,532,203 A | 7/1996 | Fory et al. |
| 5,532,233 A | 7/1996 | Weber et al. |
| 5,591,767 A | 1/1997 | Mohr et al. |
| 5,621,133 A | 4/1997 | Deninno et al. |
| 5,639,476 A | 6/1997 | Oshlack et al. |
| 5,646,173 A | 7/1997 | Bos et al. |
| 5,656,658 A | 8/1997 | Hammarberg et al. |
| 5,674,533 A | 10/1997 | Santus et al. |
| 5,684,020 A | 11/1997 | Peligion et al. |
| 5,733,566 A | 3/1998 | Lewis |
| 6,031,099 A | 2/2000 | Moltzen et al. |
| 6,235,774 B1 | 5/2001 | Fagrig et al. |
| 6,262,044 B1 | 7/2001 | Møller et al. |
| 6,313,309 B1 | 11/2001 | Baxter et al. |
| 6,436,943 B1 | 8/2002 | Stoltefuss et al. |
| 6,503,913 B1 | 1/2003 | Goldmann et al. |
| 7,019,026 B1 | 3/2006 | Andersen et al. |
| 7,282,499 B2 | 10/2007 | Arjona et al. |
| 7,297,704 B2 | 11/2007 | Sabb et al. |
| 7,414,068 B2 | 8/2008 | Lim et al. |
| 7,544,717 B2 | 6/2009 | Hom et al. |
| 7,745,462 B2 | 6/2010 | Fairhurst et al. |
| 7,884,109 B2 | 2/2011 | Ohlmeyer et al. |
| 8,227,625 B2 | 7/2012 | Corbera-Arjona et al. |
| 8,710,245 B2 | 4/2014 | Shao et al. |
| 9,216,975 B2 | 12/2015 | Napoletano et al. |
| 9,351,954 B2 | 5/2016 | Shao et al. |
| 9,758,529 B2 | 9/2017 | Chytil et al. |
| 9,856,238 B2 | 1/2018 | Xie et al. |
| 10,085,968 B2 | 10/2018 | Shao et al. |
| 10,189,825 B2 | 1/2019 | Campbell et al. |
| 10,196,403 B2 | 2/2019 | Hanania et al. |
| 10,336,732 B2 | 7/2019 | Xie et al. |
| 10,556,890 B2 | 2/2020 | Campbell et al. |
| 2003/0073687 A1 | 4/2003 | Bebbington et al. |
| 2003/0149057 A1 | 8/2003 | Want et al. |
| 2004/0180883 A1 | 9/2004 | Gilmore et al. |
| 2004/0220402 A1 | 11/2004 | Chow et al. |
| 2005/0032873 A1 | 2/2005 | Hatzenbuhler et al. |
| 2005/0075366 A1 | 4/2005 | Heidelbaugh et al. |
| 2005/0187281 A1 | 8/2005 | Hinze et al. |
| 2005/0239832 A1 | 10/2005 | John et al. |
| 2005/0267199 A1 | 12/2005 | Hom et al. |
| 2006/0047127 A1 | 3/2006 | Arjona |
| 2006/0148872 A1 | 7/2006 | Chow et al. |
| 2006/0258714 A1 | 11/2006 | Heffernan et al. |
| 2007/0032481 A1 | 2/2007 | Dvorak et al. |
| 2007/0072926 A1 | 3/2007 | Chow et al. |
| 2007/0154534 A1 | 7/2007 | Sheitman et al. |
| 2007/0185144 A1 | 8/2007 | Zhong et al. |
| 2008/0081910 A1 | 4/2008 | Saab et al. |
| 2008/0113961 A1 | 5/2008 | Nishi et al. |
| 2008/0255239 A1 | 10/2008 | Chow et al. |
| 2008/0306082 A1 | 12/2008 | Dahnke et al. |
| 2009/0069305 A1 | 3/2009 | Gaul et al. |
| 2009/0118283 A1 | 5/2009 | Defert et al. |
| 2009/0318690 A1 | 12/2009 | Sasaki et al. |
| 2010/0035887 A1 | 2/2010 | Ricciardi |
| 2010/0178299 A1 | 7/2010 | Sitkovsky et al. |
| 2010/0197714 A1 | 8/2010 | Wunsch et al. |
| 2012/0171199 A1 | 7/2012 | Dobson et al. |
| 2012/0295881 A1 | 11/2012 | Lange et al. |
| 2013/0109677 A1 | 5/2013 | Shao et al. |
| 2014/0256712 A1 | 9/2014 | Shao et al. |
| 2015/0031709 A1 | 1/2015 | Campbell et al. |
| 2016/0083399 A1 | 3/2016 | Shao et al. |
| 2016/0264597 A1 | 9/2016 | Chytil et al. |
| 2017/0001987 A1 | 1/2017 | Xie et al. |
| 2018/0028492 A1 | 2/2018 | Powel et al. |
| 2018/0030064 A1 | 2/2018 | Xie et al. |
| 2018/0057506 A1 | 3/2018 | Chytil et al. |
| 2018/0093974 A1 | 4/2018 | Xie et al. |
| 2018/0118727 A1 | 5/2018 | Campbell et al. |
| 2019/0038594 A1 | 2/2019 | Bowen et al. |
| 2019/0256525 A1 | 8/2019 | Bauer et al. |
| 2019/0308990 A1 | 10/2019 | Xie et al. |
| 2020/0129477 A1 | 4/2020 | Hopkins et al. |
| 2020/0179336 A1 | 6/2020 | Hopkins |

FOREIGN PATENT DOCUMENTS

| | | |
|---|---|---|
| CA | 2031684 | 6/1991 |
| CN | 1072411 | 5/1993 |
| CN | 1300291 | 6/2001 |
| CN | 1860112 | 11/2006 |
| CN | 100384824 | 4/2008 |
| CN | 101468986 | 7/2009 |
| CN | 101468987 | 7/2009 |
| CN | 101759710 | 6/2010 |
| CN | 102731574 | 10/2012 |
| DE | 3 827727 | 2/1990 |
| EP | 0368175 | 5/1990 |
| EP | 0416740 | 3/1991 |
| EP | 0431421 | 6/1991 |
| GB | 984365 | 2/1965 |
| JP | 01006267 | 1/1989 |
| JP | H02-243691 | 9/1990 |
| JP | H 03163068 | 7/1991 |
| JP | 049367 | 1/1992 |
| JP | 03223277 | 10/2001 |
| JP | 2002512233 | 4/2002 |
| JP | 2002512244 | 4/2002 |
| JP | 2003261566 | 9/2003 |
| JP | 2004269449 | 9/2004 |
| JP | 2005145859 | 6/2005 |
| JP | 2006117568 | 5/2006 |
| JP | 2014214130 | 11/2014 |
| JP | 2015510513 | 4/2015 |
| WO | WO 1991008205 | 6/1991 |
| WO | WO 9203434 | 3/1992 |
| WO | WO 1992003434 | 3/1992 |
| WO | WO 1992014465 | 9/1992 |
| WO | WO 1992015592 | 9/1992 |
| WO | WO 1994000441 | 1/1994 |
| WO | WO 1996004287 | 2/1996 |
| WO | WO 1996038435 | 12/1996 |
| WO | WO 1999001437 | 1/1999 |
| WO | WO 1999046237 | 9/1999 |
| WO | WO 1999046267 | 9/1999 |
| WO | WO 2000000487 | 1/2000 |
| WO | WO 2000023445 | 4/2000 |
| WO | WO 2000035915 | 6/2000 |
| WO | WO 2000043397 | 7/2000 |
| WO | WO 2000068230 | 11/2000 |
| WO | WO 2000078742 | 12/2000 |
| WO | WO 2001017516 | 3/2001 |
| WO | WO 2001019831 | 3/2001 |
| WO | WO 2001032610 | 5/2001 |
| WO | WO 2001032655 | 5/2001 |
| WO | WO 2001062233 | 8/2001 |
| WO | WO 2001072745 | 10/2001 |
| WO | WO 2002012189 | 2/2002 |
| WO | WO 2002022614 | 3/2002 |

(56) References Cited

FOREIGN PATENT DOCUMENTS

| | | |
|---|---|---|
| WO | WO 2002066443 | 8/2002 |
| WO | WO 2001080893 | 10/2002 |
| WO | WO 2002083667 | 10/2002 |
| WO | WO 2002102387 | 12/2002 |
| WO | WO 2003006455 | 1/2003 |
| WO | WO 2003035065 | 5/2003 |
| WO | WO 2003092374 | 11/2003 |
| WO | WO 2004004726 | 1/2004 |
| WO | WO 2004/018414 | 3/2004 |
| WO | WO 2004024081 | 3/2004 |
| WO | WO 2004/035589 | 4/2004 |
| WO | WO 2004035812 | 4/2004 |
| WO | WO 2004066912 | 8/2004 |
| WO | WO 2004078723 | 9/2004 |
| WO | WO 2004082687 | 9/2004 |
| WO | WO 2004087680 | 10/2004 |
| WO | WO 2004089913 | 10/2004 |
| WO | WO 2004112719 | 12/2004 |
| WO | WO 2005035518 | 4/2005 |
| WO | WO 2005072412 | 8/2005 |
| WO | WO 2005073236 | 8/2005 |
| WO | WO 2005079800 | 9/2005 |
| WO | WO 2005087779 | 9/2005 |
| WO | WO 2005111025 | 11/2005 |
| WO | WO 2006014135 | 2/2006 |
| WO | WO 2006014136 | 2/2006 |
| WO | WO 2006015259 | 2/2006 |
| WO | WO 2006030124 | 3/2006 |
| WO | WO 2006053274 | 5/2006 |
| WO | WO 2006066172 | 6/2006 |
| WO | WO 2006066950 | 6/2006 |
| WO | WO 2006089053 | 8/2006 |
| WO | WO 2006117305 | 11/2006 |
| WO | WO 2007001939 | 1/2007 |
| WO | WO 2007002681 | 1/2007 |
| WO | WO 2007006546 | 1/2007 |
| WO | WO 2007095586 | 8/2007 |
| WO | WO 2007102999 | 9/2007 |
| WO | WO 2007120594 | 10/2007 |
| WO | WO 2007126041 | 11/2007 |
| WO | WO 2008011560 | 1/2008 |
| WO | WO 2008042422 | 4/2008 |
| WO | WO 2008048981 | 4/2008 |
| WO | WO 2008058342 | 5/2008 |
| WO | WO 2008119689 | 10/2008 |
| WO | WO 2008125348 | 10/2008 |
| WO | WO 2008155132 | 12/2008 |
| WO | WO 2009009550 | 1/2009 |
| WO | WO 2009057974 | 5/2009 |
| WO | WO 2009067202 | 5/2009 |
| WO | WO 2009068467 | 6/2009 |
| WO | WO 2009072621 | 6/2009 |
| WO | WO 2009085256 | 7/2009 |
| WO | WO 2010053583 | 5/2010 |
| WO | WO 2010090716 | 8/2010 |
| WO | WO 2010092180 | 8/2010 |
| WO | WO 2010092181 | 8/2010 |
| WO | WO 2010093425 | 8/2010 |
| WO | WO 2011017389 | 2/2011 |
| WO | WO 2011036889 | 3/2011 |
| WO | WO 2011060035 | 5/2011 |
| WO | WO 2011060217 | 5/2011 |
| WO | WO 2011/068171 | 6/2011 |
| WO | WO 2011069063 | 6/2011 |
| WO | WO 2011081205 | 7/2011 |
| WO | WO 2011133729 | 10/2011 |
| WO | WO 2012020133 | 2/2012 |
| WO | WO 2012122340 | 9/2012 |
| WO | WO 2013010453 | 1/2013 |
| WO | WO 2013050334 | 4/2013 |
| WO | WO 2013067248 | 5/2013 |
| WO | WO 2013091773 | 6/2013 |
| WO | WO 2013119895 | 8/2013 |
| WO | WO 2013192346 | 12/2013 |
| WO | WO 2014078454 | 5/2014 |
| WO | WO 201410623 8 | 7/2014 |
| WO | WO 2018023072 | 2/2018 |
| WO | WO 2011094740 | 8/2018 |
| WO | WO 2018151861 | 8/2018 |
| WO | WO 2019161236 | 8/2019 |
| WO | WO 2019161238 | 8/2019 |
| WO | WO 2020118032 | 6/2020 |
| ZA | 9102744 | 2/1992 |

OTHER PUBLICATIONS

Ahmad, I and Snieckus, V., "A Convenient Entro into the Rhoeadan Skelton. Total Synthesis of (±)-cis-alpinigenine", Canadian Journal of Chemistry, 60(12):2678-2686 (1982).

Akdemir et al., "Identification of novel a7 nicotinic receptor ligands by in silico screening against the crystal structure of a chimeric a7 receptor ligand binding domain," Bioorganic and Medicinal Chemistry, 2012, 20: 5992-6002.

American Chemical Society, STN Database RN 63463-05-8 entered Nov. 16, 1984.

Answer Summary, from the search of CAPLUS, Apr. 21, 2016. {Total 29 pages.).

Antoz, F.J., et al., "The Structure and Chemistry of Actinobolin", Journal of American Chemical Society, 92(16):4933-4942 (1970).

AU Application No. 2013216935, Examination Report No. 2 dated Aug. 1, 2017.

Bakshi, et al., "Antagonism of Phencyclidine-Induced Deficits in Prepulse Inhibition by the Putative Atypical Antipsychotic Olanzapine," Psychopharamcology, 122(2):198-201, 1995.

Berardi, et al., "4-(Tetralin-1-yl)-and-4-(Naphthalen-1yl)akyl] Derivatives of 1-Cyclohexylpiperazine as σ Receptor Ligands with Agonists $σ_2$ Activity", Journal of Medicinal Chemistry, American Chemical Society, 47(9):2308-23-17 (2004).

Berardi, et al., "A Multireceptorial Binding Reinvestigation on an Extended Class of σ Ligands: N-[ω-(Indan-1-yl and Tetralin-1-yl)alkyl] Derivatives of 3,3-Dimethylpiperdine Reveal High Affinities Towards $σ_1$ and EBP Sites", Bioorganic & Medicinal Chemistry, 9(5):4325-1335 (2001).

Berardi, et al., "Novel Potent σ1 Ligands: N-[ω-(Tetralin-1-yl)alkyl] piperdine Derivatives", Journal of Medicinal Chemistry, American Chemical Society, 38(21):4255-4260 (1996).

Berge, S.M., et al., "Pharmaceutical Salts", Journal of Pharmaceutical Sciences, 66(1):1-19 (1977).

Bianchi, D.A., et al., "Model Studies towards Stephaoxocanes: Construction of the 2-oxo-4azaphenalene Core of Stephaoxocanidine and Eletefine", European Journal of Organic Chemistry, 24:4731-4736 (2003).

Boger, D.L., et al., "Thermal Cycloaddition of 1,3,5-Triazine with Enamines: Regiospecific Pyrimidine Annulation", Journal of Organic Chemistry, 47:2673-2675 (1982).

Böhme, H. and Hitzel, V., "Homoisochroman-Derivative mit basischer Seitenkette in 1-Stellung", Archiv der Pharmazie 306:948-953 (1973) No English Translation.

Böhme, H. and Ziegler, F., "The Aminomethylation of 1-cyano-isochromane and 1-cyano-isothiochromane", Arch Pharm (Weinheim), 307(4):287-290 (1974) with English Translation.

Caira "Crystalline Polymorphism of Organic Compounds" Topics in current chemistry, 1998, 163-208.

CAPULUS Search Results of Apr. 6, 2016; 102 pages.

CAS Database Registry 444792-99-8 (XP-002742897) Aug. 24, 2002; 1 page.

CAS Database Registry 444793-00-4 (XP-002742898) Aug. 24, 2002; 1 page.

CAS Database Registry 444796-01-5 (XP-002742896) Aug. 24, 2002; 1 page.

CAS Database Registry 46490-93-1 (XP-002742899) Nov. 16, 1984; 1 page.

CAS Database Registry 738532-48-4 (XP-002742900) Septembers, 2004; 1 page.

CAS Database Registry Accession No. 1022058-43-0, May 23, 2008.

CAS Database Registry Accession No. 1022339-80-5, May 25, 2008.

(56) References Cited

OTHER PUBLICATIONS

CAS Database Registry Accession No. 1022468-83-2, May 25, 2008.
CAS Database Registry Accession No. 1022813-67-7, May 27, 2008.
CAS Database Registry Accession No. 1023480-64-9, May 29, 2008.
CAS Database Registry Accession No. 1024262-27-8 Jun. 1, 2008.
CAS Database Registry Accession No. 3549452-84-9, Sep. 28, 2001.
CAS Database Registry Accession No. 3594552-83-8, Sep. 28, 2001.
CAS Database Registry Accession Nos. 131022-75-8, 1310059-007-4, 1310059-06-3, 1310059-08-5 and 1310059-09-6 as cited in the Japanese Office Action dated Mar. 14, 2017 for Japanese Application No. 2014-556702.
CAS Database Registry Accession No. 340968-07-2, Jun. 14, 2001.
CAS Database Registry Accession No. 359452-60-1, Sep. 28, 2001.
CAS Database Registry No. 1027177-28-1 Jun. 11, 2008.
CAS Database Registry No. 1935196-69-2 Jun. 20, 2016.
CAS Registry No. 724648-33-5; STN entry date Sep. 10, 2004; Chemical name: Quinazoline, 4-benzo[b]thien-2-yl-1,4-dihydro- (cited Aug. 1, 2017, obtained from https://scifinder.cas.org on Aug. 10, 2017).
CAS Registry No. 736880-30-1; STN entry date Sep. 1, 2004; Chemical name: Quinazoline, 4-benzo[b]thien-2-yl-1,4-dihydro-2-methyl- (cited Aug. 1, 2017, obtained from https://scifinder.cas.org on Aug. 10, 2017).
CAS Registry No. 775528-08-0; STN entry date Nov. 7, 2004; Chemical name: Quinazoline, 4-benzo[b]thien-2-yl-1,4-dihydro-2-methyl (cited Aug. 1, 2017, obtained from https://scifinder.cas.org on Aug. 10, 2017).
CAS Registry No. 790156-85-3; STN entry date Nov. 28, 2004; Chemical name: Quinazoline, 4-benzo[b]thien-2-yl-1,4-dihydro- (cited Aug. 1, 2017, obtained from https://scifinder.cas.org on Aug. 10, 2017).
CAS Registry No. 933704-2 1-3, Apr. 30, 2007.
CAS Registry No. 1027834-86-1, Entered STN: Jun. 13, 2008, 4 pages.
CAS Registry No. 1071058-54-2, Entered STN: Nov. 6, 2008, 4 pages.
CAS Registry No. 1541037-08-04 date unknown.
CAS Registry No. 40196-92-7, Entered STN: Nov. 16, 1984, 2 pages.
CAS Registry No. 40196-93-8, Entered STN: Nov. 16, 1984, 2 pages.
CDC.gov, "Treatment of ADHD," Jan. 30, 2016, [retrieved Mar. 16, 2019] retrieved from URL <https://www.cdc.gov/ncbddd/adhd/treatment.html>, 8 pages.
Chemical Abstracts STN REGISTRY Database, record for RN 1784628-34-7, Entered into STN on Jun. 19, 2015. (Year: 2015).
Chihara, et al., "Preparation of Benzothiiophene Derivatives as Blood Platelet Aggregation Inhibitors", Retrieved from STN Database Accession No. 1992:128652 and JP03223277a, Yoshitomi Pharmaceutuical Industries Ltd., Oct. 2, 1991.
CN Office Action in Application No. 201410333332.1, dated Nov. 2, 2015 with translation.
Corbera, et al., "A Medicinal-Chemistry-Guided Approach to Selective and Druglike Sigma 1 Ligands", ChemMedChem, 1(1):140-154 (2006).
Correll et al. "Safety and Effectiveness of SEP-363856 in Schizophrenia: Results of a 6-Month, Open-Label Extension Study", American College of Neuropsychopharmacology, Poster. Dec. 2019, 1 page.
Dammacco, M., et al., "Lithiation of N-Alkyl-(o-totyl)aziridine: Stereoselective Synthesis of Isochromans", Journal of Organic Chemistry, 74:6319-6322 with supplemental material pp. S1-S34 (2009).

Datta et al., "Studies in Sulphur Heterocycles. Part 5. Further Use of 6,7-Dihydribenzo[b]thiphen-4[5H]-one in the Synthesis of Substituted Benzo[b]thiophene Derivatives", J. Chem. Research (S), 1988, 72-73.
Davis et al., "Benzothiophene Containing Rho Kinase Inhibitors: Efficacy in an Animal Model of Glaucoma", Bioorganic & Medicinal Chemistry Letters, Jun. 1, 2010, 20(11):3361-3366.
Debernadis, J.F., et al., "Conformationally Defined Adrenergic Agents. 4. 1-(Aminomethyl)phthalans: Synthesis and Pharmacological Consequences of the Phtalan Ring Oxygen Atom", Journal of Medicinal Chemistry, 30:178-184 (1987).
Dedic et al. "SEP-363856, A Novel Psychotropic Agent With a Unique, Non-D2 Receptor Mechanism of Action", The Journal of Pharmacology and Experimental Therapeutics, vol. 371, pp. 1-14, Oct. 2019.
Dedic et al. "The Novel, Non-D2 Psychotropic Agent SEP-363856 Modulates Presynaptic Dopamine Function in Mice", American College of Neuropsychopharmacology, Poster. Dec. 9, 2019, 1 page.
Dehaven-Hudkins, et al., "Characterization of the Binding of [3H](+)pentazocine to σ Recognition Sites in Guinea Pig Brain", European Journal of Pharmacology—Molecular Pharmacology Section 227:371-378 (1992).
Deninno, M.P., et al., "Synthesis and Dopaminergic Activity of 3-Substituted 1-(Aminomethyl)-3,4-dihydro-5,6-dihydroxy-1H-2-benzopyrans: Characterization of an Auxiliary Binding Region in the D1 Receptor", Journal of Medicinal Chemistry, 34:2561-2569 (1991).
Devani et al., "Synthesis of 2-Aminothiophenes & Thieno[2,3-d]pyrimidines", Indian Journal of Chemistry, May 1976, 14B:357-360.
Disabled World Towards Tomorrow, "Neurological Disorders: Types, Research & Treatment" URL: https://www.disabled-world.com/health/neurology downloaded on Nov. 1, 2017; 5 pages.
Dobson, et al., "Pyrano Heterocycles I. The Synthesese of Isochromans and the Novel Thieno[3,2-c]pyran, Benzothieno[3,2-c]pyran, and Pyrano[4,3-b]benxofuran Systems", Journal of Hetercyclic Chemistry, 12(3):591-594, 1975, 4 pages.
Ellis, "Affective Disorders (Mood Disorders)", Healthline Part 1 of 7 Overview; URL: http://www.healthline.com/health/affective-disorders, 5 pages, downloaded Jul. 25, 2015.
Emedicine Health, "Brain Cancer: Get Facts on Treatment, Causes and Symptoms", URL: https://www,emedicinehealth.com/brain_cancer/article_em.htm?pf=2; 15 pages downloaded 2015.
EP Application No. 123747266.8, Communication Pursuant to Article 94(63) EPC dated Dec. 21, 2017.
EP Application No. 13747266.8, Partial Supplementary European Search Report dated Aug. 14, 2015; 11 pages.
EP Application No. 10835185.9, Extended European Search Report dated Apr. 4, 2013, 15 pages.
EP Patent Application No. 13747266.8, Communication Pursuant to Article 94(3) dated Nov. 18, 2016.
Extended European Search Report in EP Appln. No. 17835384.3, dated Mar. 9, 2020, 10 pages.
Frohlich et al., "A Novel Synthesis of 3,3-(Spiro)Substituted Azetidines", Heterocycles, 1994, 37(3):1897-1891.
Fujima et al. "Synthesis of (s)-3-(N-Methylamino)-1-(2-thienyl)propan-1-ol: Revisiting Eli Lilly's Resolution-Racemization-Recycle Synthesis of Duloxetine for it's Robust Processes", Organic Process Research and Development, 2006, 10(5):905-913.
Gaur,S., et al. "CoMFA and CoMSIA Studies on a set of Benzyl Piperazines, Piperadines, Pyrazinopyridoindoles, Pyrazinoisoquinolines and Semi Rigid analogs of Diphenydramine", Medicinal Chemistry Research, 13(8-9):746-757 (2004).
Ghaemi, et al., "Does Olanzapine have Antidepressant Properties? A Retrospective Preliminary Study", Bipolar Disorders, 2:196-199, 2000.
Ghasemi, et al., "The Role of NMDA Receptors in the Pathophysiology and Treatment of Mood Disorders", Neuroscience and Biobehavioral Reviews, 47:336-358, 2014.
Girke, W.P.K., "Elektrophile Aromatische Substitutionsreaktionen Mit Protonierten 1,3-Diazinen II. Darstellung und Eigenschaften

(56) References Cited

OTHER PUBLICATIONS 4-arylsubstituierter 3,4-Dichrochinazolin-Derivate", Chem Ber., 112(4): 1348-1358 (1979) [English Abstract and machine translation of entire referenc—24 pages].

Gleason, et al., "Blockade of Phencyclidine-Induced Hyperlocomotion by Olanzapine, Clozapine and Serotonin Receptor Subtype Selective Antagnoists in Mice", Psychopharmacology, 129:79-84, 1997.

Google.com [online] "Parkinson's Disease—Symptoms, Diagnosis and Treatment." Jan. 22, 2006, [Retrieved on Dec. 28, 2018] Retrieved from URL <https://www.google.com/search?q=Parkinson+disease+treatment&source=Int&tbs=cdr%3A1%2Ccd_max%3A2%2F8%2F2012&tbm=>, 2 pages.

Gould, P.L., "Sale Selection for Basic Drugs", International Journal of Pharmaceutics, 33:201-217 (1986).

Grilliot, A-L and Hart, D.J., "Guanidinium Carboxylates: Preparation of 3-Carboxyoctahydro-9aH-Pyrimidin-9a-Ylium Chloride", Heteroycles, 39(2):435-438 (1994).

Gronowitz, et al, The Reaction of 5-Bromo- and 2-Bromopyrimidine with Organolithium Compounds, Acta Chemica Scandinavica 19(7):8 pages (1965).

Hanner, et al., "Purification Molecular Cloning, and Expression of the Mammalian Sigma$_1$-Binding Site", Proc. Natl. Aca. Sci., 93:8072-8077 (1996).

Hayakawa, K., et al., "Addition Reactions of (Phenylsulfonyl)propadiene with 1-Pryrrolidinyl Enamines of Cyclic Ketones: Syntheses and Reactions of 1,3-Dienes Possessing an Allyl Sulfone Moiety", Journal of Organic Chemistry, 51:5100-5105 (1986).

Hejl, et al., "Prepulse Inhibition in Patients with Alzheimer's Disease", Neurobiology of Aging, 25:1045-1050 (2004).

Hopkins et al. "Effects of SEP-363856 on Negative Symptoms in Schizophrenia: Analysis of an Acute, Placebo-Controlled Trial of a Novel Psychotropic Agent With No Dopamine-D2/5-Ht2a Antagonist Activity", American College of Neuropsychopharmacology, Poster. Dec. 2019, 1 page.

Hopkinsmedicine.org [online] "Treatment for Tourette Syndrome: Johns Hopkins Pediatric Neurology," Apr. 2006, [Retrieved on Dec. 28, 2018] Retrieved from URL <https://www.hopkinsmedicine.org/neurology_neurosurgery/centers_clinics/pediatric-neurology/conditions/tourettes_syndrome/treatment.html>, 1 page.

Hörig, H. and Pullman, W., "From Bendch to Clinic and Back: Perspective on the 1st IQPC Translational Research Conference", Journal of Translational Medicine, 2:44, 8 pages (2004).

Ingebrigsten, T., et al., "Palladium-Catalysed Synthesis of Pyrimidines", Heterocycles, 65(11):2593-2603 (2005).

International Application No. PCT/US2013/025260, International Preliminary Report on Patentability issued by the International Searching Authority, dated Aug. 12, 2014, 10 pages.

International Application No. PCT/US2013/025260, International Search Report and Written Opinion issued by the International Searching Authority, dated Apr. 17, 2013 10 pages.

International Application No. PCT/US2016/017527 International Search Report dated Apr. 13, 2016, 8 pages.

International Application No. PCT/US2010/058884, International Search Report and Written Opinion dated Aug. 25, 2011, 10 pages.

International Application No. PCT/US2016/017539, International Search Report dated May 2, 2016, 3 pages.

International Application No. PCT/US2016/017539, Written Opinion dated May 2, 2016, 5 pages.

International Application No. PCT/US2017/044511, International Preliminary Report on Patentability issued by the International Searching Authority, dated Jan. 29, 2019, 8 pages.

International Application No. PCT/US2017/044511, International Search Report and Written Opinion dated Dec. 21, 2017, 10 pages.

International Application No. PCT/US2017/044517, International Preliminary Report on Patentability issued by the International Searching Authority, dated Jan. 29, 2019, 6 pages.

International Application No. PCT/US2017/044517, International Search Report and Written Opinion dated Jan. 11, 2018, 9 pages.

International Application No. PCT/US2018/044854, International Search Report and Written Opinion dated Apr. 10, 2018, 13 pages.

INTL Application No. PCT/US2018/000078 International Search Report and Written Opinion, dated May 25, 2018, 9 pages.

INTL Application No. PCT/US2019/018263 International Search Report and Written Opinion, dated Apr. 2, 2019, 8 pages.

INTL Application No. PCT/US2019/018265 International Search Report and Written Opinion dated May 29, 2019, 17 pages.

INTL Application No. PCT/US2019/064646, International Search Report and Written Opinion, dated Mar. 9, 2020, 13 pages.

Ito, N., et al., "A Medium-Term Rat Live Bioassy for Rapid in vivo Diction of Carcinogenic Potential of Chemicals", Cancer Science, 94(1):3-8 (2003).

Jacobs, et al., "1-Imidizolyl(alkyl)-Substituted Di- and Tetrahydroquinolines and Analogues: Syntheses and Evaluation fo Dual Inhibitors of Thromboxane A2 Synthase and Aromatase", Journal of Medicinal Chemistry, 43(9):1841-1851, 2000.

Jaskowska, J. and Kowalski, P., "N-Alkylation of Imides Using Phase Transfer Catalysts Under Solvent-Free Conditions", Journal Heterocyclic Chemistry, 45:1371-1375 (2008).

Jentsch, et al., "The Neuropsychopharmacology of Phencyclidine: From NMDA Receptor Hypfunction to the Dopamine Hypothesis of Schizophrenia", Neurpsychopharmacology, 20(3):201-225, 1999.

Jones et al. "SEP-0363856, A Novel Psychotropic Agent With a Unique, Non-D2 Mechanism of Action", European College of Neuropsychopharmacology Congress, Poster, Sep. 2019.

JP Application No. 2012-542219, Office Action dated Nov. 21, 2014, 9 pages including translation.

JP Application No. 2014-556702, Notice of Reasons for Rejection dated Jul. 19, 2016 (with translation).

JP Application No. 2014-556702, Notice of Reasons for Rejection dated Mar. 14, 2017 (with translation).

Kapur, et al., "NMDA Receptor Antagonists Ketamine and PCP Have Direct Effects on the Dopamine D2 and Serotonin 5-HT2 Receptors-Implications for Models of Schizophrenia", Molecular Psychiatry, 7:837-844, 2002.

Karran, et al., "The Amyloid Cascade Hypothesis for Alzheimer's Disease: An Appraisal for the Development of Therapeutics", Nature, 10:698-712 (2011).

Katsuki, et al., "Excitotoxic Degeneration of Hypthalamic Orexin Neurons in Slice Culture", Neurobiology of Disease, 15:61-69, 2004.

Kay et al., "The positive and negative syndrome scale (PANSS) for schizophrenia," Schizophrenia Bulletin, 1987, 13(2):261-276.

Koblan et al. "A Non-D2-Receptor-Binding Drug for the Treatment of Schizophrenia", The New England Journal of Medicine, Apr. 16, 2020, 382(16):1497-1506.

Koblan et al. "A Phase 1 Open Label Safety and Tolerability Study of Sep-363856, A Novel Non-D2 Mechanism of Action Molecule, in Patients With Schizophrenia", American College of Neuropsychopharmacology, Poster. Dec. 2016, 1 page.

Koblan et al. "Efficacy and Safety of SEP-363856 in the Treatment of Schizophrenia: A 4-Week, Randomized, Placebo-Controlled Trial of a Novel Compound With a Non-D2 Mechanism of Action", American College of Neuropsychopharmacology Annual Meeting, Poster. Dec. 2018, 1 page.

Koblan et al. "Efficacy and Safety of SEP-363856, a Novel Non-D2 Agent, in the Treatment of Schizophrenia: A 4-Week, Randomized, Placebo-Controlled Trial", European College of Neuropsychopharmacology Congress, Poster. Sep. 2019, 1 page.

Koblan et al. "Efficacy and Safety of SEP-363856, a Novel Psychotropic Agent With a Non-D2 Mechanism of Action, in the Treatment of Schizophrenia: A 4-Week, Randomized, Placebo-Controlled Trial", American Psychiatric Association, Poster. May 2019, 1 page.

Koblan et al. "Efficacy and Safety of SEP-363856, a Novel Psychotropic Agent With a Non-D2 Mechanism of Action, in the Treatment of Schizophrenia: A 4-Week, Randomized, Placebo-Controlled Trial", American Society of Clinical Psychopharmacology, Poster. May 2019, 1 page.

Koblan et al. "Efficacy and Safety of SEP-363856, a Novel Psychotropic Agent With a Non-D2 Mechanism of Action, in the

(56) References Cited

OTHER PUBLICATIONS

Treatment of Schizophrenia: A 4-Week, Randomized, Placebo-Controlled Trial", US Psychiatric and Mental Health Congress, Poster. Oct. 2019, 1 page.
Koblan et al. "Efficacy and Safety of SEP-363856, a Novel Psychotropic Agent With a Non-D2 Mechanism of Action, in the Treatment of Schizophrenia: A Randomized, Placebo-Controlled Trial", Neuroscience Education Institute, Poster. Nov. 2019, 1 page.
Koblan et al. "SEP-363856, a Novel Psychotropic Agent With a Non-D2 Mechanism of Action, for the Treatment of Schizophrenia", the 2019 Congress of the Schizophrenia International Research Society, Oral Presentation. 20 pages. Apr. 2019.
Koblan, "SEP-363856, a Candidate Antipsychotic and Antidepressant Compound With a Novel Non-D2 Mechanism of Action", 6th Biennial Schizophrenia International Research Society Conference, Oral Presentation. 31 pages. Apr. 2018.
Korneev, et al. CAS STN Abstract, publ 2009 RN 1202851-83-9.
Kostin, et al., "Lack of Hypocretin Attenuates Behavioral Changes Produced by Glutamatergic Activation of the Perifomical-Lateral Hypthalamic Area", Sleep, 37(5): 1011-1020, 2014.
Krogsgaard-Larsen, et al., Textbook of Drug Design and Discovery Madsen, U. (Ed.). (2009), Textbook of Drug Design and Discovery, Fourth Edition, Boca Raton: CRC Press. (2002).
Kumar, A., et al., "Catecholamines in a Semi-Rigid Framework: Synthesis & Biological Activity of N-Substituted I-Aminomethyl-5,6- & 6,7-dihydroxyisochromans", Indian Journal of Chemistry 26B:47-51 (1987).
Kumar, A., et al., "Phenethylamine in a Semi-Rigid Framework: Synthesis & Biological Activity of N-Substituted I-Aminomethyl-5,6- & 6,7-dimethoxyisochromans", Indian Journal of Chemistry 16B:793-796 (1978).
Langa,et al., "Generation and Phenotypic Analysis of Sigma Receptor type 1 ($\sigma$1) Knockout Mice", European Journal of Neuroscience, 18:2188-2196 (2003).
Lima, et al., Bioisosterism: A Useful Strategy for Molecular Modification and Drug Design, Current Medicinal Chemistry, 12:23-49 (2005).
Lindvall, O. and Kokaia, Z., "Stem Cells for the Treatment of Neurological Disorders", Nature, 441:1094-1096 (2006).
Lowry, et al., "Protein Measurement with the Folin Phenol Reagent", Journal Biochemistry, 193:265 (1951).
Macchia, B., et al., "Conformationally Restrained Analogs of Sympathomimetic Catecholamines, Synthesis Conformational Analysis, and Adrenergic Activity of Isochroman Derivatives", Journal of Medicinal Chemistry, 36:3077-3086 (1993).
Mahableshwarkar et al., "Replication of a statistical method to reduce pseudospecificity and enhance understanding of score changes among PANSS factors," Presented at the International Society of CNS Clinical Trials and Methodology, Paris, France, Aug. 31-Sep. 2, 2017, 1 page.
Maier, et al., "Novel Spiropiperdines as Highly Potent and Subtype Selective $\sigma$-Receptor Ligands. Part 1", Journal of Medicinal Chemistry, 45:438-448 (2002), Journal Medicinal Chemistry, 45:4923-4930 (2002).
Maier, et al., "Novel $\sigma$ Receptor Ligands, Part 2. SAR of Spiro[[2]benxopyran-1,4-piperdines] and Spiro [[2]benzofuran-1,4'-piperidines] with Carbon Substituents in Position 3", Journal Medicinal Chemistry, 45:4923-4930 (2002).
Marcus, et al., "The Efficacy and Safety of Aripiprazole as Adjunctive Therapy in Major Depressive Disorder. A Second Multicenter, Randomized, Double-Blind, Placebo-Controlled Study", Journal of Clinical Psychopharmacology, 28(2):156-165, 2008.
Mashkovskiy, Drugs, Moscow, New Wave, LLC, vol. 1, p. 11 (2002) with translation.
Mayo Clinic Symptoms and Causes, "Seasonal Affective Disorder (SAD)", URL: https://www.mayoclinic.org/diseases-conditions/seasonal-affective-disorder/syymptoms-causes; 2 pages, downloaded 2015.
Mayoclinic.org [online] "Fibromyalgia Treatment: Is Neurontin Effective?" Jul. 2009, [Retrieved Oct. 18, 2019], Retrieved from URL <https://www.mayoclinic.org/diseases-conditions/fibromyalgia/expert-answers/fibromyalgia-treatment/faq-20058273>, 3 pages.
Medicinenet.com [online] "Alzheimer's Disease Treatment, Symptoms, Stages & Life Expectancy." Jul. 2007, [Retrieved on Dec. 28, 2018], Retrieved from URL <https://www.medicinenet.com/alzheimers_disease_causes_stages_and_symptoms/article.htm#alzheimers_disease_medications>, 16 pages.
Medlineplus.gov [online] "Symptoms, Diagnosis and Treatment: Alzheimer's Disease." Fall 2010, [Retrieved on Dec. 28, 2018], Retrieved from URL <https://medlineplus.gov/magazine/issues/fall10/articles/fall10pg19.html>, 5(3): 19.
Michaeljfox.org [online] "Parkinson's Disease," May 2007, [Retrieved Dec. 28, 2018] Retrieved from URL <https://www.michaeljfox.org/understanding-parkinsons/living-with-pd/topic.php?causes>, 5 pages.
Mokrosz, et al., "Structure-Activity Relationship Studies of CNS Agents. Part 14:3 Structural Requirements for the 5-HT1A and 5-HT2A Receptor of Simple 1-(2-pyrimidinyl)piperazine Derivatives", Pharmazie, 49(H11) 6 pages (1994).
Moreno, et al., "Preclinical Models of Antipsychotic Drug Action", International Journal of Neuropsychopharmacology, 16:2131-2144, 2013.
Movassaghi, M. and Hill, M.D., "Single-Step Synthesis of Pyrimidine Derivatives", Journal of American Chemical Society, 128:14254-14255 (2006).
MX Application No. MX/a/2012/006326, Examination Report dated Jul. 4, 2013, with English translation, 6 pages.
Nakashima, T., et al., "Regulation of Folding and Photochromic Reactivity of Teraylenes Through a Host-Guest Interaction", Chem. European Journal, 17:10951-10957 (2011).
Nemade et al., "Schizophrenia Medication Treatement Options," Feb. 15, 2006, [retreived Mar. 16, 2019] retreived from URL <https://www.mentalhelp.net/articles/schizophrenia-medication-treatement-options/>, 6 pages.
Ng, et al., "Design and synthesis of hydroxy ethylamine (HEA) BACE-1 inhibitors: prime side chromane-containing inhibitors," Bioorganic & Medicinal Chemistry Letters, 2013, 23(16):4674-4679.
Nguyen et al. "Chiral Drugs: An Overview." Int. J. Biomed Sci., 2006, 2(2):85-100.
NIMH.nih.com [online] "Bipolar Disorder," Jan. 2016, [retrieved on Mar. 16, 2019] retrieved from URL <https://www.nimh.nih.gov/health/topics/bopolar-disorder/index/shtml>, 13 pages.
NIMH.nih.com [online] "Obsessive-Compulsive Disorder," Jan. 2016, [retreived on Mar. 16, 2019] retreived from URL <https://www.nimh.nih.gov/health/topics/obsessive-compulsive-disorder-ocd/index.shtml>, 10 pages.
Nishimura, Y., et al., "Syntheses and Activities of some Bactobolin Derivatives", Journal of Antibiotics, 45(5):735-741 (1992).
Nordquist, et al., "Effects of Aripiprazole/OPC-14597 on Motor Activity, Pharmacological Models of Psychosis, and Brain Activity in Rats", Neuropharmacology, 54:405-416, 2008.
NZ Application No. 600008, First Examination Report dated Mar. 11, 2013 in NZ, 3 pages.
NZ Application No. 626068 Examination Report dated Oct. 8, 2015, 3 pages.
NZ Application No. 711802 Examination Report dated Oct. 8, 2015, 5 pages.
Papillion, J.P.N., et al., "Structure-Activity Relationships, Pharmacokinetics, and in Vivo Activity of CYP11B2 and CYP11B1 Inhibitors", Journal of Medicinal Chemistry, 58:4749-4770 (2015).
Pittenger, et al., "The NMDA Receptor as a Therapeutic Target in Major Depressive Disorder", CNS & Neuroological Distorders—Drug Targets, 6(2): 101-115, 2007.
Poola et al. "Pharmacokinetics, Safety, and Tolerability of Sep-363856 in Healthy Adult Male Subjects and in Adult Patients With Schizophrenia Following Oral Administration", American College of Clinical Pharmacology, Poster. Sep. 2018, 1 page.
PUBCHEM CID 12175079, create date Febmary 7, 2007, p. 3 compound; accessed Nov. 13, 2017; 9 pages.
PUBCHEM CID 4878038, create date Sep. 17, 2005, accessed Feb. 22, 2019; 12 pages.
PUBCHEM CID 4878041, create date Sep. 17, 2005, accessed Feb. 22, 2019; 14 pages.

(56) References Cited

OTHER PUBLICATIONS

Quirion, et al., "A Proposal for the Classification of Sigma Binding Sites", Trends in Pharamcology Science, 13:85-86 (1992).
Quiroz, T., et al., "A Practical Method for the Synthesis of Pyrrolizidine, Indolizidine and Pyrroloazepinolizidine Nucleus", Tetrahedron Letters, 48:1571-1575 (2007).
Radesca, et al., "Synthesis and Receptor Binding of Enantiomeric N-Substituted cis-N-[2-(3,4-Dichlorophenyl)ethyl]-1-(1-pyrrolidinyl) cyclohexylamines as High-Affinity σ Receptor Ligands", Journal of Medicinal Chemistry, 34:3065-3074 (1991).
Ram, S., et al., "Synthesis & Structure-Activity Relationships of 1-Substituted-aminomethyl-3-phenyl/methyl-1,3-dihydroisobenzofurans & 4-Substituted-amino-1-phenyl/methylisochromans—A New Class of Antihistaminics", Indian Journal of Chemistry, Section B: Organic Chemistry Including Medicinal Chemistry, 23B(12):1261-1267 (1984).
Rekka, E., et al., Structural Features of some Diphenhydramine Analogs that Determine the Interaction with Rat Liver Cytochrome P-450, Agents and Actions, 27(1-2): 184-187 (1989).
Ross et al., "α2 Adrenoceptor Agonists as Potential Analgesic Agents. 2. Discovery of 4-(4-Imidazo)-1,3-dimethyl-6,7-dihydrothianaphthene as a High-Affinity Ligand for the α2D Adrenergic Receptor", J, Med. Chem., 2000, 43:1423-1426.
Ross, L.O., et al., "Potential Anticancer Agents. XVIII. Synthesis of Substituted 4,5-Trimethylenepyrimidines", Journal of American Chemical Society, 84(12):3108-3114 (1959).
Sakai, et al., "Facile and Efficient Synthesis of Polyfunctionalized Benzofurans: Three-Component Coupling Reactions from an Alkynylsilane, and o-Hydroxybenzaldehyde Derivative, and a Secondary Amine by a Cu(1)—Cu(II) Cooperative Calatytic System", Tetrehedron Letters, 49:3437-3440 (2008).
Salomone, A., et al., "Preparation o f Polysubstituted Isochromanes by Addition of ortho-Lithiated Aiyloxiranes to Enaminones", Journal of Organic Chemistry, 78:11059-11065 (2013).
Saxena, M., et al., "Synthesis of some Substituted Pyrazinopyridoindoles and 3D QSAR Stuies along with Related Compounds: Piperazines, Piperidines, Pyrazinoisoquinolines. And Diphenhydramine, and its Semi-Rigid Analogs as Antihistamines (H1)", Bioorganic & Medicinal Chemistry 14:8249-8258 (2006).
Schäfer, S., "Failure is an Option: Learning from Unsuccessful Proof-of-Concept Trials", Drug Discovery Today, 13(21/22):913-916 (2008).
Schmitz, et al., "Hippocampal Neuron Loss Exceeds Amyloid Plaque Load in a Transgenic Mouse Model of Alzheimer's Disease", American Journal of Pathology, 164(4):1045-1050 (2004).
Schow, et al., "Novel Sigma Receptor Ligands 2.", Bioorganic & Medicinal Chemistry Letters, 3(2):221-224 (1993).
SG Application No. 201204089-5, Written Opinion dated Sep. 20, 2013, 12 pages.
Shklyaeva et al., "2-Amino-6-(3,4-ethylenedioxythiophen-2-yl)-4-(2-thienyl)-pyrimidine: Synthesis and Properties", Russian Journal of Organic Chemistry, 2010, 46(6):938-940.
Singapore Application No. 10201401661, Search Report and Written Opinion dated Jun. 15, 2015, 10 pages.
Snyder, et al., "Receptor Mechanisms in Antipsychotic Drug Action: Focus on Sigma Receptors", Journal of Neuropsychiatry, 1(1):7-15 (1989).
Sridhar et al., "Synthesis and Anticancer Activity of Some Novel Pyrimidine Derivatives", International Journal of Pharmaceutical Sciences and Research, Sep. 29, 2011, 2(10):2562-2565.
Stanetty et al., "Heterocyclische Spiroverbindungen Spiroverbindungen: Spiro [benzo[b]thiophen-4(5H),3'-pyrrolidine]", Arch. Pharm., 1984, 317:168-176 With English Abstract.
Steliou, K., et al., "Group 14 Metal Assisted Carbon-Sulfur Bond Formation", Journal of Organic Chemistry, 50(24):4969-4971 (1985).
Strekowski, et al., "Synthesis of 2-Chloro-4,6-di(heteraryl)pyrimidines", Journal of Heterocyclic Chemistry, 27:1393-1400 (1989).
Swerdlow et al., "Seroquel Restores Sensorimotor Gating in Phencyclidine-Treated Rats," Journal of Pharmacology and Experimental Therapeutics, Dec. 1996, 279(3):1290-1299.
Toffano, M., et al., "Asymmetric Routes Towards Polyfunctionalized Pyrrolidines: Application to the Synthesis of Alkaloid Analogues", Tetrahedron: Asymmetry, 14:3365-3370 (2003).
Togna, et al., "1-Phenil-6, 7-dihydroxy-isochroman inhibits inflammatory activation of microglia," Brain Research Bulletin, 2013, 95:33-39.
Torrado, et al., "Novel Selective and Potent 5-HT Reuptake Inhibitors with 5-HT$_{1D}$ Antagonist Activity: Chemistry and Pharmacological Evaluation of a Series of Thienopyran Derivatives", Bioorganic & Medicinal Chemistry, 12(20):5277-5295, 2004, 19 pages.
Trehan, "A New Synthesis of 13-aza-18-nor-17oxo-A-nor-3-thiaestra-1,5(10), 9(11)-triene" Retrieved from STN Database Accession No. 1986:225089 & Indian Journal of Chemistry, Section 6: Organic Chemistiy Including Medicinal Chemistry, 24B(6):659-661 (1985).
Trehan, "Synthesis of 2,3,13-Triaza-18-nor-17-oxo-3-phenyl-A-nor-estra-1,5(10), 9(11)-triene & 2,3,13-Triaza-7,7-dimethyl-18-nor-17-oxo-3-phenyl-A-nor-estra-1,5(10), 9(11)-triene", Indian Journal of Chemistry, 19B:243-245 (1980).
UPMC.com [online], "Find the Best Epilepsy Treatment for You," May 23, 2015, [retreived on Mar. 16, 2019] retreived from URL <https://share.upmc.com/2015/05/epilepsy-treatement/>, 5 pages.
US Food and Drug Administration, "Highlights of Prescribing Information: Ability," FDA label, last revised Dec. 2014, 84 pages.
Van Der Stoel, et al., "Di-TT-methane Rearrangement of 4-Heteroaryl-1,4(or 3,4)-dihydropyrimidines", Journal of the Chemical Society, Perkin Transactions 1, 4 pages Nov. 2, 1978.
Vecchietti, et al. ,"(1S)-1-(Aminomethyl)-2-(arylacetyl)-1,2,3,4-tetrahydroisoquinoline and Heterocycle-Condensed Tetrahydropyridine Derivatives: Members of a Novel Class of Very Potent K Opiod Analgesics", Journal of Medicinal Chemistry, 34(8):2624-2633 1991.
Walker, et al., "Sigma Receptors: Biology and Function", Pharmacological Reviews, 42(4):355-402 (1990).
Weis, et al., "The Crystal and Molecular Structure of 4,6,6-trimethyl-2-phenyl-1,6-dihydropyrimidine", Hetercycles, 19(3):6 pages (1982).
Werber et al., "The Beneficial effect of cholinesterase inhibitors on patients suffering from Parkinson's disease and dementia," J Neural Transm., Jun. 27, 2001, 108:1319-1325.
Wilkinson et al., "Cholinesterase Inhibitors Used in the Treatment of Alzheimer's Disease," Drugs Aging., 2004, 21(7):453-478.
Williams, M., et al., "Emerging Molecular Approaches to Pain Therapy", Journal of Medicinal Chemistry, 42(9):1481-1500 (1999).
Winhusen, T.M., et al., "A Placebo-Controlled Screening Trial of Tiagabine, Sertraline and Donepezil as Cocaine Dependence Treatments", Addiction, 100(Suppl. 1):68-77 (2005).
Xi, Z., et al., Preparation of Partially Substituted 1-Halo- and 1,4-Dihalo-1,3-Dienes via Reagent-Controlled Desilyation of Halogenated 1,3-Dienes, Journal of Organic Chemistry, 71:3154-3158 (2006).
Zhong Huang, N-A, et al., "Thiation Reactions of Some Active Carbonyl Compounds with Sulfur Transfer Reagents", The Journal of Organic Chemistry, 52(2): 169-172 (1987).

HETEROARYL-ISOCHROMAN COMPOUNDS AND USES THEREOF

FIELD

Provided herein are 1-aminomethyl-5-heteroarylisochroman compounds, and pharmaceutical compositions thereof, for the treatment of central nervous system (CNS) diseases and disorders (e.g., movement disorders, epilepsy, depression, bipolar disorder, pain, schizophrenia, obsessive compulsive disorder, psychostimulation, addiction, social disorder, attention deficit hyperactivity disorder, an anxiety disorder, autism, a cognitive impairment, or a neuropsychiatric symptom such as apathy, depression, anxiety, cognitive impairment, psychosis, aggression, agitation, impulse control, and sleep disruption in neurological diseases such as Alzheimer's and Parkinson's diseases).

BACKGROUND

Central nervous system diseases and disorders affect a wide range of the population with differing severity. Neurological and psychiatric diseases and disorders include a movement disorder, epilepsy, major depression, schizophrenia, bipolar disorder, obsessive compulsive disorder (OCD), panic disorder, and posttraumatic stress disorder (PTSD), among others. These diseases and disorders affect a person's thoughts, mood, behavior and social interactions and can significantly impair daily functioning. See, e.g., *Diagnostic and Statistical Manual of Mental Disorders,* 4th Ed., American Psychiatric Association (2000) ("DSM-IV-TR"); *Diagnostic and Statistical Manual of Mental Disorders,* 5th Ed., American Psychiatric Association (2013) ("DSM-5"). Furthermore, neuropsychiatric symptoms such as apathy, depression, anxiety, cognitive impairment, psychosis, aggression, agitation, impulse control and sleep disruption are now recognized as core impairments of neurological diseases and disorders such as Alzheimer's and Parkinson's diseases.

Epilepsy is a neurological disorder characterized by recurrent, unprovoked seizures (Blume et al., Epilepsia. 2001; 42:1212-1218). These seizures are transient signs and/or symptoms due to abnormal, excessive or synchronous neuronal activity in the brain (Fisher et al., Epilepsia 46 (4): 470-2). Epilepsy should not be understood as a single disorder, but rather as a group of syndromes with vastly divergent symptoms but all involving episodic abnormal electrical activity in the brain. It is one of the most common serious neurological disorders in the United States and often requires long-term management. Each year 150,000 people in the United States are newly diagnosed as having epilepsy, with the cumulative lifetime incidence approaching 3% (Hauser et al., Epilepsia. 1991; 32:429-445; Begley et al., Epilepsia. 1994; 35:1230-1243). Patients with uncontrolled seizures experience significant morbidity and mortality and face social stigma and discrimination as well.

SUMMARY

Provided herein are compounds of Formula I:

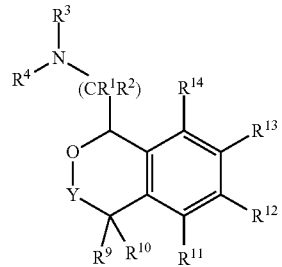

or a pharmaceutically acceptable salt thereof.
wherein:
Y is chosen from direct bond, —$C(R^5R^6)$— and —$C(R^5R^6)C(R^7R^8)$—.

$R^1$, $R^2$, $R^3$ and $R^4$ are chosen independently from H and aliphatic ($C_1$-$C_8$)hydrocarbon, wherein the aliphatic ($C_1$-$C_8$) hydrocarbon is optionally substituted with one or more of halogen, hydroxyl, ($C_1$-$C_6$)alkoxy, amino, ($C_1$-$C_6$)alkylamino and di($C_1$-$C_6$)alkylamino;

or, taken together, $R^1$ and $R^2$ may form ($C_3$-$C_6$)cycloalkyl;

$R^5$ and $R^6$ are chosen independently from H, halogen, ($C_1$-$C_6$)alkyl and ($C_1$-$C_6$)haloalkyl;

$R^7$, $R^8$, $R^9$ and $R^{10}$ are chosen independently from H, halogen, ($C_1$-$C_6$)alkyl, ($C_1$-$C_6$)haloalkyl and ($C_1$-$C_6$)alkoxy;

$R^{11}$, $R^{12}$, $R^{13}$, and $R^{14}$ are chosen independently from H, halogen, ($C_1$-$C_8$)hydrocarbyl, cyano, ($C_1$-$C_6$)haloalkyl, aminocarbonyl, ($C_1$-$C_6$))alkylaminocarbonyl, di($C_1$-$C_6$)alkylaminocarbonyl, ($C_1$-$C_6$)acyl, ($C_1$-$C_6$)alkoxy, ($C_1$-$C_6$)haloalkoxy, hydroxy($C_1$-$C_6$)alkyl, carboxy, ($C_1$-$C_6$) alkoxycarbonyl, acetoxy, nitro, amino, ($C_1$-$C_6$)alkylamino, di($C_1$-$C_6$)alkylamino, aminosulfonyl, phenoxy, benzyloxy, benzyl, aryl, alkylaryl, heteroaryl and alkylheteroaryl;

wherein one or more of $R^{11}$, $R^{12}$, $R^{13}$, and $R^{14}$ is phenoxy, benzyloxy, benzyl, aryl, alkylaryl, heteroaryl or alkylheteroaryl;

wherein said phenoxy, benzyloxy, benzyl, aryl, alkylaryl, heteroaryl or alkylheteroaryl are optionally substituted with one or more substituents selected from halogen, ($C_1$-$C_4$) alkyl, cyano, ($C_1$-$C_4$)haloalkyl, ($C_1$-$C_4$)alkoxy, aminocarbonyl, ($C_1$-$C_6$)alkylaminocarbonyl, di($C_1$-$C_6$)alkylaminocarbonyl, ($C_1$-$C_4$)acyl, ($C_1$-$C_4$)haloalkoxy, hydroxy($C_1$-$C_4$) alkyl, carboxy, ($C_1$-$C_4$)alkoxycarbonyl, acetoxy, nitro, amino, ($C_1$-$C_4$)alkylamino, and di($C_1$-$C_4$)alkylamino.

In some embodiments, provided are compositions comprising a compound disclosed herein and a pharmaceutically acceptable carrier, adjuvant, or vehicle.

In some embodiments, provided are methods for treating a neurological or psychiatric disorder in a subject, comprising administering to said subject an effective amount of a compound or composition disclosed herein.

DETAILED DESCRIPTION

The publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present inventions.

While medications exist for some aspects of these diseases and disorders, there remains a need for effective treatments for various neurological and psychiatric diseases and disorders. For example, while mood stabilizers such as lithium and valproate, antidepressants and antipsychotic drugs are used to treat mood disorders, more effective medications are necessary. Current antipsychotics may be successful in treating the positive symptoms of schizophrenia but are less effective for the negative and cognitive symptoms. Additionally, current antidepressants are typically effective only for a proportion of subjects suffering from depression. Furthermore, despite the fact that the behavioral and psychiatric symptoms of neurological disease such as Parkinson's disease and Alzheimer's disease are major reasons for the institutionalization of subjects, few drugs exist to treat them. The compounds disclosed herein address these needs.

The methods of the disclosure relate to the use of compounds and compositions disclosed herein to treat neurological or psychiatric diseases and disorders or impairments. In some embodiments, the neurological or psychiatric disorder is depression, bipolar disorder, pain, schizophrenia, obsessive compulsive disorder, addiction, social disorder, attention deficit hyperactivity disorder, an anxiety disorder, a movement disorder, epilepsy, autism, Alzheimer's disease, Parkinson's disease or cognitive impairments. In one embodiment, the disorder is depression, particularly treatment-resistant depression (TRD), major depressive disorder (MDD), unipolar depression, bipolar depression or depression associated with another disease or disorder. In some embodiments, the impairments in neurological diseases and disorders such as Alzheimer's and Parkinson's diseases include neuropsychiatric symptoms such as apathy, depression, anxiety, cognitive impairment, psychosis, aggression, agitation, impulse control disorders, and sleep disorders.

In some embodiments, provided herein are compounds of Formula I

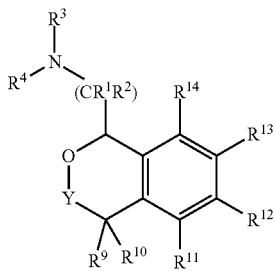

I or a pharmaceutically acceptable salt thereof,
wherein:
Y is chosen from direct bond, —$C(R^5R^6)$— and —$C(R^5R^6)C(R^7R^8)$—;
$R^1$, $R^2$, $R^3$ and $R^4$ are chosen independently from H and aliphatic $(C_1-C_8)$hydrocarbon, wherein the aliphatic $(C_1-C_8)$ hydrocarbon is optionally substituted with one or more substituents selected from halogen, hydroxyl, $(C_1-C_6)$alkoxy, amino, $(C_1-C_6)$alkylamino and di$(C_1-C_6)$alkylamino;

or, taken together, $R^1$ and $R^2$ form $(C_3-C_6)$cycloalkyl:
$R^5$ and $R^6$ are chosen independently from H, halogen, $(C_1-C_6)$alkyl and $(C_1-C_6)$haloalkyl;
$R^7$, $R^8$, $R^9$ and $R^{10}$ are chosen independently from H, halogen, $(C_1-C_6)$alkyl, $(C_1-C_6)$haloalkyl and $(C_1-C_6)$alkoxy;
$R^{11}$, $R^{12}$, $R^{13}$, and $R^{14}$ are chosen independently from H halogen, $(C_1-C_8)$hydrocarbyl, cyano, $(C_1-C_6)$haloalkyl, aminocarbonyl, $(C_1-C_6)$alkylaminocarbonyl, di$(C_1-C_6)$alkylaminocarbonyl, $(C_1-C_6)$acyl, $(C_1-C_6)$alkoxy, $(C_1-C_6)$haloalkoxy, hydroxy$(C_1-C_6)$alkyl, carboxy, $(C_1-C_6)$alkoxycarbonyl, acetoxy, nitro, amino, $(C_1-C_6)$alkylamino, di$(C_1-C_6)$alkylamino, aminosulfonyl, phenoxy, benzyloxy, benzyl, aryl, alkylaryl, heteroaryl, and alkylheteroaryl;

wherein one or more of $R^{11}$, $R^{12}$, $R^{13}$, and $R^{14}$ is phenoxy, benzyloxy, benzyl, aryl, alkylaryl, heteroaryl or alkylheteroaryl;

wherein said phenoxy, benzyloxy, benzyl, aryl, alkylaryl, heteroaryl and alkylheteroaryl are optionally substituted with one or more substituents selected from halogen, $(C_1-C_4)$alkyl, cyano, $(C_1-C_4)$haloalkyl, $(C_1-C_4)$alkoxy, aminocarbonyl, $(C_1-C_6)$alkylaminocarbonyl, di$(C_1-C_6)$alkylaminocarbonyl, $(C_1-C_4)$acyl, $(C_1-C_4)$haloalkoxy, hydroxy$(C_1-C_4)$alkyl, carboxy, $(C_1-C_4)$alkoxycarbonyl, acetoxy, nitro, amino, $(C_1-C_4)$alkylamino, and di$(C_1-C_4)$alkylamino.

In some embodiments, provided are compounds of Formula I:

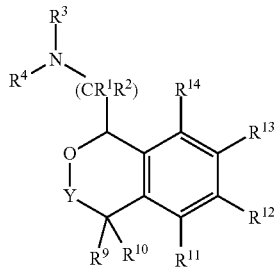

I or a pharmaceutically acceptable salt thereof,
wherein:
Y is chosen from direct bond, —$C(R^5R^6)$— and —$C(R^5R^6)C(R^7R^8)$—;
$R^1$, $R^2$, R and $R^4$ are chosen independently from H and aliphatic $(C_1-C_8)$hydrocarbon, wherein the aliphatic $(C_1-C_8)$ hydrocarbon is optionally substituted with one or more of halogen, hydroxyl, $(C_1-C_6)$alkoxy, amino, $(C_1-C_6)$alkylamino and di$(C_1-C_6)$alkylamino;
or, taken together, $R^1$ and $R^2$ may form $(C_3-C_6)$cycloalkyl;
$R^5$ and $R^6$ are chosen independently from H, halogen, $(C_1-C_6)$alkyl and $(C_1-C_6)$haloalkyl;
$R^7$, $R^8$, $R^9$ and $R^{10}$ are chosen independently from H, halogen, $(C_1-C_6)$alkyl, $(C_1-C_6)$haloalkyl and $(C_1-C_6)$alkoxy;
$R^{11}$, $R^{12}$, $R^{13}$, and $R^{14}$ are chosen independently from H, halogen, $(C_1-C_8)$hydrocarbyl, cyano, $(C_1-C_6)$haloalkyl, aminocarbonyl, $(C_1-C_6)$alkylaminocarbonyl, di$(C_1-C_6)$alkylaminocarbonyl, $(C_1-C_6)$acyl, $(C_1-C_6)$alkoxy, $(C_1-C_6)$haloalkoxy, hydroxy$(C_1-C_6)$alkyl, carboxy, $(C_1-C_6)$alkoxycarbonyl, acetoxy, nitro, amino, $(C_1-C_6)$alkylamino, di$(C_1-C_6)$alkylamino, aminosulfonyl, phenoxy, benzyloxy, benzyl, aryl, alkylaryl, heteroaryl and alkylheteroaryl;
wherein one or more of $R^{11}$, $R^{12}$, $R^{13}$, and $R^{14}$ is phenoxy, benzyloxy, benzyl, aryl alkylaryl, heteroaryl or alkylheteroaryl;
wherein said phenoxy, benzyloxy, benzyl, aryl, alkylaryl, heteroaryl or alkylheteroaryl are optionally substituted with one or more substituents selected from halogen, $(C_1-C_4)$alkyl, cyano, $(C_1-C_4)$haloalkyl, $(C_1-C_4)$alkoxy, aminocarbonyl, $(C_1-C_6)$alkylaminocarbonyl, di$(C_1-C_6)$alkylaminocarbonyl, $(C_1-C_4)$acyl, $(C_1-C_4)$haloalkoxy, hydroxy$(C_1-C_4)$alkyl, carboxy, $(C_1-C_4)$alkoxycarbonyl, acetoxy, nitro, amino, $(C_1-C_4)$alkylamino, and di$(C_1-C_4)$alkylamino.

In some embodiments. Y is —C(R$^5$R$^6$)— and the compound is of Formula II:

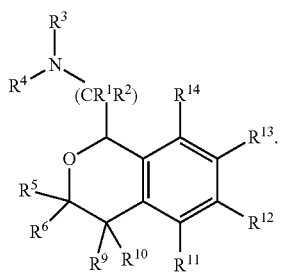

In some embodiments, Y is a direct bond and the compound is of Formula III:

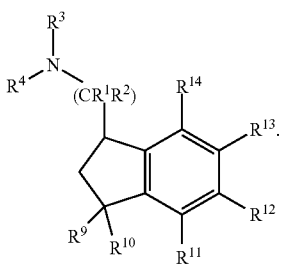

In some embodiments, Y is —C(R$^5$R$^6$)C(R$^7$R$^8$)— and the compound is of Formula IV:

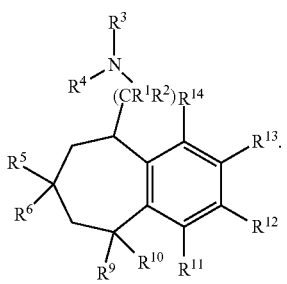

In some embodiments, the compound is of Formula Ia:

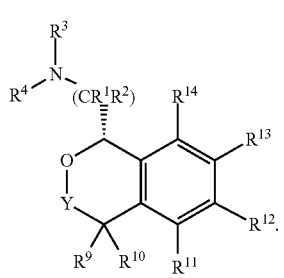

In some embodiments, the compound is of Formula Ib:

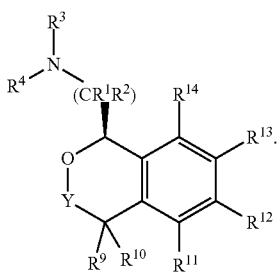

In some embodiments, the compound is of Formula IIa:

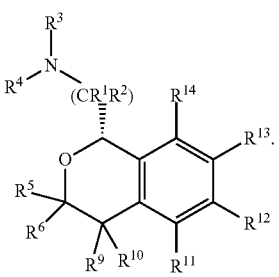

In some embodiments, the compound is of Formula IIb:

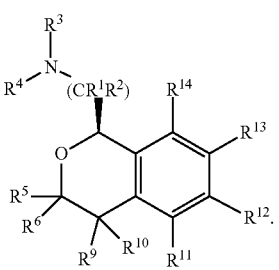

In some embodiments, the compound is of Formula IIc:

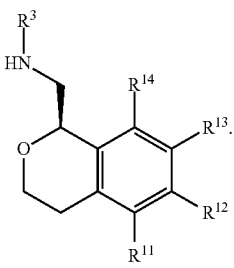

In some embodiments, the compound is of Formula IId:

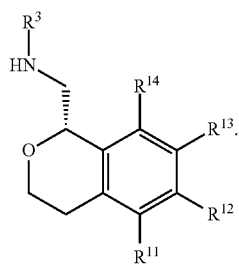
IId in some embodiments, the compound is of Formula IIe:

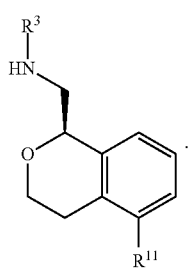
IIe

In some embodiments, the compound is of Formula IIf:

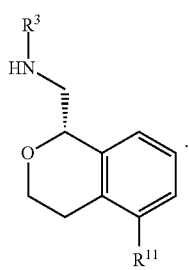
IIf

In some embodiments, the compound is of Formula IIg:

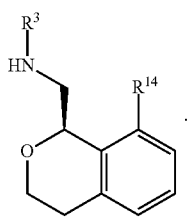
IIg

In some embodiments, the compound is of Formula IIh:

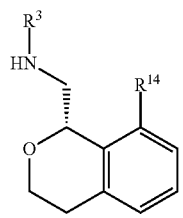
IIh

In some embodiments, the compound is of Formula IIi:

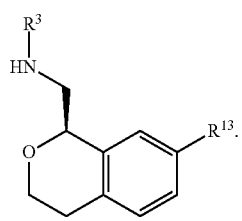
IIi

In some embodiments, the compound is of Formula IIj:

IIj

In some embodiments, the compound is of Formula IIk:

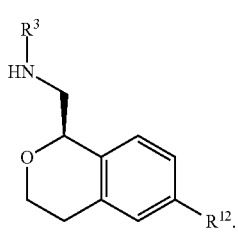
IIk

In some embodiments, the compound is of Formula IIm:

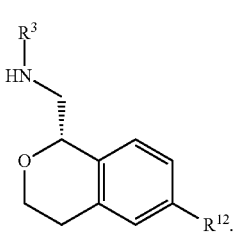
IIm

In some embodiments, the compound is of Formula IIIa:

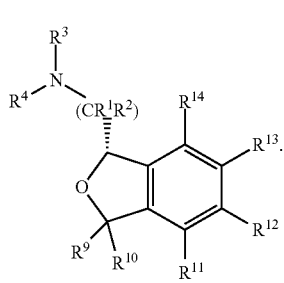

IIIa

In some embodiments, the compound is of Formula IIIb:

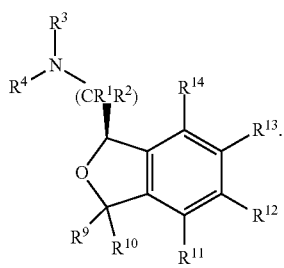

IIIb

In some embodiments, the compound is of Formula IIIc:

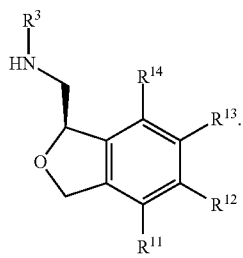

IIIc

In some embodiments, the compound is of Formula IIId:

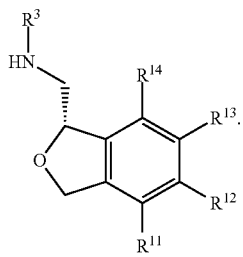

IIId

In some embodiments, the compound is of Formula IIIe:

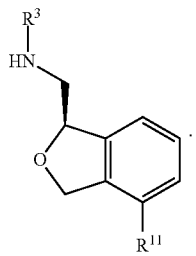

IIIe

In some embodiments, the compound is of Formula IIIf:

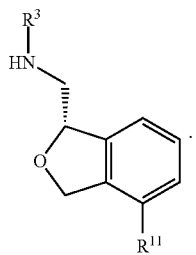

IIIf

In some embodiments, the compound is of Formula IVa:

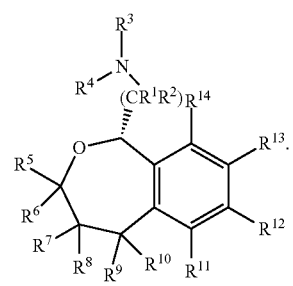

IVa

In some embodiments, the compound is of Formula IVb:

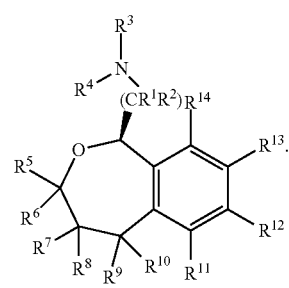

IVb

In some embodiments, the compound is of Formula IVc:

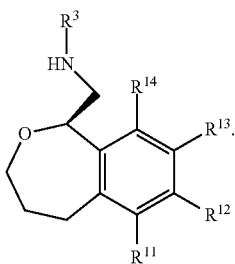

IVc

In some embodiments, the compound is of Formula IVd:

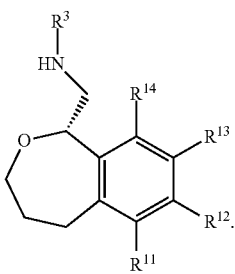

IVd

In some embodiments, the compound is of Formula IVe:

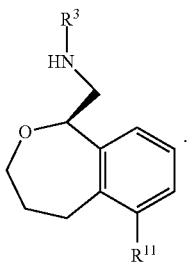

IVe

In some embodiments, the compound is of Formula IVf:

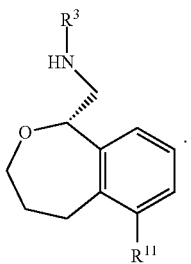

IVf

In some embodiments of Formula I, II, III, IV, Ia, Ib, IIa, IIb, IIIa, IIIb, IVa, or IVb, $R^1$ is hydrogen. In some embodiments, $R^1$ is hydrogen and $R^2$ is $(C_1-C_4)$alkyl. In some embodiments, $R^1$ is hydrogen and $R^2$ is hydrogen. In some embodiments, $R^1$ is hydrogen and $R^2$ is methyl. In some embodiments, $R^1$ and $R^2$ are each selected from hydrogen and methyl. In some embodiments, $R^1$ and $R^2$ are each independently selected from hydrogen and methyl.

In some embodiments of Formula I, II, III, IV, Ia, Ib, IIa, IIb, IIIa, IIIb, IVa, or IVb, $R^3$ and $R^4$ are chosen independently from hydrogen and $C_1-C_4$ alkyl. In some embodiments. $R^3$ is hydrogen and $R^4$ is $C_1-C_4$ alkyl. In some embodiments, $R^3$ is hydrogen and $R^4$ is hydrogen. In some embodiments, $R^3$ is hydrogen and $R^4$ is methyl. In some embodiments, $R^3$ is hydrogen and $R^4$ is ethyl. In some embodiments, $R^3$ and $R^4$ are each selected from hydrogen and methyl. In some embodiments. $R^3$ and $R^4$ are each independently selected from hydrogen and methyl.

In some embodiments of Formula I, II, III, IV, Ia, Ib, IIa, IIb, IIIa, IIIb, IVa, or IVb, $R^3$ and $R^4$ are chosen independently from hydrogen, $C_1-C_4$ alkyl, and $C_3-C_6$ cycloalkyl. In some embodiments of Formula I, II, II, IV, Ia, Ib, IIa, IIb, IIIa, IIIb, IVa, or IVb, $R^3$ and $R^4$ are chosen independently from hydrogen, methyl, ethyl, propyl, cyclopropyl, and cyclobutyl.

In some embodiments of Formula IIc, IId, IIe, IIf, IIg, IIh, IIi, IIj, IIk, IIm, IIIc, IIId, IIIe, IIIf, IVc, IVd, IVe, or IVf, $R^3$ is hydrogen, $C_1-C_4$ alkyl, or $C_3-C_6$ cycloalkyl. In some embodiments of Formula IIc, IId, IIe, IIf, IIg, IIh, IIi, IIj, IIk, or IIm, $R^3$ is hydrogen, $C_1-C_4$ alkyl, or $C_3-C_6$ cycloalkyl. In some embodiments of Formula IIIc, IIId, IIIe, or IIIf, $R^3$ is hydrogen, $C_1-C_4$ alkyl, or $C_3-C_6$ cycloalkyl. In some embodiments of Formula IVc, IVd, IVe, or IVf, $R^3$ is hydrogen, $C_1-C_4$ alkyl, or $C_3-C_6$ cycloalkyl.

In some embodiments of Formula IIc, IId, IIe, IIf, IIg, IIh, IIi, IIj, IIk, IIm, IIIc, Id, IIIe, IIIf, IVc, IVd, IVe, or IVf, R is hydrogen, methyl, ethyl, propyl, cyclopropyl, or cyclobutyl. In some embodiments of Formula IIc, IId, IIe, IIf, IIg, IIh, IIi, IIj, IIk, or IIm, $R^3$ is hydrogen, methyl, ethyl, propyl, cyclopropyl, or cyclobutyl. In some embodiments of Formula IIIc, IIId, IIIe, or IIIf, $R^3$ is hydrogen, methyl, ethyl, propyl, cyclopropyl, or cyclobutyl. In some embodiments of Formula IVc, IVd, IVe, or IVf, $R^3$ is hydrogen, methyl, ethyl, propyl, cyclopropyl, or cyclobutyl.

In some embodiments, $R^3$ of any of the formulae described herein is hydrogen.

In some embodiments. $R^3$ of any of the formulae described herein is $C_1-C_4$ alkyl. In some embodiments, $R^3$ is methyl. In some embodiments, $R^3$ is ethyl. In some embodiments. $R^3$ is propyl (e.g., n-propyl or isopropyl). In some embodiments, $R^3$ is butyl(e.g., n-butyl or t-butyl).

In some embodiments, $R^3$ of any of the formulae described herein is $C_3-C_6$ cycloalkyl. In some embodiments, $R^3$ is cyclopropyl. In some embodiments, $R^3$ is cyclobutyl. In some embodiments, $R^3$ is cyclopentyl. In some embodiments, $R^3$ is cyclohexyl.

In some embodiments of Formula I, II, IV, Ia, Ib, IIa, IIb, IVa, or IVb, $R^5$ and $R^6$ are each hydrogen. In some embodiments, $R^5$, $R^6$, $R^7$, and R are each hydrogen.

In some embodiments, $R^5$ of any of the formulae described herein is hydrogen. In some embodiments, $R^5$ of any of the formulae described herein is halogen (e.g., fluoro, chloro, or bromo). In some embodiments, $R^5$ of any of the formulae described herein is $C_1-C_6$ alkyl (e.g., methyl, ethyl, propyl, butyl, pentyl, or hexyl). In some embodiments, $R^5$ of any of the formulae described herein is $C_1-C_6$ haloalkyl (e.g., $CF_3$, $CFH_2$, $CF_2H$, or $CF_2CF_3$).

In some embodiments. $R^6$ of any of the formulae described herein is hydrogen. In some embodiments, $R^6$ of any of the formulae described herein is halogen (e.g., fluoro, chloro, or bromo). In some embodiments, $R^6$ of any of the formulae described herein is $C_1-C_6$ alkyl (e.g., methyl, ethyl, propyl, butyl, pentyl, or hexyl). In some embodiments, $R^6$ of any of the formulae described herein is $C_1-C_6$ haloalkyl (e.g., $CF_3$, $CFH_2$, $CF_2H$, or $CF_2CF_3$).

In some embodiments, $R^7$ of any of the formulae described herein is hydrogen. In some embodiments. $R^7$ of any of the formulae described herein is halogen (e.g., fluoro, chloro, or bromo). In some embodiments, $R^7$ of any of the formulae described herein is $C_1$-$C_6$ alkyl (e.g., methyl, ethyl, propyl, butyl, pentyl, or hexyl). In some embodiments, $R^7$ of any of the formulae described herein is $C_1$-$C_6$ haloalkyl (e.g., $CF_3$, $CFH_2$, $CF_2H$, or $CF_2CF_3$). In some embodiments, $R^7$ of any of the formulae described herein is $C_1$-$C_6$ alkoxy (e.g., methoxy, ethoxy, or propoxy).

In some embodiments, $R^8$ of any of the formulae described herein is hydrogen. In some embodiments, $R^8$ of any of the formulae described herein is halogen (e.g., fluoro, chloro, or bromo). In some embodiments. $R^8$ of any of the formulae described herein is $C_1$-$C_6$ alkyl (e.g., methyl, ethyl, propyl, butyl, pentyl, hexyl, etc.). In some embodiments. $R^8$ of any of the formulae described herein is $C_1$-$C_6$ haloalkyl (e.g., $CF_3$, $CFH_2$, $CF_2H$, or $CF_2CF_3$). In some embodiments, $R^7$ of any of the formulae described herein is $C_1$-$C_6$ alkoxy (e.g., methoxy, ethoxy, or propoxy).

In some embodiments of Formula I, II, III, IV, Ia, Ib, IIa, IIb, IIIa, IIIb, IVa, or IVb, $R^9$ and $R^0$ are chosen independently from hydrogen, fluoro, and methyl. In some embodiments, $R^{10}$ is hydrogen and $R^9$ is hydrogen, fluoro, or methyl. In some embodiments, $R^9$ and $R^{10}$ are each hydrogen. In some embodiments, $R^9$ is hydrogen. In some embodiments, $R^9$ is fluoro. In some embodiments. $R^9$ is methyl. In some embodiments, $R^{10}$ is hydrogen. In some embodiments, $R^{10}$ is fluoro. In some embodiments, $R^{10}$ is methyl.

In some embodiments of Formula I, II, III, IV, Ia, Ib, IIa, IIb, IIIa, IIIb, IVa, or IVb, only one of $R^{11}$, $R^{12}$, $R^{13}$, or $R^{14}$ is optionally substituted: benzyl, aryl or heteroaryl. In some embodiments, only one of $R^{11}$, $R^{12}$, $R^{13}$, or $R^{14}$ is optionally substituted: benzyl, aryl or heteroaryl; and the remainder of $R^{11}$, $R^{12}$, $R^{13}$, and $R^{14}$ are hydrogen. In some embodiments, $R^{11}$ is optionally substituted: benzyl, aryl or heteroaryl. In some embodiments, $R^{12}$ is optionally substituted: benzyl, aryl or heteroaryl. In some embodiments. $R^{13}$ is optionally substituted: benzyl, aryl or heteroaryl. In some embodiments. $R^{14}$ is optionally substituted: benzyl, aryl or heteroaryl.

In some embodiments of Formula I, II, III, IV, Ia, Ib, IIa, IIb, IIIa, IIIb, IVa, or IVb, only one of $R^{11}$, $R^{12}$, $R^{13}$, or $R^{14}$ is optionally substituted benzyl, aryl or heteroaryl. In some embodiments, only one of $R^{11}$, $R^{12}$, $R^{13}$, or $R^{14}$ is optionally substituted benzyl, aryl or heteroaryl, and the remainder of $R^{11}$, $R^{12}$, $R^{13}$, and $R^{14}$ are hydrogen. In some embodiments, $R^{11}$ is optionally substituted: benzyl, aryl or heteroaryl. In some embodiments, $R^{12}$ is optionally substituted benzyl, aryl or heteroaryl. In some embodiments, $R^{13}$ is optionally substituted benzyl, aryl or heteroaryl. In some embodiments, $R^{14}$ is optionally substituted benzyl, aryl or heteroaryl. In some embodiments, only one of $R^{11}$, $R^{12}$, $R^{13}$, or $R^{14}$ is unsubstituted benzyl, aryl or heteroaryl. In some embodiments, one of $R^{11}$, $R^{12}$, $R^{13}$, and $R^{14}$ is unsubstituted benzyl, aryl or heteroaryl, and the remaining three are hydrogen. In some embodiments, the optionally substituted benzyl, aryl or heteroaryl is selected from phenyl or a nitrogen-containing heteroaryl. In some embodiments, the optionally substituted aryl is phenyl, and the optionally substituted heteroaryl is a nitrogen-containing heteroaryl. In some embodiments, the nitrogen-containing heteroaryl is selected from pyridine, pyrimidine, pyrazine, pyridazine, thiazole, isothiazole, oxazole, isoxazole, pyrazole, imidazole and pyrrole. In some embodiments, the nitrogen-containing heteroaryl is pyridine. In some embodiments, the pyridine is at the $R^{11}$ position. In some embodiments, the pyridine is at the $R^{12}$ position. In some embodiments, the pyridine is at the $R^{13}$ position. In some embodiments, the pyridine is at the $R^{14}$ position.

In some embodiments of Formula IIc, IId, IIIc, IIId, IVc, or IVd, $R^{11}$, $R^{12}$, and $R^{13}$ are hydrogen; and $R^{14}$ is optionally substituted: benzyl, aryl or heteroaryl. In some embodiments of Formula IIc, IId, IIIc, IIId, IVc, or IVd, $R^{11}$, $R^{12}$, and $R^{13}$ are hydrogen; and $R^{14}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments of Formula IIc or IId, $R^{11}$, $R^{12}$, and $R^{13}$ are hydrogen; and $R^{14}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIIc or IIId, $R^{11}$$R^{12}$, and $R^{13}$ are hydrogen; and $R^{14}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments of Formula IVc or IVd, $R^{11}$, $R^{12}$, and $R^{13}$ are hydrogen; and $R^{14}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIIc, IIId, IIIc, IIc, IVc, or IVd, $R^{11}$, $R^{12}$, and $R^{14}$ are hydrogen; and $R^{13}$ is optionally substituted: benzyl, aryl or heteroaryl. In some embodiments of Formula IIc, IId, IIIc, IIId, IVc, or IVd, $R^{11}$, $R^{12}$, and $R^{14}$ are hydrogen; and $R^{13}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIc or IId, $R^{11}$, $R^{12}$, and $R^{14}$ are hydrogen; and $R^{13}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIIc or IIId, $R^{11}$, $R^{12}$, and $R^{14}$ are hydrogen; and $R^{13}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IVc or IIId, $R^{11}$, $R^{12}$, and $R^{14}$ are hydrogen; and $R^{13}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments of Formula IIc, IId, IIIc, IIId, IVc, or IVd, $R^{11}$, $R^{13}$, and $R^{14}$ are hydrogen; and $R^{12}$ is optionally substituted: benzyl, aryl or heteroaryl. In some embodiments of Formula IIc, IId, IIIc, IIId, IVc, or IVd, $R^{11}$, $R^{13}$, and $R^{14}$ are hydrogen; and $R^{12}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments of Formula IIc or IId, $R^{11}$, $R^{13}$, and $R^{14}$ are hydrogen and $R^{12}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIIc or IIId, $R^{11}$, $R^{13}$, and $R^{14}$ are hydrogen; and $R^{12}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments of Formula IVc or IVd, $R^{11}$, $R^{13}$, and $R^{14}$ are hydrogen; and $R^{12}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIc, IId, IIIc, IIId, IVc, or IVd, $R^{12}$, $R^{13}$, and $R^{14}$ are hydrogen; and $R^{11}$ is optionally substituted: benzyl, aryl or heteroaryl. In some embodiments of Formula IIc, IId, IIIc, IIId, IVc, or IVd, $R^{12}$, $R^{13}$, and $R^{14}$ are hydrogen; and $R^{11}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IIc or IId, $R^{12}$, $R^{13}$, and $R^{14}$ are hydrogen: and $R^{11}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments of Formula IIIc or IIId, $R^{12}$, $R^{13}$, and $R^{14}$ are hydrogen: and $R^{11}$ is phenyl, pyridine, pyrimidine, pyrazine, pyridazine, thiazole, isothiazole, oxazole, isoxazole, pyrazole, imidazole, pyrrole, or triazole: wherein the pyridine is optionally substituted with one or two $C_1$-$C_4$ alkyl.

In some embodiments of Formula IVc or IVd, $R^{12}$, $R^{13}$, and $R^{14}$ are hydrogen and $R^{11}$ is phenyl, pyridine, pyrimidine, pyrazine, pyridazine, thiazole, isothiazole, oxazole, isoxazole, pyrazole, imidazole, pyrrole, or triazole; wherein the pyridine is optionally substituted with one or two $C_1$-$C_4$ alkyl.

In some embodiments, $R^{11}$ of any of the formulae described herein is hydrogen. In some embodiments, $R^{11}$ of any of the formulae described herein is optionally substituted benzyl. In some embodiments, $R^{11}$ of any of the formulae described herein is optionally substituted aryl. In some embodiments, $R^{11}$ of any of the formulae described herein is unsubstituted aryl. In some embodiments, $R^{11}$ of any of the formulae described herein is optionally substituted phenyl. In some embodiments, $R^{11}$ of any of the formulae described herein is unsubstituted phenyl.

In some embodiments, $R^{11}$ of any of the formulae described herein is optionally substituted heteroaryl. In some embodiments, $R^{11}$ of any of the formulae described herein is pyridinyl optionally substituted with one or two $C_1$-$C_4$ alkyl (e.g., methyl, ethyl, propyl, or butyl). In some embodiments, $R^{11}$ of any of the formulae described herein is optionally substituted pyrimidinyl. In some embodiments. $R^{11}$ of any of the formulae described herein is unsubstituted pyrimidinyl. In some embodiments, $R^{11}$ of any of the formulae described herein is optionally substituted pyrazinyl. In some embodiments, $R^{11}$ of any of the formulae described herein is unsubstituted pyrazinyl. In some embodiments, $R^{11}$ of any of the formulae described herein is optionally substituted pyridazinyl. In some embodiments, $R^{11}$ of any of the formulae described herein is unsubstituted pyridazinyl. In some embodiments, $R^{11}$ of any of the formulae described herein is optionally substituted thiazolyl. In some embodiments, $R^{11}$ of any of the formulae described herein is unsubstituted thiazolyl. In some embodiments, $R^{11}$ of any of the formulae described herein is optionally substituted isothiazolyl. In some embodiments, $R^{11}$ of any of the formulae described herein is unsubstituted isothiazolyl. In some embodiments, $R^{11}$ of any of the formulae described herein is optionally substituted oxazolyl. In some embodiments, $R^{11}$ of any of the formulae described herein is unsubstituted oxazolyl. In some embodiments, $R^{11}$ of any of the formulae described herein is optionally substituted isoxazolyl. In some embodiments, $R^{11}$ of any of the formulae described herein is unsubstituted isoxazolyl. In some embodiments, $R^{11}$ of any of the formulae described herein is optionally substituted pyrazolyl. In some embodiments, $R^{11}$ of any of the formulae described herein is unsubstituted pyrazolyl. In some embodiments, $R^{11}$ of any of the formulae described herein is optionally substituted imidazolyl. In some embodiments, $R^{11}$ of any of the formulae described herein is unsubstituted imidazolyl. In some embodiments, $R^{11}$ of any of the formulae described herein is optionally substituted pyrrolyl. In some embodiments. $R^{11}$ of any of the formulae described herein is unsubstituted pyrrolyl. In some embodiments, $R^{11}$ of any of the formulae described herein is optionally substituted triazolyl. In some embodiments, $R^{11}$ of any of the formulae described herein is unsubstituted triazolyl.

In some embodiments, $R^{12}$ of any of the formulae described herein is hydrogen. In some embodiments, $R^{12}$ of any of the formulae described herein is optionally substituted benzyl. In some embodiments, $R^{12}$ of any of the formulae described herein is optionally substituted aryl. In some embodiments, $R^{12}$ of any of the formulae described herein is unsubstituted aryl. In some embodiments, $R^{12}$ of any of the formulae described herein is optionally substituted phenyl. In some embodiments, $R^{12}$ of any of the formulae described herein is unsubstituted phenyl.

In some embodiments. $R^{12}$ of any of the formulae described herein is optionally substituted heteroaryl. In some embodiments, $R^{12}$ of any of the formulae described herein is pyridinyl optionally substituted with one or two $C_1$-$C_4$ alkyl (e.g., methyl, ethyl, propyl, or butyl). In some embodiments. $R^{12}$ of any of the formulae described herein is optionally substituted pyrimidinyl. In some embodiments, $R^{12}$ of any of the formulae described herein is unsubstituted pyrimidinyl. In some embodiments, $R^{12}$ of any of the formulae described herein is optionally substituted pyrazinyl. In some embodiments. $R^{12}$ of any of the formulae described herein is unsubstituted pyrazinyl. In some embodiments, $R^{12}$ of any of the formulae described herein is optionally substituted pyridazinyl. In some embodiments, $R^{12}$ of any of the formulae described herein is unsubstituted pyridazinyl. In some embodiments, $R^{12}$ of any of the formulae described herein is optionally substituted thiazolyl. In some embodiments, $R^{12}$ of any of the formulae described herein is unsubstituted thiazolyl. In some embodiments. $R^{12}$ of any of the formulae described herein is optionally substituted isothiazolyl. In some embodiments, $R^{12}$ of any of the formulae described herein is unsubstituted isothiazolyl. In some embodiments, $R^{12}$ of any of the formulae described herein is optionally substituted oxazolyl. In some embodiments, $R^{12}$ of any of the formulae described herein is unsubstituted oxazolyl. In some embodiments, $R^{12}$ of any of the formulae described herein is optionally substituted isoxazolyl. In some embodiments, $R^{12}$ of any of the formulae described herein is unsubstituted isoxazolyl. In some embodiments, $R^{12}$ of any of the formulae described herein is optionally substituted pyrazolyl. In some embodiments, $R^{12}$ of any of the formulae described herein is unsubstituted pyrazolyl. In some embodiments, $R^{12}$ of any of the formulae described herein is optionally substituted imidazolyl. In some embodiments, $R^{12}$ of any of the formulae described herein is unsubstituted imidazolyl. In some embodiments, $R^{12}$ of any of the formulae described herein is optionally substituted pyrrolyl. In some embodiments, $R^{12}$ of any of the formulae described herein is unsubstituted pyrrolyl. In some embodiments, $R^{12}$ of any of the formulae described herein is optionally substituted triazolyl. In some embodiments, $R^{12}$ of any of the formulae described herein is unsubstituted triazolyl.

In some embodiments, $R^{13}$ of any of the formulae described herein is hydrogen. In some embodiments, $R^{13}$ of any of the formulae described herein is optionally substituted benzyl. In some embodiments. $R^{13}$ of any of the formulae described herein is optionally substituted aryl. In some embodiments, $R^{13}$ of any of the formulae described herein is unsubstituted aryl. In some embodiments, $R^{13}$ of any of the formulae described herein is optionally substituted phenyl. In some embodiments, $R^{13}$ of any of the formulae described herein is unsubstituted phenyl.

In some embodiments, $R^{13}$ of any of the formulae described herein is optionally substituted heteroaryl. In some embodiments, $R^{13}$ of any of the formulae described herein is pyridinyl optionally substituted with one or two $C_1$-$C_4$ alkyl (e.g., methyl, ethyl, propyl, or butyl). In some embodiments, $R^{13}$ of any of the formulae described herein is optionally substituted pyrimidinyl. In some embodiments. $R^{13}$ of any of the formulae described herein is unsubstituted pyrimidinyl. In some embodiments, $R^{13}$ of any of the formulae described herein is optionally substituted pyrazinyl. In some embodiments. $R^{13}$ of any of the formulae described herein is unsubstituted pyrazinyl. In some embodiments, $R^{13}$ of any of the formulae described herein is optionally substituted pyridazinyl. In some embodiments, $R^{13}$ of any of the formulae described herein is unsubstituted pyridazinyl. In some embodiments, $R^{13}$ of any of the formulae described herein is optionally substituted thiazolyl. In some embodiments, $R^{13}$ of any of the formulae described herein is unsubstituted thiazolyl. In some embodiments, $R^{13}$ of any of the formulae described herein is optionally substituted isothiazolyl. In some embodiments. $R^{13}$ of any of the formulae described herein is unsubstituted isothiazolyl. In some embodiments. $R^{13}$ of any of the formulae described herein is optionally substituted oxazolyl. In some embodiments, $R^{13}$ of any of the formulae described herein is unsubstituted oxazolyl. In some embodiments, $R^{13}$ of any of the formulae described herein is optionally substituted isoxazolyl. In some embodiments, $R^{13}$ of any of the formulae described herein is unsubstituted isoxazolyl. In some embodiments, $R^{13}$ of any of the formulae described herein is optionally substituted pyrazolyl. In some embodiments, $R^{13}$ of any of the formulae described herein is unsubstituted pyrazolyl. In some embodiments, $R^{13}$ of any of the formulae described herein is optionally substituted imidazolyl. In some embodiments, $R^{13}$ of any of the formulae described herein is unsubstituted imidazolyl. In some embodiments, $R^{13}$ of any of the formulae described herein is optionally substituted pyrrolyl. In some embodiments, $R^{13}$ of any of the formulae described herein is unsubstituted pyrrolyl. In some embodiments, $R^{13}$ of any of the formulae described herein is optionally substituted triazolyl. In some embodiments, $R^{13}$ of any of the formulae described herein is unsubstituted triazolyl.

In some embodiments, $R^{14}$ of any of the formulae described herein is hydrogen. In some embodiments, $R^{14}$ of any of the formulae described herein is optionally substituted benzyl. In some embodiments. $R^{14}$ of any of the formulae described herein is optionally substituted aryl. In some embodiments, $R^{14}$ of any of the formulae described herein is unsubstituted aryl. In some embodiments, $R^{14}$ of any of the formulae described herein is optionally substituted phenyl. In some embodiments, $R^{14}$ of any of the formulae described herein is unsubstituted phenyl.

In some embodiments, $R^{14}$ of any of the formulae described herein is optionally substituted heteroaryl. In some embodiments, $R^{14}$ of any of the formulae described herein is pyridinyl optionally substituted with one or two $C_1$-$C_4$ alkyl (e.g., methyl, ethyl, propyl, or butyl). In some embodiments, $R^{14}$ of any of the formulae described herein is optionally substituted pyrimidinyl. In some embodiments. $R^{14}$ of any of the formulae described herein is unsubstituted pyrimidinyl. In some embodiments, $R^{14}$ of any of the formulae described herein is optionally substituted pyrazinyl. In some embodiments, $R^{14}$ of any of the formulae described herein is unsubstituted pyrazinyl. In some embodiments, $R^{14}$ of any of the formulae described herein is optionally substituted pyridazinyl. In some embodiments, $R^{14}$ of any of the formulae described herein is unsubstituted pyridazinyl. In some embodiments, $R^{14}$ of any of the formulae described herein is optionally substituted thiazolyl. In some embodiments, $R^{14}$ of any of the formulae described herein is unsubstituted thiazolyl. In some embodiments, $R^{14}$ of any of the formulae described herein is optionally substituted isothiazolyl. In some embodiments, $R^{14}$ of any of the formulae described herein is unsubstituted isothiazolyl. In some embodiments, $R^{14}$ of any of the formulae described herein is optionally substituted oxazolyl. In some embodiments, $R^{14}$ of any of the formulae described herein is unsubstituted oxazolyl. In some embodiments. $R^{14}$ of any of the formulae described herein is optionally substituted isoxazolyl. In some embodiments, $R^{14}$ of any of the formulae described herein is unsubstituted isoxazolyl. In some embodiments, $R^{14}$ of any of the formulae described herein is optionally substituted pyrazolyl. In some embodiments, $R^{14}$ of any of the formulae described herein is unsubstituted pyrazolyl. In some embodiments, $R^{14}$ of any of the formulae described herein is optionally substituted imidazolyl. In some embodiments, $R^{14}$ of any of the formulae described herein is unsubstituted imidazolyl. In some embodiments, $R^{14}$ of any of the formulae described herein is optionally substituted pyrrolyl. In some embodiments, $R^{14}$ of any of the formulae described herein is unsubstituted pyrrolyl. In some embodiments. $R^{14}$ of any of the formulae described herein is optionally substituted triazolyl. In some embodiments, $R^{14}$ of any of the formulae described herein is unsubstituted triazolyl.

In some embodiments of Formula I, II, III, IV, Ia, Ib, IIa, IIb, IIIa, IIIb, IVa, or IVb, $R^1$ is hydrogen; $R^2$ is hydrogen or methyl; $R^3$ is hydrogen; and $R^4$ is hydrogen, methyl, or ethyl. In some embodiments, $R^1$, $R^2$ and $R^3$ are hydrogen, and $R^4$ is hydrogen or methyl.

In some embodiments of Formula I, II, III, IV, a, Ib, IIa, IIb, IIIa, IIIb, IVa, or IVb, $R^9$ and $R^{10}$ are each independently hydrogen, fluoro, or methyl. In some embodiments. $R^9$ and $R^{10}$ are each hydrogen. In some embodiments of Formula I, II, IV, Ia, Ib, IIa, IIb, IVa, or IVb, $R^5$, $R^6$, $R^9$ and $R^{10}$ are all hydrogen. In some embodiments of Formula I, IV, Ia, Ib, IVa, or IVb, $R^5$, R6, $R^7$, $R^8$, $R^9$ and $R^{10}$ are all hydrogen.

In some embodiments of Formula I, II, III, IV, Ia, Ib, IIa, IIb, IIa, IIIb, IVa, or IVb, $R^1$, $R^2$, $R^3$, $R^9$ and $R^{10}$ are hydrogen, $R^4$ is hydrogen or methyl, and, when present, $R^5$, $R^6$, $R^7$, and $R^8$ are all hydrogen.

In some embodiments of Formula I, II, III, IV, Ia, Ib, IIa, IIb, IIIa, IIIb, IVa, or IVb, all of $R^1$, $R^2$, $R^3$, $R^9$, $R^{10}$, and $R^{14}$, and $R^5$, $R^6$, $R^7$, and $R^8$, when present, are hydrogen; $R^4$ is hydrogen or methyl; and one of $R^{11}$, $R^{12}$ or $R^{13}$ is pyridine, and the remaining two are hydrogen.

In some embodiments of Formula I, II, III, IV, a, Ib, IIa, IIb, IIa, IIIb, IVa, or IVb, $R^{11}$ is pyridine and $R^{12}$, $R^{13}$ and $R^{14}$ are hydrogen. In some embodiments, $R^{12}$ is pyridine $R^{11}$, $R^{13}$ and $R^{14}$ are hydrogen. In some embodiments, $R^{13}$ is pyridine and $R^{11}$, $R^{12}$ and $R^{14}$ are hydrogen. In some embodiments, the pyridine is 3-pyridinyl. In some embodiments, the pyridine is 4-pyridinyl. In some embodiments, the pyridine is 2-pyridinyl. In some embodiments, $R^{11}$ is 2-pyridinyl. In other embodiments, $R^{11}$ is 3-pyridinyl. In some embodiments, $R^{11}$ is 4-pyridinyl. In yet other embodiments, $R^{11}$ is 3-pyridinyl. In some embodiments, $R^{13}$ is 4-pyridinyl. In some embodiments, $R^{12}$ is 3-pyridinyl.

In some embodiments of Formula I, III, Ia, Ib, IIa, or IIIb, $R^{11}$ is pyridine. In some embodiments, $R^{11}$ is 3-pyridinyl. In some embodiments, $R^{11}$ is 4-pyridinyl. In some embodiments, $R^{11}$ is 2-pyridinyl.

In some embodiments of Formula I, II, III, IV, Ia, Ib, IIa, IIb, IIIa, IIIb, IVa, or IVb, all of $R^1$, $R^2$, $R^3$, $R^9$, $R^{10}$, $R^{12}$, $R^{13}$ and $R^{14}$, and $R^5$, $R^6$, $R^7$ and $R^8$, when present, are hydrogen: $R^4$ is hydrogen or methyl; and $R^{11}$ is 3-pyridinyl or 4-pyridinyl.

In some embodiments of Formula I, II, III, IV, Ia, Ib, IIa, IIb, IIIa, IIIb, IVa, or IVb, all of $R^1$, $R^2$, $R^3$, $R^9$, $R^{10}$, $R^{12}$, $R^{13}$ and $R^{14}$, and $R^5$, $R^6$, $R^7$ and $R^8$, when present, are hydrogen; $R^4$ is hydrogen or methyl; and $R^{11}$ is 1-pyridinyl, 5-thiazolyl, 4-pyrimidinyl, 2-pyrazinyl, 3-isoxazolyl, 4-isoxazolyl, 5-isoxazolyl, 5-oxazolyl or 4-pyrazolyl.

In some embodiments of Formula I, the compound is:

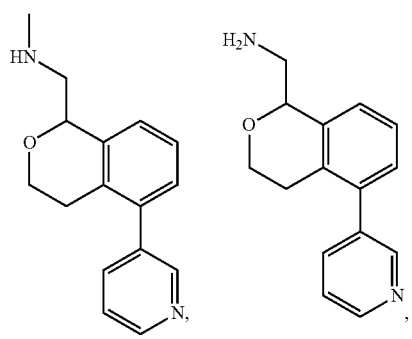

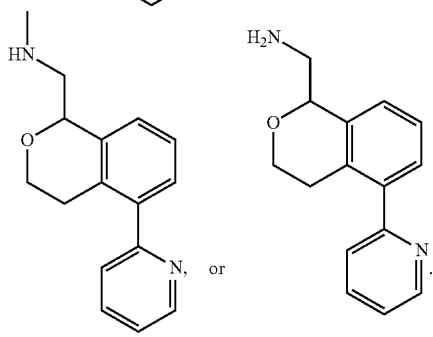

In some embodiments of Formula I, the compound is:

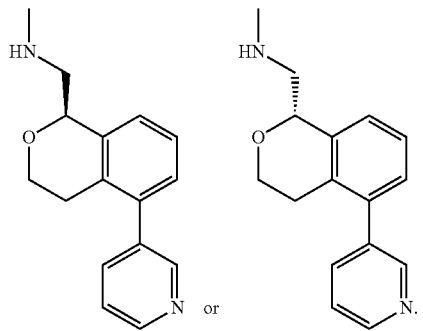 [SMILES: CNC[C@@H]1OCCc2c(-c3cccnc3)cccc21 ; CNC[C@H]1OCCc2c(-c3cccnc3)cccc21]

In some embodiments of Formula I, the compound is:

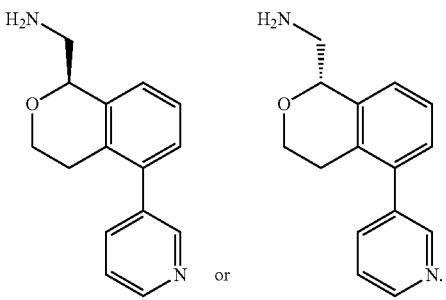 [SMILES: NC[C@@H]1OCCc2c(-c3cccnc3)cccc21 ; NC[C@H]1OCCc2c(-c3cccnc3)cccc21]

In some embodiments of Formula I, the compound is:

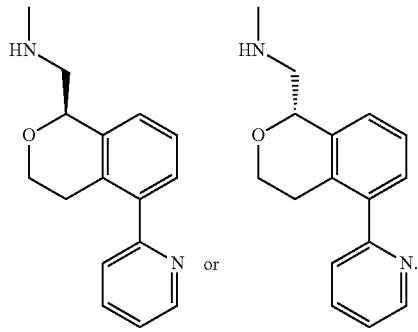 [SMILES: CNC[C@@H]1OCCc2c(-c3ccccn3)cccc21 ; CNC[C@H]1OCCc2c(-c3ccccn3)cccc21]

In some embodiments of Formula I, the compound is:

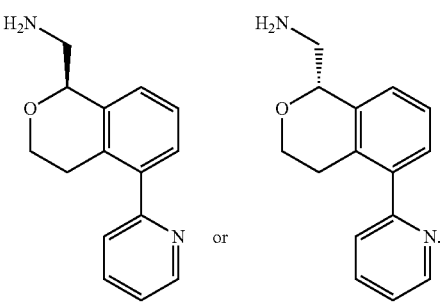 [SMILES: NC[C@@H]1OCCc2c(-c3ccccn3)cccc21 ; NC[C@H]1OCCc2c(-c3ccccn3)cccc21]

In some embodiments of Formula I, the compound is:

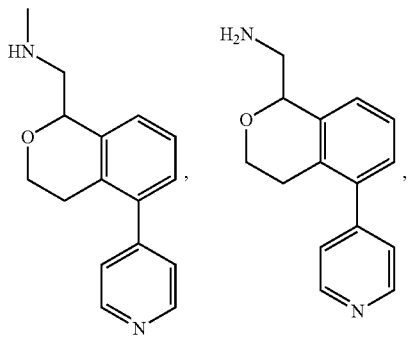

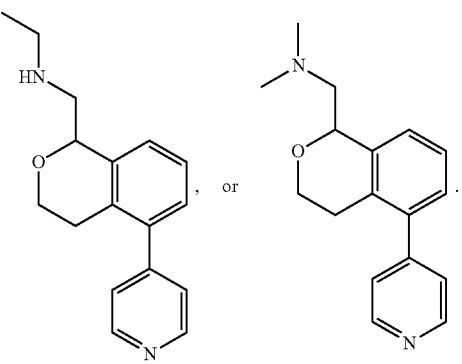

In some embodiments of Formula I, the compound is:

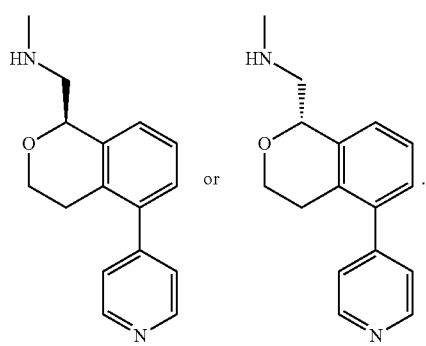 [SMILES: CNC[C@@H]1OCCc2c(-c3ccncc3)cccc21 ; CNC[C@H]1OCCc2c(-c3ccncc3)cccc21]

In some embodiments of Formula I, the compound is:

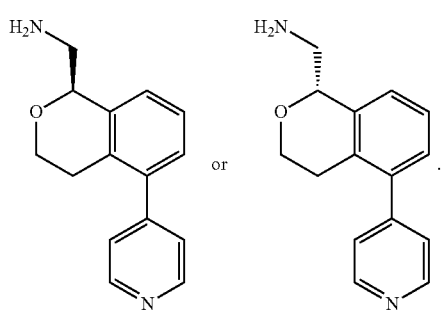 [SMILES: NC[C@@H]1OCCc2c(-c3ccncc3)cccc21 ; NC[C@H]1OCCc2c(-c3ccncc3)cccc21]

In some embodiments of Formula I, the compound is:

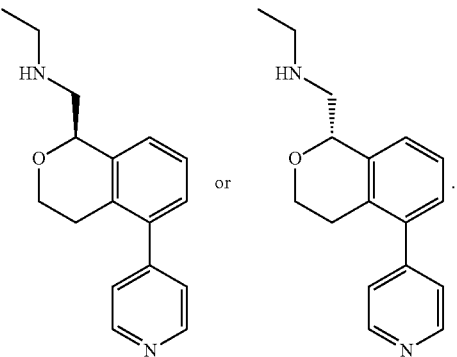 [SMILES: CCNC[C@@H]1OCCc2c(-c3ccncc3)cccc21 ; CCNC[C@H]1OCCc2c(-c3ccncc3)cccc21]

In some embodiments of Formula I, the compound is:

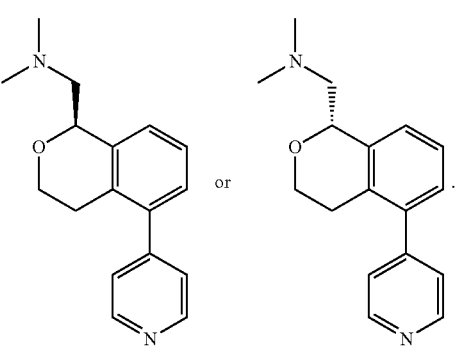 [SMILES: CN(C)C[C@@H]1OCCc2c(-c3ccncc3)cccc21 ; CN(C)C[C@H]1OCCc2c(-c3ccncc3)cccc21]

In some embodiments of Formula I, II, III, IV, Ia, Ib, IIa, IIb, IIIa, IIIb, IVa, or IVb, all of $R^1$, $R^2$, $R^3$, $R^9$, $R^{10}$, $R^{11}$, $R^{12}$ and $R^{14}$, and $R^5$, $R^6$, $R^7$ and $R^8$, when present, are hydrogen; $R^4$ is hydrogen or methyl; and $R^{13}$ is 3-pyridinyl or 4-pyridinyl.

Compounds and Definitions:

As used herein, the singular forms "a", "an" and "the" are intended to include the plural forms as well, unless the context clearly indicates otherwise.

Compounds and compositions disclosed herein include those described generally above, and are further illustrated by the classes, subclasses, and species disclosed herein. As used herein, the following definitions shall apply unless otherwise indicated. A comprehensive list of abbreviations utilized by organic chemists (i.e. persons of ordinary skill in the art) appears in the first issue of each volume of the Journal of Organic Chemistry. The definitions therein, which are typically presented in a table entitled "Standard List of Abbreviations" are the definitions used herein, unless otherwise indicated herein.

A numeric value or range of values described herein (e.g., a specific temperature or temperature range, mass, a percentage, a peak position or retention time, such as in analysis by NMR or HPLC), indicate that the value or range of values may deviate to an extent deemed reasonable to one of ordinary skill in the art while still describing the particular compound. Specifically, the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. In some embodiments, the numeric value or range of values may vary by 5%.

In some embodiments, 1 to n hydrogen atoms attached to a carbon atom in one or more of the compounds described herein may be replaced by a deuterium atom or D, where n is the number of hydrogen atoms in the molecule. As known in the art, the deuterium atom is a non-radioactive isotope of the hydrogen atom. Such deuterated compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such deuterated compounds can be synthesized by means known in the art, for example by employing starting materials in which one or more hydrogen atoms have been replaced by deuterium.

In some embodiments, other isotopes can be incorporated into one or more of the compounds described herein. Examples of other isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described in the Examples as set out below using an appropriate isotopically-labeled reagent in place of the non-labeled reagent previously employed.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

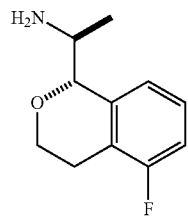

indicates a trans relationship between the two chiral centers, that is, either or both of the two representations below:

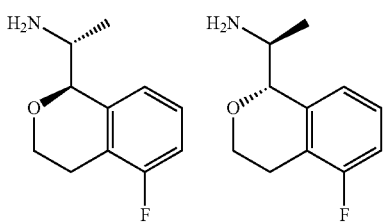

in any ratio, from pure enantiomers to racemates, while the representation:

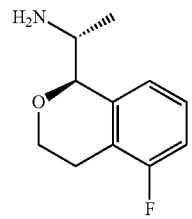

indicates pure ((R)-1-((R)-5-fluoroisochroman-1-yl)ethan-1-amine. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(R)-1-((R)-5-rel- . . . " indicates that the two chiral centers are in that relative relationship, which would be depicted in a structural diagram by solid bold and dashed lines, whereas "(R)-1-((R)-5- . . . " without the "rel" indicates a single enantiomer of that absolute configuration, which would be depicted in a structural diagram by solid and broken wedges.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer, ee=(90−10)/100=80%.

Thus, a composition containing 90% of one enantiomer and 10% of the other enantiomer is said to have an enantiomeric excess of 80%. Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In some embodiments, the compound provided herein is made up of at least about 90% by weight of one enantiomer. In some embodiments, the compound is made up of at least about 95%, 98%, or 99% by weight of one enantiomer.

In some embodiments, the compound is a racemic mixture of (S)- and (R)-isomers. In some embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 90%, about 97%, about 98%, about 99%, about 99.5%, or more. In some embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In some embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In some embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In some embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Hydrocarbyl refers to any substituent comprised of hydrogen and carbon as the only elemental constituents. $C_1$ to $C_{20}$ hydrocarbon includes, for example, alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Aromatic hydrocarbons include benzene (phenyl), naphthalene (naphthyl), anthracene, etc. Aliphatic hydrocarbons are hydrocarbons that are not aromatic; they may be saturated or unsaturated, cyclic, linear or branched, or combinations thereof. Aliphatic hydrocarbons include, for example, alkyl, alkenyl, alkynyl, cycloalkyl, cycloalkenyl, cycloalkynyl, and combinations thereof. Non-limiting examples of aliphatic hydrocarbons include isopropyl, 2-butenyl, 2-butynyl, cyclopentyl, cyclopropylmethyl, norbornyl, and the like.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. In some embodiments, cycloalkyl is a saturated or partially saturated cyclic hydrocarbon. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$)carbopolycycle refers to such systems as norbornane, decalin, indane and naphthalene. Carbocycle, if not otherwise limited, refers to monocycles, bicycles and polycycles, including bridged structures.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (hetero aliphatic) or aromatic (heteroaryl). Heterocycle, if not otherwise limited, refers to monocycles, bicycles and polycycles, including bridged structures. Examples of heterocycles include, but are not limited to, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, atrophine, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl. In some embodiments, depending on the context and valency, the heterocycle such as a heteroaryl may be written in its non-residue form, e.g., pyridine, pyrimidine, pyrazine, pyridazine, thiazole, isothiazole, oxazole, isoxazole, pyrazole, imidazole, pyrrole, etc., even though they are referring to the corresponding residue form, e.g., pyridinyl, pyrimidinyl, pyrazinyl, pyridazinyl, thiazolyl, isothiazolyl, oxazolyl, isoxazolyl, pyrazolyl, imidazolyl, pyrrolyl, etc.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

The term "halogen" means fluorine, chlorine, bromine or iodine. In some embodiments, halogen is fluorine, chlorine, or bromine. In one embodiment, halogen may be fluorine or chlorine. In some embodiments, halogen is fluorine. In some embodiments, halogen is chlorine.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, hydrocarbyl, acyl, alkoxyalkyl, hydroxy lower alkyl, carbonyl, phenyl, heteroaryl, benzenesulfonyl, hydroxy, hydrocarbyloxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido)[—C(=O)NH$_2$], alkylaminocarbonyl [—C(=O)NH-alkyl], dialkylaminocarbonyl [—C(=O)N(alkyl)$_2$], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In particular embodiments, substituents are halogen, halo($C_1$-$C_4$)hydrocarbyl, halo($C_1$-$C_4$)hydrocarbyloxy, cyano, thiocyanato, ($C_1$-$C_4$))hydrocarbylsulfinyl, ($C_1$-$C_4$)hydrocarbyl-sulfonyl, aminosulfonyl, nitro, acetyl, and acetamido. Preferred substituents are halogen, ($C_1$-$C_4$)alkyl, ($C_1$-$C_4$)alkoxy, ($C_1$-$C_4$)fluoroalkyl, ($C_1$-$C_4$)fluoroalkoxy, hydroxy, amino, ($C_1$-$C_4$)alkylamino, di($C_1$-$C_4$)alkylamino, ($C_1$-$C_4$)acylamino, ($C_1$-$C_4$)fluoroalkyl and ($C_1$-$C_4$)fluoroalkoxy.

Substituents R″ are generally defined when introduced and retain that definition throughout the specification and claims.

As used herein, and as would be understood by the person of skill in the art, the recitation of "a compound"—unless expressly further limited—is intended to include salts of that compound. Thus, for example, the recitation "a compound of Formula I" as depicted above, which contains a basic amine residue —NR$^3$R$^4$, would include salts —NHR$^3$R$^{4+}$ X$^-$ wherein X$^-$ is any counterion. In a particular embodiment, the term "compound of formula I" refers to the compound or a pharmaceutically acceptable salt thereof; this term refers to a pharmaceutically acceptable salt of the compound, even if not explicitly stated. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. In addition to therapeutic uses, such compounds are useful, for example, as analytical tools or probes in biological assays.

As used herein, "formulae" refers to any one or more of Formula I, II, III, IV, Ia, Ib, IIa, IIb, IIc, IId, IIe, IIf, IIg, IIh, IIi, IIj, IIk, IIm, IIIa, IIIb, IIIc, IIId, IIIe, IIIf, IVa, IVb, IVc, IVd, IVe, or IVf.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

Unless otherwise specified, the word "includes" (or any variation thereon, e.g., "include", "including", etc.) is intended to be open-ended. For example, "A includes 1, 2 and 3" means that A includes but is not limited to 1, 2 and 3. As used herein, the terms "comprising" or grammatical variants thereof are to be taken as specifying the stated features, integers, steps or components but do not preclude the addition of one or more additional features, integers, steps, components or groups thereof.

Unless otherwise specified, the phrase "such as" is intended to be open-ended. For example, "A can be a halogen, such as chlorine or bromine" means that A can be, but is not limited to, chlorine or bromine.

In some embodiments, provided are compositions comprising a compound disclosed herein (or a pharmaceutically acceptable salt thereof) and a pharmaceutically acceptable carrier, adjuvant, or vehicle. In some embodiments, the amount of compound in compositions is such that is effective to treat, prevent, and/or manage various neurological and/or psychiatric diseases and disorders and/or symptoms in a subject. In some embodiments, a composition is formulated for administration to a subject in need of such composition. In some embodiments, a composition is formulated for oral administration to a subject.

As used herein, the term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. The "subject" may have been independently diagnosed with a disease or disorder described herein, may currently be experiencing symptoms associated with a disease disorder described herein, or may have experienced symptoms in the past of a disease or disorder described herein, may be at risk of developing a disease or disorder described herein, or may be reporting one or more symptoms of a disease or disorder described herein, even though a diagnosis may not have been made. In some embodiments, the subject is a human who may have independently been diagnosed with a disease disorder described herein, may currently be experiencing symptoms associated with a disease or disorder described herein, or may have experienced symptoms in the past of a disease or disorder described herein, may be at risk of developing a disease or disorder described herein, or may be reporting one or more symptoms of a disease or disorder described herein, even though a diagnosis may not have been made.

In certain embodiments, provided herein is a composition (e.g., a pharmaceutical composition) comprising a compound described herein and a pharmaceutically acceptable excipient or carrier. In some embodiments, provided herein is a method of treating neurological or psychiatric diseases and disorders in a subject in need thereof in a subject, comprising administering an effective amount of a compound or a pharmaceutical composition described herein. Examples of carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Compositions of the present invention may be administered orally, parenterally, by inhalation, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Pharmaceutically acceptable compositions of this invention may be orally administered in any orally acceptable dosage form including capsules, tablets, aqueous suspensions or solutions.

The amount of compound that may be combined with the carrier materials to produce a composition in a single dosage form will vary depending upon a variety of factors, including the host treated and the particular mode of administration. It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound disclosed herein in the composition will also depend upon the particular compound in the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment of a disease or disorder is an approach for obtaining beneficial or desired results including, but not limited to, therapeutic benefit. Therapeutic benefit includes eradication and/or amelioration of the underlying disorder being treated; it also includes the eradication and/or amelioration of one or more of the symptoms associated with the underlying disorder such that an improvement is observed in the subject, notwithstanding that the subject may still be afflicted with the underlying disorder. In some embodiments, "treatment" or "treating" includes one or more of the following: (a) inhibiting the disorder (for example, decreasing one or more symptoms resulting from the disorder, and/or diminishing the extent of the disorder); (b) slowing or arresting the development of one or more symptoms associated with the disorder (for example, stabilizing the disorder and/or delaying the worsening or progression of the disorder); and/or (c) relieving the disorder (for example, causing the regression of clinical symptoms, ameliorating the disorder, delaying the progression of the disorder, and/or increasing quality of life). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, provided are methods for treating a neurological or psychiatric disease and disorder in a subject, comprising administering to the subject an effective amount of a compound of this invention (or its pharmaceutically acceptable salt), or composition comprising a compound of this invention (or its pharmaceutically acceptable salt). Neurological and/or psychiatric diseases and disorders can exhibit a variety of psychiatric and behavioral symptoms, including apathy, depression, anxiety, cognitive impairment, psychosis, aggression, agitation, poor impulse control and sleep disruptions.

In some embodiments, the neurological or psychiatric disorder is selected from a psychotic disorder, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (semantic dementia, frontotemporal dementia, dementia with depressive features, persisting, subcortical dementia, dementia with Lewy Bodies, Parkinsonism-ALS Dementia Complex, and dementia associated with Alzheimer's disease, ischemia, multi-infarct dementia, trauma, vascular problems, stroke. HIV disease, Parkinson's disease, Huntington's disease, Down syndrome, Pick's disease, Creutzfeldt-Jacob disease, perinatal hypoxia, or substance abuse), delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); eating disorders including obesity, bulimia nervosa, pica and compulsive eating disorders, bipolar disorders, including bipolar I disorder, bipolar I disorder, cyclothymic disorder, substance/medication-induced bipolar and related disorders, bipolar and related disorder due to another medical condition, other specified bipolar and related disorder, and unspecified bipolar and related disorders; depressive disorders, including unipolar depression, seasonal depression and post-partum depression, atypical depression, catatonic depression, elderly depression, endogenous depression, melancholic depression, perinatal depression, situational depression, chronic depression, premenstrual syndrome (PMS) and premenstrual dysphoric disorder (PDD), mood disorders due to a general medical condition, and substance-induced mood disorders; attention, learning and developmental disorders, such as, pervasive developmental disorder including autistic disorder, attention disorders including attention-deficit hyperactivity disorder (ADHD) and conduct disorder; disorders such as autism, and autism spectrum disorders (including Asperger's syndrome, pervasive developmental disorder, Rett Syndrome and Fragile X Syndrome), depression, benign forgetfulness, childhood learning disorders, specific learning disorders, intellectual development disorders, and closed head injury; movement disorders and symptoms, including tremors, dyskinesia, dystonia, tics, dysphonia, ataxia, myclonus, Essential Tremor, Tardive Dyskinesia. Restless Leg Syndrome, Tourettes Syndrome, Multiple System Atrophy, Multiple Sclerosis, Huntington's Disease, Parkinson's Disease and Atypical Parkinsonisms; epilepsy, including abdominal epilepsy, absence seizure, acquired epilepsy, acquired epileptiform aphasia, Aicardi syndrome, Alpes' disease, Alpers-Huttenlocher syndrome. Angelman syndrome, benign focal epilepsy, benign focal epilepsy of childhood, benign intracranial hypertension, benign rolandic epilepsy (BRE). CDKL5 disorder, childhood absense epilepsy, dentate cerebellar ataxia, Doose syndrome. Dravet syndrome, dyscognitive focal seizure, epilepsy with grand mal seizures, epilepsy with myoclonic-absences, epileptic hemiplegia, febrile seizures, focal seizure, frontal lobe epilepsy, generalized tonic-clonic seizures, genetic epilepsy, Glut1 deficiency syndrome, hypothalmic hamartoma, idiopathic epilepsy, idiopathic generalized epilepsy, idopathic localization-related epilepsies, idopathic partial epilepsy, idopathic seizure, juvenile absense epilepsy, juvenile myoclonic epilepsy, Lafora disease, Lafora progressive myoclonus epilepsy, Landau-Kleffner syndrome, Lassueur-Graham-Little syndrome. Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic partial epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor; urinary incontinence: neuronal damage including ocular damage, retinopathy or macular degeneration of the eye, tinnitus, hearing impairment and loss, and brain edema; emesis: and sleep disorders including insomnia, disturbed sleep, jet lag, hypersomnia, cataplexy, sleep apnea, obstructive sleep apnia, REM sleep behavior disorder, Restless Leg Syndrome, periodic limb movement disorder, circadian rhythm sleep disorders, delayed sleep phase disorder, sleep-walking, night terrors, bed wetting, rapid eye movement sleep behavior disorder, shift work sleep disorder, excessive daytime sleepiness, non-24-hour sleep-wake disorder, sleep paralysis and narcolepsy.

In some embodiments, the neurological or psychiatric disorder is Alzheimer's disease, Parkinson's disease, depression, cognitive impairment, stroke, schizophrenia, Down syndrome, or Fetal Alcohol Syndrome. In some embodiments, the neurological or psychiatric disorder is Alzheimer's disease. In some embodiments, the neurological or psychiatric disorder is Parkinson's disease. In some embodiments, the neurological or psychiatric disorder is depression. In some embodiments, the neurological or psychiatric disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disorder is schizophrenia. In some embodiments, the neurological or psychiatric disorder is Down syndrome. In some embodiments, the neurological or psychiatric disorder is Fetal Alcohol Syndrome.

In some embodiments, the neurological or psychiatric disorder is bipolar disorder. Bipolar disorders (including both bipolar I and bipolar 11) are serious psychiatric disorders that have a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although subjects spend considerable more time in the depressive state. Other related conditions include cyclothymic disorder.

In some embodiments, the neurological or psychiatric disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g. loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g. catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia." in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the subject suffers from a lack of normal experiences, such as anhedonia and lack of social interaction. The cognitive symptoms relate to cognitive impairment in schizophrenics, such as lack of sustained attention and deficits in decision making.

In some embodiments, the neurological or psychiatric disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

In some embodiments, the neurological or psychiatric disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, provided are methods of treating one or more symptoms of a neurological and/or psychiatric disorder provided herein. Such disorders include mood disorders, including bipolar I disorder, bipolar II disorder, bipolar depression, mania, cyclothymic disorder, substance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, agitation, aggression, delirium, catalepsy, catatonia, dissociative identity disorder, paranoid personality disorder, psychotic depression, Schizotypical Personality Disorder, Childhood Disintegrative Disorder (Heller's Syndrome), Disintegrative Psychosis, Dissociative Amnesia, Somatic Symptom Disorder, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders; and other disorders including substance abuse or dependency (e.g., nicotine, alcohol, cocaine), addiction, internet gaming disorder, eating disorders, behavior disorder, seizure, vertigo, epilepsy, agitation, aggression, neurodegenerative disease. Alzheimer's disease, Parkinson's disease, dyskinesias, Huntington's disease, dementia, premenstrual dysphoria, attention deficit disorder (ADD) and attention deficit hyperactivity disorder (ADHD)), hyperkinetic syndrome, autism, autism spectrum disorder, obsessive-compulsive disorder, pain, fibromyalgia, migraine, cognitive impairment, movement disorder, restless leg syndrome (RLS), multiple sclerosis, Primary Progressive Multiple Sclerosis, Parkinson's disease, Huntington's disease, dyskinesias multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, Rett syndrome, and Huntington's chorea. In some embodiments, the neurological and/or psychiatric disorders include agitation and aggression.

In some embodiments, the agitation and aggression are associated with Alzheimer's disease, Parkinson's disease, and/or autism.

In some embodiments, the neurological and/or psychiatric diseases and disorders are obsessive-compulsive disorder and related disorders (e.g., body dysmorphic disorder, hoarding disorder, trichotillomania, excoriation disorder).

In some embodiments, the neurological and/or psychiatric diseases and disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

Depressive disorders include major depressive disorder and dysthymia, and are associated with depressed mood (sadness), poor concentration, insomnia, fatigue, appetite disturbances, excessive guilt and thoughts of suicide.

In some embodiments, provided are methods of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome; anxieties (e.g., general anxiety disorder social anxiety disorder, panic disorder); obsessive compulsive disorder: post-menopausal vasomotor symptoms (e.g., hot flashes, night sweats); neurodegenerative disease (e.g., Parkinson's disease, Alzheimer's disease, amyotrophic lateral sclerosis, primary lateral sclerosis, progressive muscular atrophy, progressive bulbar (atrophy) palsy, pseudobulbar palsy spinal muscular atrophy diseases (e.g., SMA type I, also called Werdnig-Hoffmann disease, SMA type II, SMA type III, also called Kugelberg-Welander disease, and Kennedy Disease, also called progressive spinobulbar muscular atrophy), Hallervorden-Spatz disease, Seitelberger disease (Infantile Neuroaxonal Dystrophy), adrenoleukodystrophy, Alexander Disease, autosomal dominant cerebellar ataxia (ADCA), pure autonomic failure (Bradbury-Eggleston Syndrome), CADASIL Syndrome, and neuronal ceroids lipofuscinose disorders such as Batten Disease (Spielmeyer-Vogt-Sjögren)); manic disorder: dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present invention provides a method of treating one or more symptoms of a depressive disorder (e.g., MDD) in children, adolescents and/or young adults without increasing the risk of suicidal thinking and/or behavior.

In some embodiments, provided are methods of treating one or more symptoms including senile dementia, Early Onset Alzheimer's Disease, Alzheimer's type dementia, cognition, memory loss, amnesia/amnestic syndrome, disturbances of consciousness, coma, lowering of attention, speech disorder, agnosia, aphasia, apraxia, Mild Cognitive Impairment (MCI), benign forgetfulness, mild neurocognitive disorder, major neurocognitive disorder, neurocognitive disorder due to disease (e.g., Huntington's Disease, Parkinson's disease, Prion Disease, Traumatic Brain Injury, HIV or AIDS), Binswanger's Disease (subcortical leukoencephalopathy), and Capgras Syndrome.

In some embodiments, provided are methods of treating one or more symptoms of pain, e.g., neuropathic pain, sensitization accompanying neuropathic pain, or inflammatory pain. In some embodiments, the pain is neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use). In some embodiments, the pain is acute pain, nociceptive pain, arthritis pain, rheumatoid arthritis, osteoarthritis, joint pain, muscoskeletal pain, back pain, dorsalgia, bulging disc, hip pain, visceral pain, headache, tension headache, acute tension headache, chronic tension headache, chronic cluster headache, common migraine, classic migraine, cluster headache, mixed headache, post-traumatic headache, eye strain headache, Short-lasting Unilateral Neuralgiform (SUNCT) headache, SUNCT Syndrome, herpes zoster, acute herpes zoster, shingles, postherpetic neuralgia (shingles), causalgia, Central pain, central pain syndrome, chronic back pain, neuralgia, neuropathic pain syndrome, neuropathy, diabetic neuropathy, diabetes-related neuropathy, diabetes-related nerve pain, fibrositis, peripheral neuropathy caused by chemotherapy, peripheral nerve disease, peripheral neuropathy, nerve pain, nerve trauma, sensitization accompanying neuropathic pain, complex regional pain syndrome, compression neuropathy, craniofacial pain, chronic joint pain, chronic knee pain, chronic pain syndrome, cancer pain, trigeminal neuralgia, tic doloreaux, reflex sympathetic causalgia, painful peripheral neuropathy, spinal nerve injury, arachnoiditis, spinal pain, Bernhardt-Roth Syndrome (meralgia parasthetica), carpal tunnel syndrome, cerebrospinal fluid syndrome, Charcot-Mane-tooth disease, hereditary motor and sensory neuropathy, peroneal muscular atrophy, cluster-tic syndrome, coccygeal pain syndromes, compartment syndrome, degenerative disc disease, failed back surgery syndrome, genito-pelvic pain/penetration disorder, gout, inflammatory pain, lumbar radiculopathy, neuroma (painful scar), pain associated with multiple sclerosis, pelvic floor disorders, phantom limb pain, piriformis syndrome, psychogenic pain, radicular pain syndrome, Raeder's syndrome, referred pain, reflex sympathetic dystrophy syndrome, sciatica, sciatica pain, scoliosis, slipped disc, somatic pain, spinal stenosis, stiff-person syndrome/stiff-man syndrome, stump pain, sympathetically maintained pain, tolosa-hunt syndrome, whiplash, or pain associated with Lyme disease.

In some embodiments, provided are methods of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, provided are methods of suppressing rapid eye movement (REM) during both sleep and daytime equivalent.

In some embodiments, the present invention provides a method of suppressing or eliminating pathological or excessive REM during the night or daytime equivalent.

In some embodiments, provided are methods of treating one or more symptoms including cataplexy (sudden involuntary transient bouts of muscle weakness or paralysis while awake): nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, provided are methods of treating one or more symptoms of movement disorders, including akinesias, akinetic-rigid syndromes, dyskinesias and dystonias. Examples of akinesias and akinetic-rigid syndromes include Parkinson's disease, drug-induced Parkinsonism, postencephalitic Parkinsonism, secondary Parkinsonism, Parkinson plus syndromes, atypical Parkinsonism, idiopathic Parkinsonism, progressive supranuclear palsy, multiple system atrophy, corticobasal degeneration, Parkinsonism-ALS dementia complex and basal ganglia calcification, medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors. Examples of dyskinesias include drug (e.g. L-DOPA) induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics). Examples of dystonias include generalised dystonia, iodiopathic dystonia, drug-induced dystonia, symptomatic dystonia, paroxymal dystonia, focal dystonia, blepharospasm, oromandibular dystonia, spasmodic dysphonia, spasmodic torticollis, axial dystonia, dystonic writer's cramp and hemiplegic dystonia Other examples of movement disorders include stereotypic movement disorder, persistent (chronic) motor disorder, medication-Induced movement disorder, psychogenic movement disorders, substance/medication-Induced movement disorder, extrapyramidal movement disorders, hyperkinetic movement disorders, hypokinetic movement disorders, alternating hemiplegia, Angelman syndrome, Hallervorden-Spatz Disease, ataxia, dentate cerebellar ataxia, ataxia telangiectasia (Louis-Bar syndrome), Friedreich's Ataxia, hereditary spinal ataxia, hereditary spinal sclerosis, Machado-Joseph Disease, spinocerebellar ataxia, progressive myoclonic ataxia, athetosis, ballismus, blepharospasm (eye twitching), cerebral palsy, tardive dystonia, tardive dyskinesia, idiopathic torsion dystonia, torsion dystonia, focal dystonia, idiopathic familial dystonia, Idiopathic non-familial dystonia, cervical dystonia (spasmodic torticollis), primary dystonia, orofacial dystonia, developmental coordination disorder, bulbospinal muscular atrophy (Kennedy's Disease), Shy-Drager Syndrome, and Stiff-Person (Stiff-Man) Syndrome.

In some embodiments, provided are methods of treating one or more symptoms of epilepsy and/or seizures, including abdominal epilepsy, absence seizure, acquired epilepsy, acquired epileptiform aphasia, Aicardi syndrome, Alpers' disease, Alpers-Huttenlocher syndrome, Angelman syndrome, benign focal epilepsy, benign focal epilepsy of childhood, benign intracranial hypertension, benign rolandic epilepsy (BRE), CDKL5 disorder, childhood absence epilepsy, dentate cerebellar ataxia, Doose syndrome, Dravet syndrome, dyscognitive focal seizure, epilepsy with grand mal seizures, epilepsy with myoclonic-absences, epileptic hemiplegia, febrile seizures, focal seizure, frontal lobe epilepsy, generalized tonic-clonic seizures, genetic epilepsy, Glut1 deficiency syndrome, hypothalmic hamartoma, idiopathic epilepsy, idiopathic generalized epilepsy, idopathic localization-related epilepsies, idopathic partial epilepsy, idopathic seizure, juvenile absense epilepsy, juvenile myoclonic epilepsy, Lafora disease, Lafora progressive myoclonus epilepsy, Landau-Kleffner syndrome, Lassueur-Graham-Little syndrome. Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic partial epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor.

In some embodiments, provided are methods of treating one or more symptoms of infantile spasms. In some embodiments, provided are methods of treating one or more symptoms of primary generalized epilepsy.

In some embodiments, provided are methods of treating epilepsy and/or seizures, including abdominal epilepsy, absence seizure, acquired epilepsy, acquired epileptiform aphasia, Aicardi syndrome, Alpers' disease, Alpers-Huttenlocher syndrome, Angelman syndrome, benign focal epilepsy, benign focal epilepsy of childhood, benign intracranial hypertension, benign rolandic epilepsy (BRE), CDKL5 disorder, childhood absence epilepsy, dentate cerebellar ataxia, Doose syndrome, Dravet syndrome, dyscognitive focal seizure, epilepsy with grand mal seizures, epilepsy with myoclonic-absences, epileptic hemiplegia, febrile seizures, focal seizure, frontal lobe epilepsy, generalized tonic-clonic seizures, genetic epilepsy, Glut1 deficiency syndrome, hypothalmic hamartoma, idiopathic epilepsy, idiopathic generalized epilepsy, idopathic localization-related epilepsies, idopathic partial epilepsy, idopathic seizure, infantile spasms, juvenile absense epilepsy, juvenile myoclonic epilepsy, Lafora disease, Lafora progressive myoclonus epilepsy. Landau-Kleffner syndrome. Lassueur-Graham-Little syndrome, Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, primary generalized epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic partial epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor.

In some embodiments, provided are methods of treating epilepsy comprising administering a compound or composition disclosed herein.

In some embodiments, provided are methods of treating a neurological and/or psychiatric disease and disorder described herein, comprising administering a compound described herein in conjunction with one or more pharmaceutical agents. Suitable pharmaceutical agents that may be used in combination with the compounds of the present invention include anti-Parkinson's drugs, anti-Alzheimer's drugs, anti-depressants, anti-psychotics, anti-ischemics, CNS depressants, anti-cholinergics, nootropics, epilepsy medication, attention (e.g., ADD/ADHD) medications, sleep-promoting medications, wakefulness-promoting medications, and pain medications. In some embodiments, suitable pharmaceutical agents are anxiolytics.

Suitable anti-Parkinson's drugs include dopamine replacement therapy (e.g. L-DOPA, carbidopa, COMT inhibitors such as entacapone or tolcapone), dopamine agonists (e.g. D1 agonists, D2 agonists, mixed D1/D2 agonists, bromocriptine, pergolide, cabergoline, ropinirole, pramipexole, piribedil, or apomorphine in combination with domperidone), histamine H2 antagonists, monoamine oxidase inhibitors (such as selegiline, rasagiline, safinamideand tranylcypromine), certain atypical antipsychotics such as pimavanserin (a non-dopaminergic atypical antipsychotic and inverse agonist of the serotonin 5-HT2A receptor), and amantadine.

In some embodiments, compounds disclosed herein can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone or tolcapone, MAO A/B inhibitors, antioxidants, A2a adenosine receptor antagonists, cholinergic agonists. NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, cholinesterase inhibitors such as donepezil, galantamine or rivastigmine, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, reboxetine, vortioxetine, clorazepate, and pharmaceutically acceptable salts thereof. In some embodiments, suitable anti-depressant and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, perphenazine, thioridazine, trifluoperazine, aripiprazole, asenapine, clozapine, olanzapine, paliperidone, brexpiprazole, paliperidone, cariprazine, pimavanserin, iloperidone, lumateperone. MIN-101, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid, iloperidone, thiothixene, gabapentin, tiagabine, and pharmaceutically acceptable salts thereof.

Suitable epilepsy medications include levetiracetam, oxcarbazepine, clobazam, retigabine, zonisamide, felbamate, eslicarbazepine acetate, lacosamide, carbamazepine, tiagabine, methsuximide, progabide, valproic acid, lamotrigine, brivaracetam, rufinamide, topiramate and perampanel.

Suitable attention medications include methyl phenidate, atomoxetine, guanfacine, D-amphetamine, lisdexamphetamine, methylamphetamine, and clonidine.

Suitable sleep-promoting medications include ramelteon, triazolam, zopiclone, eszopiclone, zolpidem, temazepam, and trazodone.

Suitable wakefulness-promoting medications include Modafinil D-Amphetamine, caffeine, and armodafinil.

Suitable pain medications include dextromethorphan, tapentadol, buprenorphine, codeine, fentanyl, hydrocodone, hydromorphone, morphine, naloxegol, oxycodone, tramadol, gabapentil, difluprednate, pregabalin, acetyl salicyclic acid, bromfenac, diclofenac, diflunisal, indomethacin, ketorolac, meoxican, and naproxen. In some embodiments, compounds of the invention may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the condition, the particular agent, its mode of administration, and the like. The compounds disclosed herein are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions disclosed herein will be decided by the attending physician within the scope of sound medical judgment.

The pharmaceutically acceptable compositions disclosed herein can be administered to humans and other animals orally, rectally, parenterally, intracistemally, intravaginally, intraperitoneally, topically (as by powders, ointments, or drops), bucally, sublingually, as an oral or nasal spray, or the like, depending on the severity of the infection being treated. In some embodiments, the compounds disclosed herein may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a combination of two or more therapeutic agents may be administered together with the compounds disclosed herein. In some embodiments, a combination of three or more therapeutic agents may be administered with the compounds disclosed herein.

Other examples of agents the compounds disclosed herein may also be combined with include: vitamins and nutritional supplements, antiemetics (e.g. 5-HT3 receptor antagonists, dopamine antagonists. NK1 receptor antagonists, histamine receptor antagonists, cannabinoids, benzodiazepines, or anticholinergics), agents for treating Multiple Sclerosis (MS) such as beta interferon (e.g., Avonex® and Rebif®), dalfampridine, alemtuzumab), Copaxone®, and mitoxantrone; treatments for Huntington's disease such as tetrabenazine; treatments for asthma such as albuterol and Singulair®: anti-inflammatory agents such as corticosteroids, TNF blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, a compound disclosed herein, or a pharmaceutically acceptable salt thereof, is administered in combination with an antisense agent, a monoclonal or polyclonal antibody, or an siRNA therapeutic.

Those additional agents may be administered separately from a compound-containing composition disclosed herein, as part of a multiple dosage regimen. Alternatively, those agents may be part of a single dosage form, mixed together with a compound disclosed herein in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound disclosed herein may be administered with another therapeutic agent simultaneously or sequentially in separate unit dosage forms or together in a single unit dosage form. Accordingly, provided herein is a single unit dosage form comprising a compound of Formula I, or a pharmaceutically acceptable salt thereof, an additional therapeutic agent, and a pharmaceutically acceptable carrier, adjuvant, or vehicle. Accordingly, provided herein is a single unit dosage form comprising a compound of Formula I, or a pharmaceutically acceptable salt thereof, an additional therapeutic agent, and a pharmaceutically acceptable excipient (e.g., carrier, adjuvant, or vehicle).

The amount of both, a compound disclosed herein and additional therapeutic agent (in those compositions which comprise an additional therapeutic agent as described above) that may be combined with the carrier materials to produce a single dosage form will vary depending upon the host treated and the particular mode of administration. In some embodiments, compositions disclosed herein should be formulated so that a dosage of between 0.01-100 mg/kg body weight/day of an inventive can be administered.

In those compositions which comprise an additional therapeutic agent, that additional therapeutic agent and the compound disclosed herein may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions disclosed herein will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, provided is a medicament comprising at least one compound of Formula I, or a pharmaceutically acceptable salt thereof, and a pharmaceutically acceptable carrier, adjuvant, or vehicle. In some embodiments, provided is a medicament comprising at least one compound of Formula I, or a pharmaceutically acceptable salt thereof, and a pharmaceutically acceptable excipient (e.g., carrier, adjuvant, or vehicle).

In some embodiments, provided is the use of a compound of Formula I, or a pharmaceutically acceptable salt thereof, in the manufacture of a medicament for the treatment of a neurological and/or psychiatric disorder.

General Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, reaction sequences, purification methods, and chiral separation conditions may be employed to prepare a desired embodiment. The reactions may be scaled upwards or downwards to suit the amount of material to be prepared. In some embodiment, the compound of Formula I may be prepared following the schemes provided herein (e.g, Schemes A-C and 1-30), using suitable starting materials known in the art and/or available from a commercial source. In one embodiment, the starting materials of the schemes provided herein (e.g., Schemes A-C and 1-30) may be prepared from commercially available compounds using procedures and conditions known in the art.

In some embodiments, provided herein is a process of preparing a compound of Formula I, or a pharmaceutically acceptable salt thereof. As shown Scheme A below, reaction of an appropriately substituted Compound A1 with an appropriately substituted amino-acetaldehyde dimethyl acetal A2 in the presence of trifluoromethanesulfonic acid will afford compounds of Formula I. Accordingly, in some embodiments, provided herein is a process of preparing a compound of Formula I.

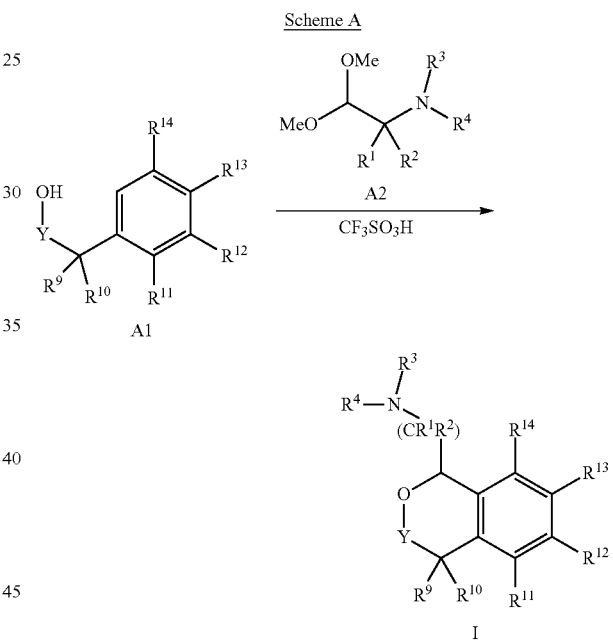

In some embodiments, provided herein is a process of preparing a compound of Formula I

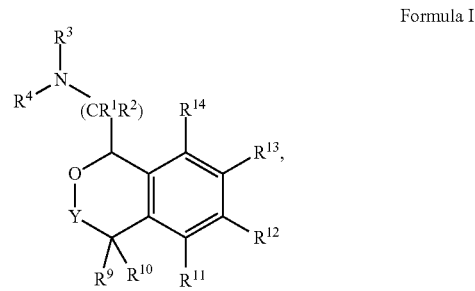

Formula I or a pharmaceutically acceptable salt thereof, comprising reacting a compound of Formula A1

Formula A1

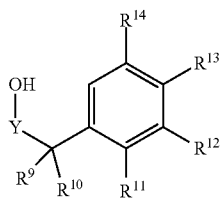

with a compound of Formula A2

Formula A2

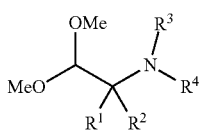

and trifluoromethanesulfonic acid,
wherein $R^1$, $R^2$, $R^3$, $R^4$, $R^9$, $R^{10}$, $R^{11}$, $R^{12}$, $R^{13}$, and $R^{14}$, are defined herein.

In some embodiments, the compound of Formula A1 is a phenethyl alcohol, phenylpropyl alcohol, or phenylbutyl alcohol.

In some embodiments, compounds provided herein can be prepared according to Scheme B shown below.

Scheme B

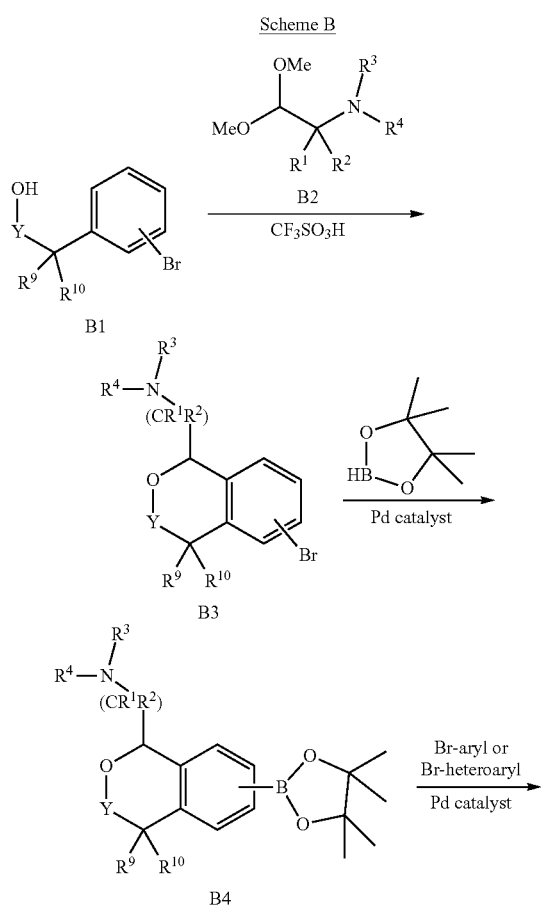

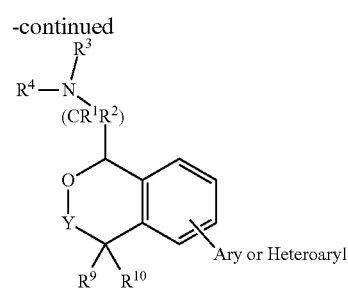

Specifically, Compound B is reacted with Compound B2 and trifluoromethanesulfonic acid to generate Compound B3. Compound B3 can be coupled with 4,4,5,5-tetramethyl-1,3,2-dioxaborolane in the presence of a palladium catalyst to generate Compound B4. Compound D1 can be coupled with an aryl bromide or heteroaryl bromide to generate Compound B5. In some embodiments, the process to prepare compounds provided herein may involve the use of an intermediate that comprises one or more protecting group. For example, the $NR^3R^4$ moiety of Compound B4 may be protected to yield Compound B4a with an $NR^3$-protecting group or Compound B4b with an $NR^4$-protecting group moiety:

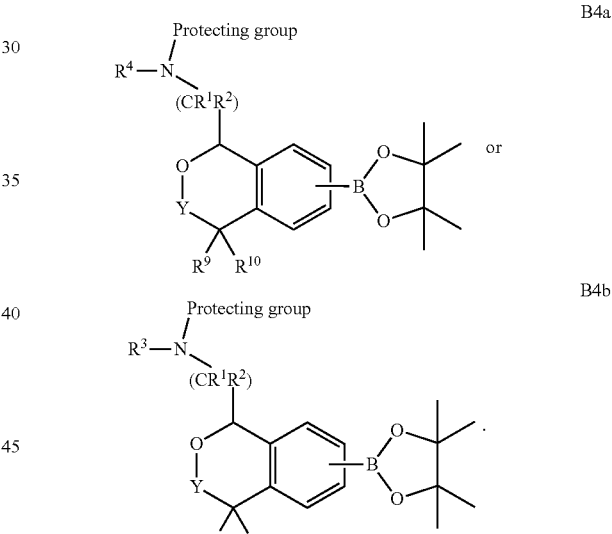

In some embodiments, the protecting group is Boc. The protecting group can be removed by methods well-known in the art.

In some embodiments, compounds provided herein can be prepared according to Scheme C below.

Scheme C

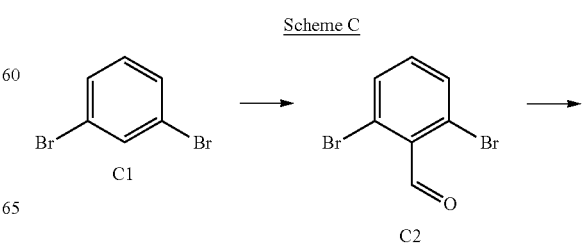

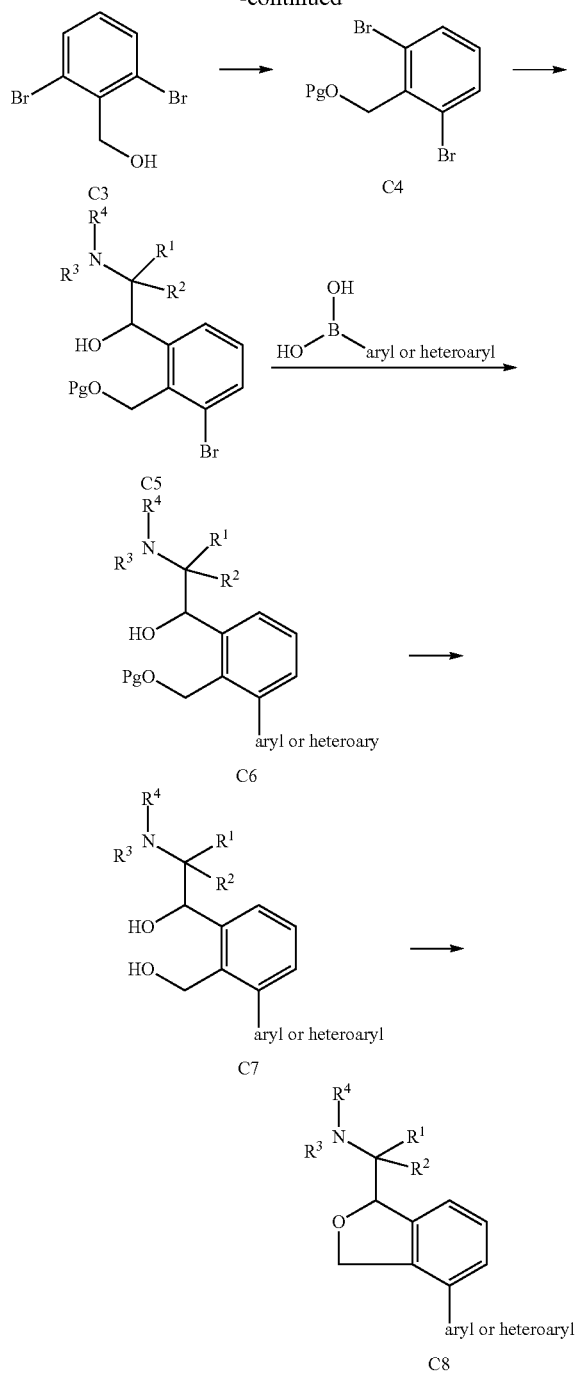

As depicted in the Examples below, in some embodiments, compounds are prepared according to the following procedures. It will be appreciated that, although the general methods depict the synthesis of certain compounds, the following methods, and other methods known to persons skilled in the art, can be applied to all compounds and subclasses and species of each of these, as described herein.

TABLE A

| Structure | Compound No. |
|---|---|
| 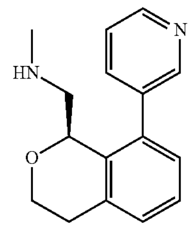 [SMILES: CNC[C@@H]1OCCc2cccc(-c3cccnc3)c21] | 1 |
| 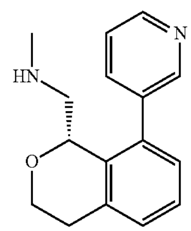 [SMILES: CNC[C@H]1OCCc2cccc(-c3cccnc3)c21] | 2 |
| 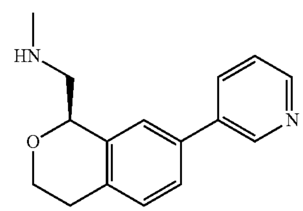 [SMILES: CNC[C@@H]1OCCc2ccc(-c3cccnc3)cc21] | 3 |
| 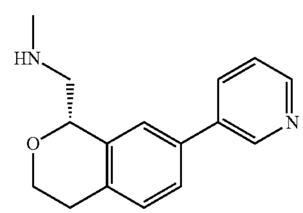 [SMILES: CNC[C@H]1OCCc2ccc(-c3cccnc3)cc21] | 4 |
| 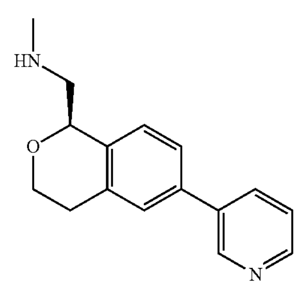 [SMILES: CNC[C@@H]1OCCc2cc(-c3cccnc3)ccc21] | 5 |

Specifically, Compound C1 can be converted to Compound C2, which is then reduced to generate compound C3. Compound C3 is protected to generate Compound C4, which is then converted to Compound C5. Compound C5 can be coupled with an aryl-B(OH)$_2$ or heteroaryl-B(OH)$_2$ to generate Compound C6. Compound C6 can be deprotected to generate Compound C7, which is then converted to Compound C8. In some embodiments, the protecting group can be TBS.

In some embodiments, stereoisomer of the compounds provided herein (e.g., R or S enantiomer) can be separated using chiral separation methods known in the art such as employing chiral column chromatography.

TABLE A-continued

| Structure | Compound No. |
|---|---|
| (structure) | 6 |
| (structure) | 7 |
| (structure) | 8 |
| (structure) | 9 |
| (structure) | 10 |
| (structure) | 11 |
| (structure) | 12 |
| (structure) | 13 |
| (structure) | 14 |
| (structure) | 15 |
| (structure) | 16 |

TABLE A-continued

| Structure | Compound No. |
|---|---|
| (isochroman with CH2-NHMe at 1-position, 5-(pyridin-4-yl) substituent) | 17 |
| (isochroman with CH2-NHMe at 1-position, 5-(pyridin-4-yl) substituent) | 18 |
| (isochroman with CH2-NH2 at 1-position, 5-(pyridin-4-yl) substituent) | 19 |
| (isochroman with CH2-NH2 at 1-position, 5-(pyridin-4-yl) substituent) | 20 |
| (isochroman with CH2-NHMe at 1-position, 6-(pyrimidin-2-yl) substituent) | 21 |
| (isochroman with CH2-NHMe at 1-position, 6-(pyrimidin-2-yl) substituent) | 22 |
| (isochroman with CH2-NHMe at 1-position, 5-(pyrimidin-2-yl) substituent) | 23 |
| (isochroman with CH2-NHMe at 1-position, 5-(pyrimidin-2-yl) substituent) | 24 |
| (isochroman with CH2-NHMe at 1-position, 7-(pyrimidin-5-yl) substituent) | 25 |
| (isochroman with CH2-NHMe at 1-position, 7-(pyrimidin-5-yl) substituent) | 26 |

TABLE A-continued
| Structure | Compound No. |
|---|---|
| 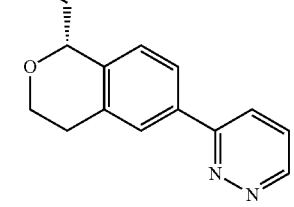 | 27 |
| 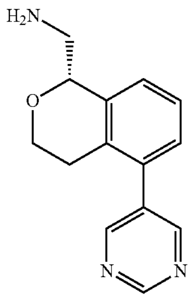 [SMILES: NC[C@H]1OCCc2c(-c3cncnc3)cccc21] | 28 |
| 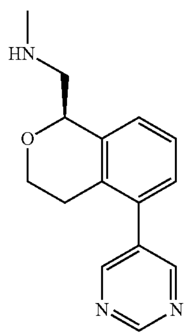 [SMILES: CNC[C@@H]1OCCc2c(-c3cncnc3)cccc21] | 29 |
| 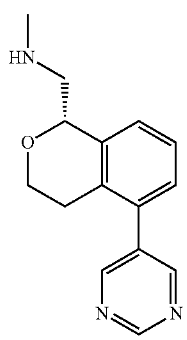 [SMILES: CNC[C@H]1OCCc2c(-c3cncnc3)cccc21] | 30 |
| 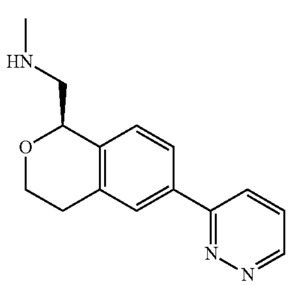 [SMILES: CNC[C@@H]1OCCc2cc(-c3cccnn3)ccc21] | 31 |
TABLE A-continued
| Structure | Compound No. |
|---|---|
| 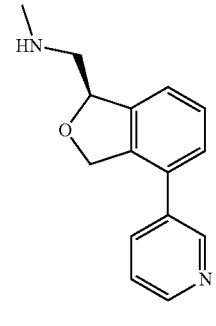 | 32 |
| 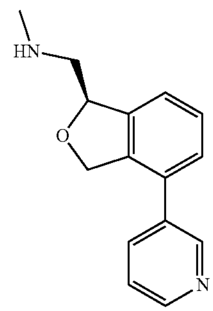 [SMILES: CNC[C@@H]1OCc2c(-c3cccnc3)cccc21] | 33 |
| 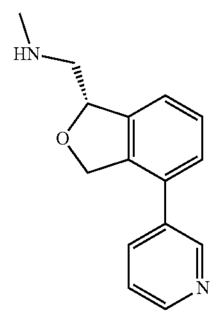 [SMILES: CNC[C@H]1OCc2c(-c3cccnc3)cccc21] | 34 |
| 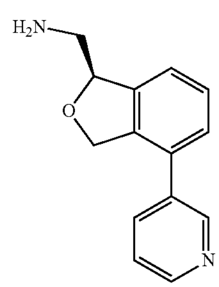 [SMILES: NC[C@@H]1OCc2c(-c3cccnc3)cccc21] | 35 |
| 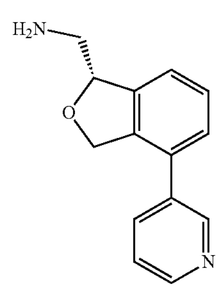 [SMILES: NC[C@H]1OCc2c(-c3cccnc3)cccc21] | 36 |

TABLE A-continued

| Structure | Compound No. |
|---|---|
| (1-(pyridin-4-yl)-1,3-dihydroisobenzofuran-1-yl)methanamine | 37 |
| (1-(pyridin-4-yl)-1,3-dihydroisobenzofuran-1-yl)methanamine stereoisomer | 38 |
| N-methyl-(1-(pyridin-4-yl)-1,3-dihydroisobenzofuran-1-yl)methanamine | 39 |
| N-methyl-(1-(pyridin-4-yl)-1,3-dihydroisobenzofuran-1-yl)methanamine stereoisomer | 40 |
| (1-(pyridin-2-yl)-1,3-dihydroisobenzofuran-1-yl)methanamine | 41 |
| (1-(pyridin-2-yl)-1,3-dihydroisobenzofuran-1-yl)methanamine stereoisomer | 42 |
| N-methyl-(isochroman-5-yl-pyridin-2-yl)methanamine | 43 |
| N-methyl-(isochroman-5-yl-pyridin-2-yl)methanamine stereoisomer | 44 |
| (isochroman-5-yl-pyridin-2-yl)methanamine | 45 |
| (isochroman-5-yl-pyridin-2-yl)methanamine stereoisomer | 46 |

TABLE A-continued
| Structure | Compound No. |
|---|---|
| 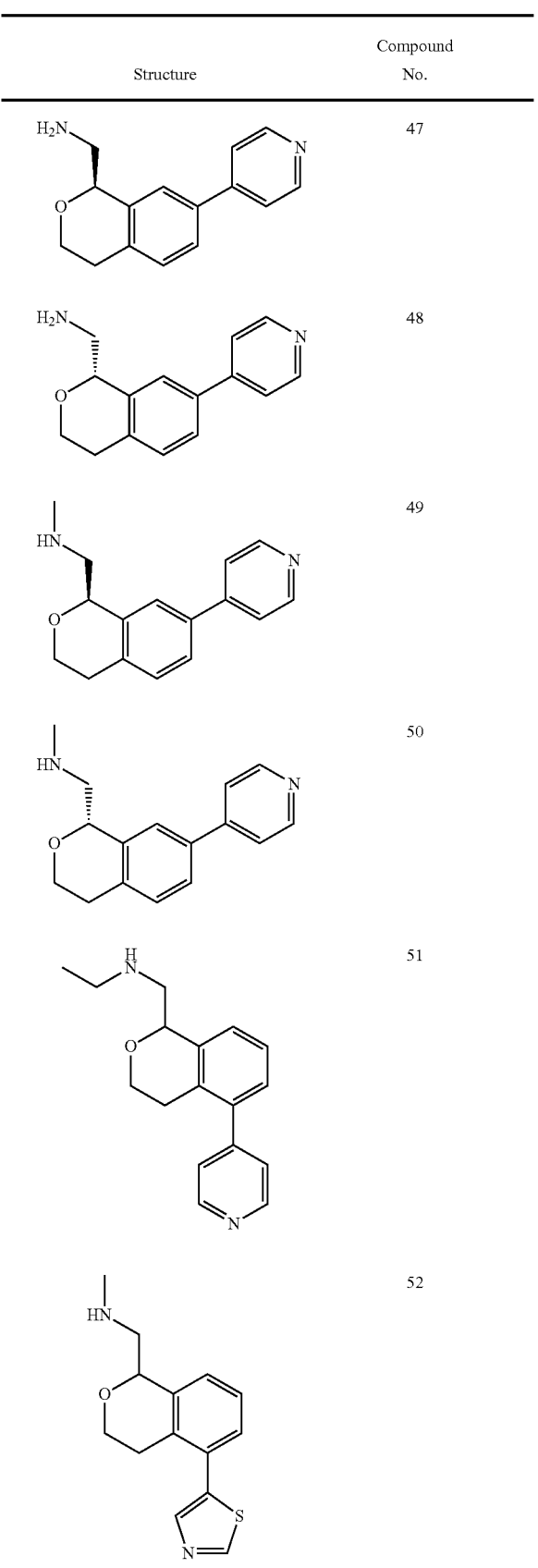 | 47 |
| 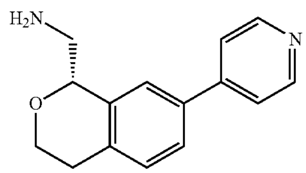 [SMILES: NC[C@H]1OCCc2ccc(-c3ccncc3)cc21] | 48 |
| 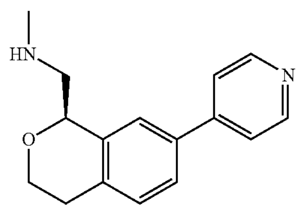 [SMILES: CNC[C@@H]1OCCc2ccc(-c3ccncc3)cc21] | 49 |
| 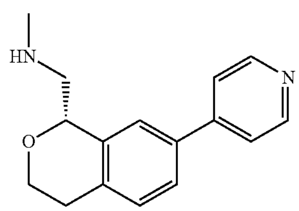 [SMILES: CNC[C@H]1OCCc2ccc(-c3ccncc3)cc21] | 50 |
| 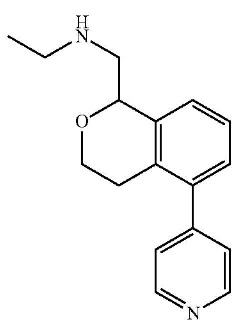 | 51 |
| 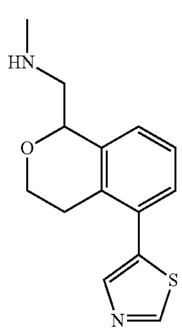 | 52 |
TABLE A-continued
| Structure | Compound No. |
|---|---|
| 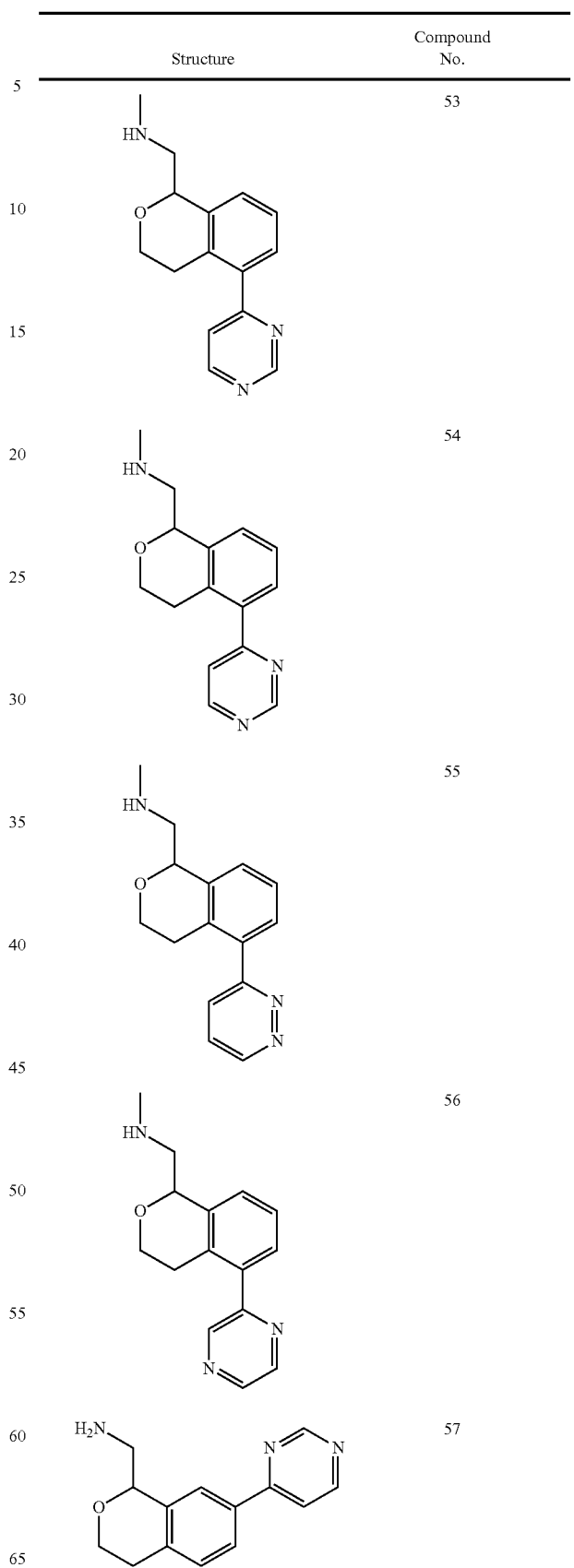 | 53 |
| 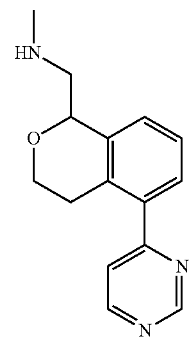 | 54 |
| 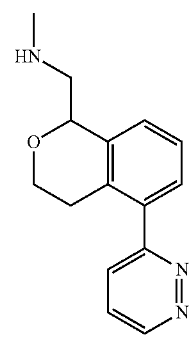 [SMILES: CNCC1OCCc2c(-c3cccnn3)cccc21] | 55 |
| 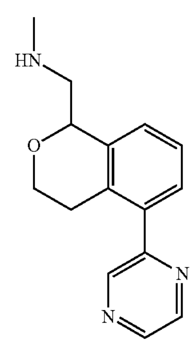 | 56 |
| 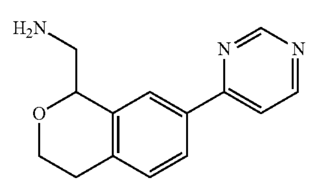 [SMILES: NCC1OCCc2ccc(-c3ccncn3)cc21] | 57 |

TABLE A-continued

| Structure | Compound No. |
|---|---|
| (isochroman with CH2-NHMe at position 1, pyrimidin-4-yl at position 7) | 58 |
| (isochroman with CH2-NH2 at position 1, thiazol-5-yl at position 5) | 59 |
| (isochroman with CH2-NH2 at position 1, pyrimidin-5-yl at position 5) | 60 |
| (isochroman with CH2-NH2 at position 1, pyridazin-4-yl at position 5) | 61 |
| (isochroman with CH2-NH2 at position 1, pyridazin-3-yl at position 5) | 62 |
| (isochroman with CH2-NH2 at position 1, pyrazin-2-yl at position 5) | 63 |
| (isochroman with CH2-NH2 at position 1, isoxazol-4-yl at position 5) | 64 |
| (isochroman with CH2-NHMe at position 1, isoxazol-4-yl at position 5) | 65 |
| (isochroman with CH2-NHEt at position 1, pyridin-4-yl at position 5) | 66 |
| (isochroman with CH2-NHEt at position 1, pyridin-4-yl at position 5) | 67 |

TABLE A-continued
| Structure | Compound No. |
|---|---|
| 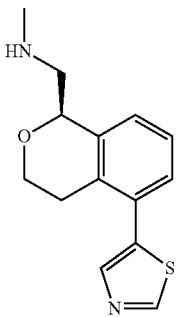 | 68 |
| 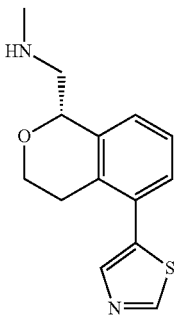 | 69 |
| 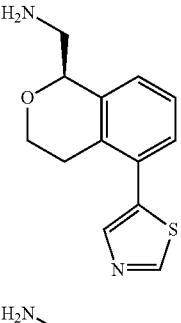 | 70 |
| 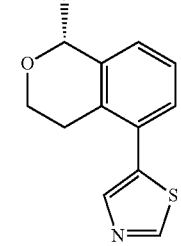 | 71 |
| 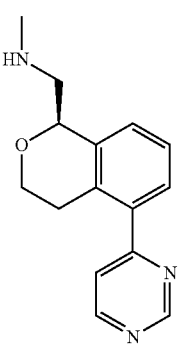 | 72 |
TABLE A-continued
| Structure | Compound No. |
|---|---|
| 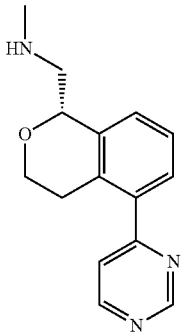 [SMILES: CNC[C@H]1OCCc2c(-c3ccncn3)cccc21] | 73 |
| 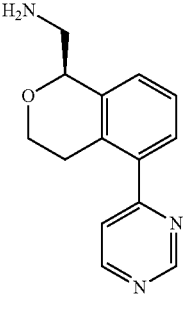 [SMILES: NC[C@@H]1OCCc2c(-c3ccncn3)cccc21] | 74 |
| 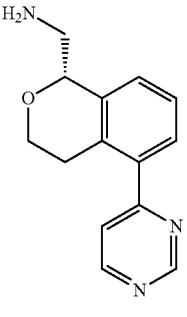 [SMILES: NC[C@H]1OCCc2c(-c3ccncn3)cccc21] | 75 |
| 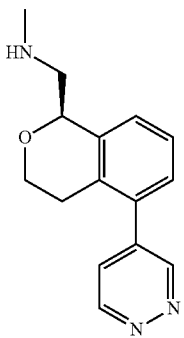 | 76 |

TABLE A-continued

| Structure | Compound No. |
|---|---|
| (isochroman-1-yl-methyl)(methyl)amine with pyridazine substituent | 77 |
| (isochroman-1-yl-methyl)amine with pyridazine substituent | 78 |
| (isochroman-1-yl-methyl)amine with pyridazine substituent | 79 |
| (isochroman-1-yl-methyl)(methyl)amine with pyrazine substituent | 80 |
| (isochroman-1-yl-methyl)(methyl)amine with pyrazine substituent | 81 |
| (isochroman-1-yl-methyl)amine with pyrazine substituent | 82 |
| (isochroman-1-yl-methyl)amine with pyrazine substituent | 83 |
| (isochroman-1-yl-methyl)(methyl)amine with isoxazole substituent | 84 |
| (isochroman-1-yl-methyl)(methyl)amine with isoxazole substituent | 85 |

TABLE A-continued

| Structure | Compound No. |
|---|---|
| (isochroman-CH2NH2 with isoxazol-4-yl at 5-position) | 86 |
| (isochroman-CH2NH2 with isoxazol-4-yl at 5-position) | 87 |
| (isochroman-CH2NH2 with isoxazol-3-yl at 5-position) | 88 |
| (isochroman-CH2NH2 with isoxazol-3-yl at 5-position) | 89 |
| (isochroman-CH2NHMe with isoxazol-3-yl at 5-position) | 90 |
| (isochroman-CH2NHMe with isoxazol-3-yl at 5-position) | 91 |
| (isochroman-CH2NH2 with isoxazol-5-yl at 5-position) | 92 |
| (isochroman-CH2NH2 with isoxazol-5-yl at 5-position) | 93 |
| (isochroman-CH2NHMe with isoxazol-5-yl at 5-position) | 94 |
| (isochroman-CH2NHMe with isoxazol-5-yl at 5-position) | 95 |

TABLE A-continued

| Structure | Compound No. |
|---|---|
| 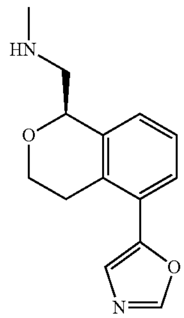 | 96 |
| 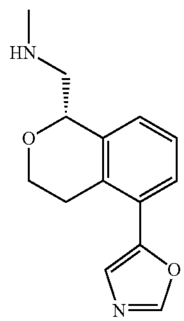 | 97 |
| 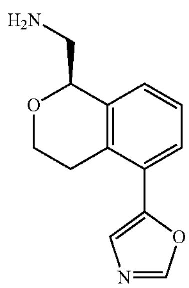 | 98 |
| 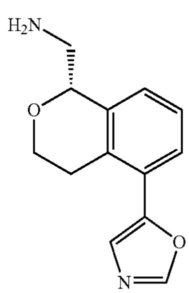 | 99 |
| 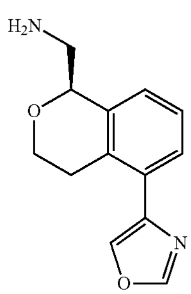 [SMILES: NC[C@@H]1OCCc2c(-c3cocn3)cccc21] | 100 |

TABLE A-continued

| Structure | Compound No. |
|---|---|
| 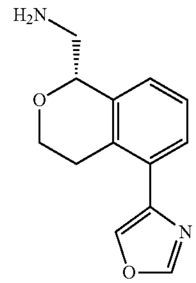 [SMILES: NC[C@H]1OCCc2c(-c3cocn3)cccc21] | 101 |
| 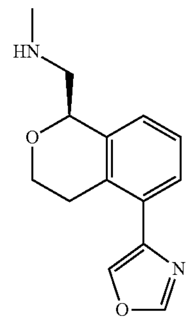 [SMILES: CNC[C@@H]1OCCc2c(-c3cocn3)cccc21] | 102 |
| 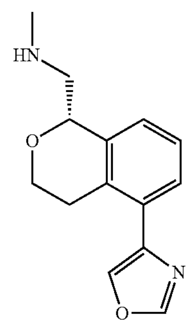 | 103 |
| 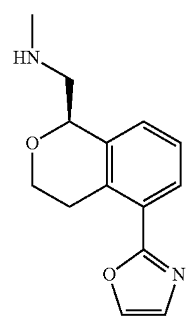 | 104 |
| 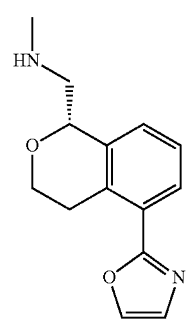 [SMILES: CNC[C@H]1OCCc2c(-c3ncco3)cccc21] | 105 |

TABLE A-continued
| Structure | Compound No. |
|---|---|
| 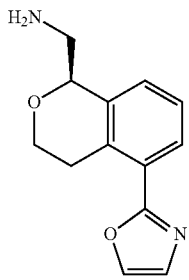 [SMILES: NC[C@@H]1OCCc2c(-c3ncco3)cccc21] | 106 |
| 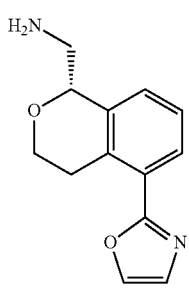 [SMILES: NC[C@H]1OCCc2c(-c3ncco3)cccc21] | 107 |
| 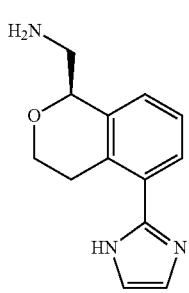 [SMILES: NC[C@@H]1OCCc2c(-c3ncc[nH]3)cccc21] | 108 |
| 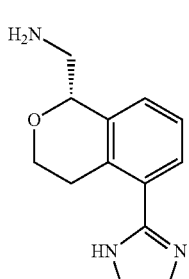 | 109 |
| 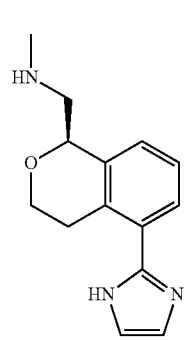 [SMILES: CNC[C@@H]1OCCc2c(-c3ncc[nH]3)cccc21] | 110 |
TABLE A-continued
| Structure | Compound No. |
|---|---|
| 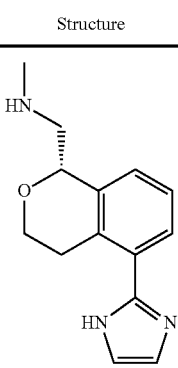 | 111 |
| 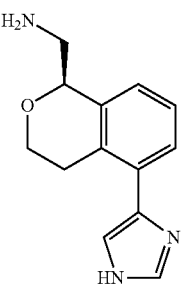 | 112 |
| 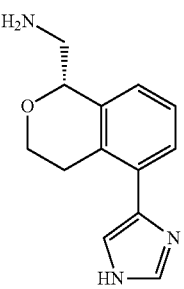 [SMILES: NC[C@H]1OCCc2c(-c3c[nH]cn3)cccc21] | 113 |
| 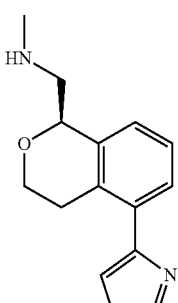 | 114 |
| 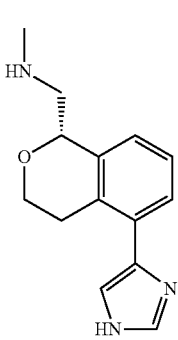 [SMILES: CNC[C@H]1OCCc2c(-c3c[nH]cn3)cccc21] | 115 |

TABLE A-continued
| Structure | Compound No. |
|---|---|
| 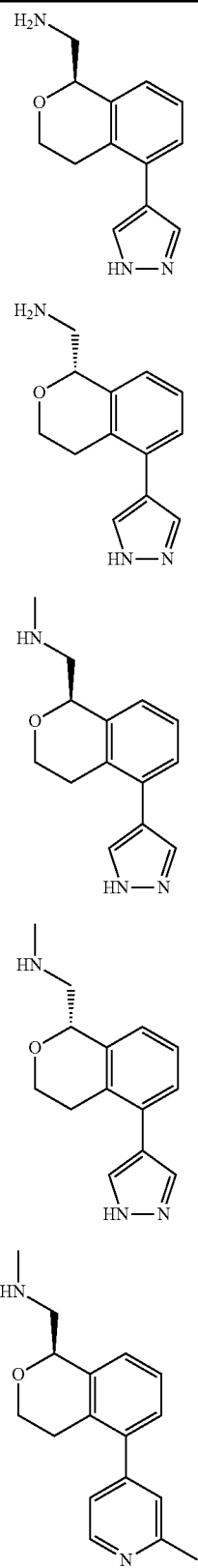 | 116 |
| 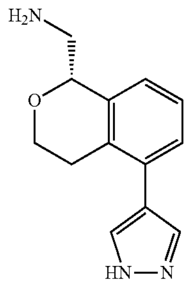 [SMILES: NC[C@H]1OCCc2c(-c3cn[nH]c3)cccc21] | 117 |
| 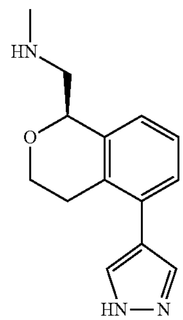 [SMILES: CNC[C@@H]1OCCc2c(-c3cn[nH]c3)cccc21] | 118 |
| 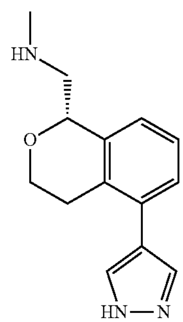 [SMILES: CNC[C@H]1OCCc2c(-c3cn[nH]c3)cccc21] | 119 |
| 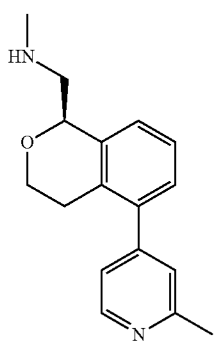 | 120 |
TABLE A-continued
| Structure | Compound No. |
|---|---|
| 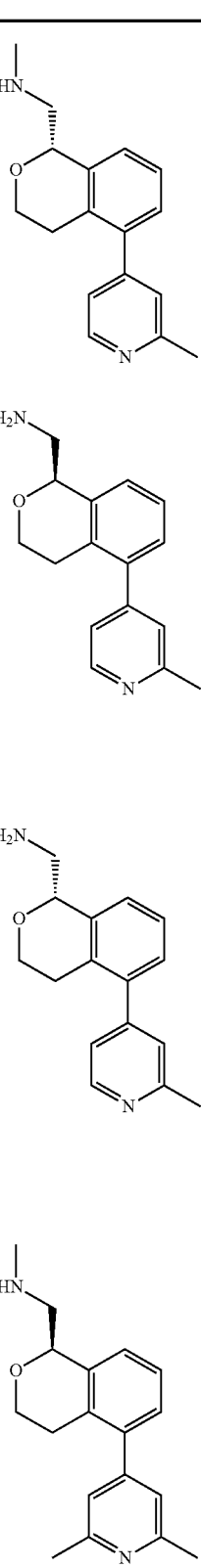 | 121 |
| 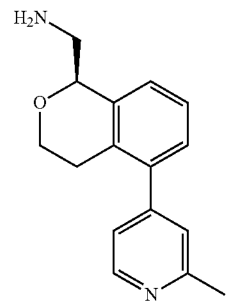 [SMILES: Cc1cc(-c2cccc3c2CCO[C@H]3CN)ccn1] | 122 |
| 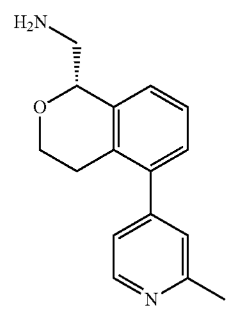 [SMILES: Cc1cc(-c2cccc3c2CCO[C@@H]3CN)ccn1] | 123 |
| 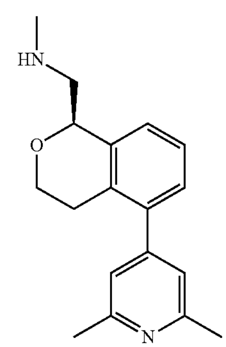 [SMILES: CNC[C@@H]1OCCc2c(-c3cc(C)nc(C)c3)cccc21] | 124 |

TABLE A-continued

| Structure | Compound No. |
|---|---|
| (isochroman-CH2NHMe with 2,6-dimethylpyridin-4-yl) | 125 |
| (isochroman-CH2NH2 with 2,6-dimethylpyridin-4-yl) | 126 |
| (isochroman-CH2NH2 with 2,6-dimethylpyridin-4-yl, different regiochemistry) | 127 |
| (isochroman-CH2NHMe with phenyl) | 128 |
| (isochroman-CH2NHMe with phenyl) | 129 |
| (isochroman-CH2NH2 with phenyl) | 130 |
| (isochroman-CH2NH2 with phenyl) | 131 |
| (isobenzofuran-CH2NHMe with pyrimidin-4-yl) | 132 |
| (isobenzofuran-CH2NHMe with pyrimidin-4-yl) | 133 |

TABLE A-continued

| Structure | Compound No. |
|---|---|
| (structure) | 134 |
| (structure) | 135 |
| (structure) | 136 |
| (structure) | 137 |
| (structure) | 138 |
| (structure) | 139 |
| (structure) | 140 |
| (structure) | 141 |
| (structure) | 142 |
| (structure) | 143 |

TABLE A-continued

| Structure | Compound No. |
|---|---|
| (isobenzofuran-CH2NH2 with isoxazole) | 144 |
| (isobenzofuran-CH2NH2 with isoxazole) | 145 |
| (isobenzofuran-CH2NHMe with isoxazole) | 146 |
| (isobenzofuran-CH2NHMe with isoxazole) | 147 |
| (benzoxepine-CH2NHMe with pyridin-4-yl) | 148 |
| (benzoxepine-CH2NHMe with pyridin-4-yl) | 149 |
| (benzoxepine-CH2NH2 with pyridin-4-yl) | 150 |
| (benzoxepine-CH2NH2 with pyridin-4-yl) | 151 |
| (benzoxepine-CH2NHMe with pyridin-3-yl) | 152 |

TABLE A-continued

| Structure | Compound No. |
|---|---|
| 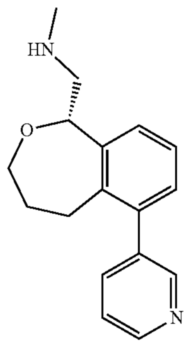 [SMILES: CNC[C@H]1OCCCc2c(-c3cccnc3)cccc21] | 153 |
| 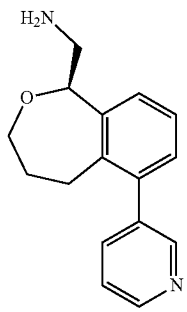 [SMILES: NC[C@@H]1OCCCc2c(-c3cccnc3)cccc21] | 154 |
| 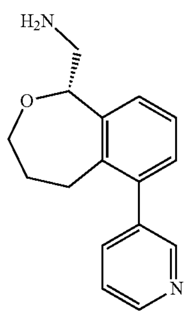 [SMILES: NC[C@H]1OCCCc2c(-c3cccnc3)cccc21] | 155 |
| 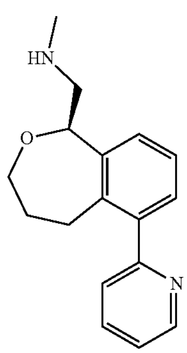 [SMILES: CNC[C@@H]1OCCCc2c(-c3ccccn3)cccc21] | 156 |
| | 157 |
| | 158 |
| | 159 |
| | 160 |

TABLE A-continued

| Structure | Compound No. |
|---|---|
| (structure) | 161 |
| (structure) | 162 |
| (structure) | 163 |
| (structure) | 164 |

TABLE A-continued

| Structure | Compound No. |
|---|---|
| (structure) | 165 |
| (structure) | 166 |
| (structure) | 167 |
| (structure) | 168 |

TABLE A-continued

| Structure | Compound No. |
|---|---|
| (structure) | 169 |
| (structure) | 170 |
| (structure) | 171 |
| (structure) | 172 |
| (structure) | 173 |

TABLE A-continued

| Structure | Compound No. |
|---|---|
| (structure) | 174 |
| (structure) | 175 |
| (structure) | 176 |
| (structure) | 177 |
| (structure) | 178 |

TABLE A-continued

| Structure | Compound No. |
|---|---|
| | 179 |
| | 180 |
| | 181 |
| | 182 |
| 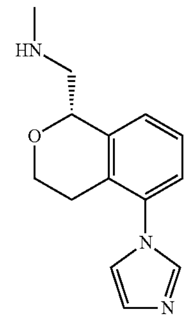 [SMILES: CNC[C@H]1OCCc2c1cccc2-n1ccnc1] | 183 |
| 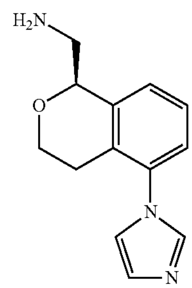 | 184 |
| 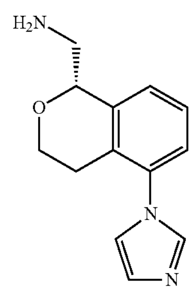 | 185 |
| 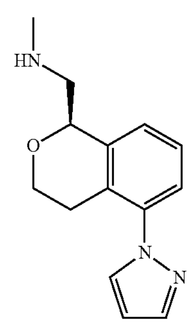 | 186 |
| 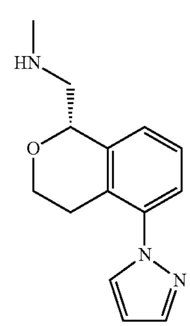 | 187 |

TABLE A-continued

| Structure | Compound No. |
|---|---|
| (structure) | 188 |
| (structure) | 189 |
| (structure) | 190 |
| (structure) | 191 |
| (structure) | 192 |
| (structure) | 193 |
| (structure) | 194 |
| (structure) | 195 |
| (structure) | 196 |

TABLE A-continued

| Structure | Compound No. |
|---|---|
| (structure) | 197 |
| (structure) | 198 |
| (structure) | 199 |
| (structure) | 200 |
| (structure) | 201 |
| (structure) | 202 |
| (structure) | 203 |

The compounds of Table A can be prepared as a pharmaceutically acceptable salt thereof. For example, the compound in Table A can be prepared as hydrochloride salt such as mono-hydrochloric acid salt or di-hydrochoric acid salt. Preparations of the compounds as a free base or the salt thereof are detailed in the examples below.

TABLE B

| Compound no | Chemical name |
|---|---|
| 1 | (R)-N-Methyl-1-(8-(pyridin-3-yl)isochroman-1-yl)methanamine bis-hydrochloride |
| 2 | (S)-N-Methyl-1-(8-(pyridin-3-yl)isochroman-1-yl)methanamine bis-hydrochloride |
| 3 | (R)-N-Methyl-1-(7-(pyridin-3-yl)isochroman-1-yl)methanamine dihydrochloride |
| 4 | (S)-N-methyl-1-(7-(pyridin-3-yl)isochroman-1-yl)methanamine dihydrochloride |
| 5 | (R)-N-Methyl(6-(pyridin-3-yl)isochroman-1-yl)methanamine bis-hydrochloride |
| 6 | (S)-N-methyl(6-(pyridin-3-yl)isochroman-1-yl)methanamine bis-hydrochloride |
| 7 | (R)-N-Methyl-1-(5-(pyridin-3-yl)isochroman-1-yl)methanamine bis-hydrochloride |

TABLE B-continued

| Compound no | Chemical name |
|---|---|
| 8 | (S)-N-Methyl(5-(pyridin-3-yl)isochroman-1-yl)methanamine bis-hydrochloride |
| 9 | (R)-(8-(Pyridin-3-yl)isochroman-1-yl)methanamine hydrochloride |
| 10 | (S)-(8-(Pyridin-3-yl)isochroman-1-yl)methanamine hydrochloride |
| 11 | (R)-(7-(pyridin-3-yl)isochroman-1-yl)methanamine hydrochloride |
| 12 | (S)-(7-(pyridin-3-yl)isochroman-1-yl)methanamine hydrochloride |
| 13 | (R)-tert-Butyl (6-(pyridin-3-yl)isochroman-1-yl)methylcarbamate hydrochloride |
| 14 | (S)-tert-Butyl (6-(pyridin-3-yl)isochroman-1-yl)methylcarbamate hydrochloride |
| 15 | (R)-(5-(Pyridin-3-yl)isochroman-1-yl)methanamine hydrochloride |
| 16 | (S)-(5-(Pyridin-3-yl)isochroman-1-yl)methanamine hydrochloride |
| 17 | (R)-N-Methyl(5-(pyridin-4-yl)isochroman-1-yl)methanamine dihydrochloride |
| 18 | (S)-N-Methyl(5-(pyridin-4-yl)isochroman-1-yl)methanamine dihydrochloride |
| 19 | (R)-(5-(Pyridin-4-yl)isochroman-1-yl)methanamine hydrochloride |
| 20 | (S)-(5-(Pyridin-4-yl)isochroman-1-yl)methanamine hydrochloride |
| 21 | (R)-N-Methyl-1-(6-(pyrimidin-2-yl)isochroman-1-yl)methanamine hydrochloride |
| 22 | (S)-N-Methyl-1-(6-(pyrimidin-2-yl)isochroman-1-yl)methanamine hydrochloride |
| 23 | (S)-N-Methyl-1-(5-(pyrimidin-2-yl)isochroman-1-yl)methanamine hydrochloride |
| 24 | (R)-N-Methyl-1-(5-(pyrimidin-2-yl)isochroman-1-yl)methanamine hydrochloride |
| 25 | (S)-N-Methyl-1-(7-(pyrimidin-5-yl)isochroman-1-yl)methanamine hydrochloride |
| 26 | (R)-N-Methyl-1-(7-(pyrimidin-5-yl)isochroman-1-yl)methanamine hydrochloride |
| 27 | (R)-(5-(Pyrimidin-5-yl)isochroman-1-yl)methanamine hydrochloride |
| 28 | (S)-(5-(Pyrimidin-5-yl)isochroman-1-yl)methanamine hydrochloride |
| 29 | (R)-N-Methyl-1-(5-(pyrimidin-5-yl)isochroman-1-yl)methanamine hydrochloride |
| 30 | (S)-N-Methyl-1-(5-(pyrimidin-5-yl)isochroman-1-yl)methanamine hydrochloride |
| 31 | (R)-N-Methyl-1-(6-(pyridazin-3-yl)isochroman-1-yl)methanamine hydrochloride |
| 32 | (S)-N-Methyl-1-(6-(pyridazin-3-yl)isochroman-1-yl)methanamine hydrochloride |
| 33 | (R)-N-Methyl-1-(4-(pyridin-3-yl)-1,3-dihydroisobenzofuran-1-yl)methanamine hydrochloride |
| 34 | (S)-N-Methyl-1-(4-(pyridin-3-yl)-1,3-dihydroisobenzofuran-1-yl)methanamine hydrochloride |
| 35 | (R)-(4-(Pyridin-3-yl)-1,3-dihydroisobenzofuran-1-yl)methanamine hydrochloride |
| 36 | (S)-(4-(Pyridin-3-yl)-1,3-dihydroisobenzofuran-1-yl)methanamine hydrochloride |
| 37 | (R)-(4-(Pyridin-4-yl)-1,3-dihydroisobenzofuran-1-yl)methanamine hydrochloride |
| 38 | (S)-(4-(Pyridin-4-yl)-1,3-dihydroisobenzofuran-1-yl)methanamine hydrochloride |
| 39 | (R)-N-Methyl-1-(4-(pyridin-4-yl)-1,3-dihydroisobenzofuran-1-yl)methanamine hydrochloride |
| 40 | (S)-N-Methyl-1-(4-(pyridin-4-yl)-1,3-dihydroisobenzofuran-1-yl)methanamine hydrochloride |
| 41 | (R)-(4-(Pyridin-2-yl)-1,3-dihydroisobenzofuran-1-yl)methanamine |
| 42 | (S)-(4-(Pyridin-2-yl)-1,3-dihydroisobenzofuran-1-yl)methanamine |
| 43 | (R)-N-Methyl-1-(5-(pyridin-2-yl)isochroman-1-yl)methanamine hydrochloride |
| 44 | (S)-N-Methyl-1-(5-(pyridin-2-yl)isochroman-1-yl)methanamine hydrochloride |
| 45 | (R)-(5-(pyridin-2-yl)isochroman-1-yl)methanamine hydrochloride |
| 46 | (S)-(5-(pyridin-2-yl)isochroman-1-yl)methanamine hydrochloride |
| 47 | (R)-(7-(pyridin-4-yl)isochroman-1-yl)methanamine hydrochloride |
| 48 | (S)-(7-(pyridin-4-yl)isochroman-1-yl)methanamine hydrochloride |
| 49 | (R)-N-Methyl-1-(7-(pyridin-4-yl)isochroman-1-yl)methanamine hydrochloride |
| 50 | (S)-N-Methyl-1-(7-(pyridin-4-yl)isochroman-1-yl)methanamine hydrochloride |
| 51 | N-((5-(pyridin-4-yl)isochroman-1-yl)methyl)ethanamine |
| 52 | N-Methyl-1-(5-(thiazol-5-yl)isochroman-1-yl)methanamine hydrochloride |
| 53 | N-Methyl-1-(5-(pyrimidin-4-yl)isochroman-1-yl)methanamine hydrochloride |
| 54 | N-Methyl-1-(5-(pyridazin-4-yl)isochroman-1-yl)methanamine hydrochloride |
| 55 | N-Methyl-1-(5-(pyridazin-4-yl)isochroman-1-yl)methanamine hydrochloride |
| 56 | N-Methyl-1-(5-(pyrazin-2-yl)isochroman-1-yl)methanamine hydrochloride |
| 57 | 7-(Pyrimidin-4-yl)isochroman-1-yl)methanamine hydrochloride |
| 58 | N-Methyl-1-(7-(pyrimidin-4-yl)isochroman-1-yl)methanamine hydrochloride |
| 59 | (5-(Thiazol-5-yl)isochroman-1-yl)methanamine hydrochloride |
| 60 | (5-(Pyrimidin-4-yl)isochroman-1-yl)methanamine hydrochloride |
| 61 | (5-(Pyridazin-4-yl)isochroman-1-yl)methanamine hydrochloride |
| 62 | (5-(Pyridazin-3-yl)isochroman-1-yl)methanaminehydrochloride |
| 63 | (5-(Pyrazin-2-yl)isochroman-1-yl)methanamine hydrochloride |
| 64 | (5-(Isoxazol-4-yl)isochroman-1-yl)methanamine hydrochloride |
| 65 | 1-(5-(Isoxazol-4-yl)isochroman-1-yl)-N-methylmethanamine hydrochloride |
| 66 | (R)-N-((5-(Pyridin-4-yl) isochroman-1-yl)methyl)ethanamine hydrochloride |
| 67 | (S)-N-((5-(Pyridin-4-yl) isochroman-1-yl)methyl)ethanamine hydrochloride |
| 68 | (R)-N-Methyl-1-(5-(thiazol-5-yl)isochroman-1-yl)methanamine hydrochloride |
| 69 | (S)-N-Methyl-1-(5-(thiazol-5-yl)isochroman-1-yl)methanamine hydrochloride |
| 70 | (R)-(5-(Thiazol-5-yl)isochroman-1-yl)methanamine hydrochloride |
| 71 | (S)-(5-(Thiazol-5-yl)isochroman-1-yl)methanamine hydrochloride |
| 72 | (R)-N-Methyl-1-(5-(pyrimidin-4-yl)isochroman-1-yl)methanamine hydrochloride |
| 73 | (S)-N-Methyl-1-(5-(pyrimidin-4-yl)isochroman-1-yl)methanamine hydrochloride |
| 74 | (R)-(5-(Pyrimidin-4-yl)isochroman-1-yl)methanamine hydrochloride |
| 75 | (S)-(5-(Pyrimidin-4-yl)isochroman-1-yl)methanamine hydrochloride |
| 76 | (R)-N-Methyl-1-(5-(pyridazin-4-yl)isochroman-1-yl)methanamine hydrochloride |
| 77 | (S)-N-Methyl-1-(5-(pyridazin-4-yl)isochroman-1-yl)methanamine hydrochloride |
| 78 | (R)-(5-(Pyridazin-4-yl)isochroman-1-yl)methanamine hydrochloride |
| 79 | (S)-(5-(Pyridazin-4-yl)isochroman-1-yl)methanamine hydrochloride |
| 80 | (R)-N-Methyl-1-(5-(pyrazine-2-yl)isochroman-1-yl)methanamine |
| 81 | (S)-N-Methyl-1-(5-(pyrazine-2-yl)isochroman-1-yl)methanamine |
| 82 | (R)-(5-(Pyrazin-2-yl)isochroman-1-yl)methanamine hydrochloride |
| 83 | (S)-(5-(Pyrazin-2-yl)isochroman-1-yl)methanamine hydrochloride |
| 84 | (R)-1-(5-(Isoxazol-4-yl)isochroman-1-yl)-N-methylmethanamine hydrochloride |
| 85 | (S)-1-(5-(Isoxazol-4-yl)isochroman-1-yl)-N-methylmethanamine hydrochloride |

TABLE B-continued

| Compound no | Chemical name |
|---|---|
| 86 | (R)-(5-(Isoxazol-4-yl)isochroman-1-yl)methanamine hydrochloride |
| 87 | (S)-(5-(Isoxazol-4-yl)isochroman-1-yl)methanamine hydrochloride |
| 88 | (R)-(5-(Isoxazol-3-yl)isochroman-1-yl)methanamine hydrochloride |
| 89 | (S)-(5-(Isoxazol-3-yl)isochroman-1-yl)methanamine hydrochloride |
| 90 | (R)-1-(5-(Isoxazol-3-yl)isochroman-1-yl)-N-methylmethanamine hydrochloride |
| 91 | (S)-1-(5-(Isoxazol-3-yl)isochroman-1-yl)-N-methylmethanamine hydrochloride |
| 92 | (R)-(5-(Isoxazol-5-yl)isochroman-1-yl)methanamine hydrochloride |
| 93 | (S)-(5-(Isoxazol-5-yl)isochroman-1-yl)methanamine hydrochloride |
| 94 | (R)-1-(5-(Isoxazol-5-yl)isochroman-1-yl)-N-methylmethanamine |
| 95 | (S)-1-(5-(Isoxazol-5-yl)isochroman-1-yl)-N-methylmethanamine |
| 96 | (R)-N-Methyl-1-(5-(oxazol-5-yl)isochroman-1-yl)methanamine hydrochloride |
| 97 | (S)-N-Methyl-1-(5-(oxazol-5-yl)isochroman-1-yl)methanamine hydrochloride |
| 98 | (R)-(5-(Oxazol-5-yl)isochroman-1-yl)methanamine hydrochloride |
| 99 | (S)-(5-(Oxazol-5-yl)isochroman-1-yl)methanamine hydrochloride |
| 100 | (R)-(5-(oxazol-4-yl)isochroman-1-yl)methanamine hydrochloride |
| 101 | (S)-(5-(oxazol-4-y1)isochroman-1-yl)methanamine hydrochloride |
| 102 | (R)-N-methyl-1-(5-(oxazol-4-yl)isochroman-1-yl)methanamine hydrochloride |
| 103 | (S)-N-methyl-1-(5-(oxazol-4-yl)isochroman-1-yl)methanamine hydrochloride |
| 104 | (R)-N-Methyl-1-(5-(oxazol-2-yl)isochroman-1-yl)methanamine hydrochloride |
| 105 | (S)-N-methyl-1-(5-(oxazol-2-yl)isochroman-1-yl)methanamine dihydrochloride |
| 106 | (R)-(5-(Oxazol-2-yl)isochroman-1-yl)methanamine hydrochloride |
| 107 | (S)-(5-(Oxazol-2-yl)isochroman-1-yl)methanamine hydrochloride |
| 108 | (R)-(5-(1H-Imidazol-2-yl)isochroman-1-yl)methanamine hydrochloride |
| 109 | (S)-(5-(1H-Imidazol-2-yl)isochroman-1-yl)methanamine hydrochloride |
| 110 | (R)-1-(5-(1H-Imidazol-2-yl)isochroman-1-yl)-N-methylmethanamine hydrochloride |
| 111 | (S)-1-(5-(1H-Imidazol-2-yl)isochroman-1-yl)-N-methylmethanamine hydrochloride |
| 112 | (R)-(5-(1H-Imidazol-4-yl)isochroman-1-yl)methanamine hydrochloride |
| 113 | (S)-(5-(1H-Imidazol-4-yl)isochroman-1-yl)methanamine hydrochloride |
| 114 | (R)-1-(5-(1H-imidazol-4-yl)isochroman-1-yl)-N-methylmethanamine hydrochloride |
| 115 | (S)-1-(5-(1H-imidazol-4-yl)isochroman-1-yl)-N-methylmethanamine hydrochloride |
| 116 | (R)-(5-(1H-pyrazol-4-yl)isochroman-1-yl)methanamine hydrochloride |
| 117 | (S)-(5-(1H-pyrazol-4-yl)isochroman-1-yl)methanamine hydrochloride |
| 118 | (R)-1-(5-(1H-pyrazol-4-yl)isochroman-1-yl)-N-methylmethanamine hydrochloride |
| 119 | (S)-1-(5-(1H-pyrazol-4-yl)isochroman-1-yl)-N-methylmethanamine hydrochloride |
| 120 | (R)-N-Methyl-1-(5-(2-methylpyridin-4-yl)isochroman-1-yl)methanamine hydrochloride |
| 121 | (S)-N-Methyl-1-(5-(2-methylpyridin-4-yl)isochroman-1-yl)methanamine hydrochloride |
| 122 | (R)-(5-(2-Methylpyridin-4-yl)isochroman-1-yl)methanamine hydrochloride |
| 123 | (S)-(5-(2-Methylpyridin-4-yl)isochroman-1-yl)methanamine hydrochloride |
| 124 | (R)-1-(5-(2,6-dimethylpyridin-4-yl)isochroman-1-yl)-N-methylmethanamine dihydrochloride |
| 125 | (S)-1-(5-(2,6-dimethylpyridin-4-yl)isochroman-1-yl)-N-methylmethanamine dihydrochloride |
| 126 | (R)-1-(5-(2,6-dimethylpyridin-4-yl)isochroman-1-yl)-N-methylmethanamine dihydrochloride |
| 127 | (S)-1-(5-(2,6-dimethylpyridin-4-yl)isochroman-1-yl)-N-methylmethanamine dihydrochloride |
| 128 | (R)-N-Methyl-1-(5-phenylisochroman-1-yl)methanamine hydrochloride |
| 129 | (S)-N-Methyl-1-(5-phenylisochroman-1-yl)methanamine hydrochloride |
| 130 | (R)-(5-Phenylisochroman-1-yl)methanamine hydrochloride |
| 131 | (S)-(5-Phenylisochroman-1-yl)methanamine hydrochloride |
| 132 | (R)-N-methyl-1-(4-(pyrimidin-4-y1)-1,3-dihydroisobenzofuran-1-yl)methanamine |
| 133 | (S)-N-methyl-1-(4-(pyrimidin-4-yl)-1,3-dihydroisobenzofuran-1-yl)methanamine |
| 134 | (R)-(4-(pyrimidin-4-yl)-1,3-dihydroisobenzofuran-1-yl)methanamine |
| 135 | (S)-(4-(pyrimidin-4-yl)-1,3-dihydroisobenzofuran-1-yl)methanamine |
| 136 | (R)-N-methyl-1-(4-(pyrazin-2-yl)-1,3-dihydroisobenzofuran-1-yl)methanamine |
| 137 | (S)-N-methyl-1-(4-(pyrazin-2-yl)-1,3-dihydroisobenzofuran-1-yl)methanamine |
| 138 | (R)-(4-(pyrazin-2-yl)-1,3-dihydroisobenzofuran-1-yl)methanamine |
| 139 | (S)-(4-(pyrazin-2-yl)-1,3-dihydroisobenzofuran-1-yl)methanamine |
| 140 | (R)-N-methyl-1-(4-(thiazol-5-yl)-1,3-dihydroisobenzofuran-1-yl)methanamine |
| 141 | (S)-N-methyl-1-(4-(thiazol-5-yl)-1,3-dihydroisobenzofuran-1-yl)methanamine |
| 142 | (R)-(4-(thiazol-5-yl)-1,3-dihydroisobenzofuran-1-yl)methanamine |
| 143 | (S)-(4-(thiazol-5-yl)-1,3-dihydroisobenzofuran-1-yl)methanamine |
| 144 | (S)-(4-(isoxazol-4-yl)-1,3-dihydroisobenzofuran-1-yl)methanamine |
| 145 | (R)-(4-(isoxazol-4-yl)-1,3-dihydroisobenzofuran-1-yl)methanamine |
| 146 | (S)-1-(4-(isoxazol-4-yl)-1,3-dihydroisobenzofuran-1-yl)-N-methylmethanamine |
| 147 | (R)-1-(4-(isoxazol-4-yl)-1,3-dihydroisobenzofuran-1-yl)-N-methylmethanamine |
| 148 | (R)-N-Methyl-1-(6-(pyridin-4-yl)-1,3,4,5-tetrahydrobenzo[c]oxepin-1-yl)methanamine |
| 149 | (S)-N-methyl-1-(6-(pyridin-4-yl)-1,3,4,5-tetrahydrobenzo[c]oxepin-1-yl)methanamine |
| 150 | (R)-(6-(Pyridin-4-yl)-1,3,4,5-tetrahydrobenzo[c]oxepin-1-y])methanamine |
| 151 | (S)-(6-(Pyridin-4-yl)-1,3,4,5-tetrahydrobenzo[c]oxepin-1-yl)methanamine |
| 152 | (R)-N-methyl-1-(6-(pyridin-3-yl)-1,3,4,5-tetrahydrobenzo[c]oxepin-1-yl)methanamine |
| 153 | (S)-N-methyl-1-(6-(pyridin-3-yl)-1,3,4,5-tetrahydrobenzo[c]oxepin-1-yl)methanamine |
| 154 | (R)-(6-(pyridin-3-yl)-1,3,4,5-tetrahydrobenzo[c]oxepin-1-yl)methanamine |
| 155 | (S)-(6-(pyridin-3-yl)-1,3,4,5-tetrahydrobenzo[c]oxepin-1-yl)methanamine |
| 156 | (R)-N-Methyl-1-(6-(pyridin-2-yl)-1,3,4,5-tetrahydrobenzo[c]oxepin-1-yl)methanamine hydrochloride |
| 157 | (S)-N-Methyl-1-(6-(pyridin-2-yl)-1,3,4,5-tetrahydrobenzo[c]oxepin-1-yl)methanamine hydrochloride |
| 158 | (R)-(6-(pyridin-2-yl)-1,3,4,5-tetrahydrobenzo[c]oxepin-1-yl)methanamine hydrochloride |
| 159 | (S)-(6-(pyridin-2-yl)-1,3,4,5-tetrahydrobenzo[c]oxepin-1-yl)methanamine hydrochloride |
| 160 | (R)-N-methyl-1-(6-(pyrazin-2-yl)-1,3,4,5-tetrahydrobenzo[c]oxepin-1-yl)methanamine |
| 161 | (S)-N-methyl-1-(6-(pyrazin-2-yl)-1,3,4,5-tetrahydrobenzo[c]oxepin-1-yl)methanamine |
| 162 | (R)-(6-(pyrazin-2-yl)-1,3,4,5-tetrahydrobenzo[c]oxepin-1-yl)methanamine |
| 163 | (S)-(6-(pyrazin-2-yl)-1,3,4,5-tetrahydrobenzo[c]oxepin-1-yl)methanamine |

TABLE B-continued

| Compound no | Chemical name |
|---|---|
| 164 | (R)-N-Methyl-1-(6-(pyrimidin-4-yl)-1,3,4,5-tetrahydrobenzo[c]oxepin-1-yl)methanamine hydrochloride |
| 165 | (S)-N-Methyl-1-(6-(pyrimidin-4-yl)-1,3,4,5-tetrahydrobenzo[c]oxepin-1-yl)methanamine hydrochloride |
| 166 | (R)-(6-(Pyrimidin-4-yl)-1,3,4,5-tetrahydrobenzo[c]oxepin-1-yl)methanamine |
| 167 | (S)-(6-(Pyrimidin-4-yl)-1,3,4,5-tetrahydrobenzo[c]oxepin-1-yl)methanamine |
| 168 | (R)-N-Methyl-1-(6-(thiazol-5-yl)-1,3,4,5-tetrahydrobenzo[c]oxepin-1-yl)methanamine hydrochloride |
| 169 | (S)-N-Methyl-1-(6-(thiazol-5-yl)-1,3,4,5-tetrahydrobenzo[c]oxepin-1-yl)methanamine hydrochloride |
| 170 | (R)-(6-(Thiazol-5-yl)-1,3,4,5-tetrahydrobenzo[c]oxepin-1-yl)methanamine hydrochloride |
| 171 | (S)-(6-(Thiazol-5-yl)-1,3,4,5-tetrahydrobenzo[c]oxepin-1-yl)methanamine hydrochloride |
| 172 | (R)-1-(6-(isoxazol-4-yl)-1,3,4,5-tetrahydrobenzo[c]oxepin-1-yl)-N-methylmethanamine |
| 173 | (S)-1-(6-(isoxazol-4-yl)-1,3,4,5-tetrahydrobenzo[c]oxepin-1-yl)-N-methylmethanamine |
| 174 | (R)-(6-(isoxazol-4-yl)-1,3,4,5-tetrahydrobenzo[c]oxepin-1-yl)methanamine |
| 175 | (S)-(6-(isoxazol-4-yl)-1,3,4,5-tetrahydrobenzo[c]oxepin-1-yl)methanamine |
| 176 | methyl({[(1R)-6-(1,3-oxazol-5-yl)-1,3,4,5-tetrahydro-2-benzoxepin-1-yl]methyl})amine hydrochloride |
| 177 | methyl({[(1S)-6-(1,3-oxazol-5-yl)-1,3,4,5-tetrahydro-2-benzoxepin-1-yl]methyl})amine hydrochloride |
| 178 | 1-[(1R)-6-(1,3-oxazol-5-yl)-1,3,4,5-tetrahydro-2-benzoxepin-1-yl]methanamine hydrochloride |
| 179 | 1-[(1S)-6-(1,3-Oxazol-5-yl)-1,3,4,5-tetrahydro-2-benzoxepin-1-yl]methanamine hydrochloride |
| 180 | (R)-N-((5-(Pyridin-4-yl)isochroman-1-yl)methyl)cyclopropanamine hydrochloride |
| 181 | (S)-N-((5-(Pyridin-4-yl)isochroman-1-yl)methyl)cyclopropanamine hydrochloride |
| 182 | (R)-1-(5-(1H-Imidazol-1-yl)isochroman-1-yl)-N-methylmethanamine hydrochloride |
| 183 | (S)-1-(5-(1H-Imidazol-1-yl)isochroman-1-yl)-N-methylmethanamine hydrochloride |
| 184 | (R)-(5-(1H-Imidazol-1-yl)isochroman-1-yl)methanamine hydrochloride |
| 185 | (S)-(5-(1H-Imidazol-1-yl)isochroman-1-yl)methanamine hydrochloride |
| 186 | (R)-1-(5-(1H-pyrazol-1-yl)isochroman-1-yl)-N-methylmethanamine |
| 187 | (S)-1-(5-(1H-pyrazol-1-yl)isochroman-1-yl)-N-methylmethanamine |
| 188 | (R)-(5-(1H-pyrazol-1-yl)isochroman-1-yl)methanamine hydrochloride |
| 189 | (S)-(5-(1H-pyrazol-1-yl)isochroman-1-yl)methanamine hydrochloride |
| 190 | (R)-1-(5-(4H-1,2,4-triazol-4-yl)isochroman-1-yl)-N-methylmethanamine |
| 191 | (S)-1-(5-(4H-1,2,4-triazol-4-yl)isochroman-1-yl)-N-methylmethanamine |
| 192 | (R)-(5-(4H-1,2,4-triazol-4-yl)isochroman-1-yl)methanamine |
| 193 | (S)-(5-(4H-1,2,4-triazol-4-yl)isochroman-1-yl)methanamine |
| 194 | (R)-N,N-dimethyl-1-(5-(pyridin-4-yl)isochroman-1-yl)methanamine |
| 195 | (S)-N,N-dimethyl-1-(5-(pyridin-4-yl)isochroman-1-yl)methanamine |
| 196 | (R)-N-methyl-1-(6-(2-methylpyridin-4-yl)-1,3,4,5-tetrahydrobenzo[c]oxepin-1-yl)methanamine dihydrochloride |
| 197 | (S)-N-methyl-1-(6-(2-methylpyridin-4-yl)-1,3,4,5-tetrahydrobenzo[c]oxepin-1-yl)methanamine dihydrochloride |
| 198 | (R)-(6-(2-methylpyridin-4-yl)-1,3,4,5-tetrahydrobenzo[c]oxepin-1-yl)methanamine dihydrochloride |
| 199 | (S)-(6-(2-methylpyridin-4-yl)-1,3,4,5-tetrahydrobenzo[c]oxepin-1-yl)methanamine dihydrochloride |
| 200 | methyl({[(1R)-6-(1,2-oxazol-5-yl)-1,3,4,5-tetrahydro-2-benzoxepin-1-yl]methyl})amine hydrochloride |
| 201 | methyl({[(1S)-6-(1,2-oxazol-5-yl)-1,3,4,5-tetrahydro-2-benzoxepin-1-yl]methyl})amine hydrochloride |
| 202 | 1-[(1R)-6-(1,2-oxazol-5-yl)-1,3,4,5-tetrahydro-2-benzoxepin-1-yl]methanamine hydrochloride |
| 203 | 1-[(1S)-6-(1,2-oxazol-5-yl)-1,3,4,5-tetrahydro-2-benzoxepin-1-yl]methanamine hydrochloride |

The compounds of Table B can be prepared as a pharmaceutically acceptable salt thereof, or the salts of Table B can be prepared as the free base thereof. For example, the compounds in Table B can be prepared as hydrochloride salt such as mono-hydrochloric acid salt or di-hydrochoric acid salt. The salts of Table B such as hydrochloric acid salt can be prepared as free base. Preparations of the compounds as a free base or the salt thereof are detailed in the examples below.

General Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, reaction sequences, purification methods, and chiral separation conditions may be employed to prepare a desired embodiment. The reactions may be scaled upwards or downwards to suit the amount of material to be prepared. In some embodiment, the compound of Formula I may be prepared following the schemes provided herein (e.g., Schemes 1-24), using suitable starting materials known in the art and/or available from a commercial source. In one embodiment, the starting materials of the schemes provided herein (e.g., Schemes 1-24) may be prepared from commercially available compounds using procedures and conditions known in the art.

Materials and Methods

Compound Analysis $^1$H NMR data were determined at 400 or 300 MHz and are reported in the form of delta (δ) values given in parts per million (ppm) relative to tetramethylsilane (TMS) as an internal standard. Conventional abbreviations used for signal shape are: s-singlet; d-doublet; t-triplet; q-quartet: m-multiplet; br-broad.

LIST OF ABBREVIATIONS

BINAP 2,2'-bis(diphenylphosphino)-1,1'-binaphthyl
boc tert-butyloxycarbonyl
Dess-Martin reagent 1,1,1-tris(acetyloxy)-1,1-dihydro-1,2-benziodoxol-3-(H)-one
DCM dichloromethane
DIEA diisopropylethylamine
DMF dimethylformamide
dppf 1,1'-Bis(diphenylphosphino)ferrocene
EDCI N-(3-dimethylaminopropyl)-N'-ethylcarbodiimide hydrochloride
EA ethyl acetate
EtOH ethanol
HOBt hydroxybenzotriazole
m-CPBA 3-chloro-perbenzoic acid
MeCN acetonitrile
MeOH methanol
NBS N-bromosuccinimide
PE petroleum ether RT or rt room temperature
t-BuONa sodium tert-butoxide
TBDMSCl tert-butyldimethylsilyl chloride
TEA triethylamine
Tf Trifluoromethanesulfonyl (trifyl)
TfOH trifluoromethanesulfonic acid (triflic acid)
THF tetrahydrofuran
TMSI iodotrimethylsilane
Xantphos 4,5-Bis(diphenylphosphino)-9,9-dimethylxanthene

EXAMPLES

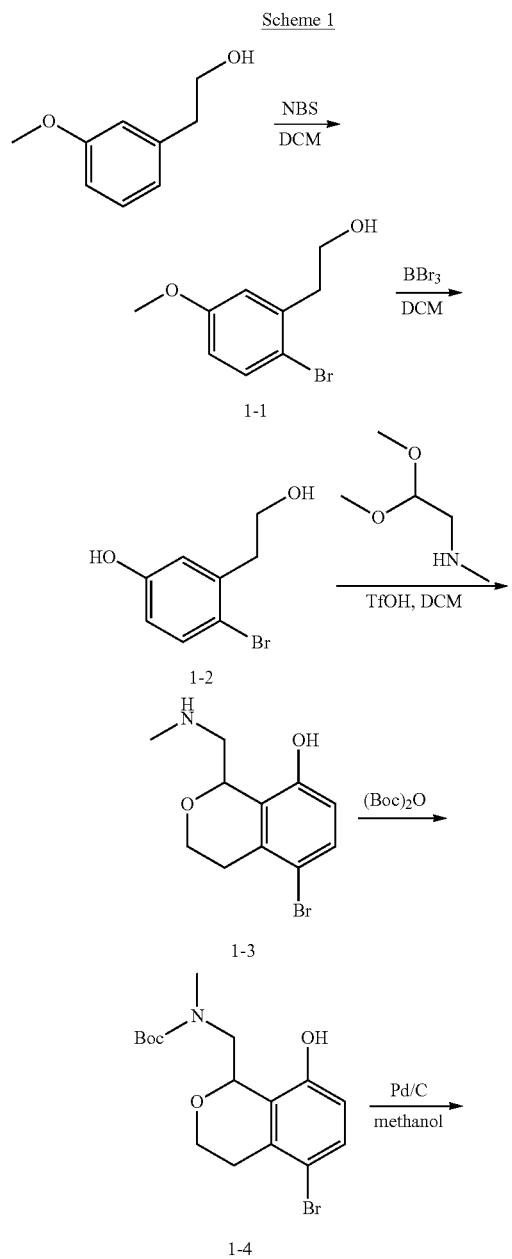
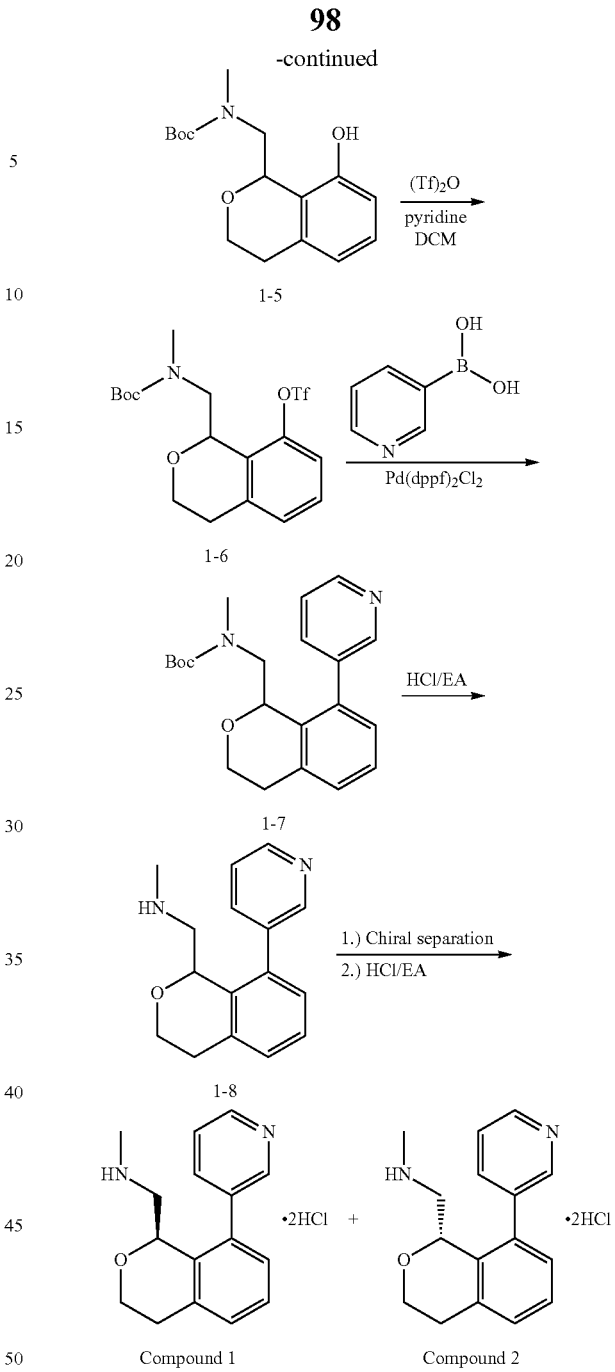

Synthesis of Compound 1 and Compound 2

2-(2-Bromo-5-methoxyphenyl) ethanol (1-1)

To a solution of 2-(3-methoxyphenyl) ethanol (10 g, 65.7 mmol) in DCM (200 mL) was added N-bromosuccinimide (12.8 g, 72.2 mmol) at 0° C. The reaction was stirred at ambient temperature for 16 h. Upon completion, a solution of NaHSO$_3$ (100 mL) was added to the reaction vessel and the resulting biphasic mixture was transferred to a separatory funnel. The layers were separated and the organic phase was washed with brine (1×100 mL). The combined organics were dried over anhydrous Na$_2$SO$_4$, filtered and concentrated in vacuo. The crude product was used for the next step without further purification. MS(ESI): m/z 213 [M−18+H]+.

4-Bromo-3-(2-hydroxyethyl) phenol (1-2)

To a solution of 2-(2-bromo-5-methoxyphenyl) ethanol (Compound 1-1) (22 g, 95.2 mmol) in DCM (200 mL) was added tribromoborane (47.5 g, 190 mmol) in DCM (50 mL) at 0° C. The reaction was stirred at ambient temperature for 3 h. Upon completion, the solution was poured into ice whiling maintaining stirring at 0° C. The mixture was filtered under reduced pressure and separated into two phases. The aqueous phase was extracted with dichloromethane (3×100 mL), combined, washed and dried. Concentration in vacuo, followed by crystallization from dichloromethane gave the desired Compound 1-2 (17 g, 82%) as a white solid. MS(ESI): m/z 199 [M−18−H]+.

5-Bromo-1-((methylamino) methyl) isochroman-8-ol (1-3)

To a solution of 4-bromo-3-(2-hydroxyethyl) phenol (Compound 1-2) (7 g, 32.2 mmol) and 2, 2-dimethoxy-N-methylethanamine (4.98 g, 41.8 mmol) in DCM (80 mL) was added trifluoromethanesulfonic acid (14.4 g, 96.6 mmol) at 0° C. The reaction was stirred at ambient temperature for 2 h. Upon completion, ice water was added to quench the reaction, and the pH was adjusted to 8 using saturated NaHCO$_3$ solution and extracted with DCM. The combined organic phases were dried over Na$_2$SO$_4$, filtered and concentrated to dryness. The crude product was used for the next step without further purification. MS(ESI): m/z 272,274 [M, M+2]+.

tert-Butyl ((5-bromo-8-hydroxyisochroman-1-yl) methyl) (methyl) carbamate (1-4)

To a solution of 5-bromo-1-((methylamino)methyl)isochroman-8-ol (Compound 1-3) (8.76 g, 32.1 mmol) in water (400 mL) was added di-tert-butyl dicarbonate (12.5 g, 57.7 mmol) and sodium bicarbonate (5.39 g, 64.2 mmol). The reaction was stirred at ambient temperature for 2 h. Upon completion, the mixture was washed with water (100 mL×2), dried with Na$_2$SO$_4$ and concentrated in vacuo. The resulting oil was triturated with DCM (100 mL), and the product (5 g, yield: 42.7%) was collected as a white solid. MS(ESI): m/z 272,274 [M−100, M−100+2]+.

Tert-butyl (8-hydroxyisochroman-1-yl) methyl (methyl) carbamate (1-5)

To a solution of tert-butyl ((5-bromo-8-hydroxyisochroman-1-yl) methyl) (methyl) carbamate (Compound 1-4) (3.1 g, 8.32 mmol) in methanol (50 mL) was added Pd/C (890 mg, 8.32 mmol). The reaction was stirred at ambient temperature for 2 h under H$_2$ atmosphere. Upon completion, the mixture was filtered and concentrated in vacuo to afford the product (2.3 g, yield: 94%) as a white solid, which was used for next step without further purification. MS(ESI): m/z 194 [M−100+1]+

1-((tert-Butoxycarbonyl (methyl)amino)methyl)isochroman-8-yl trifluoromethanesulfonate (1-6)

To a solution of tert-butyl ((8-hydroxyisochroman-1-yl) methyl) (methyl) carbamate (Compound 1-5) (2.3 g, 7.84 mmol) and pyridine (11.8 g, 150 mmol) in DCM (50 mL) was added trifluoromethanesulfonic anhydride (10.6 g, 37.6 mmol) at 0° C. The mixture was stirred at 0° C. for 30 min. Upon completion, ice water (30 mL) was added to quench the reaction. The organic phase was washed with HCl (0.12M, 50 mL×3), dried and concentrated in vacuo. The crude product was used for the next step without further purification. MS(ESI): m/z 326 [M−100+1]+ tert-Butyl methyl ((8-(pyridin-3-yl) isochroman-1-yl) methyl) carbamate (1-7)

To a solution of 1-(((tert-butoxycarbonyl)(methyl)amino)methyl)isochroman-8-yl trifluoromethanesulfonate (Compound 1-6) (3.19 g, 7.49 mmol) in toluene (60 mL) and water (10 mL) was added pyridin-3-ylboronic acid (1.83 g, 14.9 mmol), sodium carbonate (2.37 g, 22.4 mmol) and Pd(dppf)$_2$Cl$_2$ (548 mg, 749 μmol). The mixture was heated to 90° C. and stirred overnight. Upon completion, the mixture was washed with water (50 mL×2), dried and concentrated. The crude was purified by silica gel (eluted from PE:EA=20:1 to PE:EA=6:1) to get the desired Compound 1-7 (2.33 g, yield: 87.9%) as a light yellow solid. MS(ESI): m/z 355 [M+1]+

N-Methyl-1-(8-(pyridin-3-yl) isochroman-1-yl) methanamine (1-8)

To a solution of tert-butyl methyl ((8-(pyridin-3-yl) isochroman-1-yl) methyl) carbamate (Compound 1-7) (2.3 g, 6.48 mmol) in ethyl acetate (20 mL) was added HCl/ethyl acetate (3M, 5 mL). The reaction was stirred at ambient temperature for 16 h. Upon completion, the solvent was removed in vacuo. The residue was dissolved in water (30 mL) and the pH adjusted to 8. The aqueous layer was extracted with DCM (30 mL×2), and the combined organics were dried and concentrated. The desired Compound 1-8 (1.5 g, yield: 91%) was collected. MS(ESI): m/z 255 [M+1]+ rel-(R)—N-Methyl-1-(8-(pyridin-3-yl)isochroman-1-yl)methanamine bis-hydrochloride (Compound 1) and rel-(S)—N-Methyl-1-(8-(pyridin-3-yl)isochroman-1-yl)methanamine bis-hydrochloride (Compound 2)

Racemic N-methyl-1-(8-(pyridin-3-yl) isochroman-1-yl) methanamine (Compound 1-8) was loaded to a chiral column (AY-H (250×4.6 mm 5 um)) and eluted with a mobile phase consisting of mobile Phase: n-Hexane (0.1% DEA): EtOH0.1% DEA)=85:5 to afford rel-(R)—N-methyl-1-(8-(pyridin-3-yl)isochroman-1-yl)methanamine (680 mg, yield: 45.6%) and rel-(S)—N-methyl-1-(8-(pyridin-3-yl) isochroman-1-yl)methanamine (692 mg, yield: 46.3%). The free base of rel-(R)—N-methyl-1-(8-(pyridin-3-yl) isochroman-1-yl)methanamine (692 mg, 2.71 mmol) was dissolved in ethyl acetate (10 mL) and HCl/ethyl acetate (3M, 2 mL) was added at 0° C. The mixture was stirred at room temperature for 30 min. Upon completion, the solvent was removed and the residue was triturated with EA (30 mL). The mixture was filtered and dried to afford the desired product as a solid (759.64 mg, yield: 96%). MS(ESI): m/z 255 [M+1]+, ee=100% (R.T: 17.769 min). 1H NMR (free-base) (400 MHz, CDCl3) δ: 8.65~8.57 (m, 2H), 7.69~7.66 (dt, J$_1$=7.8, J$_2$=2 Hz, 1H), 7.38~7.35 (m, 1H), 7.30~7.24 (m, 1H), 7.19~7.18 (d, J=7.2 Hz, 1H), 7.04~7.02 (d, J=7.2 Hz, 1H), 5.18~5.15 (dd, J$_1$=9.2, J$_2$=2 Hz, 1H), 4.08~4.03 (m, 1H), 3.91~3.82 (m, 1H), 2.98~2.89 (m, 2H), 2.67~2.62 (m, 1H), 2.25~2.21 (dd, $J_1$=13.6, $J_2$=2.4 Hz, 1H), 2.07 (s, 3H). The free base of rel-(S)—N-methyl-1-(8-(pyridin-3-yl) isochroman-1-yl)methanamine (680 mg, 2.67 mmol) was dissolved in ethyl acetate (10 mL) and HCl/ethyl acetate (3M, 2 mL) was added at 0° C. The mixture was stirred at room temperature for 30 min. Upon completion, the solvent was removed and the residue was triturated with EA (30 mL). The mixture was filtered and dried to afford the desired product as a solid (742.8 mg, yield: 96%). MS(ESI): m/z 255 [M+1]+, ee=100% (R.T: 23.632 min). 1H NMR (400 MHz, $CD_3OD$) δ 9.06 (s, 1H), 8.97~8.95 (d, J=6 Hz, 1H), 8.76~8.74 (d, J=8 Hz, 1H), 8.26~8.22 (dd, $J_1$=8, $J_2$=6.0 Hz, 1H), 7.52~7.40 (m, 2H), 7.24~7.22 (m, 1H), 5.46~5.44 (d, J=10.4 Hz, 1H), 4.21~4.18 (m, 1H), 3.96~3.93 (m, 1H), 3.011~3.01 (m, 3H), 2.69~2.66 (dd, $J_1$=12.8, $J_2$=2.8 Hz, 1H), 2.54 (s, 3H).

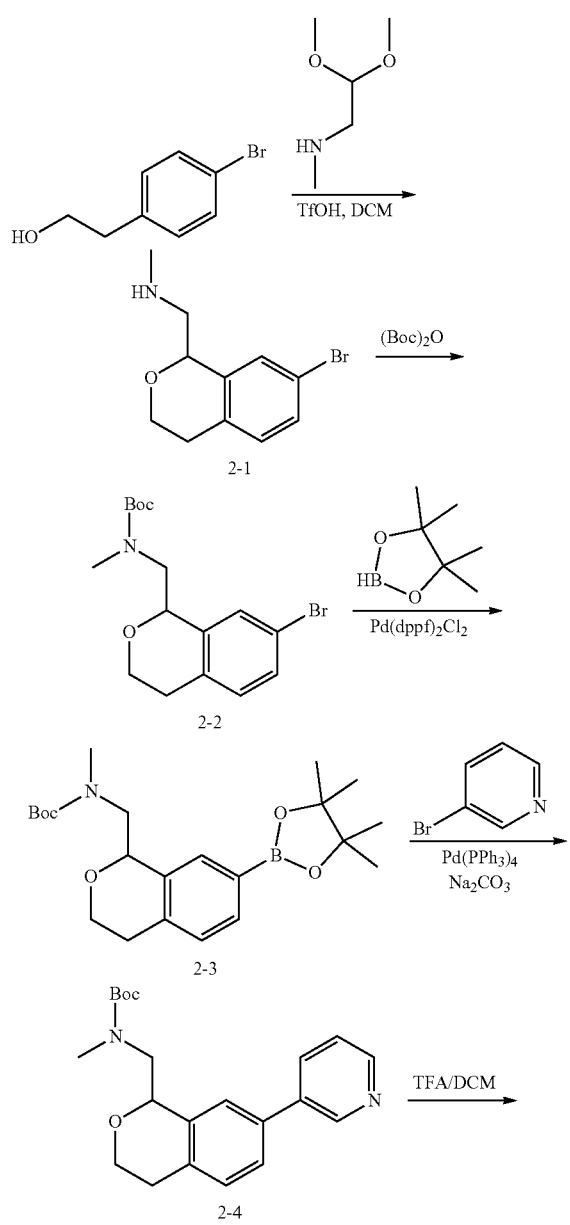

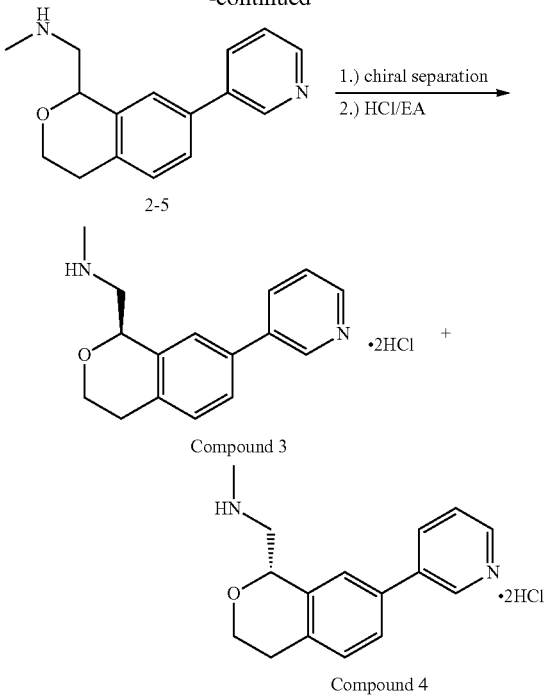

Synthesis of Compound 3 and Compound 4

1-(7-Bromoisochroman-1-yl)-N-methylmethanamine (2-1)

To a solution of 2-(4-bromophenyl)ethanol (2 g, 994 mmol) in DCM (20 mL) was added 2,2-dimethoxy-N-methyletanamine (2.35 g, 19.8 mmol). Trifluoromethane sulfonic acid (14.9 g, 99.3 mmol) was added dropwise into the mixture at 5~10° C., and the mixture was warmed to 25° C. and stirred for 1 h. Upon completion, ice water was added to quench the reaction, and the pH was adjusted to 8 using saturated $NaHCO_3$ solution and extracted with DCM. The combined organic phases were dried over $Na_2SO_4$, filtered and concentrated to dryness. The crude product was used for the next step without further purification. MS(ESI): m/z 256,258 [M, M+2]+.

tert-Butyl (7-bromoisochroman-1-yl)methyl(methyl) carbamate (2-2)

1-(7-Bromoisochroman-1-yl)-N-methylmethanamine was suspended in water (10 mL). Sodium hydroxide (5.11 g, 128 mmol) and di-tert-butyl dicarbonate (3.23 g, 14.8 mmol) were added and the reaction was stirred at ambient temperature for 2 h. The mixture was diluted with DCM (50 mL) and the mixture was washed with brine (2×30 ml). The combined organic phases were concentrated in vacuo, and the resulting oil was purified by flash column chromatography with a gradient elution of petroleum ether (100%) and ethyl acetate (0%) to petroleum ether (95%) and ethyl acetate (5%). Purification afforded tert-butyl ((7-bromoisochroman-1-yl)methyl)(methyl)carbamate (3.13 g, 8.80 mmol) as a colorless oil. MS(ESI): m/z 300 [M−55]+, purity: 100%, 214 nm; Yield 88.6%.

tert-Butyl methyl((7-(4,4,5,5-tetramethyl-1,3,2-dioxaborolan-2-yl)isochroman-1-yl)methyl)carbamate (2-3)

To a solution of tert-butyl ((7-bromoisochroman-1-yl) methyl)(methyl)carbamate (3.15 g, 8.84 mmol) in dioxane (120 mL) was added 4,4,4',4',5,5,5',5'-octamethyl-2,2'-bi(1, 3,2-dioxaborolane) (4.46 g, 17.6 mmol), Pd(dppf)$_2$C$_{12}$ (964 mg, 1.32 mmol) and potassium acetate (2.60 g, 26.5 mmol). The mixture was stirred at 100° C. under N$_2$ atmosphere overnight. Ethyl acetate (50 mL) and water (20 mL) were added to the reaction vessel and the resulting biphasic mixture was transferred to a separatory funnel. The layers were separated and the combined organic phases were dried over anhydrous Na$_2$SO$_4$. Filtration and concentration in vacuo afforded an oil which was purified by flash column chromatography with a gradient elution of petroleum ether (100%) and ethyl acetate (0%) to petroleum ether (95%) and ethyl acetate (5%) to provide tert-butyl methyl((7-(4,4,5,5-tetramethyl-1,3,2-dioxaborolan-2-yl)isochroman-1-yl) methyl)carbamate (3.00 g, 7.43 mmol) as a white solid. MS[(ESI) m/z: 304 [M−99]+, purity: 100%, 214 nm: yield: 70.5%].

tert-Butyl methyl((7-(pyridin-3-yl)isochroman-1-yl) methyl) carbamate (2-4)

To a solution of tert-butyl methyl((7-(4,4,5,5-tetramethyl-1,3,2-dioxaborolan-2-yl) isochroman-1-yl)methyl)carbamate (1.5 g, 3.71 mmol) in dioxane (8 mL) and water (2 mL) was added Pd(dppf)2Cl2 (271 mg, 0.371 mmol), sodium carbonate (786 mg, 7.42 mmol) and 3-bromopyridine (883 mg, 5.56 mmol). The mixture was stirred at 100° C. under N$_2$ atmosphere in a microwave vessel for 0.5 h. Ethyl acetate (20 mL) and water (10 mL) were added to the reaction vessel and the resulting biphasic mixture was transferred to a separatory funnel. The layers were separated and the combined organic phases were washed with saturated aqueous NaCl (2×10 mL). The combined organics were dried over anhydrous Na$_2$SO$_4$, filtered and concentrated in vacuo. The resulting oil was purified by flash column chromatography with a gradient elution of petroleum ether (100%) and ethyl acetate (0%) to petroleum ether (50%) and ethyl acetate (50%) to provide tert-butyl methyl((7-(pyridin-3-yl)isochroman-1-yl)methyl)carbamate (574 mg, 1.62 mmol) as a brown oil. MS(ESI): m/z 209 [M−55]+, purity: 96%, 214 nm; yield: 44%.

N-Methyl-1-(7-(pyridin-3-yl)isochroman-1-yl)methanamine (2-5)

The mixture of tert-butyl methyl((7-(pyridin-3-yl)isochroman-1-yl)methyl) carbamate (574 mg, 1.62 mmol) in TFA/DCM (1/2) (1 mL) was stirred at room temperature overnight. The mixture was evaporated in vacuo and re-dissolved in DCM. The pH was adjusted 8 with saturated NaHCO$_3$ solution and extracted with DCM (2×10 mL). The combined organic phases were dried over anhydrous sodium sulfate, filtered and concentrated in vacuo to give racemic N-methyl-1-(7-(pyridin-3-yl)isochroman-1-yl)methanamine (370 mg, purity: 97%, yield: 87.1) as a colorless oil. MS(ESI): m/z 254 [M+H]+.

Rel-(R)—N-Methyl-1-(7-(pyridin-3-yl)isochroman-1-yl)methanamine dihydrochloride (Compound 3) and rel-(S)—N-methyl-1-(7-(pyridin-3-yl)isochroman-1-yl)methanamine dihydrochloride (Compound 4)

Racemic N-methyl-1-(7-(pyridin-3-yl)isochroman-1-yl) methanamine methanamine (359 mg, 1.41 mmol) was resolved into its enantiomers using separative-SFC using OZ-H (4.6×250 mm 5 um column, co-solvent: MeOH (0.1% NH4OH). This afforded the enantiomers rel-(R)-tert-butyl methyl((7-(pyridin-3-yl)isochroman-1-yl)methyl)carbamate (purity: 98%, 150 mg colorless oil, yield: 81.9%) and rel-(S)-tert-butyl methyl((7-(pyridin-3-yl)isochroman-1-yl) methyl)carbamate (purity: 98%, 140 mg colorless oil, yield: 76.4%). MS(ESI): m/z 255 [M+H]+. To a solution of rel-(R)—N-methyl-1-(7-(pyridin-3-yl)isochroman-1-yl) methanamine (145 mg, 570 µmol) in ethyl acetate (10 mL) was added 3 N HCl/ethyl acetate (0.5 mL, 1.5 mmol). The mixture was stirred at r.t. for 15 mins. Upon completion, the mixture was evaporated in vacuo and triturated with ethyl acetate to afford rel-(R)—N-methyl-1-(7-(pyridin-3-yl)isochroman-1-yl)methanamine hydrochloride (Compound 3) (140 mg, purity: 99%, ee %: 100%, yield: 74.3%) as a white solid. MS (ESI): m/z 255 [M+1]+. 1H NMR (400 MHz, methanol-d4): δ 9.32 (d, J=1.2 Hz, 1H), 9.03-9.01 (m, 1H), 8.87 (d, J=5.6 Hz, 1H), 8.23-8.19 (m, 1H), 7.82-7.75 (m, 2H), 7.47 (d, J=8.0 Hz, 1H), 5.23 (d, J=7.6 Hz, 1H), 4.30-4.25 (m, 1H), 3.94-3.83 (m, 2H), 3.49-3.43 (m, 1H), 3.15-3.07 (m, 1H), 2.91-2.85 (m, 1H), 2.82 (s, 3H). To a solution of rel-(S)—N-methyl-1-(7-(pyridin-3-yl)isochroman-1-yl)methanamine (135 mg, 531 µmol) in ethyl acetate (10 ML) was added 3 N HCl/ethyl acetate (0.5 mL, 1.5 mmol). The mixture was stirred at r.t. for 15 mins. Upon completion, the mixture was evaporated in vacuo and triturated with ethyl acetate to afford rel-(S)—N-methyl-1-(7-(pyridin-3-yl)isochroman-1-yl)methanamine dihydrochloride (Compound 4)(125 mg, purity: 99%, ee %: 100%, yield: 89.8%) as a white solid. MS (ESI): m/z 255 [M+1]+. 1H NMR (400 MHz, methanol-d4): δ 9.31 (s, 1H), 9.03-9.01 (m, 1H), 8.87 (d, J=5.6 Hz, 1H), 8.23-8.19 (m, 1H), 7.82-7.75 (m, 2H), 7.47 (d, J=8.0 Hz, 1H), 5.23 (d, J=7.6 Hz, 1H), 4.30-4.25 (m, 1H), 3.94-3.82 (m, 2H), 3.48-3.42 (m, 1H), 3.15-3.07 (m, 1H), 2.91-2.85 (m, 1H), 2.82 (s, 3H).

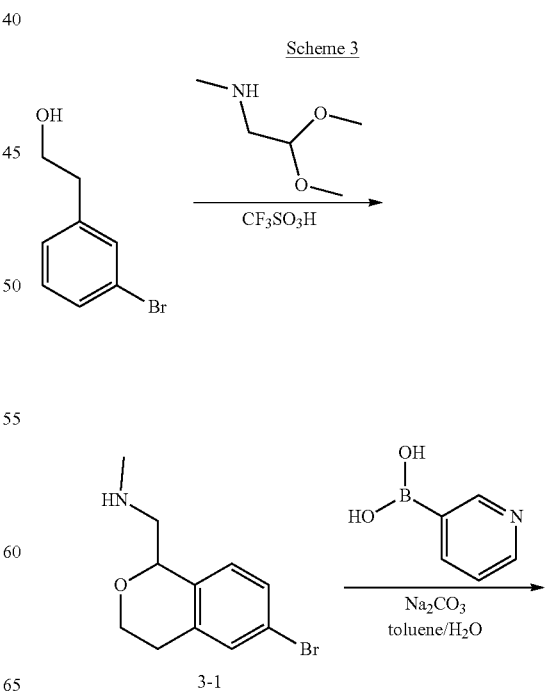

Scheme 3

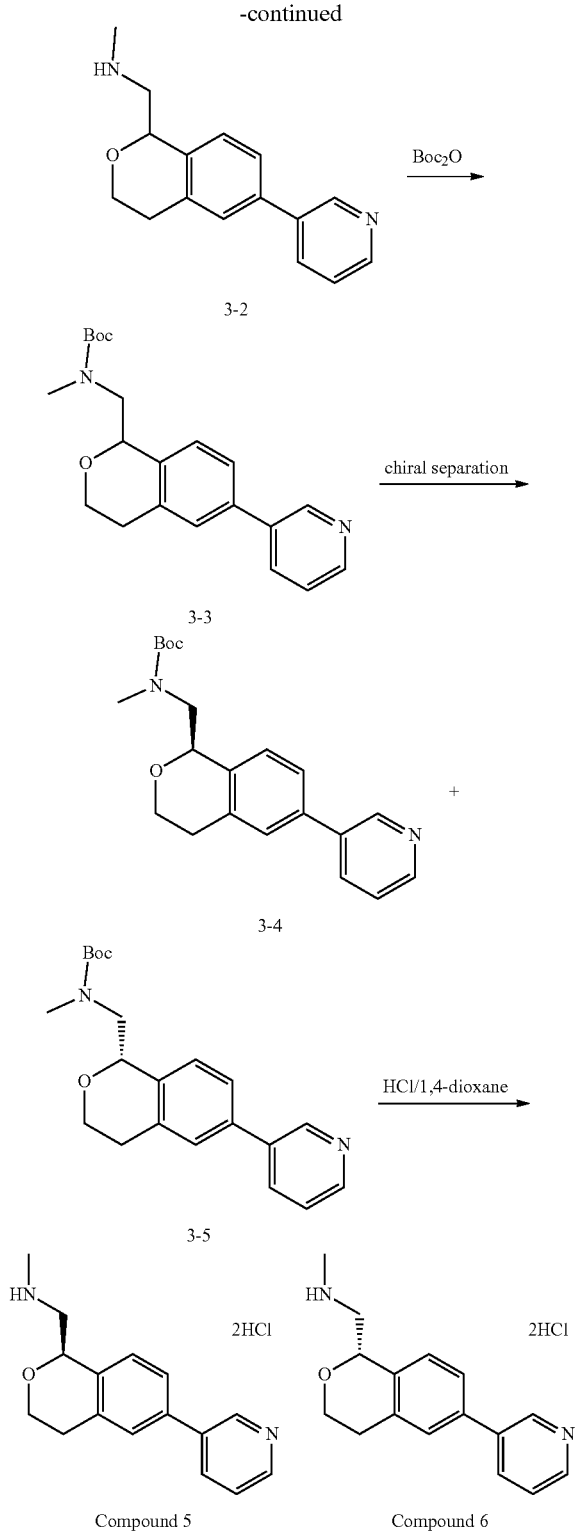

Synthesis of Compound 5 and Compound 6

1-(6-Bromoisochroman-1-yl)-N-methylmethanamine (3-1)

To a solution of 2-(3-bromophenyl) ethanol (500 mg, 2.48 mmol) and 22-dimethoxy-N-methylethanamine (0.886 g, 7.44 mmol) was added trifluoromethanesulfonic acid (6 mL) at 0° C. The reaction mixture was heated to 60° C. and stirred for 16 h. Upon completion, the reaction was cooled and neutralized with aqueous sodium bicarbonate to pH=8 at 0° C. The aqueous mixture was extracted with ethyl acetate (3×100 mL), washed with brine (1×100 mL), and dried over anhydrous sodium sulfate. Purification by column chromatography afforded the desired product (500 mg, yield: 77%) as a yellow solid. MS (ESI): m/z 256 [M+H]+.

N-Methyl-1-(6-(pyridin-3-yl)isochroman-1-yl)methanamine (3-2)

A mixture of 1-(6-bromoisochroman-1-yl)-N-methylmethanamine (1 g, 3.90 mmol), [1,1'-bis(diphenylphosphino)ferrocene] dichloropalladium (II) (285 mg, 0.1 eq), pyridin-3-ylboronic acid (527 mg, 4.29 mmol), and aq. sodium carbonate (826 mg, 6.54 mmol) in toluene (15 mL) was purged with nitrogen gas. The reaction was heated at 100° C. for 16 hours. Upon completion, the mixture was cooled, diluted with ethyl acetate (100 mL) and filtered. The filtrate was washed with water (3×100 mL), and brine (1×100 mL). The organic layer was dried over anhydrous sodium sulfate and filtered. The crude product was purified by Prep-HPLC to give N-methyl-1-(6-(pyridin-3-yl)isochroman-1-yl)methanamine (800 mg, yield 93%) as a yellow oil. MS (ESI): m/z 255 [M+H]+.

tert-Butyl methyl((6-(pyridin-3-yl)isochroman-1-yl) methyl)carbamate (3-3)

To a solution of N-methyl-1-(6-(pyridin-3-yl)isochroman-1-yl)methanamine (1.2 g, 4.71 mmol) in dichloromethane (100 mL) was added triethylamine (1.42 g, 14.1 mmol) and di-tert-butyl dicarbonate (1.23 g, 5.65 mmol). The reaction was stirred at ambient temperature for 3 h. The reaction was concentrated to dryness. Purification by Prep TLC plate (eluted with dichloromethane:methanol=10:1) gave tert-butyl methyl((6-(pyridin-3-yl)isochroman-1-yl)methyl)carbamate (1.2 g, yield: 70%) as a yellow oil. MS (ESI): m/z 355 [M+H]+.

(R)-tert-Butyl methyl((6-(pyridin-3-yl)isochroman-1-yl)methyl)carbamate (3-4) and (S)-tert-butyl methyl((6-(pyridin-3-yl)isochroman-1-yl)methyl) carbamate (3-5)

Racemic tert-butyl methyl((6-(pyridin-3-yl)isochroman-1-yl)methyl)carbamate (1.2 g, 3.38 mmol) was separated by chiral column chromatography (IC 4.6×150 mm 5 um, co-solvent MeOH (0.1% NH4OH)) to give (R)-tert-butyl methyl((6-(pyridin-3-yl) isochroman-1-yl) methyl) carbamate (500 mg, 1.41 mmol) as a yellow oil, and (S)-tert-butyl methyl((6-(pyridin-3-yl) isochroman-1-yl)methyl)carbamate (500 mg, 1.41 mmol) as a yellow oil (Yield: 83%).

(R)—N-Methyl(6-(pyridin-3-yl)isochroman-1-yl) methanamine bis-hydrochloride salt (Compound 5)

To a solution of rel-(R)-tert-butyl methyl((6-(pyridin-3-yl)isochroman-1-yl)methyl)carbamate (500 mg, 1.41 mmol) in dichloromethane (30 mL) was added HCl/1,4-dioxane (1.01 g, 28.2 mmol). The reaction was stirred at ambient temperature for 16 h. Upon completion, the mixture was concentrated to dryness. The solid was triturated with ethyl acetate and filtered to afford the desired product as a white solid. MS (ESI): m/z 255 [M+H]+. 1HNMR (400 MHz, MeOH-d4): δ 9.24 (s, 1H), 8.97 (d, J=8.0 Hz, 1H), 8.87 (d, J=5.6 Hz, 1H), 8.23-8.19 (m, 1H), 7.75 (d, J=7.6 Hz, 1H), 7.74 (s, 1H), 7.48 (d, J=7.6 Hz, 1H), 5.19 (d, J=8 Hz, 1H), 4.26-4.31 (m, 1H), 3.89-3.95 (m, 1H), 3.70 (d, J=12.8 Hz, 1H), 3.34-3.40 (m, 1H), 3.11-3.19 (m, 1H), 2.90-2.96 (m, 1H), 2.78 (s, 3H).

(S)—N-methyl(6-(pyridin-3-yl)isochroman-1-yl) methanamine bis-hydrochloride salt (Compound 6)

To a solution of (S)-tert-butyl methyl((6-(pyridin-3-yl)isochroman-1-yl) methyl)carbamate (500 mg, 1.41 mmol) in dichloromethane (30 mL) was added HCl/1,4-dioxane (1.01 g, 28.2 mmol). The reaction was stirred at ambient temperature for 16 h. Upon completion, the mixture was concentrated to dryness. The solid was triturated with ethyl acetate and filtered to afford the desired product as a white solid. MS (ESI): m/z 255 [M+H]+. 1HNMR (400 MHz, MeOH-d4): δ 9.24 (s, 1H), 8.98 (d, J=8.4 Hz, 1H), 8.88 (d, J=6 Hz, 1H), 8.20-8.24 (m, 1H), 7.76 (d, J=6.8 Hz, 1H), 7.76 (s, 1H), 7.49 (d, J=8.8 Hz, 1H), 5.21 (d, J=7.2 Hz, 1H), 4.26-4.31 (m, 1H), 3.89-3.95 (m, 1H), 3.69-3.73 (m, 1H), 3.35-3.40 (m, 1H), 3.11-3.17 (m, 1H), 2.90-2.96 (m, 1H), 2.81 (s, 3H).

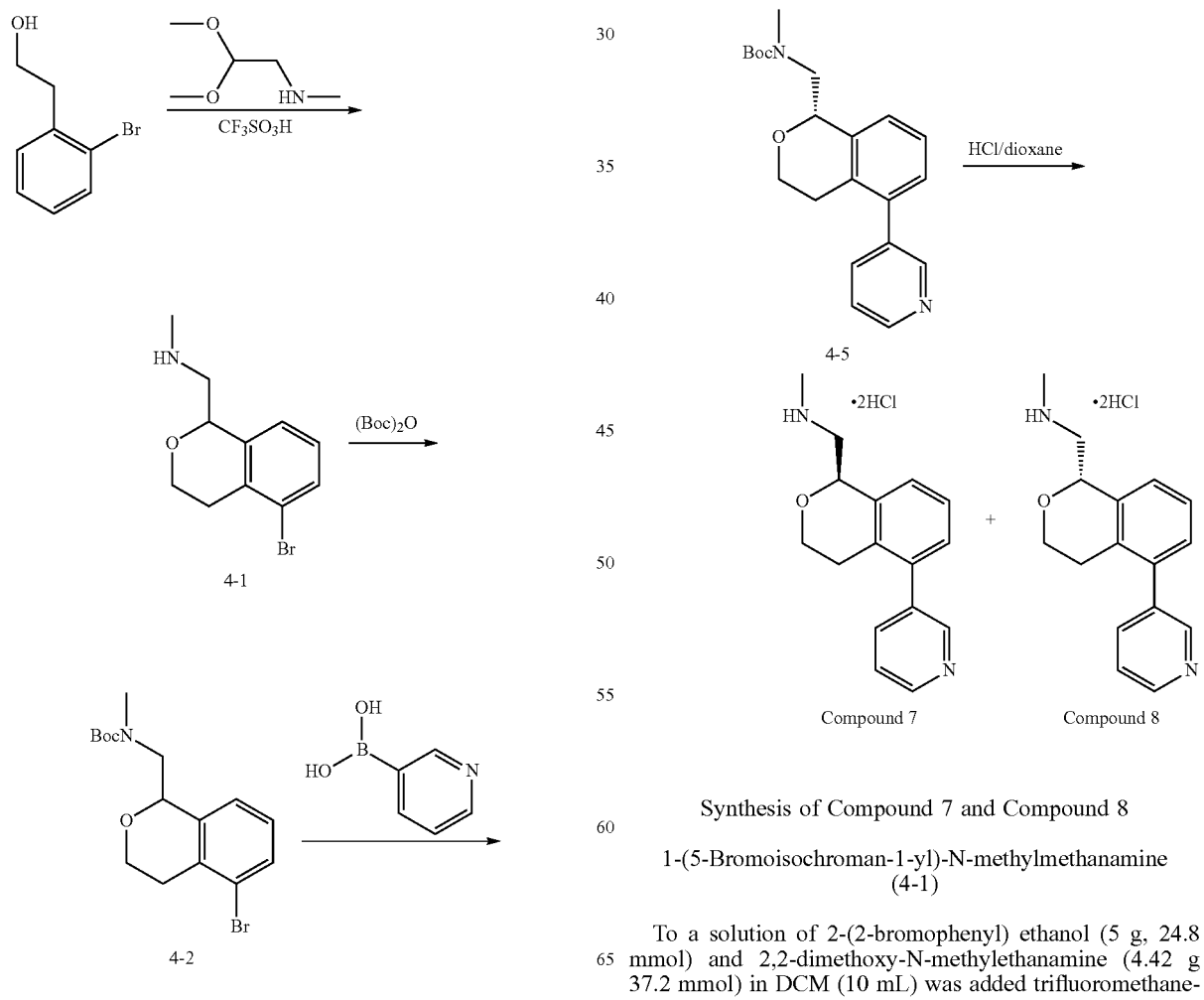

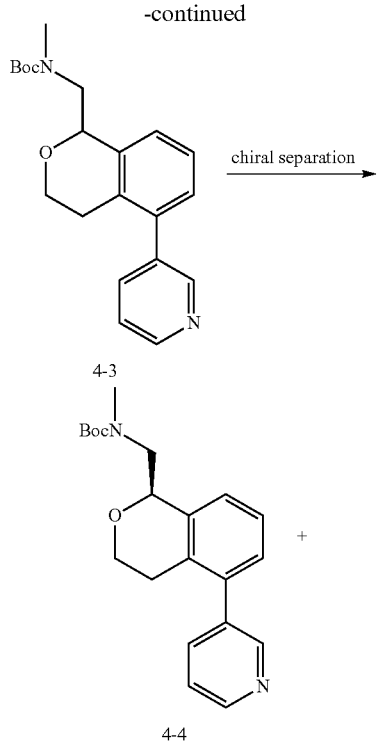

Synthesis of Compound 7 and Compound 8

1-(5-Bromoisochroman-1-yl)-N-methylmethanamine (4-1)

To a solution of 2-(2-bromophenyl) ethanol (5 g, 24.8 mmol) and 2,2-dimethoxy-N-methylethanamine (4.42 g 37.2 mmol) in DCM (10 mL) was added trifluoromethanesulfonic acid (18.6 g, 124 mmol). The reaction was stirred at ambient temperature for 3 h. Upon completion, the mixture was quenched with ice-water (50 mL). NaOH (20%) solution was added to adjust the pH to ~9. The aqueous mixture was extracted with ethyl acetate (3×100 mL), washed with brine (1×100 mL), and dried over anhydrous sodium sulfate. Filtration and concentration of solvent in vacuo afforded the desired product, which was suitable for use without further purification. MS (ESI): m/z 256,258 [M, M+2]+.

tert-Butyl (5-bromoisochroman-1-yl) methyl (methyl) carbamate (4-2)

To a solution of 1-(5-bromoisochroman-1-yl)-N-methylmethanamine (6.34 g, 24.6 mmol) in water (100 mL) was added di-tert-butyl dicarbonate (8.02 g, 36.8 mmol). The reaction was stirred at ambient temperature for 16 h. Upon completion, the mixture was extracted with EA (50 mL×2), dried and concentrated. The crude material was purified by silica gel chromatography (eluted from PE to PE:EA=50:1) to afford the desired compound (8 g, yield: 89%) as a colorless oil. MS (ESI): m/z 256, 258 [M−100, M−100+2]+.

tert-Butyl methyl (5-(pyridin-3-yl) isochroman-1-yl) methyl) carbamate (4-3)

To a solution of tert-butyl ((5-bromoisochroman-1-yl) methyl)(methyl)carbamate (3 g, 8.42 mmol) in toluene (30 mL) and water (5 mL) was added pyridin-3-ylboronic acid (1.54 g, 12.6 mmol), sodium carbonate (2.67 g, 25.2 mmol) and 1,1'-bis(diphenylphosphino)ferrocene]dichloropalladium(II) (616 mg, 842 µmol). The mixture was heated to 100° C. for 16 h under $N_2$ atmosphere. Upon completion, the reaction was cooled and EA (50 mL) was added. The mixture was filtered and the filtrate was washed with water (30 mL×2), dried and concentrated. The crude material was purified by silica gel chromatography (eluted from PE:EA=20:1 to PE:EA=3:1) to afford the desired compound (3 g, yield: 90%) as a yellow oil. MS (ESI): m/z 355 [M+H]+.

Rel-R-tert-Butyl methyl ((5-(pyridin-3-yl) isochroman-1-yl) methyl) carbamate (4-4) and rel-(S)-tert-butyl methyl ((5-(pyridin-3-yl) isochroman-1-yl) methyl) carbamate (4-5)

Racemic tert-butyl methyl ((5-(pyridin-3-yl) isochroman-1-yl) methyl) carbamate (2 g, 5.64 mmol) was loaded to a chiral column and separated (Column: OZ-H (250*4.6 mm 5 um) and Mobile Phase: MeOH (0.1% NH4OH)) to afford rel-R-tert-butyl methyl ((5-(pyridin-3-yl) isochroman-1-yl) methyl) carbamate (4-4) (660 mg, yield: 33%) and rel-(S)-tert-butyl methyl ((5-(pyridin-3-yl) isochroman-1-yl) methyl) carbamate (4-5) (320 mg, yield: 16%).

(R)—N-Methyl(5-(pyridin-3-yl)isochroman-1-yl) methanamine bis-hydrochloride (Compound 7)

To a solution of rel-(R)-tert-butyl methyl ((5-(pyridin-3-yl) isochroman-1-yl) methyl) carbamate (659 mg, 1.86 mmol) in DCM (10 mL) was added HCl/dioxane (4M, 3 mL). The reaction was stirred at ambient temperature for 16 h. Upon completion, the solvent was removed and the residue was washed with EA, the mixture was filtered and the off-white solid (469.64 mg, yield: 86.9%) was collected. MS (ESI): m/z 255 [M+1]+. 1H NMR (400 MHz, $CD_3OD$) δ 9.01 (s, 1H), 8.95~8.94 (d, J=5.2 Hz, 1H), 8.75~8.73 (d, J=8.2 Hz, 1H), 8.25~8.22 (m, 1H), 7.52~7.45 (m, 2H), 7.42~7.39 (m, 1H), 5.29~5.20 (m, 1H), 4.20~4.16 (m, 1H), 3.84~3.75 (m, 1H), 3.71~3.68 (dd, $J_1$=12.8, $J_2$=2.8 Hz, 1H), 3.42~3.35 (m, 1H), 3.07~2.97 (m, 1H), 2.82 (s, 3H), 2.63-2.58 (m, 1H).

(S)—N-Methyl(5-(pyridin-3-yl)isochroman-1-yl) methanamine bis-hydrochloride (Compound 8)

To a solution of rel-(S)-tert-butyl methyl ((5-(pyridin-3-yl) isochroman-1-yl) methyl) carbamate (319 mg, 0.902 mmol) in DCM (10 mL) was added HCl/dioxane (4M, 2 mL). The reaction was stirred at ambient temperature for 16 h. Upon completion, the solvent was removed and the residue was washed with ethyl acetate. The mixture was filtered and the off-white solid (265 mg, yield: 98%) was collected. MS (ESI): m/z 255 [M+1]+. 1H NMR (400 MHz, $CD_3OD$) δ 9.01 (s, 1H), 8.95~8.93 (d, J=6 Hz, 1H), 8.74~8.72 (d, J=8 Hz, 1H), 8.25~8.21 (m, 1H), 7.49~7.45 (m, 2H), 7.41~7.39 (m, 1H), 5.25~5.23 (m, 1H), 4.20~4.16 (m, 1H), 3.83~3.77 (m, 1H), 3.71~3.67 (dd, $J_1$=12.8, $J_2$=2.4 Hz, 1H), 3.42~3.36 (m, 1H), 3.02~2.99 (m, 1H), 2.81 (s, 3H), 2.62~2.57 (m, 1H).

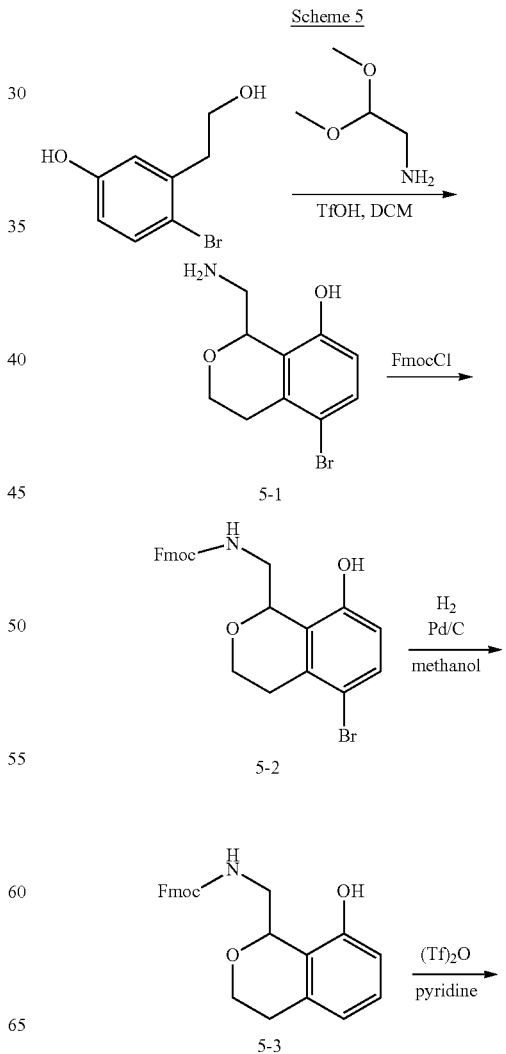

Scheme 5

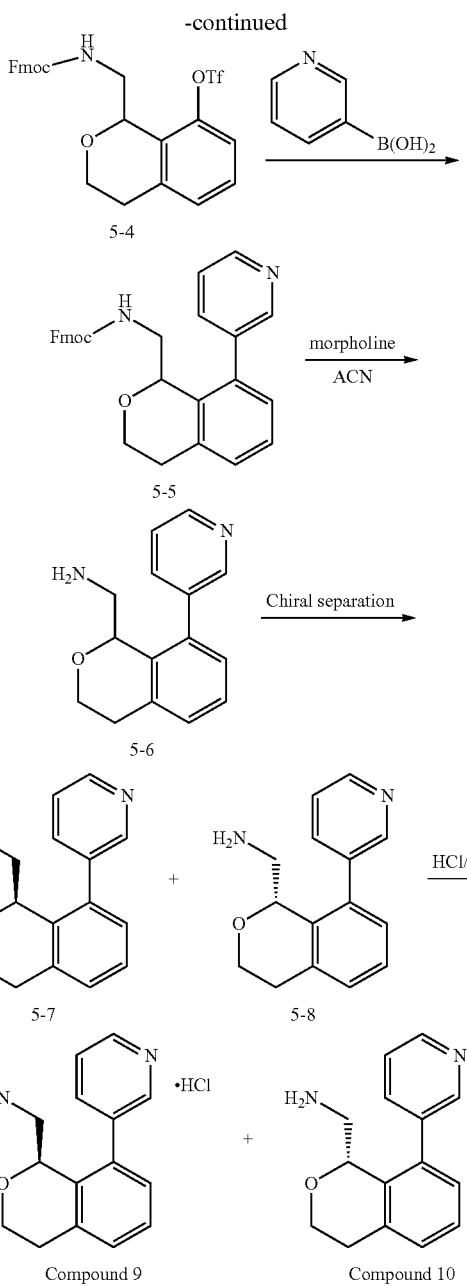

mL) was added (9H-fluoren-9-yl) methyl carbonochloridate (8.87 g, 34.3 mmol) and sodium bicarbonate (3.84 g, 45.8 mmol). The reaction was stirred at ambient temperature for 3 h. Upon the completion, the organic solvent was removed and the aqueous phase was extracted with DCM (50 mL×3), dried and concentrated. The crude was purified by silica gel (eluted from PE:EA=50:1 to PE:EA:DCM=100:30:5) to get the desired compound (5.38 g, yield: 48.9%) as a white solid. MS (ESI): m/z 480,482 [M+H, M+2+H]+.

(9H-Fluoren-9-yl) methyl (8-hydroxyisochroman-1-yl) methylcarbamate (5-3)

To a solution of (9H-fluoren-9-yl) methyl ((5-bromo-8-hydroxyisochroman-1-yl) methyl) carbamate (4 g, 8.32 mmol) in methanol (80 mL) was added Pd/C (890 mg, 8.32 mmol). The reaction was stirred at ambient temperature for 16 h under $H_2$ atmosphere. Upon completion, the mixture was filtered and the filtrate was concentrated. The crude material (2.3 g) was dissolved in ethyl acetate (200 mL), washed with water, dried and concentrated to get the desired material as a white solid (1.1 g). MS (ESI): m/z 402 [M+H]+.

1-((((9H-Fluoren-9-yl) methoxy) carbonylamino) methyl) isochroman-8-yltrifluoromethanesulfonate (5-4)

To a solution of (9H-fluoren-9-yl) methyl ((8-hydroxyisochroman-1-yl) methyl) carbamate (1.5 g, 3.73 mmol) and pyridine (2.35 g, 29.8 mmol) in DCM (80 mL) was added trifluoromethanesulfonic anhydride (2.10 g, 7.46 mmol) at 0° C. The reaction was stirred at 0° C. for 30 min. Upon completion, the reaction was quenched with ice water (50 mL); the organic phase was washed with HCl (0.12M, 30 mL×3), dried and concentrated to dryness. The crude product was used for the next step without further purification. MS (ESI): m/z 534 [M+H]+.

(9H-Fluoren-9-yl) methyl (8-(pyridin-3-yl) isochroman-1-yl) methylcarbamate (5-5)

To a solution of 1-(((((9H-fluoren-9-yl) methoxy) carbonyl) amino) methyl) isochroman-8-yl trifluoromethanesulfonate (1.03 g, 1.93 mmol) in toluene (30 mL) and water (5 mL) was added pyridin-3-ylboronic acid (474 mg, 3.86 mmol), sodium carbonate (613 mg, 5.79 mmol) and palladiumtriphenylphosphane (1:4) (223 mg, 193 μmol). The mixture was heated to 90° C. and stirred overnight. Upon completion, the reaction was quenched with water (50 mL×2), dried and concentrated in vacuo. The crude was purified by pre-TLC (PE:EA=2:1) to get the desired compound (705 mg, yield: 79%) as a white solid. MS (ESI): m/z 463 [M+H]+.

(8-(Pyridin-3-yl) isochroman-1-yl) methanamine (5-6)

To a solution of (9H-fluoren-9-yl) methyl ((8-(pyridin-3-yl) isochroman-1-yl) methyl) carbamate (0.7 g, 1.51 mmol) in CH3CN (20 mL) was added morpholine (1.04 g. 12.0 mmol). The reaction mixture was heated to 70° C. and stirred at that temperature for 5 h. Upon the completion, the mixture was purified by pre-HPLC to get the desired compound (0.3 g. yield: 82%) as a colorless oil. MS (ESI): m/z 241 [M+H]+.

Synthesis of Compound 9 and Compound 10

1-(Aminomethyl)-5-bromoisochroman-8-ol (5-1)

To a solution of 4-bromo-3-(2-hydroxyethyl) phenol (5 g, 23.0 mmol) and 2,2-dimethoxyethanamine (3.62 g, 34.5 mmol in DCM (50 mL) was added trifluoromethanesulfonic acid (10.3 g, 69.0 mmol) at 0° C. Upon completion, ice water (50 mL) was added to quench the reaction and the organic solvent was removed. The resulting mixture was suitable for use in the next step without further purification. MS (ESI): m/z 258,260 [M, M+2]+.

(9H-Fluoren-9-yl) methyl (5-bromo-8-hydroxyisochroman-1-yl) methylcarbamate (5-2)

To a solution of 1-(aminomethyl)-5-bromoisochroman-8-ol (5.93 g, 22.9 mmol) in 1, 4-dioxane (50 mL) and water (50 rel-(R)-(8-(Pyridin-3-yl)isochroman-1-yl)methanamine (5-7) and rel-(S)-(8-(pyridin-3-yl)isochroman-1-yl)methanamine (5-8)

Racemic (8-(Pyridin-3-yl) isochroman-1-yl) methanamine was loaded to a chiral column and separated (Column: IC (250×4.6 mm 5 um) and Mobile Phase: methanol(0.2% Methanol Ammonia)) to afford rel-(R)-(8-(pyridin-3-yl)isochroman-1-yl)methanamine (5-7) (106 mg, yield: 35%) as a colorless oil and rel-(S)-(8-(pyridin-3-yl) isochroman-1-yl)methanamine (5-8) (102 mg, yield: 34%) as a colorless oil.

(R)-(8-(Pyridin-3-yl)isochroman-1-yl)methanamine hydrochloride (Compound 9)

To a solution of rel-(R)-(8-(pyridin-3-yl) isochroman-1-yl) methanamine (0.106 g, 441 μmol) in EA (5 mL) was added HCl/EA (1 mL) at 0° C. The reaction was stirred at ambient temperature for 30 min. Upon completion, the solvent was removed in vacuo. The residue was triturated with ethyl acetate (30 mL), filtered and dried to afford the desired compound (63.74 mg, yield: 52.2%) as a yellow solid. MS (ESI): m/z 241 [M+H]+ ee value=98% (R.T: 3.56 min). 1H NMR (400 MHz, CD$_3$OD) δ 9.07 (s, 1H), 8.97 (s, 1H), 8.75~8.73 (d, J=6.8 Hz, 1H), 8.25 (s, 1H), 7.46~7.41 (m, 2H), 7.23~7.22 (d, J=6.8 Hz, 1H), 5.38~5.35 (d, J=9.2 Hz, 1H), 4.22~4.12 (m, 1H), 4.00~3.91 (m, 1H), 3.00~2.91 (m, 3H), 2.67~2.64 (d, J=12.4 Hz, 1H).

(S)-(8-(Pyridin-3-yl)isochroman-1-yl)methanamine hydrochloride (Compound 10)

To a solution of rel-(S)-(8-(pyridin-3-yl) isochroman-1-yl) methanamine (0.102 g, 420 μmol) in ethyl acetate (5 mL) was added HCl/ethyl acetate (1 mL) at 0° C. The reaction was stirred at ambient temperature for 30 min. Upon completion, the solvent was removed in vacuo. The residue was triturated with ethyl acetate (30 mL), filtered and dried to afford the desired compound (75.73 mg, yield: 64.9%) as a yellow solid. MS (ESI): m/z 241 [M+H]+, ee value=95% (R.T: 5.98 min). 1H NMR (400 MHz, CD$_3$OD) δ 9.07 (s, 1H), 8.97 (s, 1H), 8.74 (d, J=7.2 Hz, 1H), 8.24 (s, 1H), 7.48~7.41 (m, 2H), 7.23~7.21 (d, J=6.4 Hz, 1H), 5.37~4.35 (d, J=9.2 Hz, 1H), 4.23~4.11 (m, 1H), 4.01~3.90 (m, 1H), 3.10~2.89 (m, 3H), 2.67~2.64 (d, J=12.8 Hz, 1H).

Synthesis of rel-(R)-(7-(pyridin-3-yl)isochroman-1-yl)methanamine hydrochloride (Compound 11) and rel-(S)-(7-(pyridin-3-yl)isochroman-1-yl)methanamine hydrochloride (Compound 12)

The title compounds were prepared using the procedure described in Scheme 2, substituting (7-bromoisochroman-1-yl)methanamine for 1-(7-bromoisochroman-1-yl)-N-methylmethanamine. Chiral separation and deprotection afforded rel-(R)-(7-(pyridin-3-yl)isochroman-1-yl)methanamine hydrochloride (Compound 11) (200 mg, purity: 100%, e.e. value: 99%, yield: 71%) as a white solid. MS (ESI): m/z 241 [M+H]+. 1H NMR (400 MHz, methanol-d4): δ. 9.30 (d, J=1.2 Hz, 1H), 9.02 (d, J=8.0 Hz, 1H), 8.86 (d, J=5.6 Hz, 1H), 8.23-8.20 (m, 1H), 7.81-7.76 (m, 2H), 7.46 (d, J=8.0 Hz, 1H), 5.16 (d, J=7.2 Hz, 1H), 4.29-4.24 (m, 1H), 3.93-3.87 (m, 1H), 3.77-3.73 (m, 1H), 3.38-3.33 (m, 1H), 3.15-3.10 (m, 1H), 2.90-2.85 (m, 1H). Chiral separation and deprotection also afforded rel-(S)-(7-(pyridin-3-yl)isochroman-1-yl)methanamine hydrochloride (Compound 12) (180 mg, purity: 100%, ee value: 100%, yield: 70%) as a white solid. MS (ESI): m/z 241 [M+H]+. 1H NMR (400 MHz, methanol-d4) δ 9.28 (d J=1.6 Hz, 1H), 9.00-8.98 (m, 1H), 8.86 (d, J=5.6 Hz, 1H), 8.21-8.18 (m, 1H) 7.79-7.74 (m, 2H), 7.46 (d, J=8.0 Hz, 1H) 5.15 (d, J=6.8 Hz, 1H), 4.30-4.25 (m, 1H), 3.93-3.87 (m, 1H), 3.76-3.72 (m, 1H), 3.37-3.31 (m, 1H), 3.15-3.07 (m, 1H), 2.91-2.85 (m, 1H).

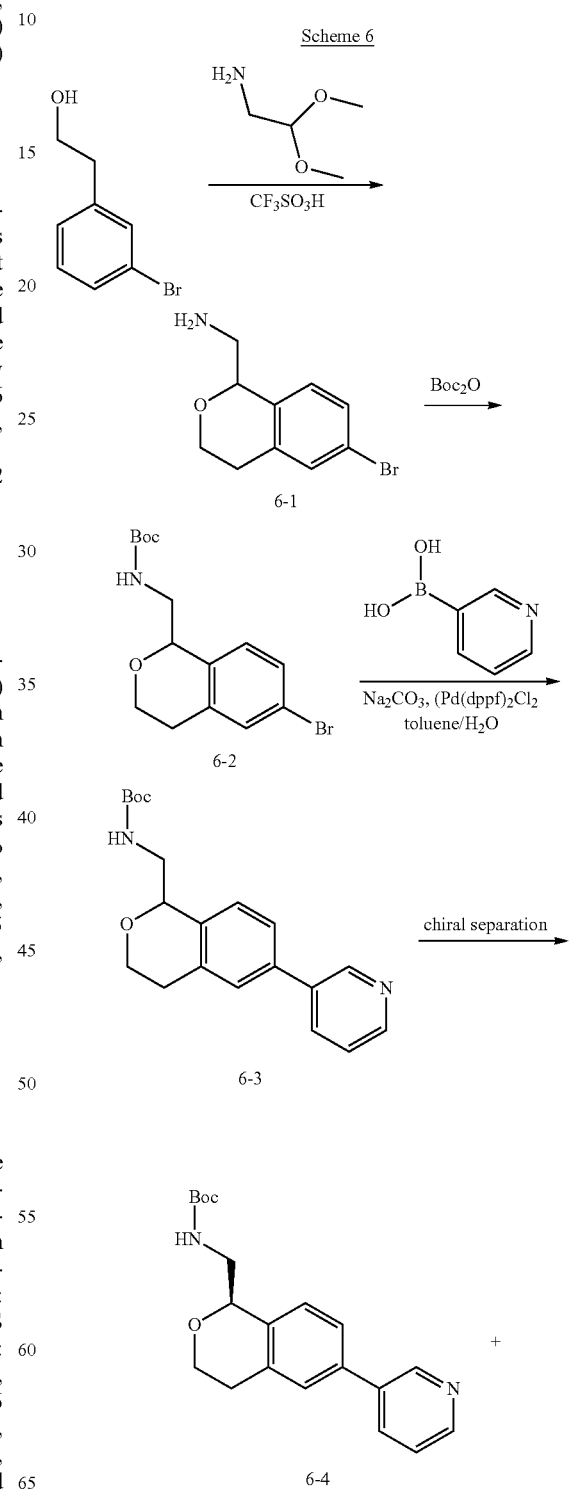

Scheme 6

115

-continued

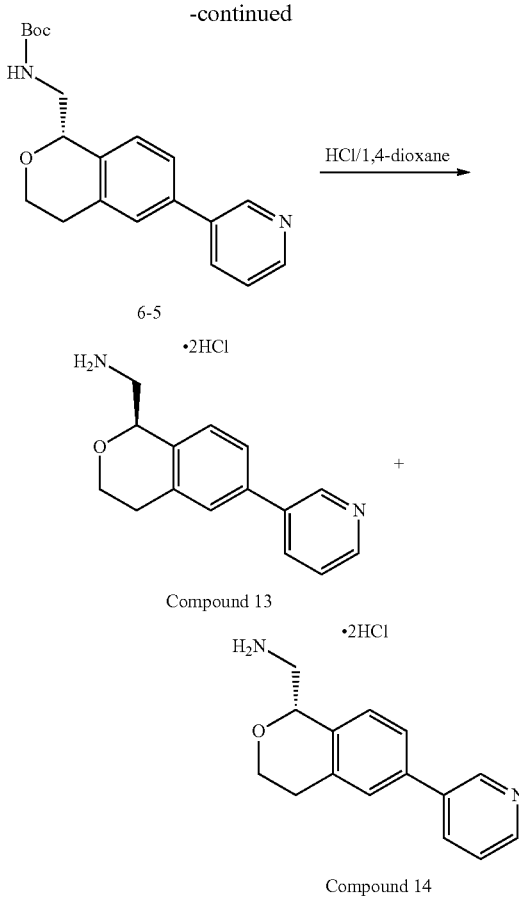

Synthesis of Compound 13 and Compound 14

(6-Bromoisochroman-1-yl)methanamine (6-1)

To a solution of 2-(3-bromophenyl) ethanol (2 g, 9.94 mmol) and 2,2-dimethoxy ethanamine (1.56 g, 14.90 mmol) was added trifluoromethanesulfonic acid (7 mL) at 0° C. The reaction was stirred at ambient temperature for 1 h. Upon completion, the mixture was neutralized with aq. sodium bicarbonate, extracted with EA and dried over sodium sulfate. The organic layer was filtered and concentrated to dryness in vacuo. The mixture was used for next step without further purification.

tert-Butyl (6-bromoisochroman-1-yl)methylcarbamate (6-2)

To a solution of (6-bromoisochroman-1-yl)methanamine (2.4 g, 9.91 mmol) in water (150 mL) and tetrahydrofuran (10 mL) was added di-tert-butyl dicarbonate (2.57 g, 11.8 mmol). Sodium hydroxide (1.18 g, 29.7 mmol) was added, and the reaction was stirred at room temperature for 16 h. The reaction mixture was washed with dichloromethane (150 mL×3), and the organic layer were combined and concentrated to dryness. The crude material was purified by column chromatography (dichloromethane:methanol=15:1) to give tert-butyl ((6-bromoisochroman-1-yl)methyl)carbamate as a colorful oil (2.4 g, yield 70%). MS (ESI): m/z 342 [M+H]+.

116 tert-Butyl (6-(pyridin-3-yl)isochroman-1-yl)methylcarbamate (6-3)

A mixture of tert-butyl ((6-bromoisochroman-1-yl) methyl)carbamate (3 g, 8.76 mmol), [1,1'-Bis(diphenylphosphino)ferrocene]dichloropalladium(II) (640 mg, 0.1 eq), pyridin-3-ylboronic acid (1.38 g, 11.3 mmol), and aq. sodium carbonate (1.85 g, 17.5 mmol) in toluene (60 mL) was degassed by purging with nitrogen. The mixture was then heated at 100° C. for 16 hours. The mixture was diluted with ethyl acetate and filtered. The filtrate was washed with water and brine. The organic layer was dried over sodium sulfate, filtered. The crude product was purified by column chromatography (PE:EA=1:1) to give tert-butyl ((6-(pyridin-3-yl)isochroman-1-yl)methyl)carbamate 2.8 g (yield 90%) as yellow oil. MS (ESI): m/z 341 [M+H]+.

(R)-tert-Butyl (6-(pyridin-3-yl)isochroman-1-yl) methylcarbamate (6-4) and (S)-tert-butyl (6-(pyridin-3-yl)isochroman-1-yl)methylcarbamate (6-5)

Racemic tert-butyl ((6-(pyridin-3-yl)isochroman-1-yl) methyl)carbamate (3 g, 8.81 mmol) was charged to a chiral column (OZ-H 250×4.6 mm 5 μm. Co-Solvent MeOH (0.2% Methanol Ammonia)) and separated to give (R)-tert-butyl (6-(pyridin-3-yl)isochroman-1-yl) methylcarbamate (6-4) (1.1 g) as yellow oil and (S)-tert-butyl (6-(pyridin-3-yl) isochroman-1-yl) methylcarbamate (6-5) 1.1 g (yield 72%) as yellow oil. MS (ESI): m/z 341 [M+H]+.

(R)-tert-Butyl (6-(pyridin-3-yl)isochroman-1-yl) methylcarbamate hydrochloride salt (Compound 13)

To a solution of (R)-tert-butyl ((6-(pyridin-3-yl)isochroman-1-yl)methyl)carbamate (300 mg, 881 μmol) in ethyl acetate (20 mL) was added HCl/1,4-dioxane (316 mg, 8.81 mmol). The reaction was stirred at ambient temperature for 16 h. The mixture was concentrated to give the title compound (237 mg, yield 86%) as white solid. MS (ESI): m/z 241 [M+H]+. 1H NMR (400 MHz, MeOH-d4): δ 9.24-9.23 (d, J=1.2 Hz, 1H), 8.97-8.95 (m, 1H), 8.87 (d, J=4.4 Hz, 1H), 8.22-8.19 (m, 1H), 7.75 (d, J=6 Hz, 1H), 7.75 (s, 1H), 7.48 (d, J=6.4 Hz, 1H), 5.13-5.12 (d, J=5.2 Hz, 1H), 4.31-4.27 (m, 1H), 3.95-3.90 (m, 1H), 3.65-3.61 (m, 1H), 3.29-3.25 (m, 1H), 3.19-3.13 (m, 1H), 2.95-2.90 (m, 1H).

(S)-tert-Butyl (6-(pyridin-3-yl)isochroman-1-yl) methylcarbamate hydrochloride salt (Compound 14)

To a solution of (S)-tert-butyl ((6-(pyridin-3-yl)isochroman-1-yl)methyl)carbamate (300 mg, 881 μmol) in ethyl acetate (20 mL) was added HCl/1,4-dioxane (316 mg, 8.81 mmol). The reaction was stirred at ambient temperature for 16 h. The mixture was concentrated to give title compound (250 mg, yield 91%) as white solid. MS (ESI): m/z 241 [M+H]+. 1H NMR (400 MHz, MeOH-d4): δ 9.23 (d, J=1.2 Hz, 1H), 8.96-8.93 (m, 1H), 8.86 (d, J=4 Hz, 1H), 8.20-8.18 (m, 1H), 7.75 (d, J=6 Hz, 1H), 7.74 (s, 1H), 7.47 (d, J=6 Hz, 1H), 5.11 (d, J=5.6 Hz 1H), 4.31-4.27 (m, 1H), 3.95-3.90 (m, 1H), 3.64-3.61 (m, 1H), 3.29-3.25 (m, 1H), 3.19-3.13 (m, 1H), 2.96-2.92 (m, 1H).

Scheme 7

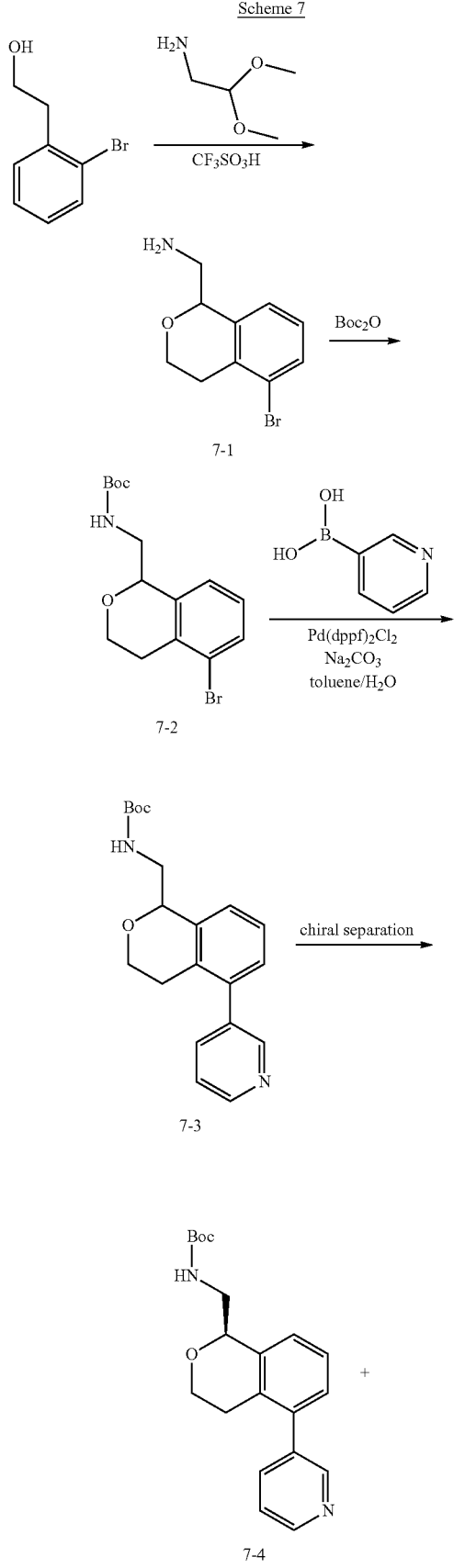

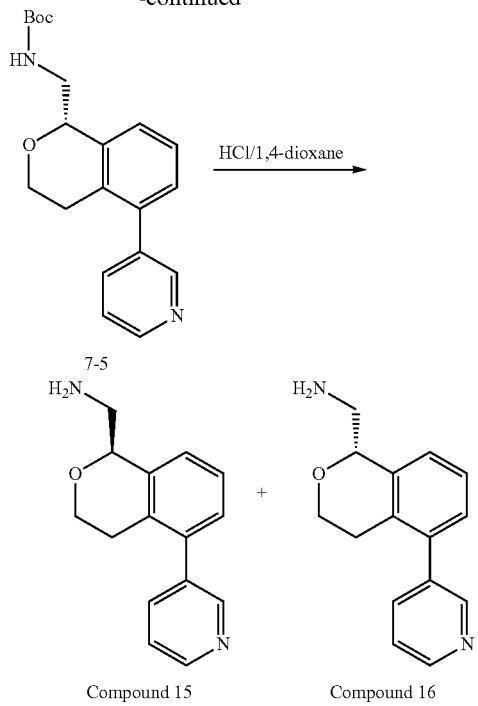

Compound 15     Compound 16

Synthesis of Compound 15 and Compound 16

(5-Bromoisochroman-1-yl)methanamine (7-1)

A mixture of 2-(2-bromophenyl)ethanol (2.5 g, 14.9 mmol) and 2,2-dimethoxyethanamine (3.12 g, 29.8 mmol) was added trifluoromethanesulfonic acid (8 mL) in ice bath. The reaction was warmed to room temperature and stirred for 2 h. Upon completion, the reaction was quenched with water, neutralized and extracted with DCM. The combined organics were concentrated to dryness in vacuo. The crude material was suitable for use without further purification.

tert-Butyl (5-bromoisochroman-1-yl)methylcarbamate (7-2)

To a solution of (5-bromoisochroman-1-yl)methanamine (3.5 g) in water (80 mL) was added di-tert-butyl dicarbonate (3.84 g, 17.6 mmol) and sodium bicarbonate (3.71 g, 44.8 mmol). Tetrahydrofuran (15 mL) was added to the mixture, and the reaction was stirred at ambient temperature for 16 h. The mixture was concentrated, and then purified by column chromatography (PE:EA=15:1) to give tert-butyl((5-bromoisochroman-1-yl)methyl)carbamate (3.8 g) as white solid. MS(ESI): m/z 342 [M+H]+.

tert-Butyl (5-(pyridin-3-yl)isochroman-1-yl)methylcarbamate (7-3)

To tert-butyl (5-bromoisochroman-1-yl)methylcarbamate (2.10 g, 6.13 mmol) and sodium carbonate (1.29 g, 12.2 mmol), [1,1'-Bis(diphenylphosphino) ferrocene]dichloropalladium(II) (448 mg, 0.1 eq) was added pyridine-3-ylboronic(978 mg, 7.96 mmol) in toluene (50 mL) and H2O (10 mL). The reaction mixture was heated to 90° C. and stirred at that temperature for 16 h under N2 protection. Upon the completion, the mixture was filtered and then concentrated to give the residue. The residue was purified by column chromatography (PE:EA=2:1) to give the product 1.9 g as colorless oil (yield 90%). MS(ESI): m/z 341 [M+H]+

(R)-tert-Butyl (5-(pyridin-3-yl)isochroman-1-yl) methylcarbamate (7-4) and (S)-tert-butyl (5-(pyridin-3-yl)isochroman-1-yl)methylcarbamate (7-5)

Racemic tert-butyl (5-(pyridin-3-yl)isochroman-1-yl) methylcarbamate (1.9 g) was charged to a chiral column (OZ-H 250×4.6 mm 5 um, Co-Solvent MeOH) to give (R)-tert-butyl (5-(pyridin-3-yl)isochroman-1-yl)methylcarbamate (7-4) (0.7 g) and (S)-tert-butyl (5-(pyridin-3-yl) isochroman-1-yl)methylcarbamate (7-5) (0.75 g).

(R)-(5-(Pyridin-3-yl)isochroman-1-yl)methanamine hydrochloride (Compound 15)

To a solution of (R)-tert-butyl (5-(pyridin-3-yl)isochroman-1-yl)methylcarbamate (350 mg, 1.02 mmol) in ethyl acetate (20 mL) was added HCl/1,4-dioxane (3.4 mL, 10.2 mmol). The reaction was stirred at ambient temperature for 16 h. Upon completion, the mixture was concentrated to give (R)-(5-(pyridin-3-yl)isochroman-1-yl)methanamine hydrochloride (Compound 15) (222 mg, yield: 90.2%) as a yellow solid. MS(ESI): m/z 241 [M+H]+. 1H NMR (400 MHz, CD$_3$OD): δ 9.22 (s, 1H), 8.94 (s, 1H), 8.73 (s, 1H), 8.22-8.24 (m, 1H), 7.40-7.52 (m, 3H), 5.14-5.16 (d, J=8 Hz, 1H), 4.17-4.20 (m, 1H), 3.78-3.82 (m, 1H), 3.60-3.63 (m, 1H), 3.25-3.33 (m, 1H), 2.99-3.03 (m, 1H), 2.58-2.62 (m, 1H).

(S)-(5-(Pyridin-3-yl)isochroman-1-yl)methanamine hydrochloride (Compound 16)

To a solution of (S)-tert-butyl (5-(pyridin-3-yl)isochroman-1-yl)methylcarbamate (350 mg, 1.02 mmol) in ethyl acetate (20 mL) was added HCl/1,4-dioxane (3.4 mL, 10.2 mmol). The reaction was stirred at ambient temperature for 16 h. Upon completion, the mixture was concentrated to give (S)-(5-(pyridin-3-yl)isochroman-1-yl)methanamine hydrochloride (Compound 16) (221 mg) as a yellow solid (yield 88.9%). MS(ESI): m/z 241 [M+H]+. 1H NMR (400 MHz, CD$_3$OD): δ 9.01 (s, 1H), 8.95 (s, 1H), 8.74 (s, 1H), 8.22-8.24 (m, 1H), 7.40-7.51 (m, 3H), 5.15-5.16 (d, J=6 Hz, 1H), 4.18-4.20 (m, 1H), 3.78-3.81 (m, 1H), 3.60-3.63 (m, 1H), 3.26-3.33 (m, 1H), 3.02-3.03 (m, 1H), 2.59-2.62 (m, 1H).

Scheme 8

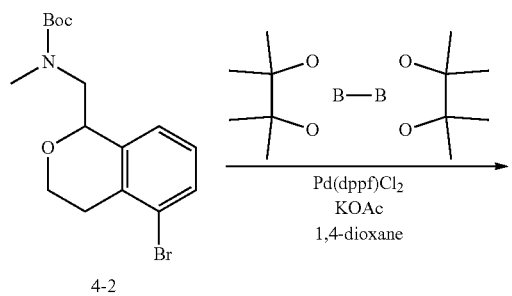

4-2

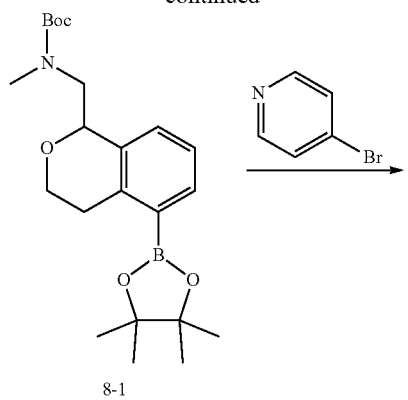

8-1

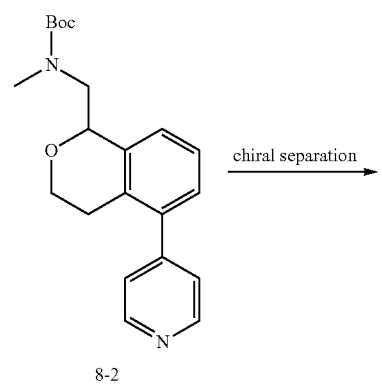

8-2

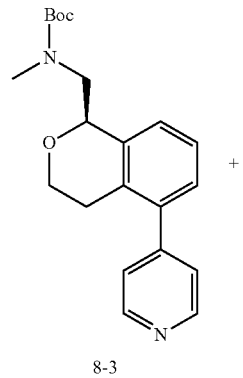

8-3

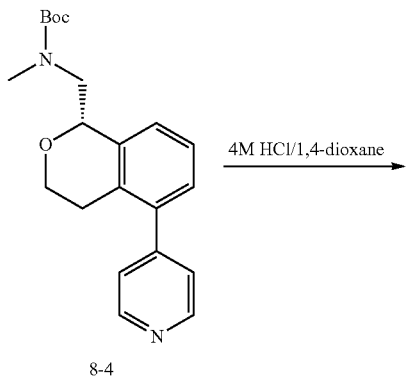

8-4

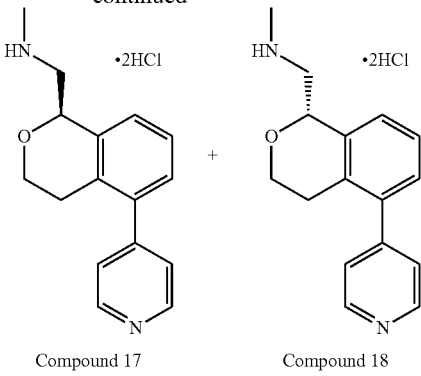

Compound 17     Compound 18

Synthesis of Compound 17 and Compound 18 tert-Butyl methyl((5-(4,4,5,5-tetramethyl-1,3,2-dioxaborolan-2-yl)isochroman-1-yl)methyl)carbamate (8-1)

A reaction flask was charged with 1,1'-bis(diphenylphosphino)ferrocene-palladium(II)dichloride (806 mg, 1.46 mmol), potassium acetate (2.86 g, 29.2 mmol), and 4,4,4',4',5,5,5',5'-octamethyl-2,2'-bi(1,3,2-dioxaborolane) (5.54 g, 21.9 mmol), and was flushed with nitrogen. 1,4-dioxane (80 mL) and tert-butyl ((5-bromoisochroman-1-yl)methyl)(methyl)carbamate (prepared as described previously in Scheme 4)(5.20 g, 14.60 mmol) were then added. After stirring at 90° C. for 16 h, the mixture was concentrated, diluted with ethyl acetate (200 mL) and filtered. The filtrate was washed with brine (3×50 mL). The organic layer was dried over with sodium sulfate, filtered and then concentrated to give tert-butyl methyl((5-(4,4,5,5-tetramethyl-1,3,2-dioxaborolan-2-yl)isochroman-1-yl)methyl)carbamate as brown oil (3.9 g, crude), MS (ESI): m/z 404 [M+H]+.

tert-Butyl methyl((5-(pyridin-4-yl)isochroman-1-yl)methyl)carbamate (8-2)

To 4-bromopyridine (2.21 g, 14.52 mmol) and sodium carbonate (2.05 g, 194 mmol), [1,1'-Bis(diphenylphosphino)ferrocene]dichloropalladium(II) (707 mg, 0.1 eq) was added tert-butyl methyl((5-(4,4,5,5-tetramethyl-1,3,2-dioxaborolan-2-yl)isochroman-1-yl)methyl)carbamate (crude, 3.9 g, 9.68 mmol) in toluene (60 mL) and H$_2$O (12 mL). The reaction mixture was heated to 90° C. and stirred at that temperature for 16 h under N$_2$ protection. Upon completion, the mixture was filtered and then concentrated to dryness. The residue was purified by column chromatography (eluted from petroleum ether to petroleum ether/ethyl acetate=1/1) to give tert-butyl methyl((5-(pyridin-4-yl)isochroman-1-yl)methyl)carbamate as a colorless oil (2.5 g, yield: 73%), MS (ESI): m/z 355 [M+H]+.

(R)-tert-butyl methyl((5-(pyridin-4-yl)isochroman-1-yl)methyl)carbamate (8-3) and (S)-tert-butyl methyl((5-(pyridin-4-yl)isochroman-1-yl)methyl)carbamate (8-4)

Racemic tert-butyl methyl((5-(pyridin-4-yl)isochroman-1-yl)methyl)carbamate (3.5 g) was separated by chiral column chromatography (As—H 250×4.6 mm 5 um. Co-Solvent MeOH (0.2% Methanol Ammonia)) to give (R)-tert-butyl methyl((5-(pyridin-4-yl)isochroman-1-yl)methyl)carbamate (8-3) (1.2 g) and (S)-tert-butyl methyl((5-(pyridin-4-yl)isochroman-1-yl)methyl)carbamate (8-4) (1.2 g).

(R)—N-Methyl(5-(pyridin-4-yl)isochroman-1-yl)methanamine dihydrochloride salt (Compound 17)

To a solution of (R)-tert-butyl methyl((5-(pyridin-4-yl)isochroman-1-yl)methyl)carbamate (450 mg, 1.26 mmol) in ethyl acetate (20 mL) was added 4 M HCl/1,4-dioxane (3.9 mL, 12.6 mmol, 4M). The reaction was stirred at ambient temperature for 16 h. Upon completion, the mixture was concentrated in vacuo to give a residue which was washed with (petroleum ether/ethyl acetate=10/1, 100 mL) to give the desired product as yellow solid (241 mg, yield: 73%), MS (ESI): m/z 255 [M+H]+. 1HNMR (400 MHz, CD$_3$OD): δ 8.96-8.98 (d, J=5.2 Hz, 2H), 8.20-8.21 (d, J=5.2 Hz, 2H), 7.45-7.53 (m, 3H), 5.26-5.27 (m, 1H), 4.18-4.22 (m, 1H), 3.69-3.82 (m, 2H), 3.39-3.44 (m, 1H), 3.09-3.13 (m, 1H), 2.83 (s, 3H), 2.65-2.68 (m, 1H).

(S)—N-Methyl(5-(pyridin-4-yl)isochroman-1-yl)methanamine dihydrochloride salt (Compound 18)

To a solution of (S)-tert-butyl methyl((5-(pyridin-4-yl)isochroman-1-yl)methyl)carbamate (450 mg, 1.26 mmol) in ethyl acetate (20 mL) was added 4 M HCl/1,4-dioxane (3.15 mL, 12.6 mmol, 4M). The reaction was stirred at ambient temperature for 16 h. Upon completion, the mixture was concentrated in vacuo to give a residue which was washed with (petroleum ether/ethyl acetate=10/1, 100 mL) to yield the desired product as a yellow solid (250 mg, yield: 77.8%), MS (ESI): m/z 255 [M+H]+. 1HNMR (400 MHz, CD$_3$OD): δ 8.96-8.98 (d, J=5.2 Hz, 2H), 8.20-8.21 (d, J=5.2 Hz, 2H), 7.45-7.53 (m, 3H), 5.26-5.27 (m, 1H), 4.18-4.22 (m, 1H), 3.69-3.82 (m, 2H), 3.39-3.44 (m, 1H), 3.09-3.13 (m, 1H), 2.83 (s, 3H), 2.65-2.68 (m, 1H).

Scheme 9

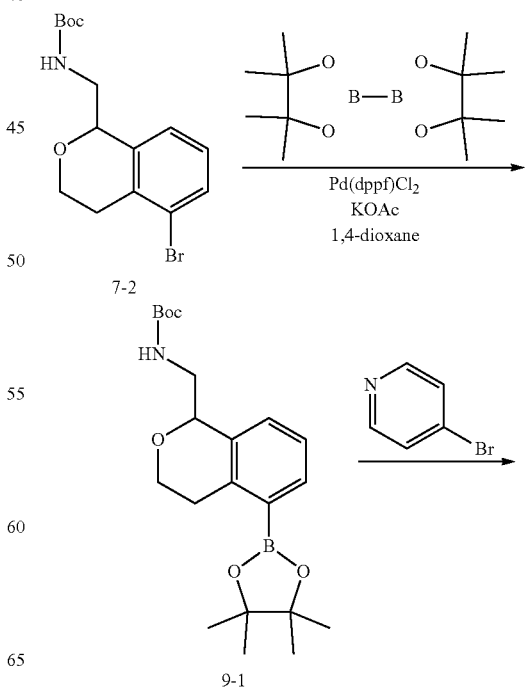

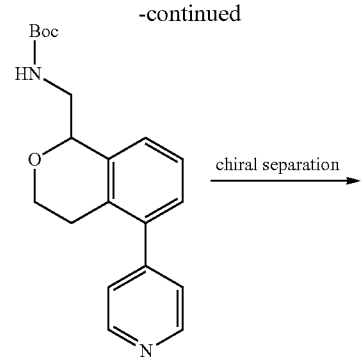

5,5,5'-octamethyl-2,2'-bi(1,3,2-dioxaborolane) (2.26 g, 8.93 mmol). 1,4-dioxane (50 mL) was added and the flask was flushed with nitrogen, tert-Butyl (5-bromoisochroman-1-yl)methylcarbamate (7-2) (prepared as described previously in Scheme 7) (1.8 g, 5.25 mmol) was then added. After being stirred at 90° C. for 16 h, the mixture was concentrated, diluted with ethyl acetate (200 mL) and filtered. The filtrate was washed with brine (3×50 mL). The organic was dried over sodium sulfate, filtered and then concentrated to give tert-butyl (5-(4,4,5,5-tetramethyl-1,3,2-dioxaborolan-2-yl)isochroman-1-yl)methylcarbamate as brown oil (3.6 g, crude), MS (ESI): m/z 334 [M−55]+.

tert-Butyl (5-(pyridin-4-yl)isochroman-1-yl)methyl-carbamate (9-2)

To 4-bromopyridine (1.45 g, 9.24 mmol) and sodium carbonate (1.63 g, 15.4 mmol), [1,1'-Bis(diphenylphosphino) ferrocene]dichloropalladium(II) (563 mg, 0.77 mmol) was added tert-butyl ((5-(4,4,5,5-tetramethyl-1,3,2-dioxaborolan-2-yl)isochroman-1-yl)methyl)carbamate (crude, 3 g, 7.70 mmol) in toluene (50 mL) and H$_2$O (10 mL). The reaction mixture was heated to 90° C. and stirred at that temperature for 16 h under N$_2$ protection. Upon the completion, the mixture was filtered and then concentrated to give the residue. The residue was purified by column chromatography (eluted from petroleum ether to petroleum ether/ethyl acetate=1/1) to give tert-butyl (5-(pyridin-4-yl)isochroman-1-yl)methylcarbamate as colorless oil (2 g, yield: 76.4%). MS (ESI): m/z 285 [M−55]+.

(R)-tert-Butyl (5-(pyridin-4-yl)isochroman-1-yl)methylcarbamate (9-3) and (S)-tert-butyl (5-(pyridin-4-yl)isochroman-1-yl)methylcarbamate (9-4)

Racemic tert-butyl (5-(pyridin-4-yl)isochroman-1-yl)methylcarbamate (4.2 g) was charged to a chiral column (As—H 250×4.6 mm 5 um, Co-Solvent MeOH (1% Methanol Ammonia)) and separated to give (R)-tert-butyl (5-(pyridin-4-yl)isochroman-1-yl)methylcarbamate (1.4 g) and (S)-tert-butyl (5-(pyridin-4-yl)isochroman-1-yl)methylcarbamate (1.4 g).

(R)-(5-(Pyridin-4-yl)isochroman-1-yl)methanamine hydrochloride salt (Compound 19)

To a solution of (R)-tert-butyl (5-(pyridin-4-yl)isochroman-1-yl) methylcarbamate (500 mg, 1.46 mmol) in ethyl acetate (20 mL) was added 4 M HCl/1,4-dioxane (3.6 mL, 14.5 mmol, 4M). The reaction was stirred at ambient temperature for 16 h. Upon completion, the mixture was concentrated to give (R)-(5-(pyridin-4-yl)isochroman-1-yl) methanamine hydrochloride salt as a white solid. (0.27 g, yield: 76%). MS (ESI): m/z 241 [M+H]+. 1HNMR (400 MHz, CD$_3$OD): δ 8.94-8.96 (d, J=5.2 Hz, 2H), 8.18-8.20 (d, J=4.8 Hz, 2H), 7.45-7.54 (m, 3H), 5.16-5.17 (m, 1H), 4.17-4.21 (m, 1H), 3.60-3.81 (m, 2H), 3.27-3.33 (m, 1H), 3.07-3.13 (m, 1H), 2.63-2.67 (m, 1H).

(S)-(5-(Pyridin-4-yl)isochroman-1-yl)methanamine hydrochloride salt (Compound 20)

To a solution of (S)-tert-butyl (5-(pyridin-4-yl)isochroman-1-yl)methylcarbamate (500 mg, 1.46 mmol) in ethyl acetate (20 mL) was added 4 M HCl/1,4-dioxane (3.6 mL, 14.5 mmol, 4M). The reaction was stirred at ambient temperature for 16 h. Upon completion, the mixture was con- Synthesis of Compound 19 and Compound 20 tert-Butyl (5-(4,4,5,5-tetramethyl-1,3,2-dioxaborolan-2-yl)isochroman-1-yl)methylcarbamate (9-1)

A flask was charged with 1,1'-Bis(diphenylphosphino) ferrocene-palladium(II)dichloride (384 mg, 0.525 mmol), potassium acetate (1030 mg, 10.51 mmol), and 4,4,4',4',5, centrated to give (S)-(5-(pyridin-4-yl)isochroman-1-yl)methanamine hydrochloride salt as a white solid (0.26 g, yield: 75.4%), MS (ESI): m/z 241 [M+H]+. 1HNMR (400 MHz, CD$_3$OD): δ 8.94-8.96 (d, J=5.2 Hz, 2H), 8.18-8.19 (d, J=5.2 Hz, 2H), 7.44-7.54 (m, 3H), 5.16-5.17 (m, 1H), 4.17-4.21 (m, 1H), 3.60-3.82 (m, 2H), 3.27-3.37 (m, 1H), 3.07-3.13 (m, 1H), 2.63-2.67 (m, 1H).

Scheme 10

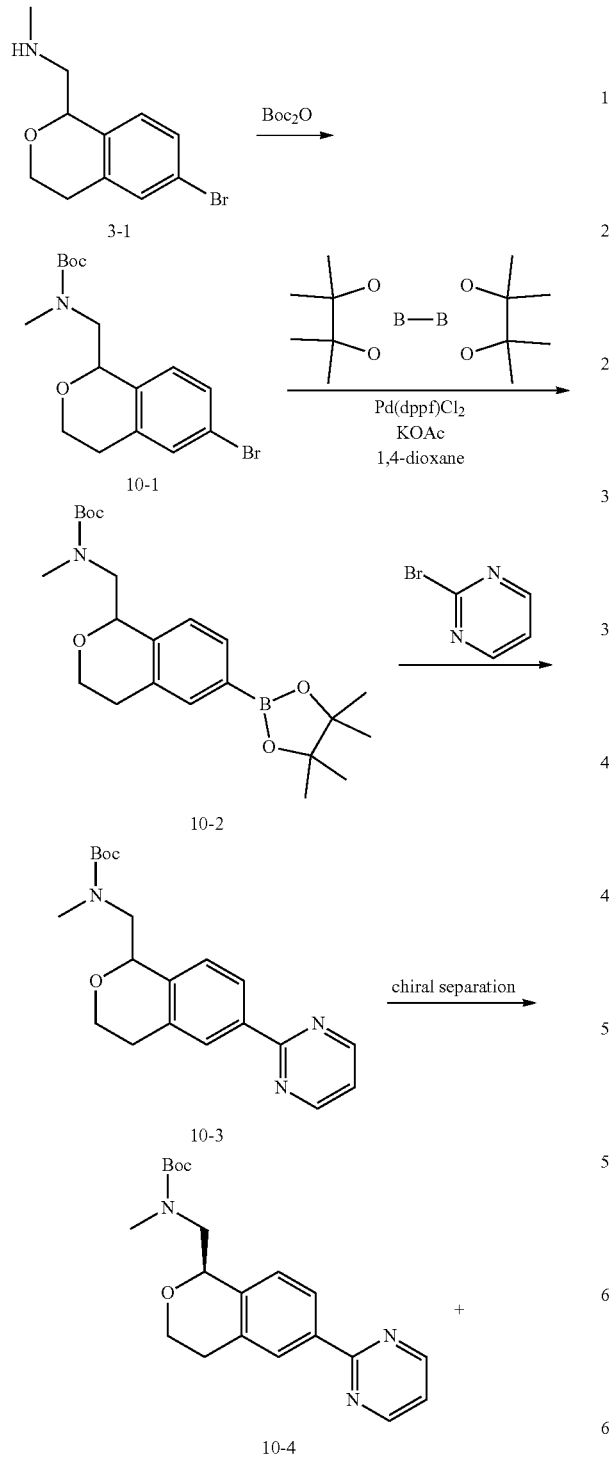

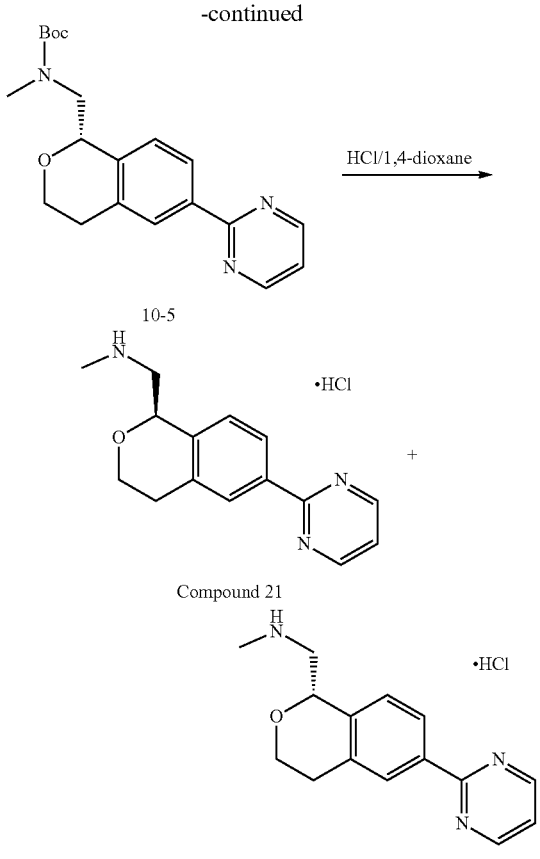

Synthesis of Compound 21 and Compound 22

(tert-Butyl (6-bromoisochroman-1-yl)methyl (methyl)carbamate (10-1)

To a solution of 1-(6-bromoisochroman-1-yl)-N-methyl-methanamine (3-1) (prepared as previously described in Scheme 3) (2.6 g, 10.1 mmol) in dichloromethane (30 mL) was added di-tert-butyl dicarbonate (2.42 g, 11.1 mmol) and triethylamine (2.04 g, 20.2 mmol). The reaction was stirred at ambient temperature for 2 h. The solvent was removed and the residue was purified by flash column chromatography (petroleum ether:ethyl acetate=9:1) to provide tert-butyl ((6-bromoisochroman-1-yl)methyl)(methyl)carbamate (3.40 g, yield 93%) as a yellow oil. MS: m/z=356 [M+H]+.

(tert-Butyl methyl((6-(4,4,5,5-tetramethyl-1,3,2-dioxaborolan-2-yl)isochroman-1-yl)methyl)carbamate (10-2)

A flask charged with 1,1'-Bis(diphenylphosphino)ferrocene-palladium(I)dichloride dichloromethane complex (409 mg, 0.1 eq), potassium acetate (1.10 g, 11.22 mmol), and 4,4,4',4',5,5,5',5'-octamethyl-2,2'-bi(1,3,2-dioxaborolane) (2.41 g, 9.52 mmol) was flushed with nitrogen. 1,4-dioxane (30 mL) and tert-butyl ((6-bromoisochroman-1-yl) methyl)(methyl)carbamate (2 g, 5.61 mmol) were then added. The reaction was stirred at 100° C. for 16 h. The reaction was cooled, concentrated and diluted with ethyl acetate (100 mL) and filtered. The filtrate was washed with brine (3×100 mL). The organic layer was dried over anhydrous sodium sulfate, filtered and then concentrated to give crude (tert-butyl methyl((6-(4,4,5,5-tetramethyl-1,3,2-dioxaborolan-2-yl)isochroman-1-yl)methyl)carbamate (2.7 g, yield 86%) ESI: m/z=304 [M−100+H]+, 348 [M−55]+.

tert-Butyl methyl((6-(pyrimidin-2-yl)isochroman-1-yl)methyl)carbamate (10-3)

A mixture of tert-butyl methyl((6-(4,4,5,5-tetramethyl-1,3,2-dioxaborolan-2-yl)isochroman-1-yl)methyl) carbamate (1.3 g, 3.22 mmol), [1,1'-Bis (diphenylphosphino)ferrocene] dichloropalladium (II) (213 mg, 0.1 eq), 2-bromopyrimidine (464 mg, 2.92 mmol), and aq. sodium carbonate (620 mg, 5.85 mmol) in toluene (20 mL) was degassed by purging with nitrogen. The mixture was then heated at 100° C. for 16 hours. The reaction was cooled, diluted with ethyl acetate (150 mL) and filtered. The filtrate was concentrated. The crude product was purified by silica gel chromatography eluted with petroleum ether:ethyl acetate=6:1 to give tert-butyl methyl ((6-(pyrimidin-2-yl) isochroman-1-yl)methyl) carbamate (970 mg, yield 90%) as a yellow oil. ESI: m/z=256 [M−100+H]+.

(R)-tert-Butyl methyl((6-(pyrimidin-2-yl)isochroman-1-yl)methyl)carbamate (10-4) and (S)-tert-butyl methyl((6-(pyrimidin-2-yl)isochroman-1-yl)methyl)carbamate (10-5)

Racemic tert-butyl methyl((6-(pyrimidin-2-yl)isochroman-1-yl)methyl)carbamate (2.6 g, 7.31 mmol) was charged to a chiral column (OJ-H (250*4.6 mm 5 um), Mobile Phase: MeOH (0.1% NH4OH)) and separated to give (R)-tert-butyl methyl((6-(pyrimidin-2-yl) isochroman-1-yl)methyl) carbamate (620 mg, yield 23%) as a yellow oil, and (S)-tert-butyl methyl((6-(pyrimidin-2-yl) isochroman-1-yl)methyl) carbamate (1.2 g, yield 46%) as a yellow oil.

(R)—N-Methyl-1-(6-(pyrimidin-2-yl)isochroman-1-yl)methanamine hydrochloride salt (Compound 21)

To a solution of (R)-tert-butyl methyl ((6-(pyrimidin-2-yl)isochroman-1-yl)methyl)carbamate (690 mg, 1.94 mmol) in dichloromethane (20 mL) was added HCl/1,4-dioxane (4M, 2.9 mL). The reaction was stirred at ambient temperature for 16 h. Upon completion, the mixture was concentrated to dryness and triturated with ethyl acetate. The filter cake was washed with 100 mL of ethyl acetate and dried in vacuum to afford the desired product as a yellow solid (533 mg, yield 93%). ESI: m/z=256 [M+H]+. 1HNMR (400 MHz, MeOH-d4): δ 9.20-9.18 (m, 2H), 8.26 (d, J=7.2 Hz, 2H), 7.85-7.83 (m, 1H), 7.52 (d, J=8.4 Hz, 1H), 5.23 (d, J=7.6 Hz, 1H), 4.32-4.27 (m, 1H), 3.96-3.90 (m, 1H), 3.74-3.70 (m, 1H), 3.43-3.37 (m, 1H), 3.20-3.12 (m, 1H), 2.97-2.91 (m, 1H), 2.81 (s, 3H).

(S)—N-Methyl-1-(6-(pyrimidin-2-yl)isochroman-1-yl)methanamine hydrochloride salt (Compound 22)

To a solution of (S)-tert-butyl methyl((6-(pyrimidin-2-yl) isochroman-1-yl)methyl)carbamate (1.2 g, 3.37 mmol) in dichloromethane (30 mL) was added HCl/1,4-dioxane (5.05 mL, 20.2 mmol, 4 M). The reaction was stirred at ambient temperature for 16 h. Upon completion, the mixture was concentrated to dryness and the residue was washed with ethyl acetate to give the desired product as a yellow solid (538 mg, yield: 55%). ESI: m/z=256 [M+H]+. 1 HNMR (400 MHz, MeOH-d4): δ 9.17 (d, J=4.4 Hz, 2H), 8.28 (d, J=6.4 Hz, 2H), 7.82 (t, J=8.4 Hz, 1H), 7.53 (d, J=6.0 Hz, 1H), 5.25-5.23 (m, 1H), 4.32-4.28 (m, 1H), 3.97-3.92 (m, 1H), 3.75-3.72 (m, 1H), 3.43-3.33 (m, 1H), 3.19-3.14 (m, 1H), 2.98-2.83 (m, 1H), 2.81 (s, 3H).

Synthesis of Compound 23 and Compound 24

(S)—N-Methyl-1-(5-(pyrimidin-2-yl)isochroman-1-yl)methanamine hydrochloride salt (Compound 23)

The title compound was prepared using the procedure described in Scheme 8, substituting 2-bromopyrimidine for 4-bromopyridine. The title compound was isolated as a white solid (441 mg, yield: 81.6%). ESI: m/z=256 [M+1]+, ee %=97% (R.T.: 4.59 min) 1H NMR (400 MHz, CD₃OD) δ 9.20~9.18 (d, J=5.6 Hz, 2H), 7.85~7.82 (t, J=5.2 Hz, 1H), 7.74~7.72 (t, J=4.4 Hz, 1H), 7.53~7.2 (d, J=4.6 Hz 2H), 5.24~5.21 (m, 1H), 4.23~4.17 (m, 1H), 3.84~3.78 (m, 1H), 3.70~3.66 (dd, $J_1$=12.8. $J_2$=2.8 Hz, 1H), 3.42~3.37 (m, 1H), 3.30~3.25 (m, 1H), 2.92~2.88 (m, 1H), 2.80 (s, 3H).

(R)—N-Methyl-1-(5-(pyrimidin-2-yl)isochroman-1-yl)methanamine hydrochloride (Compound 24)

The title compound was prepared using the procedure described in Scheme 8, substituting 2-bromopyrimidine for 4-bromopyridine. The title compound was isolated as a white solid (397 mg, yield: 64.5%). ESI: m/z=256 [M+1]+, ee %=100% (R.T.: 3.97 min). 1H NMR (400 MHz, CD₃OD) δ 9.29~9.28 (d, J=5.6 Hz, 2H), 7.97~7.95 (t, J=5.6 Hz, 1H), 7.75~7.73 (dd, $J_1$=6.8, $J_2$=1.2 Hz, 1H), 7.59~7.53 (m, 2H), 5.26~5.24 (m, 1H), 4.23~4.18 (m, 1H), 3.85~3.79 (m, 1H), 3.72~3.68 (dd, $J_1$=12.8, $J_2$=3.0 Hz, 1H), 3.43~3.37 (m, 1H), 3.28~3.26 (m, 1H), 2.95~2.90 (m, 1H), 2.81 (s, 3H).

Synthesis of Compound 25 and Compound 26

Rel-(S)—N-Methyl-1-(7-(pyrimidin-5-yl)isochroman-1-yl)methanamine hydrochloride (Compound 25)

The title compound was prepared using the procedure shown in Scheme 2, substituting 5-bromopyrimidine for 3-bromopyridine. Trituration with ethyl acetate afforded the desired product as a white solid. (90 mg, purity: 95%, ee %: 100%, yield: 80.1%). MS (ESI): m/z=256 [M+1]+. 1H NMR (400 MHz, DMSO-d6): δ 9.38 (brs, 1H), 9.20 (s, 3H), 8.88 (brs, 1H), 7.74-7.72 (m, 2H), 7.38 (d, $J_2$=6.4 Hz, 1H), 5.20 (d, $J_2$=7.2 Hz, 1H), 4.15-4.11 (m, 1H), 3.85-3.80 (m, 1H), 3.76-3.72 (m, 1H), 3.32-3.27 (m, 1H), 2.97-2.91 (m, 1H), 2.85-2.80 (m, 1H), 2.62-2.60 (m, 3H).

Rel-(R)—N-Methyl-1-(7-(pyrimidin-5-yl)isochroman-1-yl)methanamine hydrochloride (Compound 26)

The title compound was prepared using the procedure shown in Scheme 2, substituting 5-bromopyrimidine for 3-bromopyridine. Trituration with ethyl acetate afforded the desired product as a white solid. (140 mg, purity: 100%, ee %: 100%, yield: 85.3%) as a white solid. MS (ESI): m/z=256 [M+1]+. 1H NMR (400 MHz, DMSO-d6): δ 9.38 (brs, 1H), 9.20 (s, 3H), 8.88 (brs, 1H), 7.74-7.72 (m, 2H), 7.38 (d, $J_2$=6.4 Hz, 1H), 5.20 (d, $J_2$=7.2 Hz, 1H), 4.15-4.11 (m, 1H), 3.85-3.80 (m, 1H), 3.76-3.72 (m, 1H), 3.32-3.27 (m, 1H), 2.97-2.91 (m, 1H), 2.85-2.80 (m, 1H), 2.62-2.60 (m, 3H).

Scheme 11

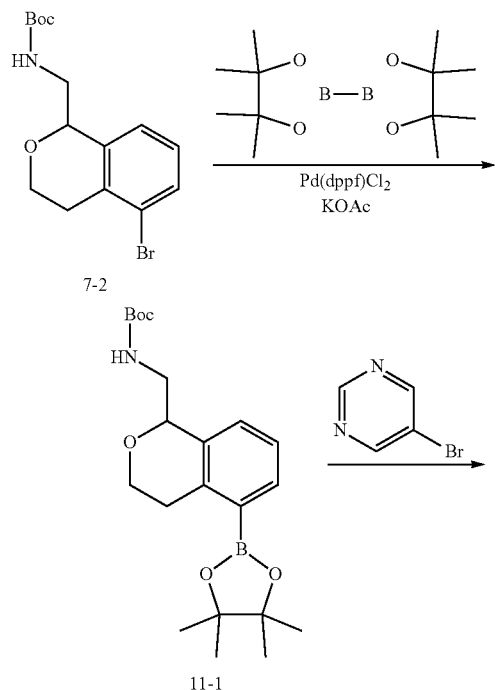

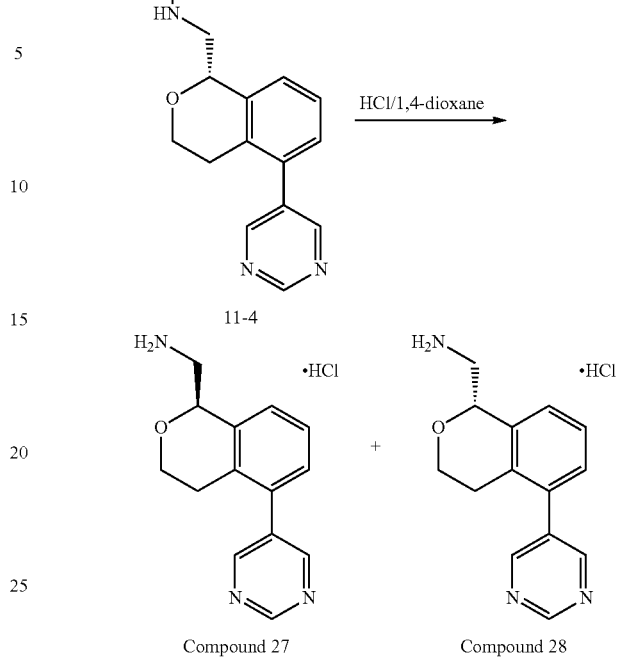

Compound 27    Compound 28

Synthesis of Compound 27 and Compound 28 tert-Butyl (5-(4,4,5,5-tetramethyl-1,3,2-dioxaborolan-2-yl)isochroman-1-yl)methylcarbamate (11-1)

A flask charged with 1,1'-Bis(diphenylphosphino)ferrocene-palladium(II)dichloride (320 mg, 0.1 eq), potassium acetate (859 mg, 8.76 mmol), 4,4,4',4',5,5,5',5'-octamethyl-2,2'-bi(1,3,2-dioxaborolane) (1.88 g, 7.44 mmol) and 1,4-dioxane (30 mL) was flushed with nitrogen, tert-Butyl ((6-bromoisochroman-1-yl)methyl)(methyl)carbamate (prepared as described previously in Scheme 7) (1.5 g, 4.38 mmol) was then added. After being stirred at 90° C. for 16 h, the reaction was monitored by LCMS. The mixture was concentrated, then diluted with ethyl acetate (200 mL), filtered. The filtrate was washed with brine (3×100 mL). The organic was dried over with sodium sulfate, filtered and then concentrated to give the crude product 3 g as a brown oil which was suitable for use without further purification. ESI: m/z=290 [M−100+H]+, 334 [M−55]+.

tert-Butyl (5-(pyrimidin-5-yl)isochroman-1-yl)methylcarbamate (11-2)

To a mixture of 5-bromopyrimidine (1.46 g, 9.24 mmol) and sodium carbonate (1.63 g, 15.4 mmol), [1,1'-Bis(diphenylphosphino) ferrocene]dichloropalladium(II) (563 mg, 0.1 eq) was added tert-butyl ((5-(4,4,5,5-tetramethyl-1,3,2-dioxaborolan-2-yl)isochroman-1-yl)methyl)carbamate (crude, 3 g, 7.70 mmol) in toluene (30 mL) and H2O (8 mL). The reaction mixture was heated to 90° C. and stirred at that temperature for 16 h under N2 protection. Upon the completion, the mixture was filtered and then concentrated to give the residue. The residue was purified by column chromatography (PE:EA=1:1) to yield the product (2.2 g, yield: 86%) as a colorless oil. ESI: m/z=286 [M−55]+.

(R)-ter-butyl (5-(pyrimidin-5-yl)isochroman-1-yl) methylcarbamate (11-3) and (S)-tert-butyl (5-(pyrimidin-5-yl)isochroman-1-yl)methylcarbamate (11-4)

Racemic tert-butyl ((5-(pyrimidin-5-yl)isochroman-1-yl) methyl)carbamate (5.5 g) was charged to a chiral column (OZ-H 250*4.6 mm 5 um, Co-Solvent MeOH (0.2% Methanol Ammonia)) and separated to give (R)-tert-butyl ((5-(pyrimidin-5-yl) isochroman-1-yl)methyl)carbamate (1.2 g, yield: 21.8%), (S)-tert-butyl ((5-(pyrimidin-5-yl) isochroman-1-yl)methyl)carbamate (1.2 g, yield: 21.8%).

rel-(R)-(5-(Pyrimidin-5-yl)isochroman-1-yl)methanamine hydrochloride salt (Compound 27)

To a solution of rel-(R)-tert-butyl ((5-(pyrimidin-5-yl) isochroman-1-yl)methyl)carbamate (700 mg, 2.05 mmol) in ethyl acetate (20 mL) was added HCl/1,4-dioxane (449 mg, 12.5 mmol). The reaction was stirred at ambient temperature for 16 h. Upon completion, the mixture was concentrated to give the product (500 mg, yield 88.0%), which was purified by Prep-HPLC to give (R)-(5-(pyrimidin-5-yl)isochroman-1-yl)methanamine (400 mg). To a solution of rel-(R)-(5-(pyrimidin-5-yl)isochroman-1-yl)methanamine (350 mg, 1.45 mmol) in ethyl acetate (20 mL) was added HCl/ethyl acetate (156 mg, 4.35 mmol). The reaction was stirred at ambient temperature for 15 min. Upon completion, the mixture was concentrated to give the title compound (350 mg, yield: 61.3%) as a yellow solid. ESI: m/z=242 [M+H]+. 1HNMR (400 MHz, DMSO-d6): δ 9.22 (s, 1H), 8.88 (s, 2H), 8.30 (s, 2H), 7.38-7.40 (d, J=4.8 Hz, 2H), 7.29-7.32 (m, 1H), 5.08-5.10 (d, J=8 Hz, 1H), 3.97-4.02 (m, 1H), 3.65-3.71 (m, 1H), 3.40-3.45 (m, 1H), 3.05-3.12 (m, 1H), 2.77-2.84 (m, 1H), 2.50-2.62 (m, 1H).

rel-(S)-(5-(Pyrimidin-5-yl)isochroman-1-yl)methanamine hydrochloride salt (Compound 28)

To a solution of rel-(S)-tert-butyl ((5-(pyrimidin-5-yl) isochroman-1-yl)methyl)carbamate (700 mg, 2.05 mmol) in ethyl acetate (20 mL) was added HCl/1,4-dioxane (3.1 mL, 12.5 mmol). The reaction was stirred at ambient temperature for 16 h. Upon the completion, the mixture was concentrated to give the product (500 mg, yield 88.0%), which was purified by Prep-HPLC to give (S)-(5-(pyrimidin-5-yl)isochroman-1-yl) methanamine (400 mg). To a solution of (S)-(5-(pyrimidin-5-yl) isochroman-1-yl)methanamine (300 mg, 1.24 mmol) in ethyl acetate (20 mL) was added HCl/ethyl acetate (1.3 mL, 3.72 mmol). The reaction was stirred at ambient temperature for 15 min. Upon completion, the mixture was concentrated to give the title compound (222 mg, yield: 40%) as a yellow solid. ESI: m/z=242 [M+H]+. 1HNMR (400 MHz, DMSO-d6): δ 9.22 (s, 1H), 8.88 (s, 2H), 8.25 (s, 3H), 7.38-7.40 (m, 2H), 7.29-7.32 (m, 1H), 5.06-5.09 (d, J=9.2 Hz, 1H), 3.97-4.01 (m, 1H), 3.66-3.72 (m, 1H), 3.43-3.44 (m, 1H), 3.08-3.12 (m, 1H), 2.77-2.80 (m, 1H), 2.58-2.63 (m, 1H).

Synthesis of Compound 29 and Compound 30

The title compounds were prepared using the procedure shown in Scheme 11, substituting tert-butyl methyl((5-(4,4,5,5-tetramethyl-1,3,2-dioxaborolan-2-yl)isochroman-1-yl) methyl)carbamate (8-2) for tert-butyl (5-(4,4,5,5-tetramethyl-1,3,2-dioxaborolan-2-yl)isochroman-1-yl) methylcarbamate.

rel-(R)—N-Methyl-1-(5-(pyrimidin-5-yl)isochroman-1-yl)methanamine hydrochloride salt (Compound 29)

ESI: m/z=256 [M+H]+ 1H NMR (400 MHz, DMSO-d6): δ 9.60 (brs, 1H), 9.22 (s, 1H), 8.96 (brs, 1H), 8.89 (s, 2H), 8.78 (brs, 1H), 7.40-7.36 (m, 2H), 7.30-7.28 (m, 1H), 5.24-5.22 (d, J=9.2 Hz, 1H), 4.01-3.96 (m, 1H), 3.72-3.66 (m, 1H), 3.55-3.50 (m, 1H). 3.24-3.21 (m, 1H), 2.80-2.74 (m, 1H), 2.64-2.59 (m, 1H), 2.49-2.48 (m, 3H).

rel-(S)—N-Methyl-1-(5-(pyrimidin-5-yl)isochroman-1-yl)methanamine hydrochloride salt (Compound 30)

ESI: m/z=242 [M+H]+. 1H NMR (400 MHz, DMSO-d6): δ 9.58 (brs, 1H), 9.22 (s, 1H), 8.96 (brs, 1H), 8.89 (s, 2H), 8.78 (brs, 1H), 7.41-7.36 (m, 2H), 7.30-7.28 (m, 1H), 5.24-5.22 (d, J=9.2 Hz, 1H), 4.01-3.96 (m, 1H), 3.72-3.66 (m, 1H), 3.55-3.50 (m, 1H), 3.24-3.21 (m, 1H), 2.80-2.74 (m, 1H), 2.64-2.59 (m, 1H), 2.60-2.58 (m, 3H).

Synthesis of Compound 31 and Compound 32

The title compounds were prepared using the procedure shown in Scheme 10, substituting 3-bromopyridazine for 2-bromopyrimidine.

Rel-(R)—N-Methyl-1-(6-(pyridazin-3-yl)isochroman-1-yl)methanamine hydrochloride (Compound 31)

The desired material was obtained as a white solid (100 mg, purity: 100%, ee %: 100%, yield: 81.2%). MS (ESI): m/z 256 [M+1]+. 1H NMR (400 MHz, DMSO-d6): δ 9.25-9.24 (m, 1H), 9.10 (brs, 1H), 8.74 (brs, 1H), 8.30-8.28 (m, 1H), 8.04 (d, J=4.4 Hz, 2H), 7.85-7.82 (m, 1H), 7.45-7.43 (m, 1H), 5.18 (d, J=6.8 Hz, 1H), 4.18-4.14 (m, 1H), 3.88-3.84 (m, 1H), 3.62-3.58 (m, 1H), 3.34-3.27 (m, 1H), 3.03-2.98 (m, 1H), 2.92-2.89 (m, 1H), 2.64-2.60 (m, 3H).

Rel-(S)—N-Methyl-1-(6-(pyridazin-3-yl)isochroman-1-yl)methanamine hydrochloride (Compound 32)

The desired material was obtained as a white solid. MS (ESI): m/z=56 [M+1]+. 1H NMR (400 MHz, DMSO-d6): δ 9.25-9.24 (m, 1H), 9.10 (brs, 1H), 8.74 (brs, 1H), 8.30-8.28 (m, 1H), 8.04 (d, J=4.4 Hz, 2H), 7.85-7.82 (m, 1H), 7.45-7.43 (m, 1H), 5.18 (d, J=6.8 Hz, 1H), 4.18-4.14 (m, 1H), 3.88-3.84 (m, 1H), 3.62-3.58 (m, 1H), 3.34-3.27 (m, 1H), 3.03-2.98 (m, 1H), 2.92-2.89 (m, 1H), 2.64-2.60 (m, 3H).

Scheme 12

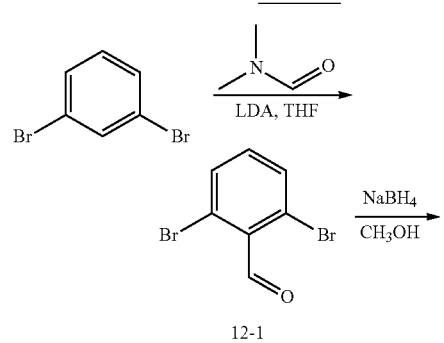

12-1

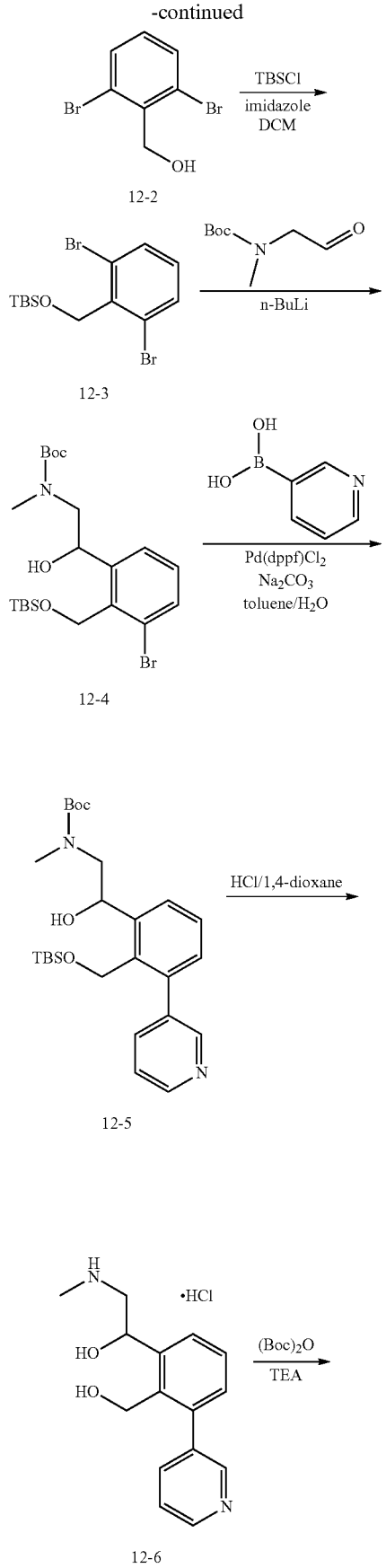
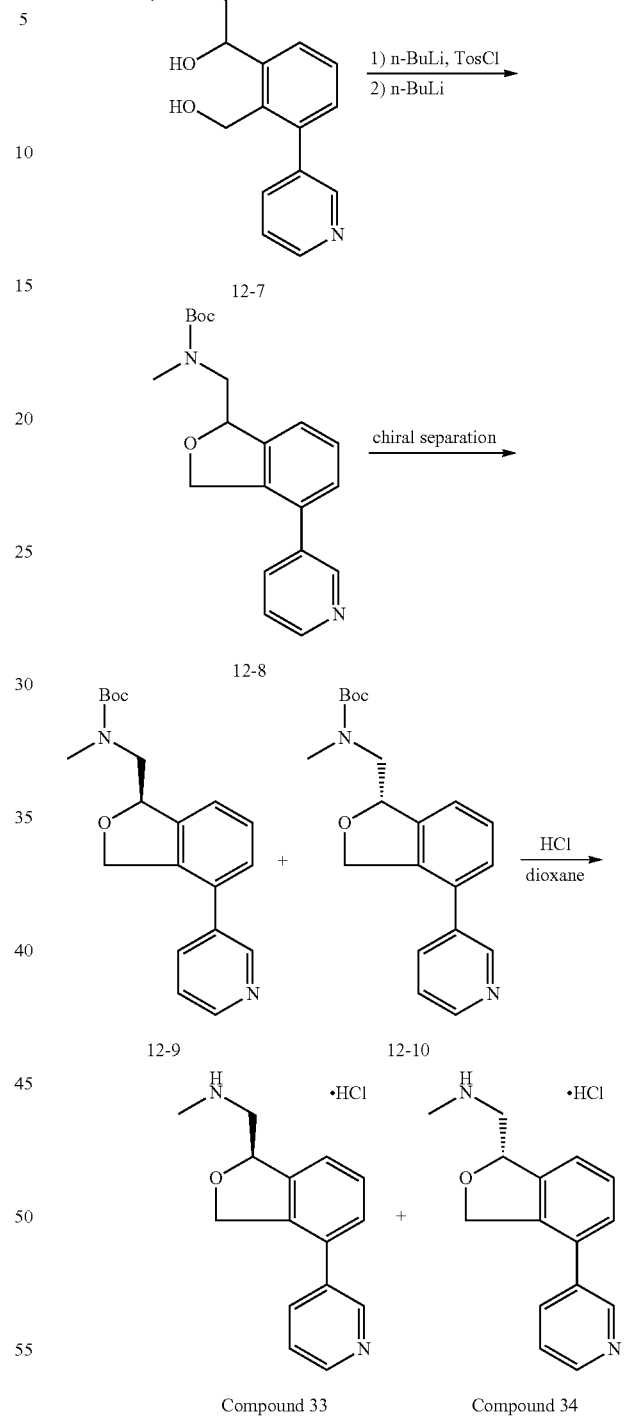
Synthesis of Compound 33 and Compound 34
2,6-Dibromobenzaldehyde (12-1)
To a solution of 1,3-dibromobenzene (10 g. 42.3 mmol) in tetrahydrofuran (100 mL) was added lithium diisopropylazanide (5.43 g, 50.7 mmol) at −78° C., The reaction was stirred at −78° C. for 1 h. N,N-Dimethylformamide (3.70 g, 50.7 mmol) was added, and the reaction was stirred at −78° C. for 2 h. Upon completion, 5N HCl (60 mL) was added to the reaction and the mixture was allowed to warm to rt. The mixture was extracted with diethyl ether (2×100 mL). The combined organic layers were washed with brine (3×100 mL), then dried over sodium sulfate. Filtration and removal of the solvent afforded the product (11.5 g) as yellow solid that was suitable for use without further purification.

(2,6-Dibromophenyl)methanol (12-2)

To a solution of 2,6-dibromobenzaldehyde (11.9 g, 45.46 mmol) in methanol (100 mL) was added sodium borohydride (2.57 g, 68.18 mmol) at 0° C. The reaction was stirred at rt for 16 h. Upon completion, water (100 mL) was added to the reaction, and the mixture was extracted with ethyl acetate (3×150 mL). The combined organic phases were dried over anhydrous $Na_2SO_4$, filtered and concentrated to dryness in vacuo to give the residue. The crude material was purified by column chromatography (PE:EA=10:1) to give (2,6-dibromophenyl)methanol (9 g, yield 74%) as a white solid.

tert-Butyl(2,6-dibromobenzyloxy)dimethylsilane (12-3)

To a solution of (2,6-dibromophenyl)methanol (5 g, 18.8 mmol) in dichloromethane (50 mL) was added tert-butylchlorodimethylsilane (4.25 g, 28.2 mmol) and 1H-imidazole (1.91 g, 28.2 mmol) at 0° C. The reaction was stirred at ambient temperature for 16 h. Upon completion, the mixture was washed with water (3×100 mL), the organic layer was dried over $Na_2SO_4$. The organic layer was filtered and concentrated to dryness. Purification by column chromatography (PE) gave the product (7 g, yield: 95%).

tert-Butyl 2-(3-bromo-2-((tert-butyldimethylsilyloxy) methyl) phenyl)-2-hydroxyethyl(methyl)carbamate (124)

To a solution of tert-butyl((2,6-dibromobenzyl)oxy)dimethylsilane (2.5 g, 6.57 mmol) in diethyl ether (30 mL) was added n-butyllithium (462 mg, 7.22 mmol) at −78° C. The reaction was stirred at −78° C. for 1 h. tert-butyl methyl(2-oxoethyl)carbamate (1.25 g, 7.22 mmol) was added to the mixture. The mixture was stirred at −78° C. for 3 h. Upon completion, aq. NH$_4$Cl (8 mL) was added to quench the reaction at −78° C. Then the mixture was extracted with ethyl acetate (3×50 mL) and the combined organic dried and filtered. The mixture was concentrated to give the crude product 4 g as yellow oil that was suitable for use without further purification. ESI: m/z=496 [M+23]+ tert-Butyl(2,6-dibromobenzyloxy)dimethylsilane (12-5)

To tert-butyl 2-(3-bromo-2-((tert-butyldimethylsilyloxy) methyl)phenyl)-2-hydroxyethyl (methyl)carbamate (6.5 g, 13.6 mmol) and sodium carbonate (2.88 g, 27.2 mmol), pyridin-3-ylboronic acid (2 g, 16.3 mmol) and [1,1'-Bis (diphenylphosphino) ferrocene] dichloropalladium(II) (995 mg, 1.36 mmol) was added toluene (60 mL) and H$_2$O (13.6 mL). The reaction mixture was heated to 90° C. and stirred for 16 h. Upon completion, the reaction was cooled and filtered. The filtrate was concentrated to give a residue that was purified by column chromatography (PE: ethyl acetate=4:1) to give tert-butyl (2-hydroxy-2-(2-(hydroxymethyl)-3-(pyridin-3-yl)phenyl)ethyl)(methyl)carbamate (5.8 g, yield 88%) as yellow oil. ESI: m/z=473 [M+H]+.

2-Hydroxy-2-(2-(hydroxymethyl)-3-(pyridin-3-yl) phenyl)-N-methylethanaminium chloride (12-6)

To a solution of tert-butyl (2-(2-(((tert-butyldimethylsilyl) oxy)methyl)-3-(pyridin-3-yl)phenyl)-2-hydroxyethyl) (methyl)carbamate (400 mg, 846 μmol) in ethyl acetate (10 mL) was added HCl/1,4-dioxane (304 mg, 8.45 mmol). The reaction was stirred at ambient temperature for 3 h, then concentrated to give the crude product (200 mg) as yellow solid which was used for next step without further purification. MS: (ESI: m/z=259 [M+H]+.

tert-Butyl 2-hydroxy-2-(2-(hydroxymethyl)-3-(pyridin-3-yl)phenyl)ethyl(methyl)carbamate (12-7)

To a solution of 1-(2-(hydroxymethyl)-3-(pyridin-3-yl) phenyl)-2-(methylamino)ethanol (3 g, 11.6 mmol, crude) in dichloromethane (50 mL) was added triethylamine (3.52 g, 34.8 mmol) and di-tert-butyl dicarbonate (3.03 g, 13.9 mmol). The reaction was stirred at ambient temperature for 5 h. The reaction was washed with water (3×30 mL), and the combined organic layers were dried over sodium sulfate. The organic layer was filtered and concentrated to dryness. The crude material was purified by column chromatography (DCM:MeOH=20:1) to give tert-butyl (2-hydroxy-2-(2-(hydroxymethyl)-3-(pyridin-3-yl)phenyl)ethyl) (methyl) carbamate (3.3 g, yield 79%) as a yellow solid. ESI: m/z=359 [M+H]+.

tert-Butyl methyl((4-(pyridin-3-yl)-1,3-dihydroisobenzofuran-1-yl)methyl)carbamate (12-8)

To a solution of tert-butyl (2-hydroxy-2-(2-(hydroxymethyl)-3-(pyridin-3-yl)phenyl)ethyl)(methyl)carbamate (1.79 g, 5 mmol) in tetrahydrofuran (20 mL) at −78° C. was added n-butyllithium (2.5 M, 2.19 mL, 5.50 mmol) dropwise over a period of 5 min at −78° C. The reaction was stirred at −78° C. for 30 min. A solution of tosyl chloride (1.04 g, 5.50 mmol) in tetrahydrofuran (20 mL) as added dropwise over a period of 5 min at −78° C. The reaction was stirred at −78° C. for 30 min. Another equivalent of n-butyllithium (2.5 M, 2.19 mL, 5.50 mmol) was added dropwise over a period of 5 mins at −78° C. The reaction was stirred at 25° C. for 16 h. Upon completion, the reaction was carefully quenched with water (80 mL) at 0° C., and extracted with ethyl acetate (3×100 mL). The combined organic layers were dried over anhydrous sodium sulfate, and concentrated in vacuo. The crude material was purified by silica column chromatography (eluted with methanol:dichloromethane from 1/100 to 1/20) to give the crude product, which was purified by reverse silica gel chromatography (eluted with acetonitrile in water from 0% to 60%, 0.1% NH4OH in water) to give tert-butyl methyl((4-(pyridin-3-yl)-1,3-dihydroisobenzofuran-1-yl)methyl)carbamate as a yellow oil (250 mg, yield: 14.7%), MS ESI: m/z=341 [M+H]+.

(R)-tert-Butyl methyl((4-(pyridin-3-yl)-1,3-dihydroisobenzofuran-1-yl)methyl)carbamate (12-9) and (S)-tert-butyl methyl((4-(pyridin-3-yl)-1,3-dihydroisobenzofuran-1-yl)methyl)carbamate (12-10)

Racemic tert-butylmethyl((4-(pyridin-3-yl)-1,3-dihydroisobenzofuran-1-yl)methyl) carbamate (300 mg, 881

(R)—N-Methyl-1-(4-(pyridin-3-yl)-1,3-dihydroisobenzofuran-1-yl)methanamine hydrochloride salt (Compound 33)

To a solution of (R)-tert-butyl methyl((4-(pyridin-3-yl)-1,3-dihydroisobenzofuran-1-yl)methyl)carbamate (140 mg, 411 μmol) in ethyl acetate (10 mL) was added HCl/EA (88.5 mg, 2.46 mmol). The reaction was stirred at ambient temperature for 30 mins. Upon completion, the mixture was concentrated to give a solid that was triturated with ether to afford the desired product (114 mg) as a yellow solid. (yield: 99%) 1H NMR (400 MHz, MeOH-d4): δ 9.07 (s, 1H), 8.91 (d, J=5.2 Hz, 1H), 8.79-8.77 (m, 1H), 8.23-8.20 (m, 1H), 7.67-7.59 (m, 3H), 5.64-5.62 (d, J=8 Hz, 1H), 5.44-5.04 (m, 1H), 5.35-5.33 (m, 1H), 3.64-3.60 (m, 1H), 3.35-3.30 (m, 1H), 2.81 (s, 3H).

(S)—N-Methyl-1-(4-(pyridin-3-yl)-1,3-dihydroisobenzofuran-1-yl)methanamine hydrochloride salt (Compound 34)

To a solution of (S)-tert-butyl methyl((4-(pyridin-3-yl)-1,3-dihydroisobenzofuran-1-yl)methyl)carbamate (140 mg, 411 μmol) in ethyl acetate (10 mL) was added HCl/EA (88.5 mg, 2.46 mmol). The reaction was stirred at ambient temperature for 30 min. Upon completion, the mixture was concentrated to give a solid that was triturated with ether to afford the desired product (114 mg) as a yellow solid. (yield: 97%) 1H NMR (400 MHz, MeOH-d4): δ 9.07 (s, 1H), 8.92 (d, J=6 Hz, 1H), 8.80-8.77 (m, 1H), 8.24-8.20 (m, 1H), 7.67-7.58 (m, 3H), 5.64-5.62 (d, J=8 Hz, 1H), 5.44-5.04 (m, 1H), 5.36-5.32 (m, 1H), 3.64-3.60 (m, 1H), 3.35-3.30 (m, 1H), 2.81 (s, 3H).

Scheme 13

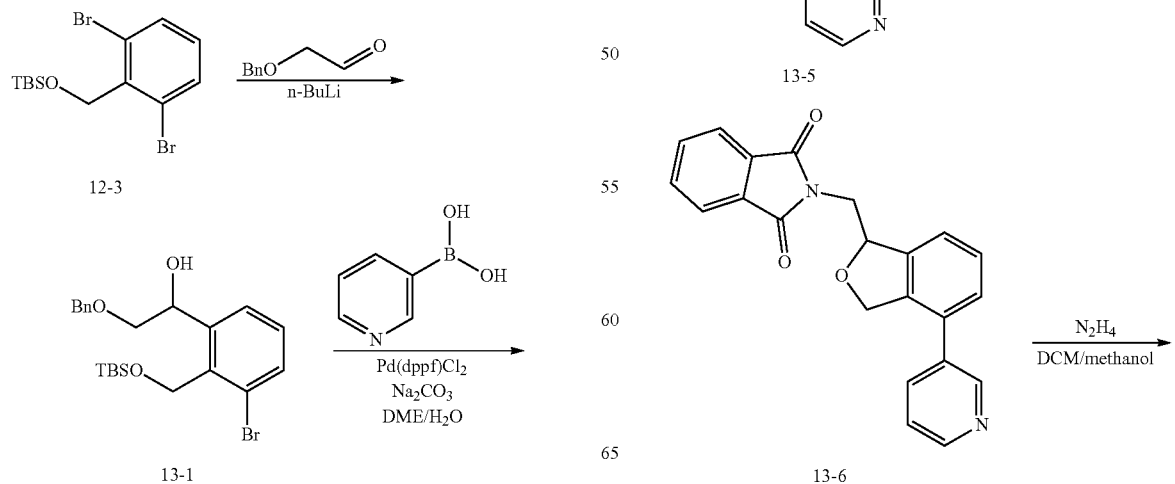

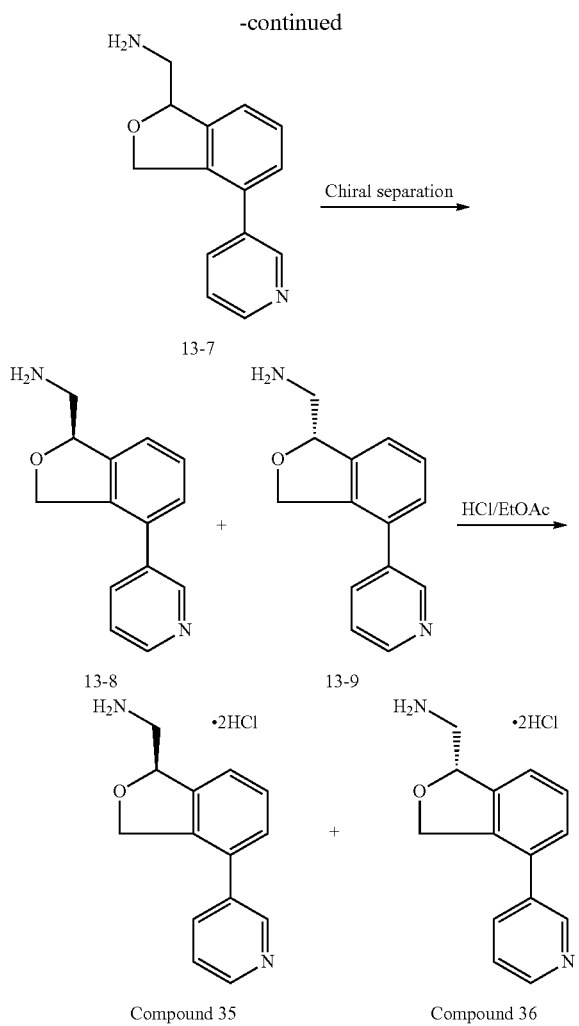

13-7

13-8    13-9

Compound 35    Compound 36

Synthesis of Compound 35 and Compound 36

2-(Benzyloxy)-1-(3-bromo-2-(((tert-butyldimethylsilyl)oxy)methyl)phenyl)ethanol (13-1)

To a solution of tert-butyl((2,6-dibromobenzyl)oxy)dimethylsilane (prepared as described previously in Scheme 12) (9 g, 23.6 mmol) in diethyl ether (100 mL) at −78° C. was added n-butyllithium (2.5 M, 9.44 mL, 23.6 mmol) dropwise over a period of 5 min. The reaction was stirred at −78° C. for 30 min. A solution of 2-(benzyloxy)acetaldehyde (3.88 g, 25.9 mmol) in diethyl ether (5 mL) was added dropwise over a period of 5 min at −78° C. The reaction was stirred at −78° C. for 6 h. Upon completion, the reaction was carefully quenched with water at 0° C., and extracted with ethyl acetate (3×100 mL). The combined organics were dried over anhydrous sodium sulfate, and concentrated in vacuo to dryness. Purification by silica column chromatography (eluted from petroleum ether to petroleum ether/ethyl acetate=5/1) gave 2-(benzyloxy)-1-(3-bromo-2-(((tert-butyldimethylsilyl)oxy)methyl)phenyl) ethanol as a white solid (5.8 g, yield: 54.7%), MS (ESI): m/z=473 [M+Na]+.

2-(Benzyloxy)-1-(2-(((tert-butyldimethylsilyl)oxy)methyl)-3-(pyridin-3-yl)phenyl)ethanol (13-2)

To a solution of 2-(benzyloxy)-1-(3-bromo-2-(((tert-butyldimethylsilyl)oxy) methyl)phenyl)ethanol (6.6 g, 14.6 mmol) in 1, 2-dimethoxyethane/water=5/1 (180 mL) was added sodium carbonate (3.09 g, 29.2 mmol), pyridin-3-ylboronic acid (2.69 g, 21.9 mmol) and 1,1'-Bis(diphenylphosphino)ferrocene-palladium(II)dichloride dichloromethane complex (596 mg, 730 μmol). The reaction was stirred at 80° C. for 16 h. Upon completion, the reaction was filtered through celite and extracted with ethyl acetate (3×100 mL). The combined organic layers were dried over anhydrous sodium sulfate, and concentrated to dryness in vacuo. Purification by silica column chromatography (eluted from petroleum ether to petroleum ether/ethyl acetate=2/1) to give 2-(benzyloxy)-1-(2-(((tert-butyldimethylsilyl)oxy)methyl)-3-(pyridin-3-yl)phenyl)ethanol as a yellow oil (5.4 g, yield: 82.3%), MS (ESI)=m/z 450 [M+H]+.

2-(Benzyloxy)-1-(2-(hydroxymethyl)-3-(pyridin-3-yl)phenyl)ethanol (13-3)

To a solution of 2-(benzyloxy)-1-(2-(((tert-butyldimethylsilyl)oxy)methyl)-3-(pyridin-3-yl)phenyl)ethanol (5.4 g, 12.0 mmol) in tetrahydrofuran (50 mL) was added tetrabutylammonium fluoride (3.13 g, 12.0 mmol). The reaction was stirred at ambient temperature for 3 h. Upon completion, the reaction was concentrated to give a residue which was diluted with ethyl acetate (200 mL), neutralized with saturated sodium bicarbonate solution, washed with brine (4×50 mL), dried over anhydrous sodium sulfate and concentrated. The crude product was purified by silica gel chromatography (eluted with dichloromethane/methanol from 1000/1 to 40/1) to give 2-(benzyloxy)-1-(2-(hydroxymethyl)-3-(pyridin-3-yl)phenyl)ethanol as a yellow solid (3 g, yield: 74.6%), MS (ESI): m/z=336 [M+H]+.

2-(Benzyloxy)-1-(2-(hydroxymethyl)-3-(pyridin-3-yl)phenyl)ethanol (13-4)

To a solution of 2-(benzyloxy)-1-(2-(hydroxymethyl)-3-(pyridin-3-yl)phenyl)ethanol (2.6 g, 7.75 mmol) in tetrahydrofuran (40 mL) at −78° C. was added n-butyllithium (3.46 mL, 2.5 M, 8.52 mmol) dropwise over a period of 5 min. The reaction was stirred at −78° C. for 30 min. A solution of 4-methylbenzene-1-sulfonyl chloride (1.62 g, 8.52 mmol) in tetrahydrofuran (10 mL) was added dropwise over a period of 5 mins. The reaction was stirred at −78° C. for 1 h. Additional n-butyllithium (3.71 mL, 2.5 M, 9.29 mmol) was added dropwise over a period of 5 mins. The reaction was stirred at 0° C. for 3 h. Upon completion, the reaction was quenched with water (150 mL) at 0° C., extracted with ethyl acetate (3, 150 mL), dried over anhydrous sodium sulfate and concentrated to dryness. The crude product was purified by silica gel chromatography (eluted with dichloromethane/methanol from 100/1 to 30/1) to give 3-(1-((benzyloxy)methyl)-1,3-dihydroisobenzofuran-4-yl)pyridine as a yellow oil (1.1 g, yield: 44.8%), MS (ESI): m/z=318 [M+H]+.

(4-(Pyridin-3-yl)-1,3-dihydroisobenzofuran-1-yl)methanol (13-5)

To a solution of 3-(1-((benzyloxy)methyl)-1,3-dihydroisobenzofuran-4-yl)pyridine (1.1 g, 3.46 mmol) in dichloromethane (50 mL) at 0° C. was added trifluoromethanesulfonic acid (2.77 g, 20.7 mmol). The reaction was stirred at 0° C. for 1 h. Upon completion, the reaction was neutralized with saturated sodium bicarbonate solution, extracted with dichloromethane (3×100 mL) and dried over anhydrous sodium sulfate. Filtration gave a residue which was purified by Prep-TLC (eluted with dichloromethane/ methanol=20/1) to give (4-(pyridin-3-yl)-1,3-dihydroisobenzofuran-1-yl)methanol as a yellow oil (550 mg, yield: 69.9%). MS (ESI): m/z=228 [M+H]+.

2-((4-(Pyridin-3-yl)-1,3-dihydroisobenzofuran-1-yl)methyl)isoindoline-1,3-dione (13-6)

To a solution of (4-(pyridin-3-yl)-1,3-dihydroisobenzofuran-1-yl)methanol (450 mg, 1.98 mmol) in dichloromethane (25 mL) under nitrogen atmosphere was added isoindoline-1,3-dione (407 mg, 2.77 mmol), triphenylphosphine (776 mg, 2.96 mmol) and diethyl azodicarboxylate (515 mg, 2.96 mmol). The reaction was stirred at ambient temperature under nitrogen atmosphere for 3 h. Upon completion, the reaction was diluted with water (50 mL), extracted with dichloromethane (3×50 mL) and dried over anhydrous sodium sulfate. Concentration in vacuo gave a residue that was recrystallized with methanol to give 2-((4-(pyridin-3-yl)-1,3-dihydroisobenzofuran-1-yl)methyl)isoindoline-1,3-dione as a white solid (460 mg, yield: 65%), MS (ESI): m/z=357 [M+H]+.

4-(Pyridin-3-yl)-1,3-dihydroisobenzofuran-1-yl)methanamine (13-7)

To a solution of 2-((4-(pyridin-3-yl)-1,3-dihydroisobenzofuran-1-yl)methyl) isoindoline-1,3-dione (760 mg, 2.13 mmol) in dichloromethane/methanol=1/1 (100 mL) was added hydrazine hydrate (80%, 662 mg, 10.6 mmol). The reaction mixture was heated to 60° C. and stirred for 16 h. Upon completion, the reaction mixture was cooled to rt and the white precipitate that formed was filtered and washed with dichloromethane (100 mL). The filtrate was concentrated in vacuo, re-dissolved in dichloromethane (200 mL) and filtered again and the filtrate was concentrated in vacuo. The crude product was purified by reverse silica gel chromatography (eluted with acetonitrile in water from 0% to 20%, 0.1% ammonium hydroxide in water) to give (4-(pyridin-3-yl)-1,3-dihydroisobenzofuran-1-yl)methanamine as a yellow oil (200 mg, yield: 41.5%), MS (ESI): m/z=227 [M+H]+.

(R)-(4-(Pyridin-3-yl)-1,3-dihydroisobenzofuran-1-yl)methanamine (13-8) and (S)-(4-(pyridin-3-yl)-1,3-dihydroisobenzofuran-1-yl)methanamine (13-9)

Racemic (4-(pyridin-3-yl)-1,3-dihydroisobenzofuran-1-yl)methanamine (200 mg, 883 μmol) was charged to a Chiral HPLC column (Co-Solvent: MeOH (0.2% Methanol Ammonia): Column: AD-H (4.6*250 mm, 5 um)) and separated to give (R)-(4-(pyridin-3-yl)-1,3-dihydroisobenzofuran-1-yl)methanamine as yellow oil (95 mg, yield: 47.7%), ee: 95% and (S)-(4-(pyridin-3-yl)-1,3-dihydroisobenzofuran-1-yl)methanamine as yellow oil (95 mg, yield: 47.7%), ee: 96%.

(R)-(4-(Pyridin-3-yl)-1,3-dihydroisobenzofuran-1-yl)methanamine hydrochloride (Compound 35)

(R)-(4-(Pyridin-3-yl)-1,3-dihydroisobenzofuran-1-yl)methanamine (95 mg, 419 μmol) was dissolved in ethyl acetate (10 mL). 3 M HCl/ethyl acetate (2 mL) was added, and the reaction was stirred at ambient temperature for 5 min. Upon completion, the reaction was concentrated in vacuo to give a residue which was washed with (petroleum ether/ethyl acetate=50/1, 50 mL) to give the desired product as a white solid (76 mg, yield: 59.4%), MS (ESI): m/z=227 [M+H]+. 1HNMR (400 MHz, CD₃OD): δ 9.70 (s, 1H), 8.91-8.93 (d, J=4.2 Hz, 1H), 8.77-8.79 (m, 1H), 8.20-8.24 (m, 1H), 7.58-7.67 (m, 3H), 5.57-5.59 (m, 1H), 5.31-5.43 (m, 2H), 3.52-3.56 (dd, J1=4.0 Hz, J2=13.6 Hz, 1H), 3.22-3.27 (m, 1H).

(S)-(4-(Pyridin-3-yl)-1,3-dihydroisobenzofuran-1-yl)methanamine hydrochloride (Compound 36)

(S)-(4-(Pyridin-3-yl)-1,3-dihydroisobenzofuran-1-yl)methanamine (95 mg, 419 μmol) was dissolved in ethyl acetate (10 mL). 3M HCl/ethyl acetate (2 mL) was added, and the reaction was stirred at ambient temperature for 5 min. Upon completion, the reaction was concentrated in vacuo to give a residue which was washed with (petroleum ether/ethyl acetate=50/1, 50 mL) to give the desired product as a white solid (76 mg, yield: 61.2%), MS (ESI): m/z=227 [M+H]+. 1HNMR (400 MHz, CD₃OD): δ 8.86-8.87 (d, J=2.0 Hz, 1H), 8.74-8.76 (dd, J1=5.2 Hz, J2=1.2 Hz, 1H), 8.37-8.40 (m, 1H), 7.88-7.91 (m, 1H), 7.56-7.61 (m, 3H), 5.55-5.57 (m, 1H), 5.28-5.38 (m, 2H), 3.49-3.54 (m, 1H), 3.21-3.27 (m, 1H).

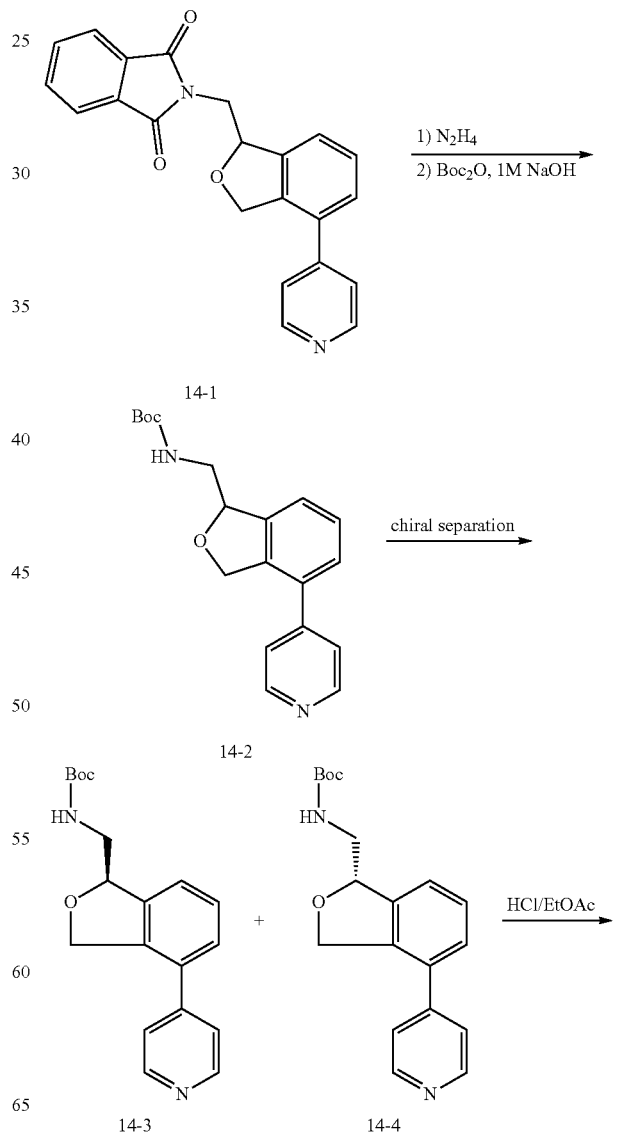

Scheme 14

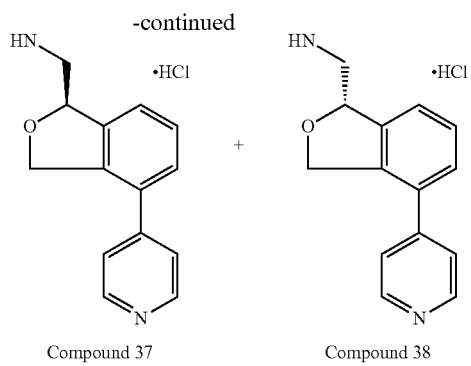

Compound 37        Compound 38

Synthesis of Compound 37 and Compound 38 tert-Butyl (4-(pyridin-4-yl)-1,3-dihydroisobenzofuran-1-yl)methylcarbamate (14-2)

To a solution of 2-((4-(pyridin-4-yl)-1,3-dihydroisobenzofuran-1-yl)methyl) isoindoline-1,3-dione (14-1) (1.26 g, 3.53 mmol) (prepared using the procedure described in Scheme 13 substituting pyridin-4-ylboronic acid for pyridin-3-ylboronic acid) in DCM/EtOH=1/1 (100 mL) was added diazene (1.13 g, 35.3 mmol). The reaction was stirred at 80° C. for 16 h. Then the reaction mixture was cooled to rt and the white precipitate that formed was filtered. The precipitate was washed with dichloromethane (100 mL) and the filtrate was concentrated in vacuo. The residue was diluted with THF (50 mL) and water (50 mL), and 4 M NaOH (1.76 mL, 4 M, 7.06 mmol) and di-tertbutyl dicarbonate (1.54 g, 7.06 mmol) were added. The reaction was stirred at ambient temperature for 3 h. Upon completion, the mixture was extracted with ethyl acetate (3.50 mL), dried over anhydrous sodium sulfate and concentrated. The crude product was purified by silica gel chromatography (eluted from petroleum ether to petroleum ether/ethyl acetate=5/1) to give tert-butyl (4-(pyridin-4-yl)-1,3-dihydroisobenzofuran-1-yl) methylcarbamate as a yellow oil, 600 mg, Yield: 52.1%. MS (ESI) m/z=327 [M+H]+.

(R)-tert-Butyl (4-(pyridin-4-yl)-1,3-dihydroisobenzofuran-1-yl)methylcarbamate (14-3) and (S)-tert-butyl (4-(pyridin-4-yl)-1,3-dihydroisobenzofuran-1-yl)methylcarbamate (14-4)

Racemic tert-butyl ((4-(pyridin-4-yl)-1,3-dihydroisobenzofuran-1-yl)methyl)carbamate (540 mg, 1.65 mmol) was charged to a chiral column ((Column: AD-H (250*4.6 mm 5 um); Mobile Phase: MeOH (0.2% Methanol Ammonia)) and separated to give (R)-tert-butyl ((4-(pyridin-4-yl)-1,3-dihydroisobenzofuran-1-yl)methyl)carbamate as a yellow oil (250 mg, yield: 46.4%, 100% ee) and (S)-tert-butyl ((4-(pyridin-4-yl)-1,3-dihydroisobenzofuran-1-yl)methyl) carbamate as yellow oil (250 mg, yield: 46.4%, 99% ee).

rel-(R)-(4-(Pyridin-4-yl)-1,3-dihydroisobenzofuran-1-yl)methanamine hydrochloride salt (Compound 37)

To a solution of (R)-tert-butyl ((4-(pyridin-4-yl)-1,3-dihydroisobenzofuran-1-yl)methyl)carbamate (250 mg, 765 μmol) in ethyl acetate (10 mL) was added 3 M HCl/ethyl acetate (10.1 mL, 3 M. 30.5 mmol). The reaction was stirred at ambient temperature for 16 h. Then it was concentrated in vacuo to give a residue which was washed with ethyl acetate(50 mL) to give a yellow solid (88% purity). Purification by reverse silica gel chromatography (eluted with acetonitrile in water from 0% to 40%, 0.1% ammonium hydroxide in water) gave the desired product as a yellow oil which was re-dissolved in ethyl acetate (10 mL). 3 M HCl/ethyl acetate (0.5 mL) was added, and the reaction was stirred at ambient temperature for 5 min. The reaction was concentrated in vacuo to give a residue which was washed with ethyl acetate (10 mL) to give the desired product as a yellow solid (120 mg, 99% purity, yield: 52.6%), MS (ESI)=m/z 227 [M+H]+, 100% ee, 1HNMR (400 MHz, CD$_3$OD): δ 8.98 (d, J=6.8 Hz, 1H), 8.25 (d, J=6.8 Hz, 1H), 7.81-7.78 (m, 1H), 7.69-7.65 (m, 2H), 5.60-5.58 (m, 1H), 5.50-5.39 (m, 2H), 3.57-3.53 (m, 1H), 3.29-3.24 (m, 1H).

rel-(S)-(4-(Pyridin-4-yl)-1,3-dihydroisobenzofuran-1-yl)methanamine hydrochloride salt (Compound 38)

To a solution of (S)-tert-butyl ((4-(pyridin-4-yl)-1,3-dihydroisobenzofuran-1-yl)methyl)carbamate (250 mg, 765 μmol) in ethyl acetate (10 mL) was added 3 M HCl/ethyl acetate (10.1 mL, 3 M, 30.5 mmol). The reaction was stirred at ambient temperature for 16 h. The reaction was concentrated in vacuo to give a yellow solid. Purification by reverse phase chromatography (eluted with acetonitrile in water from 0% to 40%, 0.1% ammonium hydroxide in water) afforded the desired product which was dissolved in ethyl acetate (10 mL). 3 M HCl/ethyl acetate (0.5 mL) was added, and the reaction was stirred at ambient temperature for 5 min. The reaction was concentrated in vacuo to give a residue which was washed with petroleum ether/ethyl acetate (50/1, 10 mL) to give the desired product as a yellow solid (46 mg, 99% purity, yield: 19.9%), MS (ESI)=m/z 227 [M+H]+, 100% ee, 1HNMR (400 MHz, CD$_3$OD): 1H NMR δ 8.96 (d, J=6.8 Hz, 1H), 8.26 (d, J=6.8 Hz, 1H), 7.82-7.79 (m, 1H), 7.69-7.66 (m, 2H), 5.61-5.59 (m, 1H), 5.52-5.39 (m, 2H), 3.58-3.54 (m, 1H), 3.30-3.25 (m, 1H).

Scheme 15

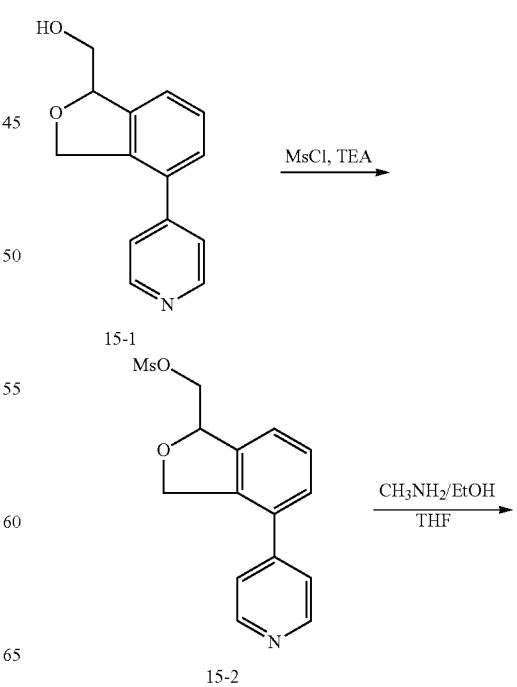

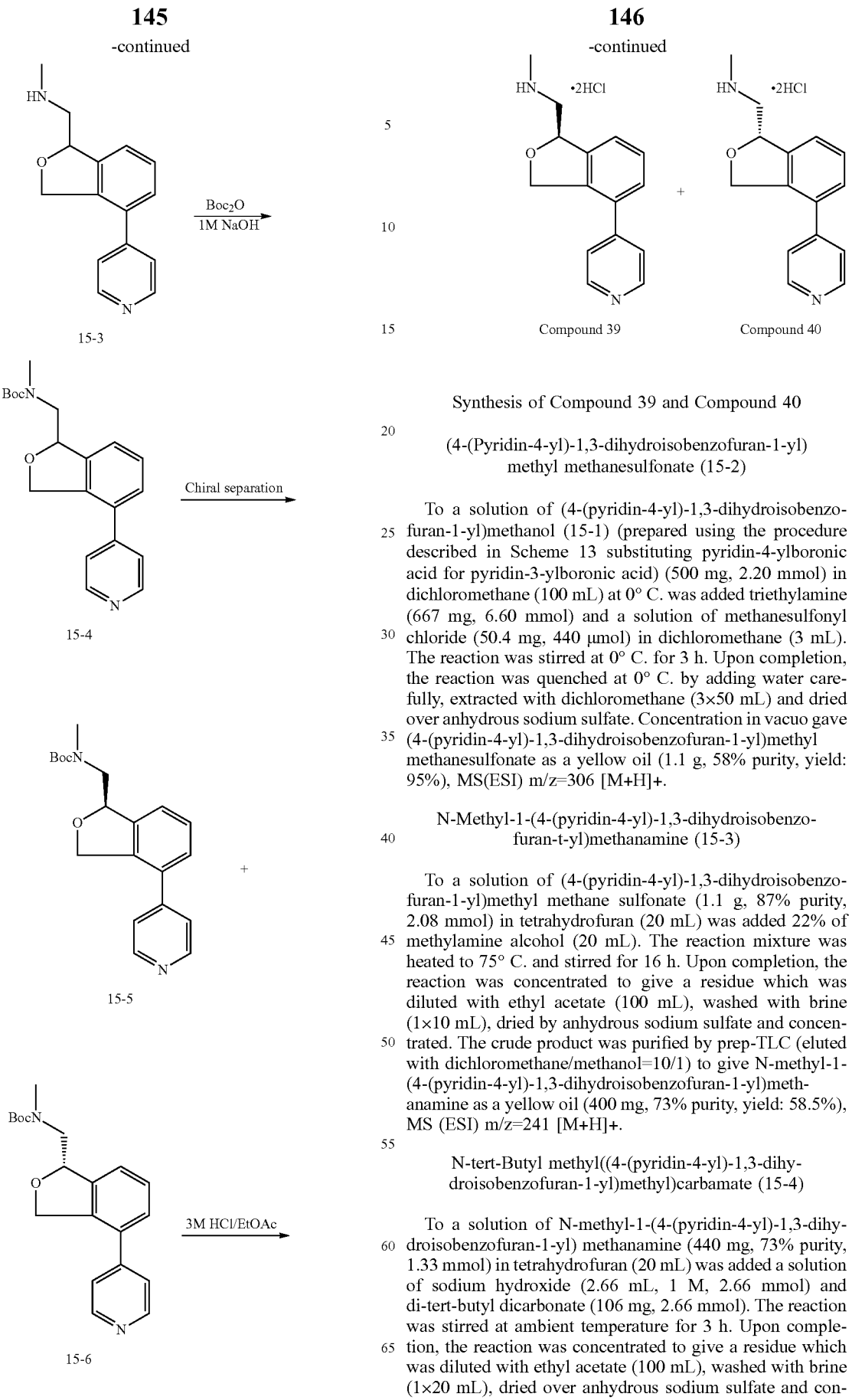

Compound 39   Compound 40

Synthesis of Compound 39 and Compound 40

(4-(Pyridin-4-yl)-1,3-dihydroisobenzofuran-1-yl)methyl methanesulfonate (15-2)

To a solution of (4-(pyridin-4-yl)-1,3-dihydroisobenzofuran-1-yl)methanol (15-1) (prepared using the procedure described in Scheme 13 substituting pyridin-4-ylboronic acid for pyridin-3-ylboronic acid) (500 mg, 2.20 mmol) in dichloromethane (100 mL) at 0° C. was added triethylamine (667 mg, 6.60 mmol) and a solution of methanesulfonyl chloride (50.4 mg, 440 µmol) in dichloromethane (3 mL). The reaction was stirred at 0° C. for 3 h. Upon completion, the reaction was quenched at 0° C. by adding water carefully, extracted with dichloromethane (3×50 mL) and dried over anhydrous sodium sulfate. Concentration in vacuo gave (4-(pyridin-4-yl)-1,3-dihydroisobenzofuran-1-yl)methyl methanesulfonate as a yellow oil (1.1 g, 58% purity, yield: 95%), MS(ESI) m/z=306 [M+H]+.

N-Methyl-1-(4-(pyridin-4-yl)-1,3-dihydroisobenzofuran-t-yl)methanamine (15-3)

To a solution of (4-(pyridin-4-yl)-1,3-dihydroisobenzofuran-1-yl)methyl methane sulfonate (1.1 g, 87% purity, 2.08 mmol) in tetrahydrofuran (20 mL) was added 22% of methylamine alcohol (20 mL). The reaction mixture was heated to 75° C. and stirred for 16 h. Upon completion, the reaction was concentrated to give a residue which was diluted with ethyl acetate (100 mL), washed with brine (1×10 mL), dried by anhydrous sodium sulfate and concentrated. The crude product was purified by prep-TLC (eluted with dichloromethane/methanol=10/1) to give N-methyl-1-(4-(pyridin-4-yl)-1,3-dihydroisobenzofuran-1-yl)methanamine as a yellow oil (400 mg, 73% purity, yield: 58.5%), MS (ESI) m/z=241 [M+H]+.

N-tert-Butyl methyl((4-(pyridin-4-yl)-1,3-dihydroisobenzofuran-1-yl)methyl)carbamate (15-4)

To a solution of N-methyl-1-(4-(pyridin-4-yl)-1,3-dihydroisobenzofuran-1-yl) methanamine (440 mg, 73% purity, 1.33 mmol) in tetrahydrofuran (20 mL) was added a solution of sodium hydroxide (2.66 mL, 1 M, 2.66 mmol) and di-tert-butyl dicarbonate (106 mg, 2.66 mmol). The reaction was stirred at ambient temperature for 3 h. Upon completion, the reaction was concentrated to give a residue which was diluted with ethyl acetate (100 mL), washed with brine (1×20 mL), dried over anhydrous sodium sulfate and concentrated. The crude product was purified by Prep-TLC (eluted with petroleum ether/ethyl acetate=5/3) to give tert-butyl methyl((4-(pyridin-4-yl)-1,3-dihydroisobenzofuran-1-yl)methyl)carbamate as a yellow oil (400 mg, yield: 88.4%), MS (ESI)=m/z 341 [M+H]+.

(R)-tert-Butyl methyl((4-(pyridin-4-yl)-1,3-dihydroisobenzofuran-1-yl)methyl)carbamate (15-5) and (S)-tert-butyl methyl((4-(pyridin-4-yl)-1,3-dihydroisobenzofuran-1-yl)methyl)carbamate (15-6)

Racemic tert-butyl methyl((4-(pyridin-4-yl)-1,3-dihydroisobenzofuran-1-yl)methyl)carbamate (400 mg, 1.17 mmol) was charged to a chiral column (Column: AY-H (250*4.6 mm 5 um); Mobile Phase: MeOH (0.2% Methanol Ammonia)) and separated to give (R)-tert-butylmethyl((4-(pyridin-4-yl)-1,3-dihydroisobenzofuran-1-yl)methyl)carbamate as a yellow oil (170 mg, yield: 42.7%, 100% ee) and (S)-tert-butylmethyl((4-(pyridin-4-yl)-1,3-dihydroisobenzofuran-1-yl)methyl)carbamate as yellow oil (175 mg, yield: 43.9%, 99% ee).

(R)—N-Methyl-1-(4-(pyridin-4-yl)-1,3-dihydroisobenzofuran-1-yl)methanamine hydrochloride salt (Compound 39)

To a solution of rel-(R)-tert-butyl methyl((4-(pyridin-4-yl)-1,3-dihydroisobenzofuran-1-yl)methyl)carbamate (170 mg, 499 μmol) in ethyl acetate (20 mL) was added 3 M HCl/ethyl acetate (6.63 mL, 3 M, 19.9 mmol). The reaction was stirred at ambient temperature for 16 h. Upon completion, the reaction was concentrated in vacuo to give a residue which was washed with (petroleum ether/ethyl acetate=50/1, 50 mL) to give the desired product as a yellow solid (150 mg, 98% purity, yield: 94.8%), MS (ESI): m/z 241 [M+H]+, 100% ee, 1H NMR δ 8.95 (d, J=6.8 Hz, 1H), 8.25 (d, J=6.8 Hz, 1H), 7.81-7.79 (m, 1H), 7.68-7.65 (m, 2H), 5.65-5.63 (m, 1H), 5.52-5.40 (m, 2H), 3.65-3.61 (m, 1H), 3.37-3.32 (m, 1H), 2.81 (s, 3H).

(S)—N-Methyl-1-(4-(pyridin-4-yl)-1,3-dihydroisobenzofuran-1-yl)methanamine hydrochloride salt (Compound 40)

To a solution of rel-(S)-tert-butyl methyl((4-(pyridin-4-yl)-1,3-dihydroisobenzofuran-1-yl)methyl)carbamate (170 mg, 499 μmol) in ethyl acetate (20 mL) was added 3 M HCl/ethyl acetate (726 mg, 6.63 mL, 3 M, 19.9 mmol). The reaction was stirred at ambient temperature for 16 h. Upon completion, the reaction was concentrated in vacuo to give a residue which was washed with (petroleum ether/ethyl acetate=50/1, 50 mL) to give the desired product as a yellow solid (152 mg, 99% purity, yield: 95.4%), MS (ESI): m/z 241 [M+H]+, 100% ee, 1H NMR δ 8.96 (d, J=6.8 Hz, 1H), 8.26 (d, J=6.8 Hz, 1H), 7.82-7.78 (m, 1H), 7.67-7.66 (m, 2H), 5.66-5.64 (m, 1H), 5.53-5.40 (m, 2H), 3.65-3.61 (m, 1H), 3.38-3.32 (m, 1H), 2.82 (s, 3H).

Scheme 16

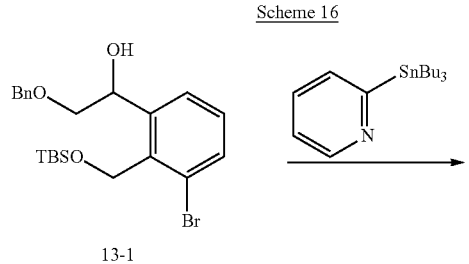

13-1

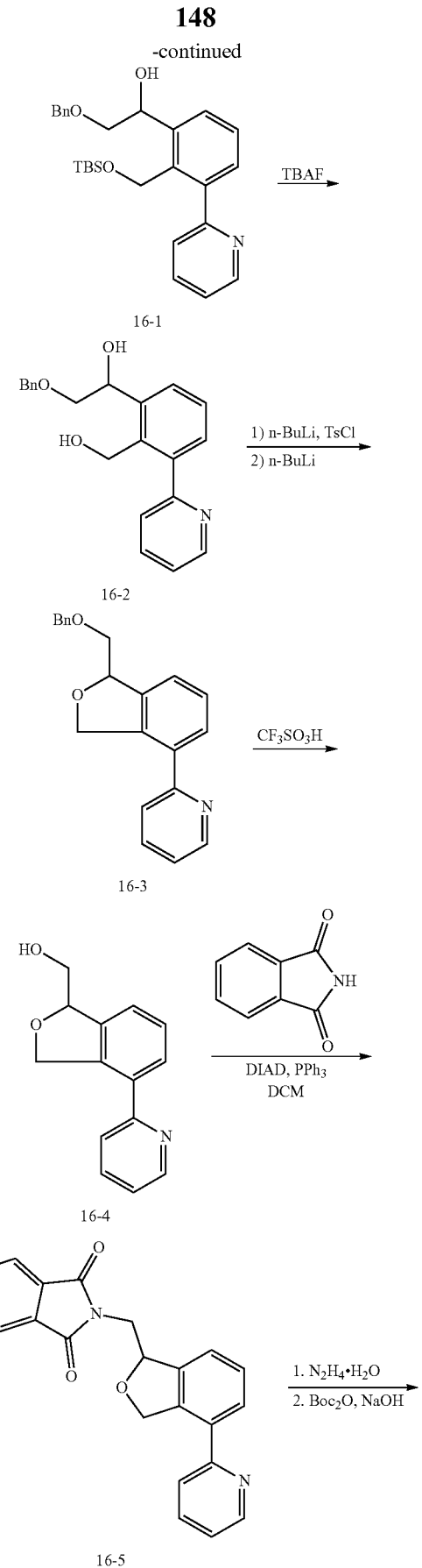

-continued

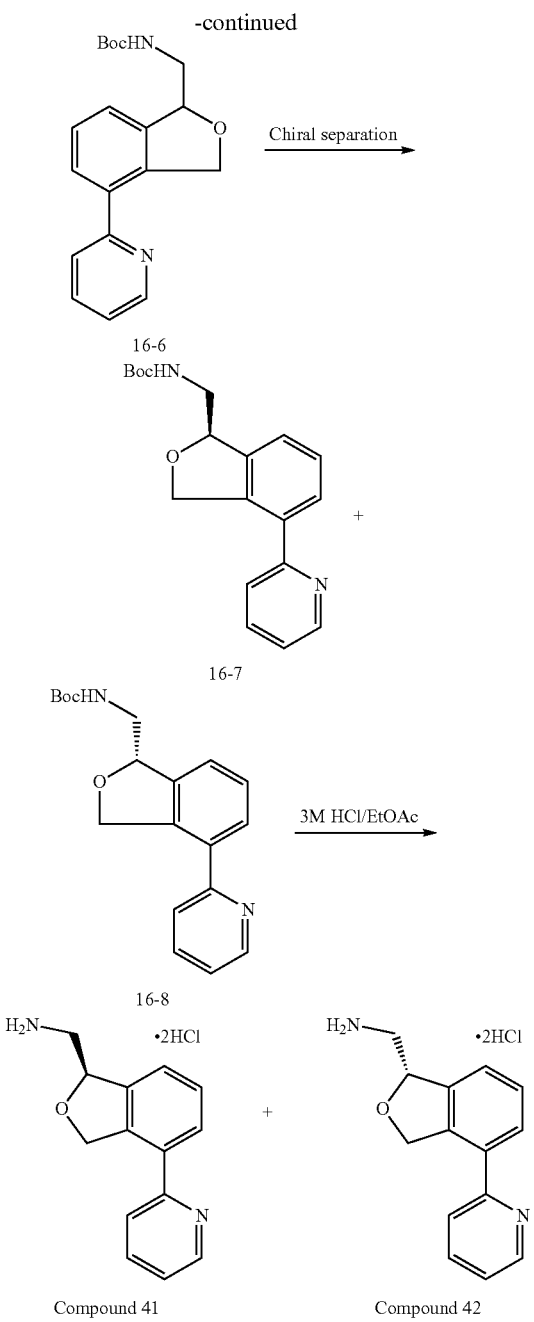

Synthesis of Compound 41 and Compound 42

2-(Benzyloxy)-1-(2-(((tert-butyldimethylsilyl)oxy)methyl)-3-(pyridin-2-yl)phenyl)ethanol (16-1)

To a solution of 2-(benzyloxy)-1-(3-bromo-2-(((tert-butyldimethylsilyl)oxy)methyl)phenyl)ethanol (prepared as described previously in Scheme 13) (4.5 g, 9.96 mmol) in 1,4-dioxane (50 mL) was added lithium chloride (843 mg, 19.9 mmol), 2-(tributylstannyl)pyridine (5.48 g, 14.9 mmol) and tetrakis(triphenylphosphane) palladium (575 mg, 498 µmol). The reaction was stirred at 110° C. under nitrogen atmosphere for 48 h. Upon completion, the reaction was filtered through celite and concentrated in vacuo to give dryness. The residue was diluted with water (100 mL), extracted with ethyl acetate (3×100 mL), dried over anhydrous sodium sulfate and concentrated in vacuo to dryness. The residue was purified by silica gel chromatography (eluted from petroleum ether to petroleum ether/ethyl acetate=1/1) to give 2-(benzyloxy)-1-(2-(((tert-butyldimethylsilyl)oxy)methyl)-3-(pyridin-2-yl)phenyl)ethanol as a yellow oil, 3.5 g, Yield: 78.2%, MS (ESI): m/z 450 [M+H]+.

2-(Benzyloxy)-1-(2-(hydroxymethyl)-3-(pyridin-2-yl)phenyl)ethanol (16-2)

To a solution of 2-(benzyloxy)-1-(2-(((tert-butyldimethylsilyl)oxy)methyl)-3-(pyridin-2-yl)phenyl)ethanol (5.4 g, 12.0 mmol) in tetrahydrofuran (50 mL) was added tetrabutylammonium fluoride (3.13 g, 12.0 mmol). The reaction was stirred at ambient temperature for 3 h. Upon completion, the reaction was concentrated to give a residue which was diluted with ethyl acetate (200 mL), neutralized with saturated sodium bicarbonate solution, washed with brine (4×50 mL) and dried over anhydrous sodium sulfate. Filtration and concentration to dryness afforded the crude product, which was purified by silica gel chromatography (eluted with dichloromethane/methanol from 1000/1 to 40/1) to give 2-(benzyloxy)-1-(2-(hydroxymethyl)-3-(pyridin-2-yl)phenyl)ethanol as a yellow oil, 3 g, Yield: 74.6%, MS (ESI): m/z 336 [M+H]+.

2-(Benzyloxy)-1-(2-(hydroxymethyl)-3-(pyridin-2-yl)phenyl)ethanol (16-3)

To a solution of 2-(benzyloxy)-1-(2-(hydroxymethyl)-3-(pyridin-2-yl)phenyl)ethanol (2.6 g, 7.75 mmol) in tetrahydrofuran (40 mL) at −78° C. was added n-butyllithium (3.46 mL, 2.5 M, 8.52 mmol) dropwise over a period of 5 min. The reaction was stirred at −78° C. for 30 min. A solution of 4-methylbenzene-1-sulfonyl chloride (1.62 g, 8.52 mmol) in tetrahydrofuran (10 mL) was added dropwise over a period of 5 min. The reaction was stirred at −78° C. for 1 h. An additional equivalent of n-butyllithium (3.71 mL, 2.5 M, 9.29 mmol) was added dropwise over a period of 5 min. The reaction was stirred at 0° C. for 3 h. Upon completion, the reaction was quenched with water (150 mL) at 0° C., extracted with ethyl acetate (3×150 mL), dried over anhydrous sodium sulfate and concentrated to dryness in vacuo. The crude product was purified by silica gel chromatography (eluted with dichloromethane/methanol from 1000/1 to 30/1) to give 2-(1-((benzyloxy)methyl)-1,3-dihydroisobenzofuran-4-yl)pyridine as a yellow oil (1.1 g, Yield: 44.8%. MS (ESI): m/z 318 [M+H]+.

(4-(Pyridin-2-yl)-1,3-dihydroisobenzofuran-1-yl)methanol (16-4)

To a solution of 2-(1-((benzyloxy)methyl)-1,3-dihydroisobenzofuran-4-yl)pyridine (2.2 g, 6.93 mmol) in dichloromethane (25 mL) at 0° C. was added trifluoromethanesulfonic acid (2.31 g, 15.4 mmol) dropwise. The reaction was stirred at 0° C. for 1 h. Upon completion, the reaction was neutralized with saturated sodium bicarbonate solution, extracted with dichloromethane (3×100 mL), dried over anhydrous sodium sulfate and concentrated to dryness. Purification by Prep-TLC (eluted with dichloromethane/methanol=20/1) gave (4-(pyridin-2-yl)-1,3-dihydroisobenzofuran-1-yl)methanol as a yellow oil, 1 g. Yield: 63.6%, MS (ESI): m/z 228 [M+H]+.

2-((4-(Pyridin-2-yl)-1,3-dihydroisobenzofuran-1-yl)methyl)isoindoline-1,3-dione (16-5)

To a solution of (4-(pyridin-2-yl)-1,3-dihydroisobenzofuran-1-yl)methanol (900 mg, 3.96 mmol) in dichloromethane (50 mL) at 0° C. was added isoindoline-1,3-dione (698 mg, 4.75 mmol), triphenylphosphine (1.34 g, 5.14 mmol) and (E)-diisopropyl azodicarboxylate (1.19 g, 5.93 mmol). The reaction was stirred at ambient temperature under nitrogen atmosphere for 16 h. Upon completion, the reaction was diluted with water (50 mL), extracted with dichloromethane (3×50 mL), dried over anhydrous sodium sulfate and concentrated to dryness in vacuo. The residue was recrystallized with methanol to give 24(4-(pyridin-2-yl)-1,3-dihydroisobenzofuran-1-yl)methyl)isoindoline-1,3-dione as a yellow solid, 1 g, Yield: 70.9%, MS (ESI): m/z 357 [M+H]+.

4-(Pyridin-2-yl)-1,3-dihydroisobenzofuran-1-yl)methanamine (16-6)

To a solution of 2-((4-(pyridin-2-yl)-1,3-dihydroisobenzofuran-1-yl)methyl)isoindoline-1,3-dione (1.26 g, 3.53 mmol) in DCM/EtOH=1/1 (100 mL) was added diazene (1.13 g, 35.3 mmol). The reaction was stirred at 80° C. for 16 h. Upon completion, the reaction mixture was cooled to rt and the white precipitate that formed was filtered off. The precipitate was washed with dichloromethane (100 mL) and the filtrate was concentrated in vacuo. The precipitate was re-dissolved in THF (50 mL) and water (50 mL). 4 M NaOH (1.76 mL, 4 M, 7.06 mmol) and di-tert-butyl dicarbonate (1.54 g, 7.06 mmol) were added, and the reaction was stirred at ambient temperature for 3 h. Upon completion, the mixture was extracted with ethyl acetate (3×50 mL), dried over anhydrous sodium sulfate and concentrated to dryness. The crude product was purified by silica gel chromatography (eluted from petroleum ether to petroleum ether/ethyl acetate=5/1) to give tert-butyl ((4-(pyridin-2-yl)-1,3-dihydroisobenzofuran-1-yl)methyl)carbamate as a yellow oil, 600 mg, Yield: 52.1%, MS (ESI): n, 327 [M+H]+.

rel-(R)-tert-Butyl ((4-(pyridin-2-yl)-1,3-dihydroisobenzofuran-1-yl)methyl)carbamate (16-7) and rel-(S)-tert-butyl ((4-(pyridin-2-yl)-1,3-dihydroisobenzofuran-1-yl)methyl)carbamate (16-8)

Racemic tert-butyl ((4-(pyridin-2-yl)-1,3-dihydroisobenzofuran-1-yl)methyl)carbamate (450 mg, 1.37 mmol) was charged to a chiral column (SFC-80 (Thar, Waters), column: OJ 20×250 mm, 10 um (Daicel), column temperature: 35° C., mobile phase: CO2/MeOH (0.2% Methanol Ammonia) =90/10, flow rate: 70 g/min, back pressure: 100 bar, detection wavelength: 254 nm, cycle time: 4.0 min) and separated to give rel-(R)-tert-butyl ((4-(pyridin-2-yl)-1,3-dihydroisobenzofuran-1-yl)methyl)carbamate as a yellow oil, 190 mg, Yield: 42.2%, retention time: 3.63 min, 100% ee, P1 and rel-(S)-tert-butyl ((4-(pyridin-2-yl)-1,3-dihydroisobenzofuran-1-yl)methyl)carbamate as a yellow oil, 150 mg, Yield: 33.3%, retention time: 4.33 min, 100% ee, P2.

(R)-(4-(Pyridin-2-yl)-1,3-dihydroisobenzofuran-1-yl)methanamine (Compound 41)

To a solution of rel-(R)-tert-butyl ((4-(pyridin-2-yl)-1,3-dihydroisobenzofuran-1-yl)methyl)carbamate (190 mg, 582 µmol) in ethyl acetate (5 mL) was added 3 M HCl/EtOAc (5.8 mL, 3 M, 17.4 mmol). The reaction was stirred at ambient temperature for 16 h. Upon completion, the reaction was concentrated in vacuo to give a residue which was washed with ethyl acetate (50 mL) to give the desired product as a white solid, 70 mg, Yield: 58.3%. MS (ESI): m/z 227 [M+H]+, retention time: 17.491 min, 100% ee. 1H NMR (400 MHz, CD$_3$OD): δ 8.92-9.94 (d, J=5.6 Hz, 1H), 8.69-8.72 (t, J=8.0 Hz, 1H), 8.22-8.24 (d, J=8.0 Hz, 1H), 8.08-8.11 (t, J=6.4 Hz, 1H), 7.80-7.82 (m, 1H), 7.69-7.72 (m, 2H), 5.60-5.62 (d, J=6.8 Hz, 1H), 5.36-5.50 (m, 2H), 3.55-3.58 (m, 1H), 3.23-3.29 (m, 1H).

(S)-(4-(Pyridin-2-yl)-1,3-dihydroisobenzofuran-1-yl)methanamine (Compound 42)

To a solution of rel-(S)-tert-butyl ((4-(pyridin-2-yl)-1,3-dihydroisobenzofuran-1-yl)methyl)carbamate (150 mg, 459 µmol) in ethyl acetate (5 mL) was added 3 M HCl/EtOAc (4.56 mL, 3 M, 13.7 mmol). The reaction was stirred at ambient temperature for 16 h. Upon completion, the reaction was concentrated in vacuo to give a residue which was washed with ethyl acetate (50 mL) to give the desired product as a yellow solid, 80 mg, Yield: 58.3%. MS (ESI): m/z 227 [M+H]+, retention time: 25.176 min, 99% ee. 1H NMR (400 MHz, CD$_3$OD): δ 8.92-9.94 (d, J=5.6 Hz, 1H), 8.69-8.72 (t, J=8.0 Hz, 1H), 8.22-8.24 (d, J=8.0 Hz, 1H), 8.08-8.11 (t, J=6.4 Hz, 1H), 7.80-7.82 (m, 1H), 7.69-7.72 (m, 2H), 5.60-5.62 (d, J=6.8 Hz, 1H), 5.36-5.50 (m, 2H), 3.55-3.58 (m, 1H), 3.23-3.29 (m, 1H).

Scheme 17

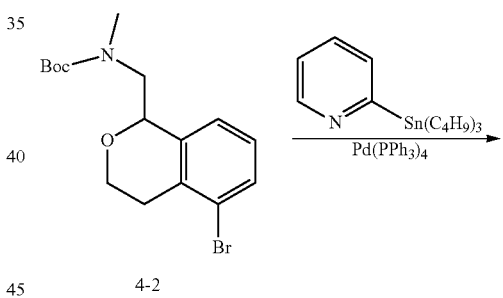

4-2

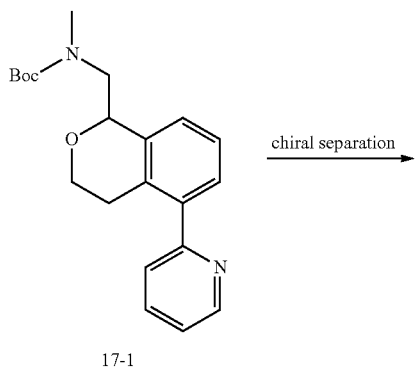

17-1

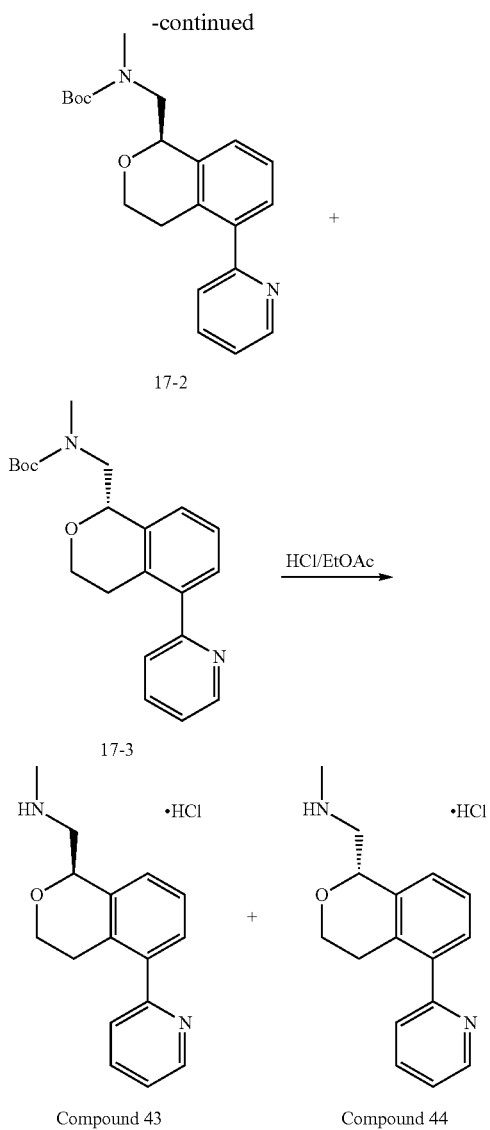

Synthesis of Compound 43 and Compound 44 tert-Butyl methyl((5-(pyridin-2-yl)isochroman-1-yl)methyl)carbamate (17-1)

To a solution of tert-butyl ((5-bromoisochroman-1-yl)methyl)(methyl)carbamate (4-2) (prepared as described previously in Scheme 4) (1 g, 2.80 mmol) in toluene (5 mL) was added 2-(tributylstannyl)pyridine (1.23 g, 3.35 mmol) and tetrakis(triphenylphosphane) palladium (323 mg, 280 µmol) and sodium carbonate (593 mg, 5.60 mmol). The reaction was stirred at 110° C. for 12 h. Upon completion, water (5 mL) was added to the reaction vessel and the resulting biphasic mixture was transferred to a separatory funnel. The layers were separated and the aqueous phase was washed with EtOAc (2×50 mL). The combined organics were dried over anhydrous $Na_2SO_4$, filtered and concentrated in vacuo. The resulting oil was purified by flash column chromatography (petroleum ether/EtOAc 20:1 to 10:1 to 5:1) to provide tert-butyl methyl((5-(pyridin-2-yl)isochroman-1-yl)methyl)carbamate (1 g, purity: 97%, Yield: 91.7%) as a colorless oil. MS (ESI): m/z 355 [M+H]+.

(R)-tert-Butyl methyl((5-(pyridin-2-yl)isochroman-1-yl)methyl)carbamate (17-2) and (S)-tert-butyl methyl((5-(pyridin-2-yl)isochroman-1-yl)methyl)carbamate (17-3)

Tert-butyl methyl((5-(pyridin-2-yl)isochroman-1-yl)methyl)carbamate (800 mg, 2.24 mmol) was charged to a chiral column (repetitive-SFC using AY-90 (4.6×250 mm 5 um), co-solvent: n-Hexane(0.1% DEA):EtOH (0.1% DEA) =90:10, column temperature: 40° C. flow rate: 1.0 mL/min. detection wavelength: 214 nm and cycle time: 22 min.) and separated into its enantiomers (R)-tert-butyl methyl((5-(pyridin-2-yl)isochroman-1-yl)methyl)carbamate and (S)-tert-butyl methyl((5-(pyridin-2-yl)isochroman-1-yl)methyl)carbamate. Each enantiomer was concentrated to dryness in vacuo. MS (ESI): m/z 355 [M+H]+, 17-2: purity: 98%, 200 mg colorless oil, yield: 50.1%; 17-3: purity: 98%, 200 mg colorless oil, yield: 50.0%.

rel-(R)—N-Methyl-1-(5-(pyridin-2-yl)isochroman-1-yl)methanamine hydrochloride salt (Compound 43)

A mixture of (R)-tert-butyl methyl((5-(pyridin-2-yl)isochroman-1-yl)methyl)carbamate (200 mg, 564 µmol) in TFA/DCM (1/2) (5 mL) was stirred overnight at rt. Upon completion, the reaction mixture was concentrated in vacuo to give a residue, which was suspended in aq $NaHCO_3$ solution and extracted with DCM (20 mL×2). The combined organic layers were dried and concentrated in vacuo to get the desired product as its free base (135 mg, purity: 100%, yield: 94.4%) as a colorless oil. MS (ESI): m/z 255 [M+H]+. rel-(R)—N-Methyl-1-(5-(pyridin-2-yl)isochroman-1-yl)methanamine (135 mg, 530 µmol) was re-dissolved in 3N HCl/EtOAc (2 mL) and stirred at r.t. for 15 mins. Upon completion, the mixture was evaporated in vacuo to get the crude product which was purified by recrystallization (with EtOAc) and dried in vacuo to get the desired product (125 mg, purity: 100%, ee %: 98%, yield: 72.1%) as a white solid. MS (ESI): m/z 255 [M+H]+. 1H NMR (400 MHz, methanol-d4): δ 8.97 (d, J=4.0 Hz, 1H), 8.78 (d, J=7.6 Hz, 1H), 8.25-8.18 (m, 2H), 7.60-7.57 (m, 3H), 5.28 (d, J=8.4 Hz, 1H), 4.24-4.19 (m, 1H), 3.87-3.71 (m, 2H), 3.44-3.33 (m, 1H), 3.10-3.06 (m, 1H)), 2.83 (s, 3H), 2.65-2.61 (m, 1H).

rel-(S)—N-Methyl-1-(5-(pyridin-2-yl)isochroman-1-yl)methanamine hydrochloride salt (Compound 44)

A mixture of (S)-tert-butyl methyl((5-(pyridin-2-yl)isochroman-1-yl)methyl)carbamate (200 mg, 564 µmol) in TFA/DCM (1/2) (5 mL) was stirred at r.t. overnight. The mixture was concentrated in vacuo to give a residue, which was suspended in saturated aq $NaHCO_3$ solution and extracted with DCM (20 mL×2). The combined organic layers were dried and concentrated in vacuo to get the desired product as its free base (137 mg, purity: 98%, yield: 95.8%) as a colorless oil. MS (ESI): m/z 255 [M+H]+. rel-(S)—N-methyl-1-(5-(pyridin-2-yl)isochroman-1-yl)methanamine (135 mg, 530 µmol) was re-dissolved in 3N HCl/EtOAc (2 mL) and stirred at room temperature for 15 mins. Upon completion, the mixture was evaporated to dryness in vacuo and triturated with EtOAc) to get the desired product as its hydrochloride salt. (129 mg, purity: 100%, ee %: 98%, yield: 74.4%) as a white solid. MS (ESI): m/z 255 [M+H]+. 1H NMR (400 MHz, methanol-d4): δ 8.97 (S, 1H), 8.78 (d, J=7.2 Hz, 1H), 8.26-8.17 (m, 2H), 7.61-7.57 (m, 3H), 5.29 (d, J=8.0 Hz, 1H), 4.24-4.19 (m, 1H), 3.87-3.72 (m, 2H), 3.45-3.33 (m, 1H), 3.10-3.07 (m, 1H)), 2.84 (s, 3H), 2.65-2.62 (m, 1H).

Synthesis of rel-(R)-(5-(pyridin-2-yl)isochroman-1-yl)methanamine hydrochloride (Compound 45) and rel-(S)-(5-(pyridin-2-yl)isochroman-1-yl)methanamine hydrochloride (Compound 46)

The title compounds were synthesized using the procedure described in Scheme 17, substituting tert-butyl ((5-bromoisochroman-1-yl)methyl)carbamate (7-2, prepared as described in Scheme 7) for tert-butyl ((5-bromoisochroman-1-yl)methyl)(methyl)carbamate, rel-(R)-(5-(Pyridin-2-yl)isochroman-1-yl)methanamine hydrochloride was obtained as a white solid (95 mg, purity: 100%, ee %: 1000%, yield: 73%). MS (ESI): m/z 241 [M+H]+. 1H NMR (400 MHz, methanol-d4): δ 8.97 (d, J=5.6 Hz, 1H), 8.80-8.74 (m, 1H), 8.25-8.16 (m, 2H), 7.62-7.57 (m, 3H), 5.21-5.19 (m, 1H), 4.23-4.18 (m, 1H), 3.86-3.80 (m, 1H), 3.67-3.63 (m, 1H), 3.30-3.28 (m, 1H), 3.11-3.05 (m, 1H), 2.65-2.60 (m, 1H). rel-(S)-(5-(pyridin-2-yl)isochroman-1-yl)methanamine hydrochloride was obtained as a white solid (95 mg, purity: 98%, ee %: 100%, yield: 71.6%). MS (ESI): m/z 241 [M+H]+. 1H NMR (400 MHz, methanol-d4): δ 8.95 (d, J=4.8 Hz, 1H), 8.78-8.73 (m, 1H), 8.24-8.15 (m, 2H), 7.59-7.54 (m, 3H), 5.19-5.16 (m, 1H), 4.23-4.18 (m, 1H), 3.86-3.80 (m, 1H), 3.67-3.63 (m, 1H), 3.29-3.25 (m, 1H), 3.10-3.02 (m, 1H), 2.66-2.60 (m, 1H).

Synthesis of (R)-(7-(pyridin-4-yl)isochroman-1-yl)methanamine hydrochloride (Compound 47) and (S)-(7-(pyridin-4-yl)isochroman-1-yl)methanamine hydrochloride (Compound 48) The title compounds were synthesized using the procedure described in Scheme 6, substituting pyridin-4-ylboronic acid for pyridin-3-ylboronic acid, and substituting tert-Butyl (7-bromoisochroman-1-yl)methylcarbamate for tert-butyl (6-bromoisochroman-1-yl)methylcarbamate. (R)-(7-(Pyridin-4-yl)isochroman-1-yl)methanamine hydrochloride (Compound 47) was obtained as a white solid. MS(ESI): m/z 241 [M+H]+, purity: 100%, retention time: 3.67 min, ee %: 100%, 240 mg off-white solid obtained, yield: 92.6%, 1H-NMR (400 MHz, CD₃OD): δ 8.89 (d, J=4.8 Hz, 2H), 8.46 (d, J=5.2 Hz, 2H), 7.93 (d, J=8.4 Hz, 2H), 7.52 (d, J=8.0 Hz, 1H), 5.17 (d, J=7.6 Hz, 1H), 4.31~4.26 (m, 1H), 3.95~3.89 (m, 1H), 3.76 (d, J=11.6 Hz, 1H), 3.38 (m, 1H), 3.18-3.10 (m, 1H), 2.93~2.89 (m 1H). (S)-(7-(Pyridin-4-yl)isochroman-1-yl)methanamine hydrochloride (Compound 48) was obtained as a white solid MS(ESI): m/z 241 [M+H]+, purity: 1000%, retention time: 3.17 min, ee value: 100%, 80 mg white solid obtained, yield: 30.8%, 1H-NMR (400 MHz, CD₃OD): δ 8.89 (d, J=6.4 Hz, 2H), 8.46 (d, J=7.2 Hz, 2H), 7.93 (d, J=8.0 Hz, 2H), 7.53 (d, J=8.0 Hz, 1H), 5.17 (d J=6.8 Hz, 1H), 4.31~4.26 (m, 1H), 3.95~3.89 (m, 1H), 3.77~3.74 (m, 1H), 3.39 (m, 1H), 3.18~3.10 (m, 1H), 2.94-2.89 (m, 1H).

Scheme 18

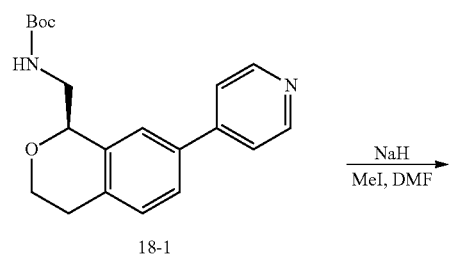

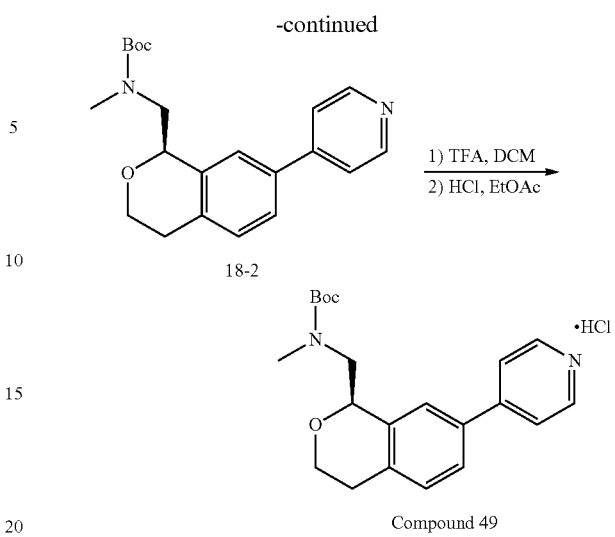

Compound 49

Synthesis of (R)—N-Methyl-1-(7-(pyridin-4-yl)isochroman-1-yl)methanamine hydrochloride (Compound 49)

(R)-tert-Butyl methyl((7-(pyridin-4-yl)isochroman-1-yl) methyl)carbamate (18-2)

To a solution of rel-(R)-tert-butyl ((7-(pyridin-4-yl)isochroman-1-yl)methyl) carbamate (18-1) (prepared using the procedure in Scheme 6, substituting pyridin-4-ylboronic acid for pyridin-3-ylboronic acid, and substituting tert-butyl (7-bromoisochroman-1-yl)methylcarbamate for tert-butyl (6-bromoisochroman-1-yl)methylcarbamate) (400 mg, 1.17 mmol) in DMF (10 mL) was added NaH (60% in oil) (56.1 mg, 2.34 mmol) and MeI (332 mg, 2.34 mmol) at 0° C. The mixture was stirred at this temperature for 3 h. Upon completion, the reaction was quenched into excess water, extracted with ether (50 mL×2), dried and concentrated to dryness in vacuo. Purification by prep. TLC eluted with PE:EtOAc=3:1 gave the desired product. MS(ESI): m/z 355 [M+H]+, purity: 100%, 260 mg yellow oil obtained, yield: 62.8%.

(R)—N-Methyl-1-(7-(pyridin-4-yl)isochroman-1-yl) methanamine hydrochloride (Compound 49)

To a solution of rel-(R)-tert-butyl methyl((7-(pyridin-4-yl)isochroman-1-yl)methyl) carbamate (260 mg, 733 µmol) in DCM (6 mL) was added TFA (500 mg, 4.39 mmol). The mixture was stirred at room temperature overnight. Upon completion, the reaction was concentrated in vacuo and partitioned between 10% aq. NaOH and DCM (50 mL×3). The combined organics were dried and evaporated under reduced pressure to yield the free base. The free base was re-dissolved in EtOAc (3 mL) and 3N HCl/EtOAc (0.3 mL, 786 µmol) was added at 0° C. The reaction was stirred for 15 mins. Upon completion, the mixture was concentrated in vacuo triturated with EtOAc (20 mL) and dried in vacuo to get the desired product. MS(ESI): m/z 255 [M+H]+, ee value: 100%, retention time: 19.44 min, purity: 100%, 120 mg white solid obtained, yield: 93.7%, 1H-NMR (400 MHz, CD₃OD): δ 8.90 (d, J=6.4 Hz, 2H), 8.49 (d, J=6.4 Hz, 2H), 7.96 (s, 1H), 7.94 (d, J=8.4 Hz, 1H), 7.53 (d, J=8.0 Hz, 1H), 5.25 (d, J=8.0 Hz, 1H), 4.32-4.27 (m, 1H), 3.96~3.84 (m, 2H), 3.49-3.43 (m, 1H), 3.18-3.10 (m, 1H), 2.94 (m, 1H), 2.83 (s, 3H).

Synthesis of (S)—N-Methyl-1-(7-(pyridin-4-yl)isochroman-1-yl)methanamine hydrochloride (Compound 50)

The title compound was prepared using the procedure shown in Scheme 18, substituting rel-(S)-tert-butyl ((7-(pyridin-4-yl)isochroman-1-yl)methyl) carbamate for rel-(R)-tert-butyl ((7-(pyridin-4-yl)isochroman-1-yl)methyl) carbamate. The title compound was obtained as a white solid, MS(ESI): m/z 241 [M+H]+, purity: 100%, retention time: 3.17 min, ee value: 100%, 80 mg white solid obtained, yield: 30.8%, 1H NMR (400 MHz, CD$_3$OD): δ 8.89 (d, J=6.4 Hz, 2H), 8.46 (d, J=7.2 Hz, 2H), 7.93 (d, J=8.0 Hz, 2H), 7.53 (d, J=8.0 Hz, 1H), 5.17 (d, J=6.8 Hz, 1H), 4.31~4.26 (m, 1H), 3.95~3.89 (m, 1H), 3.77~3.74 (m, 1H), 3.39 (m, 1H), 3.18~3.10 (m, 1H), 2.94~2.89 (m, 1H).

Scheme 19

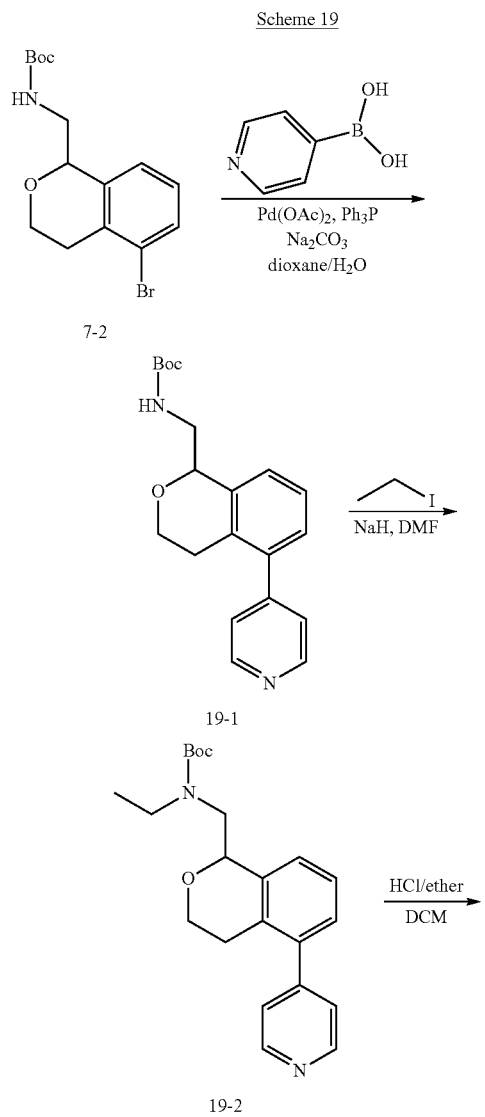

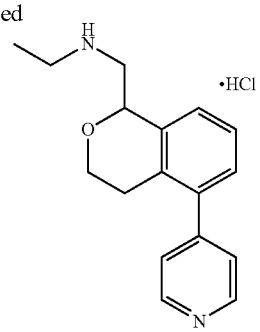

Compound 51

Synthesis of N-((5-(pyridin-4-yl)isochroman-1-yl)methyl)ethanamine (Compound 51)

tert-Butyl ((5-(pyridin-4-yl)isochroman-1-yl)methyl) carbamate (19-1)

To a solution of tert-butyl ((5-bromoisochroman-1-yl)methyl)carbamate (2 g, 5.84 mmol) (prepared as described in Scheme 7) in dioxane/H$_2$O (20 mL/15 mL) was added pyridin-4-ylboronic acid (860 mg, 7.00 mmol), diacetoxypalladium (131 mg, 584 µmol), triphenylphosphine (153 mg, 584 µmol) and Na$_2$CO$_3$ (1.53 g, 14.5 mmol). The reaction was stirred at 80° C. for 16 h under N$_2$. Water (20 mL) was added to the reaction vessel and the resulting biphasic mixture was transferred to a separatory funnel. The layers were separated and the aqueous phase was extracted with EtOAc (3×50 mL). The combined organics were dried over anhydrous Na$_2$SO$_4$, filtered and concentrated in vacuo. The resulting oil was purified by flash column chromatography with a gradient elution of hex (90%) and EtOAc (10%) to hex (55%) and EtOAc (45%) to provide tert-butyl ((5-(pyridin-4-yl)isochroman-1-yl)methyl)carbamate (1.20 g, 3.52 mmol) as a yellow oil that was suitable for use without further purification.

tert-Butyl ethyl((5-(pyridin-4-yl)isochroman-1-yl) methyl)carbamate (19-2)

To a solution of tert-butyl ((5-(pyridin-4-yl)isochroman-1-yl)methyl)carbamate (250 mg, 734 µmol) in DMF (3 mL) was added sodium hydride (58.3 mg, 1.46 mmol) slowly at 0° C. The reaction was stirred at 0° C. for 30 min. Iodoethane (114 mg, 734 µmol) was added and the reaction was stirred at ambient temperature for 3 h. Saturated aqueous NH$_4$Cl (10 mL) and EtOAc (20 mL) were added to the reaction vessel and the resulting biphasic mixture was transferred to a separatory funnel. The layers were separated and the aqueous phase was extracted with EtOAc (2×20 mL). The combined organics were washed with H2O and brine, dried over anhydrous Na$_2$SO$_4$, filtered and concentrated in vacuo. The resulting oil was purified by flash column chromatography with an isocratic elution of hex (85%) and EtOAc (15%) to hex (60%) and EtOAc (40%) to provide tert-butyl ethyl((5-(pyridin-4-yl)isochroman-1-yl) methyl)carbamate (170 mg, 461 µmol) as a yellow glass.

N-((5-(Pyridin-4-yl)isochroman-1-yl)methyl) ethanamine hydrochloride salt (Compound 51)

A solution of tert-butyl ethyl((5-(pyridin-4-yl)isochroman-1-yl)methyl)carbamate (170 mg, 461 µmol) in DCM (1 mL) and HCl-Et2O (5 mL) was stirred at ambient temperature for 4 h. The reaction mixture was concentrated. The resulting solid was washed with Et2O (10 mL) and dried in vacuo to provide N-((5-(pyridin-4-yl)isochroman-1-yl) methyl)ethanamine HCl salt (108 mg, 405 μmol) as an off-white solid. MS(ESI): m/z 269 [M+1]+. 1H NMR (300 MHz, d6-DMSO) δ: 9.45 (brs, 1H), 8.95 (d, J=6.6 Hz, 2H), 8.32 (brs, 1H), 8.03 (d, J=6.6 Hz, 2H), 7.47 (m, 2H), 7.38 (m, 1H), 5.26 (m, 1H), 4.03 (m, 1H), 3.73 (m, 1H), 3.52 (m, 1H), 3.24 (m, 1H), 3.07 (m, 2H), 2.88 (m, 1H), 2.63 (m, 1H), 1.26 (t, J=7.2 Hz, 3H).

N-Methyl-1-(5-(thiazol-5-yl)isochroman-1-yl)methanamine hydrochloride (Compound 52)

The title compound was prepared using the procedure shown in Scheme 8, substituting 5-bromothiazole for 4-bromopyridine, and omitting the chiral separation step. Deprotection of the Boc-protected intermediate afforded the crude material that was triturated with ethyl acetate to afford the desired compound (270 mg, purity: 98%, yield: 71.6%). MS (ESI): m/z 247 [M+H]+, 1H NMR (400 MHz, DMSO-d6): δ 9.22 (s, 1H), 8.01 (s, 1H), 7.39-7.31 (m, 3H), 5.14 (d, J=6.8 Hz, 1H), 4.05-4.02 (m, 1H), 3.76-3.71 (m, 1H), 3.53-3.50 (m, 1H), 3.29-3.25 (m, 1H), 2.86-2.83 (m, 1H), 2.62 (s, 3H).

N-Methyl-1-(5-(pyrimidin-4-yl)isochroman-1-yl) methanamine hydrochloride salt (Compound 53)

The title compound was prepared using the procedure shown in Scheme 8, substituting 4-chloropyrimidine for 4-bromopyridine, and omitting the chiral separation step. Deprotection of the Boc-protected intermediate afforded the crude material that was triturated with ethyl acetate to afford the desired compound (120 mg, purity: 100%, yield: 60.6%) as a light red solid. MS (ESI): m/z 255 [M+H]+. 1H NMR (400 MHz, methanol-d4): δ 9.59 (s, 1H), 9.18 (d, J=5.6 Hz, 1H), 8.27 (s, 1H), 7.74-7.73 (m, 1H), 7.56-7.54 (m, 2H), 5.27 (d, J=8.0 Hz, 1H), 4.23-4.20 (m, 1H), 3.72-3.68 (m, 1H), 3.44-3.40 (m, 1H), 3.34-3.32 (m, 1H), 2.93-2.90 (m, 1H), 2.82 (s, 3H).

N-Methyl-1-(5-(pyridazin-4-yl)isochroman-1-yl) methanamine hydrochloride salt (Compound 54)

The title compound was prepared using the procedure shown in Scheme 8, substituting 4-bromopyridazine for 4-bromopyridine, and omitting the chiral separation step. Deprotection of the Boc-protected intermediate afforded the crude material that was triturated with ethyl acetate to afford the desired compound (170 mg, purity: 97%, yield: 55.0%) as a light red solid. MS (ESI): m/z 255 [M+H]+. 1H NMR (400 MHz, methanol-d4): δ 9.73 (d, J=1.6 Hz, 1H), 9.67 (d, J=6.0 Hz, 1H), 8.63-8.61 (m, 1H), 7.57-7.53 (m, 3H), 5.27-5.24 (m, 1H), 4.24-4.19 (m, 1H), 3.84-3.78 (m, 1H), 3.73-3.69 (m, 1H), 3.43-3.40 (m, 1H), 3.21-3.14 (m, 1H), 3.83 (s, 3H), 2.75-2.69 (m, 1H).

N-Methyl-1-(5-(pyridazin-4-yl)isochroman-1-yl) methanamine hydrochloride salt (Compound 55)

The title compound was prepared using the procedure shown in Scheme 8, substituting 3-chloropyridazine for 4-bromopyridine, and omitting the chiral separation step. Deprotection of the Boc-protected intermediate afforded the crude material that was triturated with ethyl acetate to afford the desired compound (170 mg, purity: 100%, yield: 50.3%) as a light red solid. MS (ESI): m/z 255 [M+H]+. 1H NMR (400 MHz, methanol-d4): δ 9.66 (d, J=4.8 Hz, 1H), 8.77 (d, J=8.4 Hz, 1H), 8.65-8.62 (m, 1H), 7.66-7.58 (m, 3H), 5.27 (d, J=7.2 Hz, 1H), 4.23-4.20 (m, 1H), 3.85-3.81 (m, 1H), 3.73-3.70 (m, 1H), 3.44-3.39 (m, 1H), 3.21-3.14 (m, 1H), 2.83-2.75 (m, 4H).

N-Methyl-1-(5-(pyrazin-2-yl)isochroman-1-yl)methanamine hydrochloride salt (Compound 56)

The title compound was prepared using the procedure shown in Scheme 8, substituting 2-chloropyrazine for 4-bromopyridine, and omitting the chiral separation step. Deprotection of the Boc-protected intermediate afforded the crude material that was triturated with ethyl acetate to afford the desired compound (95 mg, purity: 97%, yield: 49.9%) as a light red solid. MS (ESI): m/z 255 [M+H]+. 1H NMR (400 MHz, methanol-d4): δ 8.98 (s, 2H), 8.78 (s, 1H), 7.55-7.48 (m, 3H), 5.24 (d, J=9.2 Hz, 1H), 4.22-4.16 (m, 1H), 3.83-3.78 (m, 1H), 3.71-3.68 (m, 1H), 3.43-3.38 (m, 1H), 2.82 (s, 3H), 2.77-2.73 (m, 1H).

7-(Pyrimidin-4-yl)isochroman-1-yl)methanamine hydrochloride (Compound 57)

The title compound was prepared using the procedure shown in Scheme 11, substituting 4-chloropyrimidine for 4-bromopyridine, and omitting the chiral separation step. Deprotection of the Boc-protected intermediate afforded the crude material that was triturated with ethyl acetate to afford the desired compound (100 mg, purity: 100%, yield: 72.7%) as a white solid. MS (ESI): m/z 242 [M+H]+. 1H NMR (400 MHz, methanol-d4): δ 9.49 (s, 1H), 9.07 (d, J=6.0 Hz, 1H), 8.57 (d, J=6.4 Hz, 1H), 8.30 (d, J=5.6 Hz, 2H), 7.52 (d, J=5.6 Hz, 1H), 5.17 (d, J=6.4 Hz, 1H), 4.31-4.26 (m, 1H), 3.96-3.90 (m, 1H), 3.76-3.72 (m, 1H), 3.38-3.35 (m, 1H), 3.20-3.12 (m, 2H), 2.95-2.91 (m, 1H).

N-Methyl-1-(7-(pyrimidin-4-yl)isochroman-1-yl) methanamine hydrochloride salt (Compound 58)

The title compound was prepared using the procedure shown in Scheme 19, substituting methyl iodide for ethyl iodide, and substituting tert-butyl ((7-(pyrimidin-4-yl)isochroman-1-yl)methyl)carbamate for tert-butyl ((5-(pyridin-4-yl)isochroman-1-yl)methyl)carbamate. Trituration with ethyl acetate afforded the desired compound (140 mg, purity: 95%, yield: 63.4%) as a white solid. MS (ESI): m/z 255 [M+H]+. 1H NMR (400 MHz, methanol-d4): δ 9.40 (s, 1H), 9.00 (d, J=6.0 Hz, 1H), 8.41-8.39 (m, 1H), 8.24-8.23 (m, 2H), 7.50 (d, J=8.4 Hz, 1H), 5.22 (d, J=7.2 Hz, 1H), 4.31-4.27 (m, 1H), 3.96-3.91 (m, 1H), 3.82-3.78 (m, 1H), 3.14-3.12 (m, 1H), 2.94-2.90 (m, 2H), 2.82 (s, 3H).

(5-(Thiazol-5-yl)isochroman-1-yl)methanamine hydrochloride salt (Compound 59)

The title compound was prepared using the procedure described in Scheme 11, substituting 5-bromothiazole for 5-bromopyrimidine, and omitting the chiral separation step. Deprotection of the Boc-protected intermediate afforded the crude material that was triturated with ethyl acetate to afford the desired product (274 mg, Yield=84%). MS (ESI): m/z 247 [M+H]+, 1H NMR (400 MHz, methanol-d4): δ 9.99 (s, 1H), 8.40 (s, 1H), 7.50-7.40 (m, 3H), 5.14 (d, J=7.2 Hz, 1H), 4.24-4.21 (m, 1H), 3.85-3.81 (m, 1H), 3.62-3.59 (m, 1H), 3.30-3.24 (m, 1H), 3.10-3.06 (m, 1H), 2.77 (d, J=16.4 Hz, 1H).

(5-(Pyrimidin-4-yl)isochroman-1-yl)methanamine hydrochloride salt (Compound 60)

The title compound was prepared using the procedure described in Scheme 11, substituting 4-chloropyrimidine for 5-bromopyrimidine, and omitting the chiral separation step. Deprotection of the Boc-protected intermediate afforded the crude material that was triturated with ethyl acetate to afford the desired product (207 mg, yield: 63%) as an orange solid. MS (ESI): m/z 242 [M+H]+. 1H NMR (400 MHz, methanol-d4): δ 9.54 (s, 1H), 9.13 (d, J=6.0 Hz, 1H), 8.18 (d, J=6.0 Hz, 1H), 7.69 (t, J=4.4 Hz, 1H), 7.54-7.52 (m, 2H), 5.19-5.17 (m, 1H), 4.22-4.17 (m, 1H), 3.83-3.77 (m, 1H), 3.63-3.59 (m, 1H), 3.30-3.25 (m, 2H), 2.91-2.86 (m, 1H).

(5-(Pyridazin-4-yl)isochroman-1-yl)methanamine hydrochloride salt (Compound 61)

The title compound was prepared using the procedure described in Scheme 11, substituting 4-bromopyridazine for 5-bromopyrimidine, and omitting the chiral separation step. Deprotection of the Boc-protected intermediate afforded the crude material that was triturated with ethyl acetate to afford the desired product (457 mg, yield: 63%) as a grey white solid. MS (ESI): m/z 242 [M+H]+. 1H NMR (400 MHz, methanol-d4): δ 9.76 (s, 1H), 9.69 (d, J=5.6 Hz, 1H), 8.68-8.67 (m, 1H), 7.56-7.51 (m, 3H), 5.20-5.19 (m, 1H), 4.23-4.18 (m, 1H), 3.84-3.78 (m, 1H), 3.65-3.61 (m, 1H), 3.31-3.28 (m, 1H), 3.21-3.14 (m, 1H), 2.75-2.70 (m, 1H).

(5-(Pyridazin-3-yl)isochroman-1-yl)methanaminehydrochloride salt (Compound 62)

The title compound was prepared using the procedure described in Scheme 11, substituting 3-chloropyridazine for 5-bromopyrimidine, and omitting the chiral separation step. Deprotection of the Boc-protected intermediate afforded the crude material that was triturated with ethyl acetate to afford the desired product (266 mg, yield: 70.5%) as a light red solid. MS (ESI): m/z 242 [M+H]+. 1H NMR (400 MHz, methanol-d4): δ 9.68-9.66 (m, 1H), 8.79-8.77 (m, 1H), 8.66-8.62 (m, 1H), 7.65-7.62 (m, 1H), 7.58-7.55 (m, 2H), 5.22-5.19 (m, 1H), 4.23-4.18 (m, 1H), 3.85-3.79 (m, 1H), 3.66-3.62 (m, 1H), 3.34-3.28 (m, 1H), 3.21-3.14 (m, 1H), 2.79-2.74 (m, 1H).

(5-(Pyrazin-2-yl)isochroman-1-yl)methanamine hydrochloride salt (Compound 63)

The title compound was prepared using the procedure described in Scheme 11, substituting 2-chloropyrazine for 5-bromopyrimidine, and omitting the chiral separation step. Deprotection of the Boc-protected intermediate afforded the crude material that was triturated with ethyl acetate to afford the desired product (240 mg, yield: 68.9%) as a light red solid. MS (ESI): m/z 242 [M+H]+. 1H NMR (400 MHz, methanol-d4): δ 8.93-8.91 (m, 2H), 8.74 (s, 1H), 7.52-7.43 (m, 3H), 5.17-5.15 (m, 1H), 4.20-4.15 (m, 1H), 3.82-3.76 (m, 1H), 3.63-3.59 (m, 1H), 3.33-3.27 (m, 1H), 3.18-3.10 (m, 1H), 2.75-2.71 (m, 1H).

(5-(Isoxazol-4-yl)isochroman-1-yl)methanamine hydrochloride salt (Compound 64)

The title compound was prepared using the procedure described in Scheme 11, substituting 4-bromoisoxazole for 5-bromopyrimidine, and omitting the chiral separation step. Deprotection of the Boc-protected intermediate afforded the crude material that was triturated with ethyl acetate to afford the desired product (106 mg, yield: 42.4%) as an orange solid. MS (ESI): m/z 242 [M+H]+. 1H NMR (400 MHz, methanol-d4): δ 8.92 (s, 1H), 8.71 (s, 1H), 7.43-7.26 (m, 3H), 5.12-5.10 (m, 1H), 4.25-4.20 (m, 1H), 3.85-3.79 (m, 1H), 3.60-3.56 (m, 1H), 3.27-3.21 (m, 1H), 3.09-3.01 (m, 1H), 2.77-2.71 (m, 1H).

1-(5-(Isoxazol-4-yl)isochroman-1-yl)-N-methylmethanamine hydrochloride salt (Compound 65)

The title compound was prepared using the procedure shown in Scheme 11, substituting 4-bromoisoxazole for 4-bromopyridine, and omitting the chiral separation step. Deprotection of the Boc-protected intermediate afforded the crude material that was triturated with ethyl acetate to afford the desired product (106 mg, yield: 42.4%) as an orange solid. MS (ESI): m/z 242 [M+H]+. 1H NMR (400 MHz, D2O): δ 8.68 (s, 1H), 8.55 (s, 1H), 7.30-7.24 (m, 2H), 7.14-7.12 (m, 1H), 5.13-5.10 (m, 1H), 4.05-3.99 (m, 1H), 3.73-3.67 (m, 1H), 3.49-3.35 (m, 2H), 2.85-2.77 (m, 1H), 2.67 (s, 3H), 2.65-2.58 (m, 1H).

rel-(R)-(5-(Thiazol-5-yl)isochroman-1-yl)methanamine hydrochloride salt (Compound 70)

The title compound was prepared using the procedure described in Scheme 9, substituting 5-bromothiazole for 4-bromopyridine. (322 mg, Yield: 40%). MS (ESI): m/z 247 [M+H]$^+$. $^1$H NMR (400 MHz, Methanol-d$_4$): δ 10.08 (s, 1H), 8.47 (s, 1H), 7.54-7.46 (m, 3H), 5.18-5.15 (m, 1H), 4.26-4.21 (m, 1H), 3.87-3.81 (m, 1H), 3.64-3.60 (m, 1H), 3.31-3.26 (m 1H), 3.14-3.07 (m, 1H), 2.83-2.77 (m, 1H).

rel-(S)-(5-(Thiazol-5-yl)isochroman-1-yl)methanamine hydrochloride salt (Compound 71)

The title compound was prepared using the procedure described in Scheme 9, substituting 5-bromothiazole for 4-bromopyridine. (509 mg, Yield: 63%). MS (ESI): m/z 247 [M+H]$^-$. $^1$H NMR (400 MHz, Methanol-d$_4$): δ 10.08-10.05 (m, 1H), 8.46-8.45 (m, 1H), 7.54-7.46 (m, 3H), 5.17-5.15 (m, 1H), 4.26-4.21 (m, 1H), 3.87-3.81 (m, 1H), 3.64-3.60 (m, 1H), 3.31-3.25 (m, 1H), 3.14-3.06 (m, 1H), 2.82-2.76 (m, 1H).

rel-tert-Butyl (R)-methyl((5-(thiazol-5-yl)isochroman-1-yl)methyl)carbamate

To a solution of sodium hydride (138 mg, 5.76 mmol) in DMF (30 mL) was added rel-(R)-tert-butyl ((5-(thiazol-5-yl)isochroman-1-yl)methyl)carbamate (prepared as shown in Scheme 9 substituting 5-bromothiazole for 4-bromopyridine)(1 g, 2.88 mmol) at 0° C. The solution was stirred at 0° C. for 1 h. Iodomethane (817 mg, 5.76 mmol) was added. The reaction was stirred at ambient temperature for 3. Water (90 mL) and EA (20 mL) was added to the reaction vessel and the resulting biphasic mixture was transferred to a separatory funnel. The layers were separated and the aqueous phase was washed with EtOAc (2×30 mL). The combined organics were washed with brine (2×50 mL), dried over anhydrous Na$_2$SO$_4$, filtered and concentrated in vacuo. The crude was purified by pre-HPLC to get the desired compound (0.9 g, purity: 100%, Yield: 87%) as a yellow oil. MS (ESI): m/z 261 [M−100+H]+.

rel-(R)—N-Methyl-1-(5-(thiazol-5-yl)isochroman-1-yl)methanamine hydrochloride salt (Compound 68)

A solution of rel-(R)-tert-butyl methyl((5-(thiazol-5-yl)isochroman-1-yl)methyl)carbamate (1 g, 2.77 mmol) in 3 M HCl/EtOAc (30 mL) was stirred at room temperature for 12 h. The mixture was concentrated in vacuo to get the crude product, washed with EtOAc (30 mL), and dried in vacuo to yield the desired product (587 mg, Yield: 70%). MS (ESI): m/z 261 [M+H]+. $^1$H NMR (400 MHz, Methanol-$d_4$): δ 10.12 (s, 1H), 8.49 (s, 1H), 7.54-7.45 (m, 3H), 5.25-5.22 (m, 1H), 4.27-4.22 (m, 1H), 3.88-3.82 (m, 1H), 3.72-3.68 (m, 1H), 3.42-3.35 (m, 1H), 3.14-3.07 (m, 1H), 2.82-2.77 (m, 4H).

rel-tert-Butyl (S)-methyl((5-(thiazol-5-yl)isochroman-1-yl)methyl)carbamate

To a solution of sodium hydride (138 mg, 5.76 mmol) in DMF (30 mL) was added rel-(S)-tert-butyl ((5-(thiazol-5-yl)isochroman-1-yl)methyl)carbamate (1 g, 2.88 mmol) at 0° C. Then the solution was stirred at 0° C. for 1 h. Iodomethane (817 mg, 5.76 mmol) was added. The reaction was stirred at ambient temperature for 3 h. Water (90 mL) and ethyl acetate (20 mL) was added to the reaction vessel and the resulting biphasic mixture was transferred to a separatory funnel. The layers were separated and the aqueous phase was washed with ethyl acetate (2×30 mL). The combined organics were washed with saturated aqueous NaCl (2×50 mL), dried over anhydrous $Na_2SO_4$, filtered and concentrated in vacuo. The crude was purified by pre-HPLC to get the desired compound (0.9 g, purity: 100%, Yield: 87%) as a yellow oil. MS (ESI): m/z 261 [M −100+H]+.

rel-(S)—N-Methyl-1-(5-(thiazol-5-yl)isochroman-1-yl)methanamine hydrochloride salt (Compound 69)

To a solution of rel-(S)-tert-butyl methyl((5-(thiazol-5-yl)isochroman-1-yl)methyl)carbamate (1.3 g, 3.60 mmol) in 3 M HCl/EtOAc (30 mL) was stirred at room temperature for 12 h. The mixture was concentrated in vacuo to get the crude material, washed with EtOAc (30 mL), and dried in vacuo to yield the desired product (712 mg Yield: 67%). MS(ESI): m/z 261 [M+H]+. $^1$H NMR (400 MHz, Methanol-$d_4$): δ 10.01 (s, 1H), 8.43 (s, 1H), 7.53-7.46 (m, 3H), 5.24-5.21 (m, 1H), 4.27-4.22 (m, 1H), 3.88-3.81 (m, 1H), 3.71-3.67 (m, 1H), 3.41-3.36 (m, 1H), 3.14-3.06 (m, 1H), 2.82-2.77 (m, 4H).

rel-(R)-(5-(Isoxazol-4-yl)isochroman-1-yl)methanamine hydrochloride salt (Compound 86)

The title compound was prepared using the procedure described in Scheme 9, substituting 4-bromoisoxazole for 4-bromopyridine. (353 mg, Yield: 73%) as a light yellow solid. MS (ESI): m/z 231 [M+H]+. $^1$H NMR (400 MHz, Methanol-d4): δ 8.92 (s, 1H), 8.71 (s, 1H), 7.44-7.26 (m, 3H), 5.12-5.09 (m, 1H), 4.25-4.20 (m, 1H), 3.85-3.79 (m, 1H), 3.59-3.55 (m, 1H), 3.27-3.22 (m, 1H), 3.09-3.01 (m, 1H), 2.77-2.72 (m, 1H).

rel-(S)-(5-(Isoxazol-4-yl)isochroman-1-yl)methanamine hydrochloride salt (Compound 87)

The title compound was prepared using the procedure described in Scheme 9, substituting 4-bromoisoxazole for 4-bromopyridine. (340 mg, Yield: 68%) as a light yellow solid. MS (ESI): m/z 231 [M+H]+. $^1$H NMR (400 MHz, Methanol-d4): δ 8.92 (s, 1H), 8.71 (s, 1H), 7.44-7.26 (m, 3H), 5.12-5.09 (m, 1H), 4.25-4.20 (m, 1H), 3.85-3.79 (m, 1H), 3.59-3.55 (m, 1H), 3.27-3.22 (m, 1H), 3.09-3.01 (m, 1H), 2.77-2.72 (m, 1H).

rel-(R)-1-(5-(Isoxazol-4-yl)isochroman-1-yl)-N-methylmethanamine hydrochloride salt (Compound 84)

The title compound was prepared using the procedure described in Scheme 8, substituting 4-bromoisoxazole for 4-bromopyridine. (252 mg, Yield: 68%) as a light orange solid. MS (ESI): m/z 245 [M+H]+. $^1$H NMR (400 MHz, Methanol-$d_4$): δ 8.93 (s, 1H), 8.71 (s, 1H), 7.44-7.27 (m, 3H), 5.19-5.17 (m, 1H), 4.26-4.21 (m, 1H), 3.86-3.80 (m, 1H), 3.67-3.64 (m, 1H), 3.38-3.34 (m, 1H), 3.09-3.01 (m, 1H), 2.80 (s, 3H), 2.77-2.72 (m, 1H).

rel-(S)-1-(5-(Isoxazol-4-yl)isochroman-1-yl)-N-methylmethanamine hydrochloride salt (Compound 85)

The title compound was prepared using the procedure described in Scheme 8, substituting 4-bromoisoxazole for 4-bromopyridine. (305 mg, Yield: 73%) as a light orange solid. MS (ESI): m/z 245 [M+H]+. $^1$H NMR (400 MHz, Methanol-$d_4$): δ 8.93 (s, 1H), 8.71 (s, 1H), 7.44-7.27 (m, 3H), 5.20-5.17 (m, 1H), 4.26-4.21 (m, 1H), 3.86-3.80 (m, 1H), 3.68-3.64 (m, 1H), 3.38-3.34 (m, 1H), 3.09-3.01 (m, 1H), 2.81 (s, 3H), 2.79-2.72 (m, 1H).

rel-(R)-(5-(Pyridazin-4-yl)isochroman-1-yl)methanamine hydrochloride salt (Compound 78)

The title compound was prepared using the procedure described in Scheme 9, substituting 4-bromopyridazine for 4-bromopyridine. (733 mg, Yield: 99%) as a light brown solid. MS (ESI): m/z 242 [M+H]+. $^1$H NMR (400 MHz, Methanol-d4): δ 9.76 (s, 1H), 9.70 (d, J=5.6 Hz, 1H), 8.68-8.66 (m, 1H), 7.56-7.53 (m, 3H), 5.21-5.18 (m, 1H), 4.24-4.19 (m 1H), 3.84-3.78 (m, 1H), 3.65-3.61 (m, 1H), 3.32-3.28 (m, 1H), 3.22-3.14 (m, 1H), 2.75-2.71 (m, 1H).

rel-(S)-(5-(Pyridazin-4-yl)isochroman-1-yl)methanamine hydrochloride salt (Compound 79)

The title compound was prepared using the procedure described in Scheme 9, substituting 4-bromopyridazine for 4-bromopyridine. (679 mg, Yield: 90%) as a light brown solid. MS (ESI): m/z 242 [M+H]+. $^1$H NMR (400 MHz, Methanol-d4): δ 9.77 (s, 1H), 9.71 (d, J=5.6 Hz, 1H), 8.70-8.66 (m, 1H), 7.60-7.57 (m, 3H), 5.22-5.19 (m, 1H), 4.24-4.19 (m, 1H), 3.84-3.78 (m, 1H), 3.66-3.62 (m, 1H), 3.32-3.28 (m, 1H), 3.23-3.15 (m, 1H), 2.75-2.71 (m, 1H).

rel-tert-butyl (R)-Methyl((5-(pyridazin-4-yl)isochroman-1-yl)methyl)carbamate To a solution of sodium hydride (143 mg, 6.00 mmol) in DMF (40 mL) was added rel-(R)-tert-butyl ((5-(pyridazin-4-yl)isochroman-1-yl)methyl)carbamate (1.02 g, 3 mmol) in DMF (10 mL) at 0° C. Then the solution was stirred at 0° C. for 1 h. Iodomethane (425 mg, 3.00 mmol) was added at 0° C. The reaction was stirred at ambient temperature for 3 h. water (60 mL) was added to the reaction vessel, ethyl acetate (50 mL) was added, resulting biphasic mixture was transferred to a separating funnel. The layers were separated and the aqueous phase was washed with ethyl acetate (2×50 mL). The combined organics were washed with saturated aqueous NaCl (2×50 mL) and dried over anhydrous Na$_2$SO$_4$, filtered and concentrated in vacuo. The resulting oil was purified by normal phase HPLC with a gradient elution of petroleum ether (100%) and ethyl acetate (0%) to petroleum ether (10%) and ethyl acetate (95%) to provide rel-(R)-tert-butyl methyl((5-(pyridazin-4-yl)isochroman-1-yl)methyl) carbamate (950 mg, 2.67 mmol, Yield: 89%) as a brown oil. MS(ESI): m/z 356 [M+H]$^+$.

rel-(R)—N-Methyl-1-(5-(pyridazin-4-yl)isochroman-1-yl)methanamine hydrochloride salt (Compound 76)

To a solution of rel-(R)-tert-butyl methy((5-(pyridazin-4-yl)isochroman-1-yl)methyl) carbamate (0.95 g, 2.66 mmol) in 3 M HCl/ethyl acetate (30 mL) was stirred at room temperature for 12 h. The mixture was concentrated in vacuo to get the crude, washed with ethyl acetate (30 mL), dried in vacuo to yield the desired product (611 mg, Yield: 69%) as a light brown solid. MS (ESI): m/z 256 [M+H]$^+$. $^1$H NMR (400 MHz, Methanol-d4): δ 9.76 (s, 1H), 9.69 (d, J=5.6 Hz, 1H), 8.68-8.66 (m, 1H), 7.60-7.54 (m, 3H), 5.28-5.26 (m, 1H), 4.24-4.19 (m, 1H), 3.85-3.79 (m, 1H), 3.72 (dd, J=2.8 Hz, 1H), 3.44-3.39 (m, 1H), 3.22-3.14 (m, 1H), 2.83 (s, 3H), 2.75-2.71 (m, 1H).

rel-tert-butyl (S)-Methyl((5-(pyridazin-4-yl)isochroman-1-yl)methyl)carbamate

To a solution of sodium hydride (143 mg, 6.00 mmol) in DMF (40 mL) was added rel-(S)-tert-butyl ((5-(pyridazin-4-yl)isochroman-1-yl)methyl)carbamate (1.02 g, 3 mmol) in DMF (10 mL) at 0° C. Then the solution was stirred at 0° C. for 1 h. Iodomethane (425 mg, 3.00 mmol) in DMF (2 mL) was added at 0° C. The reaction was stirred at ambient temperature for 3 h. water (60 mL) was added to the reaction vessel, ethyl acetate (50 mL) was added, resulting biphasic mixture was transferred to a separating funnel. The layers were separated and the aqueous phase was washed with ethyl acetate (2×50 mL). The combined organics were washed with saturated aqueous NaCl (2×50 mL) and dried over anhydrous Na$_2$SO$_4$, filtered and concentrated in vacuo. The resulting oil was purified by normal phase HPLC with a gradient elution of petroleum ether (100%) and ethyl acetate (0%) to petroleum ether (10%) and ethyl acetate (95%) to provide rel-(R)-tert-butyl methyl((5-(pyridazin-4-yl)isochroman-1-yl)methyl)carbamate (940 mg, 2.64 mmol, Yield: 88%) as a brown oil. MS (ESI): m/z 356 [M+H]$^+$.

rel-(S)—N-Methyl-1-(5-(pyridazin-4-yl)isochroman-1-yl)methanamine hydrochloride salt (Compound 77)

To a solution of rel-(S)-tert-butyl methyl((5-(pyridazin-4-yl)isochroman-1-yl)methyl)carbamate (0.95 g, 2.66 mmol) in 3 M HCl/ethyl acetate (30 mL) was stirred at room temperature for 12 h. The mixture was concentrated in vacuo to get the crude, washed with ethyl acetate (30 mL), dried in vacuo to yield the desired product (584 mg, Yield: 66%) as a light brown solid. MS (ESI): m/z 256 [M+H]$^+$. $^1$H NMR (400 MHz, Methanol-d4): δ 9.76 (s, 1H), 9.69 (d, J=5.6 Hz, 1H), 8.68-8.66 (m, 1H), 7.60-7.54 (m, 3H), 5.28-5.26 (m, 1H), 4.24-4.19 (m, 1H), 3.85-3.79 (m, 1H), 3.72 (dd, J=2.8 Hz, 1H), 3.44-3.39 (m, 1H), 3.22-3.14 (m, 1H), 2.83 (s, 3H), 2.75-2.71 (m, 1H).

rel-(R)—N-Methyl-1-(5-(pyrazine-2-yl)isochroman-1-yl)methanamine (Compound 80)

The title compound was prepared using the procedure described in Scheme 8, substituting 2-chloropyrazine for 4-bromopyridine. (730 mg, 2.85 mmol) (Purity: 100%, Yield: 75%) as a white solid. MS (ESI): m/z 256 [M+H]$^+$. $^1$H NMR (400 MHz, Methanol-d4): δ 9.08-9.04 (m, 2H), 8.83 (s, 1H), 7.58-7.48 (m, 3H), 5.26 (d, J=9.2 Hz, 1H), 4.22-4.17 (m, 1H), 3.83-3.77 (m, 1H), 3.71-3.68 (m, 1H), 3.43-3.38 (m, 1H), 2.82 (s, 3H), 2.80-2.74 (m, 1H).

rel-(S)—N-Methyl-1-(5-(pyrazine-2-yl)isochroman-1-yl)methanamine (Compound 81)

The title compound was prepared using the procedure described in Scheme 8, substituting 2-chloropyrazine for 4-bromopyridine. (700 mg, purity: 100%, Yield: 94%) as a white solid. MS (ESI): m/z 256 [M+H]$^+$. $^1$H NMR (400 MHz, Methanol-d4): δ 9.07-9.03 (m, 2H), 8.82 (s, 1H), 7.57-7.49 (m, 3H), 5.26 (d, J=9.2 Hz, 1H), 4.22-4.17 (m, 1H), 3.83-3.78 (m, 1H), 3.71-3.68 (m, 1H), 3.43-3.38 (m, 1H), 2.82 (s, 3H), 2.82-2.75 (m, 1H).

rel-(R)-(5-(Pyrazin-2-yl)isochroman-1-yl)methanamine hydrochloride salt (Compound 82)

The title compound was prepared using the procedure described in Scheme 9, substituting 2-chloropyrazine for 4-bromopyridine. (1.14 mg, Yield: 90%) as a white solid. MS (ESI): m/z 242 [M+H]$^+$. $^1$H NMR (400 MHz, Methanol-d4): δ 9.05-9.03 (m, 2H), 8.82 (s, 1H), 7.57-7.46 (m, 3H), 5.19-5.16 (m, 1H), 4.21-4.16 (m, 1H), 3.82-3.76 (m, 1H), 3.63-3.60 (m, 1H), 3.34-3.27 (m, 1H), 3.18-3.13 (m, 1H), 2.79-2.73 (m, 1H).

rel-(S)-(5-(Pyrazin-2-yl)isochroman-1-yl)methanamine hydrochloride salt (Compound 83)

The title compound was prepared using the procedure described in Scheme 9, substituting 2-chloropyrazine for 4-bromopyridine. (1.1 g, Yield: 92%) as a white solid. MS (ESI): m/z 242 [M+H]$^+$. $^1$H NMR (400 MHz, methanol-d4): δ 9.08-9.05 (m, 2H), 8.83 (s, 1H), 7.57-7.47 (m, 3H), 5.19-5.17 (m, 1H), 4.21-4.16 (m, 1H), 3.83-3.78 (m, 1H), 3.61-3.61 (m, 1H), 3.34-3.27 (m, 1H), 3.17-3.15 (m, 1H), 2.79-2.74 (m, 1H).

rel-(R)-(5-(Pyrimidin-4-yl)isochroman-1-yl)methanamine hydrochloride salt (Compound 74)

The title compound was prepared using the procedure described in Scheme 9, substituting 4-chloropyrimidine for 4-bromopyridine. (501 mg, Purity: 100%, Yield: 71%) as a light yellow solid. MS (ESI): m/z 242 [M+H]$^+$. $^1$HNMR (400 MHz, Methanol-d4): δ 9.55 (s, 1H), 9.15 (d, J=5.6 Hz, 1H), 8.21 (d, J=6 Hz, 1H), 7.71-7.69 (m, 1H), 7.56-7.51 (m, 2H), 5.17 (d, J=11.6 Hz, 1H), 4.23-4.18 (m, 1H), 3.83-3.77 (m, 1H), 3.61 (d, J=16 Hz, 1H), 3.30-3.27 (m, 2H), 2.88 (m, 1H).

rel-(S)-(5-(Pyrimidin-4-yl)isochroman-1-yl)methanamine hydrochloride salt (Compound 75)

The title compound was prepared using the procedure described in Scheme 9, substituting 4-chloropyrimidine for 4-bromopyridine. (459 mg, Yield: 48%) as a light yellow solid. MS (ESI): m/z 241 [M+H]⁺. ¹HNMR (400 MHz, Methanol-d4): δ 9.55 (s, 1H), 9.15 (d, J=5.6 Hz, 1H), 8.21 (d, J=6 Hz, 1H), 7.71-7.69 (m, 1H), 7.56-7.51 (m, 2H), 5.17 (d, J=11.6 Hz, 1H), 4.23-4.18 (m, 1H), 3.83-3.77 (m, 1H) 0.3.61 (d, J=16 Hz, 1H), 3.30-3.27 (m, 2H), 2.88 (d, J=20.4 Hz, 1H).

rel-(R)—N-Methyl-1-(5-(pyrimidin-4-yl)isochroman-1-yl)methanamine hydrochloride salt (Compound 72)

The title compound was prepared using the procedure described in Scheme 8, substituting 4-chloropyrimidine for 4-bromopyridine. (621 mg, Yield: 61%) as a light yellow solid. MS (ESI): m/z 256 [M+H]⁺. ¹HNMR (400 MHz, Methanol-d4): δ 9.55 (s, 1H), 9.15 (d, J=8.4 Hz, 1H), 8.22 (d, J=13.2 Hz, 1H), 7.71 (s, 1H), 7.55 (d, J=13.2 Hz, 2H), 5.25 (d, J=11.2 Hz, 1H), 4.24-4.19 (m, 1H), 3.81 (m, 1H), 3.69 (d, J=15.6 Hz, 1H), 3.40 (m, 1H), 3.33-3.27 (m, 1H), 2.89 (m, 1H), 2.82 (s, 3H).

rel-(S)—N-Methyl-1-(5-(pyrimidin-4-yl)isochroman-1-yl)methanamine hydrochloride salt (Compound 73)

The title compound was prepared using the procedure described in Scheme 8, substituting 4-chloropyrimidine for 4-bromopyridine. (1.07 g, Yield: 87%). MS (ESI): m z 256 [M+H]⁺. ¹HNMR (400 MHz, Methanol-d4): δ 9.55 (s, 1H), 9.15 (d, J=8.4 Hz, 1H), 8.22 (d, J=13.2 Hz, 1H), 7.71 (s, 1H), 7.55 (d, J=13.2 Hz, 2H), 5.25 (d, J=11.2 Hz, 1H), 4.24-4.19 (m, 1H), 3.81 (m, 1H), 3.69 (d, J=15.6 Hz, 1H), 3.40 (m, 1H), 3.33-3.27 (m, 1H), 2.89 (m, 1H), 2.82 (s, 3H).

rel-(R)—N-Methyl-1-(5-(2-methylpyridin-4-yl)isochroman-1-yl)methanamine hydrochloride salt (Compound 120)

The title compound was prepared using the procedure described in Scheme 8, substituting 4-bromo-2-methylpyridine for 4-bromopyridine. (310 mg, Yield: 78%). MS (ESI): m/z 269.1 [M+H]⁺. ¹H NMR (400 MHz, Methanol-d4): δ 8.76 (d, J=6.4 Hz, 1H), 8.01 (s, 1H), 7.95 (d, J=6.0 Hz, 1H), 7.53-7.46 (m, 2H), 7.42 (d, J=7.2 Hz, 1H), 5.23 (d, J=6.4 Hz, 1H), 4.22-4.17 (m, 1H), 3.89-3.77 (m, 1H), 3.70 (d, J=11.2 Hz, 1H), 3.42-3.36 (m, 1H), 3.08-3.05 (m, 1H), 2.88 (s, 3H), 2.82 (s, 3H), 2.64 (d, J=12.8 Hz, 1H).

rel-(S)—N-Methyl-1-(5-(2-methylpyridin-4-yl)isochroman-1-yl)methanamine hydrochloride salt (Compound 121)

The title compound was prepared using the procedure described in Scheme 8, substituting 4-bromo-2-methylpyridine for 4-bromopyridine. (310 mg. Yield: 84%). MS (ESI): m/z 269.1 [M+H]⁺. ¹H NMR (400 MHz, Methanol-d4): δ 8.76 (d, J=6.4 Hz, 1H), 8.01 (s, 1H), 7.95 (d, J=6.0 Hz, 1H), 7.53-7.46 (m, 2H), 7.42 (d, J=7.2 Hz, 1H), 5.23 (d, J=6.4H. 1H), 4.22-4.17 (m, 1H), 3.89-3.77 (m, 1H), 3.70 (d, J=11.2 Hz, 1H), 3.42-3.36 (m, 1H), 3.08-3.05 (m, 1H), 2.88 (s, 3H), 2.82 (s, 3H), 2.64 (d, J=12.8 Hz, 1H).

rel-(R)-(5-(2-Methylpyridin-4-yl)isochroman-1-yl)methanamine hydrochloride salt (Compound 122)

The title compound was prepared using the procedure described in Scheme 9, substituting 4-bromo-2-methylpyridine for 4-bromopyridine. (310 mg, Yield: 58%). MS (ESI): m/z 255.1 [M+H]⁺. ¹H NMR (400 MHz, Methanol-d4): δ 8.76 (d, J=6.4 Hz, 1H), 8.01 (s, 1H), 7.95 (d, J=6.0 Hz, 1H), 7.53-7.46 (m, 2H), 7.42 (d, J=7.2 Hz, 1H), 5.16 (d, J=6.4 Hz, 1H), 4.21-4.16 (m, 1H), 3.82-3.76 (m, 1H), 3.61 (d, J=11.2 Hz, 1H), 3.29-3.26 (m, 1H), 3.08-3.06 (m, 1H), 2.88 (s, 3H), 2.64 (d, J=13.6 Hz, 1H).

rel-(S)-(5-(2-Methylpyridin-4-yl)isochroman-1-yl)methanamine hydrochloride salt (Compound 123)

The title compound was prepared using the procedure described in Scheme 9, substituting 4-bromo-2-methylpyridine for 4-bromopyridine. (350 mg, Yield: 17%). MS (ESI): m/z 255.1 [M+H]⁺. ¹H NMR (400 MHz, Methanol-d4): δ 8.76 (d, J=6.4 Hz, 1H), 8.01 (s, 1H), 7.95 (d, J=6.0 Hz, 1H), 7.51-7.44 (m, 2H), 7.42 (d, J=7.2 Hz, 1H), 5.16 (d, J=6.4 Hz, 1H), 4.20-4.17 (m, 1H), 3.79-3.76 (m, 1H), 3.61 (d, J=11.2 Hz, 1H), 3.29-3.26 (m, 1H), 3.10-3.02 (m, 1H), 2.87 (s, 3H), 2.64 (d, J=16.4 Hz, 1H).

rel-(S)-(5-(Oxazol-5-yl)isochroman-1-yl)methanamine hydrochloride salt (Compound 99)

The title compound was prepared using the procedure shown in Scheme 7, substituting oxazole, palladium acetate and X-PHOS for pyridin-3-ylboronic acid and Pd(dppf)₂Cl₂ respectively. White solid (900 mg, Yield: 98%). MS (ESI): m/z 231 [M+H]⁺. ¹H NMR (400 MHz, Methanol-d₄): δ 8.81 (s, 1H), 7.73 (d, J=7.6 Hz, 1H), 7.65 (s, 1H), 7.45 (t, J=8.0 Hz, 1H), 7.37 (d, J=7.6 Hz, 1H), 5.13 (dd, J=2.8 Hz, 8.8 Hz, 1H), 4.25-4.31 (m, 1H), 3.84-3.90 (m, 1H), 3.59 (dd. J=2.8/12.8 Hz, 1H), 3.27 (dd. J=8.8/13.2 Hz, 1H), 3.11-3.17 (m, 1H), 2.87 (td, J=3.6/16.8 Hz, 1H).

rel-(R)-(5-(Oxazol-5-yl)isochroman-1-yl)methanamine hydrochloride salt (Compound 98)

The title compound was prepared using the procedure shown in Scheme 7, substituting oxazole, palladium acetate and X-PHOS for pyridin-3-ylboronic acid and Pd(dppf)₂Cl₂ respectively. White solid. (900 mg, Yield: 98%). MS (ESI): m/z 231 [M+H]⁺. ¹H NMR (400 MHz, Methanol-d₄): δ 8.81 (s, 1H), 7.73 (d, J=7.6 Hz, 1H), 7.65 (s, 1H), 7.45 (t, J=8.0 Hz, 1H), 7.37 (d, J=7.6 Hz, 1H), 5.13 (dd, J=2.8 Hz, 8.8 Hz, 1H), 4.25-4.31 (m, 1H), 3.84-3.90 (m, 1H), 3.59 (dd, J=2.8/12.8 Hz, 1H), 3.27 (dd, J=8.8/13.2 Hz, 1H), 3.11-3.17 (m, 1H), 2.87 (td, J=3.6/16.8 Hz, 1H).

rel-(S)—N-Methyl-1-(5-(oxazol-5-yl)isochroman-1-yl)methanamine hydrochloride salt (Compound 97)

The title compound was prepared using the procedure shown in Scheme 4, substituting oxazole, palladium acetate and X-PHOS for pyridin-3-ylboronic acid and Pd(dppf)₂Cl₂ respectively. White solid. (800 mg, Yield: 75%). MS (ESI): m/z 245 [M+H]⁺. ¹H NMR (400 MHz, Methanol-d₄): δ 8.43 (s, 1H), 7.71 (d, J=7.6 Hz, 1H), 7.47 (s, 1H), 7.43 (t, J=8.0 Hz, 1H), 7.33 (d, J=7.6 Hz, 1H), 5.19 (dd, J=2.8 Hz, 8.8 Hz, 1H), 4.26-4.31 (m, 1H), 3.84-3.90 (m, 1H), 3.66 (dd, J=2.8/12.8 Hz, 1H), 3.35-3.40 (m, 1H), 3.10-3.18 (m, 1H), 2.86 (td, J=3.6/16.4 Hz, 1H), 2.80 (s, 3H).

rel-(R)—N-Methyl-1-(5-(oxazol-5-yl)isochroman-1-yl)methanamine hydrochloride salt (Compound 96)

The title compound was prepared using the procedure shown in Scheme 4, substituting oxazole, palladium acetate and X-PHOS for pyridin-3-ylboronic acid and Pd(dppf)$_2$Cl$_2$ respectively. White solid. (950 mg, Yield: 89%). MS (ESI): M/z 245 [M+H]$^+$. $^1$H NMR (400 MHz, methanol-d$_4$): δ 8.43 (s, 1H), 7.71 (d, J=7.6 Hz, 1H), 7.47 (s, 1H), 7.43 (t, J=8.0 Hz, 1H), 7.33 (d, J=7.6 Hz, 1H), 5.19 (dd, J=2.8 Hz, 8.8 Hz, 1H), 4.26-4.31 (m, 1H), 3.84-3.90 (m, 1H), 3.66 (dd, J=2.8/12.8 Hz, 1H), 3.35-3.40 (m, 1H), 3.10-3.18 (m, 1H), 2.86 (td. J=3.6/16.4 Hz, 1H), 2.80 (s, 3H).

rel-(R)-(5-(1H-Imidazol-4-yl)isochroman-1-yl)methanamine hydrochloride salt (Compound 112)

The title compound was prepared as shown in Scheme 9, substituting 4-bromo-1H-imidazole for 4-bromopyridine. (450 mg, Yield: 70%) as a white solid. MS (ESI): m/z 230 [M+H]$^+$, $^1$H NMR (400 MHz, Methanol-d$_4$): δ 9.09 (s, 1H), 7.78 (s, 1H), 7.52-7.45 (m, 3H), 5.15 (d, J=9.2 Hz, 1H), 4.25-4.23 (m, 1H), 3.87-3.82 (m, 1H), 3.63-3.60 (m, 1H), 3.28-3.23 (m, 1H), 3.12-3.06 (m, 1H), 2.80-2.75 (m, 1H).

rel-(S)-(5-(1H-Imidazol-4-yl)isochroman-1-yl)methanamine hydrochloride salt (Compound 113)

The title compound was prepared as shown in Scheme 9, substituting 4-bromo-1H-imidazole for 4-bromopyridine. (510 mg, purity: 99%, Yield: 80%) as a white solid. MS (ESI): m/z 230 [M+H]$^+$, $^1$H NMR (400 MHz, Methanol-d$_4$): δ 9.09 (s, 1H), 7.78 (s, 1H), 7.53-7.43 (m, 3H), 5.15 (d, J=7.2 Hz, 1H), 4.26-4.21 (m, 1H), 3.88-3.81 (m, 1H), 3.64-3.60 (m, 1H), 3.29-3.23 (m, 1H), 3.14-3.06 (m, 1H), 2.80-2.75 (m, 1H).

rel-(R)-1-(5-(1H-imidazol-4-yl)isochroman-1-yl)-N-methylmethanamine hydrochloride salt (Compound 114)

The title compound was prepared as shown in Scheme 8, substituting 4-bromo-1H-imidazole for 4-bromopyridine. (370 mg, purity: 99%, Yield: 81%) as a white solid. MS (ESI): m/z 244 [M+H]$^+$. $^1$H NMR (400 MHz, Methanol-d$_4$): δ 9.10 (s, 1H), 7.79 (s, 1H), 7.53-7.46 (m, 3H), 5.14 (d, J=8.8 Hz, 1H), 4.27-4.22 (m, 1H), 3.88-3.82 (m, 1H), 3.72-3.68 (m, 1H), 3.40-3.34 (m, 1H), 3.14-3.07 (m, 1H), 2.82-2.76 (m, 4H).

rel-(S)-1-(5-(1H-imidazol-4-yl)isochroman-1-yl)-N-methylmethanamine hydrochloride salt (Compound 115)

The title compound was prepared as shown in Scheme 8, substituting 4-bromo-1H-imidazole for 4-bromopyridine. White solid (370 mg, purity: 97%, Yield: 84%). MS (ESI): m/z 244 [M+H]$^+$, $^1$H NMR (400 MHz, methanol-d$_4$): δ 9.10 (s, 1H), 7.79 (s, 1H), 7.53-7.45 (m, 3H), 5.24 (d, J=7.6 Hz, 1H), 4.27-4.22 (m, 1H), 3.88-3.82 (m, 1H), 3.72-3.68 (m, 1H), 3.40-3.34 (m, 1H), 3.13-3.07 (m, 1H), 2.82-2.75 (m, 4H).

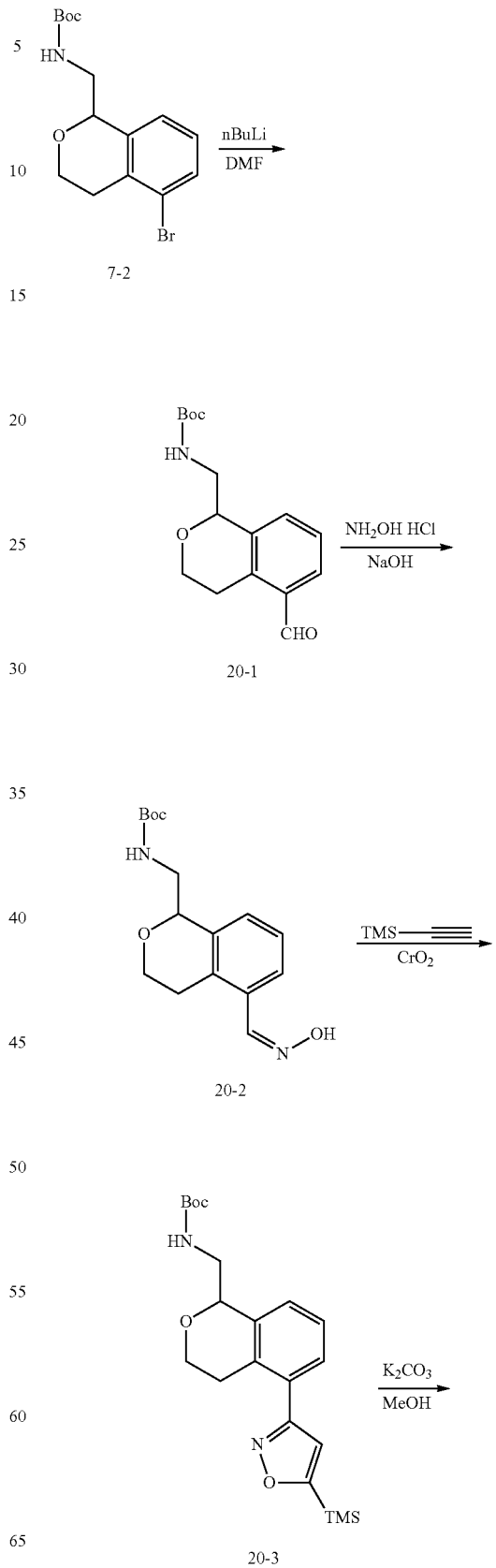

Scheme 20

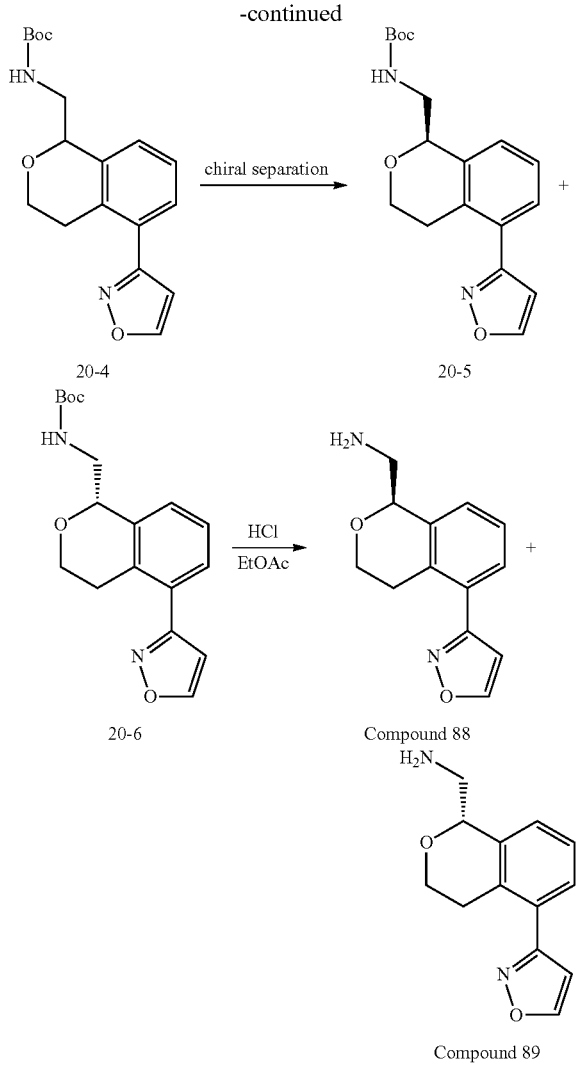

Synthesis of Compound 88 and Compound 89 tert-Butyl ((5-formylisochroman-1-yl)methyl)carbamate (20-1)

To a solution of tert-butyl ((5-bromoisochroman-1-yl)methyl)carbamate (Intermediate 7-2) (5 g, 12.8 mmol) in tetrahydrofuran (50 mL) was added n-butyllithium (2.04 g, 32.0 mmol) at −78° C., the reaction was stirred at −78° C. for 1 h. DMF (2.80 g, 38.4 mmol) was added to the mixture. The reaction was stirred at −78° C. for 2 h. Upon completion, the mixture was quenched with aq. ammonium chloride, diluted with ethyl acetate, washed with brine (3×50 mL). The organic layer was dried over sodium sulfate, filtered and concentrated to give the crude product, then it was purified by column chromatography (petroleum ether:ethyl acetate=4:1) to give tert-butyl ((5-formylisochroman-1-yl)methyl)carbamate as yellow oil (1.7 g, Yield: 34%). MS (ESI): m/z 314 [M+Na]$^+$.

(Z)-tert-Butyl ((5-((hydroxyimino)methyl)isochroman-1-yl)methyl)carbamate (20-2)

To a solution of tert-butyl ((5-formylisochroman-1-yl)methyl)carbamate (2.3 g, 7.89 mmol) in ethanol (40 mL) was added hydroxylamine hydrochloride (1.48 g, 21.3 mmol) and a solution of sodium hydroxide (1.70 g, 42.6 mmol) in deionized water (3 mL). The reaction was allowed to reflux overnight under an atmosphere of nitrogen. The mixture was then worked up with water and extracted with ethyl acetate (3×100 mL). The organic extracts dried over anhydrous sodium sulfate and the solvent evaporated under reduced pressure. The crude product was purified by silica-gel chromatograph column using a mixture of ethyl acetate: petroleum ether (1:4) as eluent. The product was dried in vacuo to give (Z)-tert-butyl ((5-((hydroxyimino)methyl)isochroman-1-yl)methyl)carbamate as a light-yellow oil (1.9 g, yield: 79%). MS (ESI): m/z 329 [M+Na]$^+$.

tert-Butyl ((5-(5-(trimethylsilyl)isoxazol-3-yl)isochroman-1-yl)methyl)carbamate (20-3)

To a solution of (Z)-tert-butyl ((5-((hydroxyimino)methyl)isochroman-1-yl)methyl)carbamate (2 g, 6.52 mmol) in acetonitrile (5 mL) was added ethynyltrimethylsilane (1.91 g, 19.5 mmol) and chromium(IV) oxide (5.46 g, 65.1 mmol). The reaction mixture was heated to 80° C. and stirred at that temperature for 16 h. The mixture was cooled down to room temperature. Then it was filtered and washed with DCM, the filtrate was concentrated. Then it was diluted with DCM (20 mL), washed with brine (2×10 mL). The organic layer was dried over sodium sulfate, filtered and concentrated to give the crude product. Then it was purified with column chromatography (petroleum ether:ethyl acetate=4:1) to give tert-butyl ((5-(5-(trimethylsilyl)isoxazol-3-yl)isochroman-1-yl)methyl)carbamate (1.12 g, Yield: 41%). MS (ESI): m/z 303 [M−100+H]$^+$, 425 [M+Na]$^+$.

Tert-Butyl ((5-(isoxazol-3-yl)isochroman-1-yl)methyl)carbamate (20-4)

To a solution of tert-butyl ((5-(5-(trimethylsilyl)isoxazol-3-yl)isochroman-1-yl)methyl) carbamate (1.5 g, 3.72 mmol) in methanol (15 mL) was added potassium carbonate (102 mg, 744 μmol). The reaction was stirred at ambient temperature for 2 h. The product was found based on LCMS, and then water (10 mL) was added to the mixture and the resulting mixture was extracted three times with DCM (20 mL). The combined organic phases were dried over sodium sulfate, filtered and evaporated to dry under reduced pressure to give product (1 g, Yield: 79%). MS (ESI): m/z 231 [M−100+H]$^+$.

(R)-tert-Butyl ((5-(isoxazol-3-yl)isochroman-1-yl)methyl)carbamate (20-5) and (S)-tert-butyl ((5-(isoxazol-3-yl)isochroman-1-yl)methyl)carbamate (20-6)

Tert-butyl ((5-(isoxazol-3-yl)isochroman-1-yl)methyl) carbamate (2 g, 6.05 mmol) was separated twice by column: AD 20×250 mm, 5 μm (Daicel), mobile phase: CO$_2$/Ethanol (1% Methanol Ammonia)=80/20, flow rate: 70 g/min, back pressure: 100 bar cycle time: 7 min, sample solution: 2 g dissolved in 60 ml methanol, injection volume: 0.5 mL to give (R)-tert-butyl ((5-(isoxazol-3-yl)isochroman-1-yl) methyl)carbamate (300 mg, retention time 2.26 min, ee 100%, Yield: 15%) and (S)-tert-butyl ((5-(isoxazol-3-yl) isochroman-1-yl)methyl)carbamate (600 mg, retention time 2.8 min, ee 98.8%, Yield: 30%). Total yield: 45%.

rel-(R)-(5-(Isoxazol-3-yl)isochroman-1-yl)methanamine hydrochloride salt (Compound 88)

To a solution of (R)-tert-butyl ((5-(isoxazol-3-yl)isochroman-1-yl)methyl)carbamate (290 mg, 877 μmol) in ethyl acetate (25 mL) was added HCl/Ethyl acetate (638 mg, 17.5 mmol). The reaction was stirred at ambient temperature for 5 h. The mixture was concentrated to give rel-(R)-(5-(isoxazol-3-yl)isochroman-1-yl)methanamine hydrochloride (0.216 g, Yield 91%) as yellow solid MS (ESI): m/z 231 [M+H]⁺. ¹H NMR (400 MHz, Methanol-d4): δ 8.79 (d, J=1.6 Hz, 1H), 7.55 (d, J=7.6 Hz, 1H), 7.45-7.36 (m, 2H), 6.78 (d, J=1.6 Hz, 1H), 5.13-5.11 (m, 1H), 4.24-4.19 (m, 1H), 3.85-3.79 (m, 1H), 3.60-3.56 (m, 1H), 3.28-3.25 (m, 1H), 3.18-3.10 (m, 1H), 2.92-2.86 (m, 1H).

rel-(S)-(5-(Isoxazol-3-yl)isochroman-1-yl)methanamine hydrochloride salt (Compound 89)

To a solution of (S)-tert-butyl ((5-(isoxazol-3-yl)isochroman-1-yl)methyl)carbamate (590 mg, 1.78 mmol) in ethyl acetate (50 mL) was added HCl/Ethyl acetate (1.29 g, 35.6 mmol). The mixture was concentrated to give rel-(S)-(5-(isoxazol-3-yl)isochroman-1-yl)methanamine (0.398 g, Yield: 83%) as yellow solid. MS (ESI): m/z 231 [M+H]⁺. ¹H NMR (400 MHz, Methanol-d4): δ 8.79 (d, J=2.0 Hz, 1H), 7.55 (d, J=7.2 Hz, 1H), 7.45-7.36 (m, 2H), 6.78 (d, J=2.0 Hz, 1H), 5.14-5.11 (m, 1H), 4.24-4.19 (m, 1H), 3.85-3.79 (m, 1H), 3.60-3.56 (m, 1H), 3.28-3.25 (m, 1H), 3.18-3.10 (m, 1H), 2.92-2.86 (m, 1H).

rel-(R)-1-(5-(Isoxazol-3-yl)isochroman-1-yl)-N-methylmethanamine hydrochloride salt (Compound 90)

The title compound was prepared using the procedure shown in Scheme 20, substituting tert-butyl ((5-bromoisochroman-1-yl)methyl)(methyl)carbamate (Intermediate 4-2) for tert-butyl ((5-bromoisochroman-1-yl)methyl)carbamate. White solid (0.364 g, Yield: 81%). MS (ESI): m/z 245 [M+H]⁺. ¹H NMR (400 MHz, Methanol-d4): δ 8.79 (s, 1H), 7.55 (d, J=7.2 Hz, 1H), 7.45-7.38 (m, 2H), 6.78 (s, 1H), 5.21-5.19 (m, 1H), 4.25-4.20 (m, 1H), 3.85-3.80 (m, 1H), 3.68-3.65 (m, 1H), 3.40-3.35 (m, 1H), 3.18-3.10 (m, 1H), 2.91-2.88 (m, 1H), 2.80 (s, 3H).

rel-(S)-1-(5-(Isoxazol-3-yl)isochroman-1-yl)-N-methylmethanamine hydrochloride salt (Compound 91)

The title compound was prepared using the procedure shown in Scheme 20, substituting tert-butyl ((5-bromoisochroman-1-yl)methyl)(methyl)carbamate (Intermediate 4-2) for tert-butyl ((5-bromoisochroman-1-yl)methyl)carbamate. White solid (0.422 g, Yield: 73%). MS (ESI): m/z 245 [M+H]⁺. ¹H NMR (400 MHz, Methanol-d4): δ 8.79 (d, J=1.6 Hz, 1H), 7.56 (d, J=7.2 Hz, 1H), 7.45-7.38 (m, 2H), 6.78 (d, J=1.6 Hz, 1H), 5.20-5.18 (m, 1H), 4.2-4.20 (m, 1H), 3.86-3.80 (m, 1H), 3.68-3.64 (m, 1H), 3.41-3.36 (m, 1H), 3.18-3.10 (m 1H), 2.92-2.87 (m, 1H), 2.80 (s, 3H).

Scheme 21

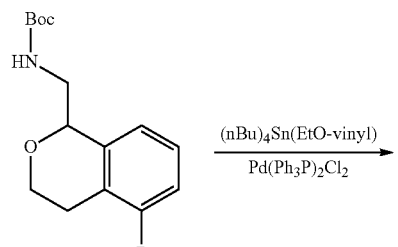

7-2

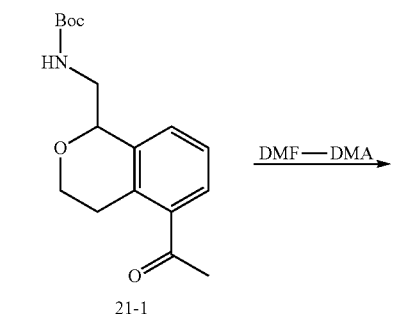

21-1

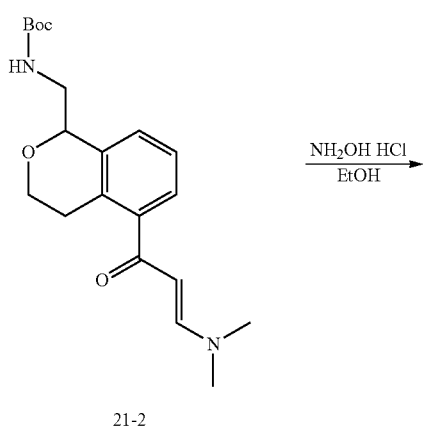

21-2

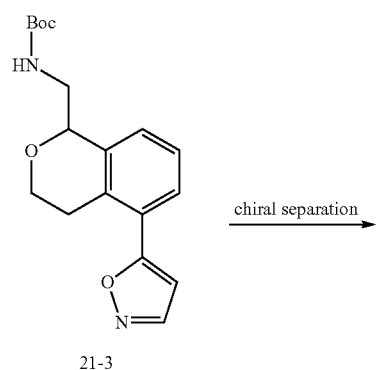

21-3

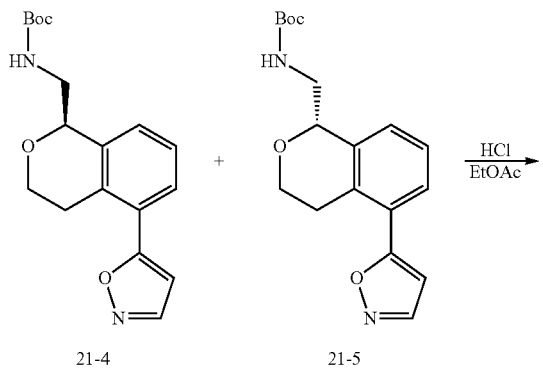

21-4    21-5

-continued

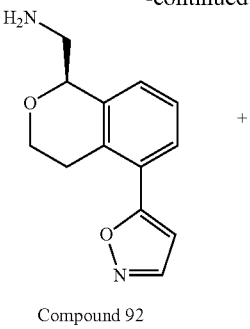

Compound 92

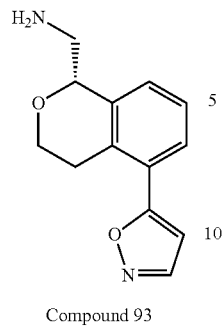

Compound 93

Synthesis of Compound 92 and Compound 93

Tert-Butyl ((5-acetylisochroman-1-yl)methyl)(methyl)carbamate (21-1)

To a solution of tert-butyl ((5-bromoisochroman-1-yl)methyl)(methyl)carbamate (Intermediate 7-2) (7.58 g, 21.3 mmol) in 1,4-dioxane (100 mL) was added tributyl(1-ethoxyvinyl)stannane (7.7 g, 21.3 mmol) and Pd(Ph$_3$P)$_2$Cl$_2$ (299 mg, 426 µmol). The reaction mixture was heated to 90° C. and stirred at that temperature for 16 h. After cooling to room temperature, the reaction was treated with ethyl acetate (100 mL) and washed with 15 percent citric acid aqueous solution (2×50 mL), H$_2$O (50 mL) and brine (50 mL). The organic layer was dried over Na$_2$SO$_4$ and concentrated in vacuo. The residue was purified by flash chromatography on silica gel (ethyl acetate:petroleum ether=1:5) to give desired compound (5.3 g, Yield 78%). MS (ESI): m/z 219 [M+1−100]$^+$ (E)-r-Butyl ((5-(3-(dimethylamino)acryloyl)isochroman-1-yl)methyl)(methyl)carbamate (21-2)

Tert-butyl ((5-acetylisochroman-1-yl)methyl)(methyl)carbamate (5.3 g, 16.5 mmol) was dissolved in DMF-DMA (60 mL). The reaction mixture was heated to 110° C. and stirred at that temperature for 24 h. The reaction mixture was concentrated to dry, water (150 mL) was added to the reaction vessel and the resulting biphasic mixture was transferred to a separating funnel. The layers were separated and the aqueous phase was washed with ethyl acetate (3×100 mL). The combined organics were dried over anhydrous Na$_2$SO$_4$, filtered and concentrated in vacuo. The crude product was purified via silica chromatography, eluting with ethyl acetate to afford the title compound as brown oil (6.0 g, Yield: 82%). MS (ESI): m/z 375 [M+H]$^+$ Tert-Butyl ((5-(isoxazol-5-yl)isochroman-1-yl)methyl)(methyl)carbamate (21-3)

To a solution of (E)-tert-butyl ((5-(3-(dimethylamino)acryloyl)isochroman-1-yl)methyl)(methyl)carbamate (6.0 g, 16.0 mmol) in EtOH (100 mL) was added hydroxylamine hydrochloride (2.22 g, 32.0 mmol). The reaction mixture was heated to 90° C. and stirred at that temperature for 16 h. The reaction mixture was concentrated, saturated aqueous NaHCO$_3$(150 mL) was added to the reaction vessel and the resulting biphasic mixture was transferred to a separating funnel. The layers were separated and the aqueous phase was washed with ethyl acetate (3×100 mL). The combined organics were dried over anhydrous Na$_2$SO$_4$, filtered and concentrated in vacuo. The residue was purified by silica chromatography, eluting with ethyl acetate:petroleum ether=1:4 to afford the title compound (4.4 g, Yield 80%). MS (ESI): m/z 353 [M+Na]$^+$ rel-(R)-tert-Butyl ((5-(isoxazol-5-yl)isochroman-1-yl)methyl)(methyl)carbamate (21-4) and rel-(S)-tert-butyl ((5-(isoxazol-5-yl)isochroman-1-yl)methyl)(methyl)carbamate (21-5)

Tert-butyl ((5-(isoxazol-5-yl)isochroman-1-yl)methyl)(methyl)carbamate (3.2 g, 9.29 mmol) was separated into its enantiomers rel-(R)-tert-butyl ((5-(isoxazol-5-yl)isochroman-1-yl)methyl)(methyl)carbamate and rel-(R)-tert-butyl ((5-(isoxazol-5-yl)isochroman-1-yl)methyl)(methyl)carbamate by using HPLC-AY, Rel-(R)-tert-butyl ((5-(isoxazol-5-yl)isochroman-1-yl)methyl)(methyl)carbamate (1.5 g, Yield: 47%) was obtained as white solid. rel-(R)-tert-butyl ((5-(isoxazol-5-yl)isochroman-1-yl)methyl)(methyl)carbamate (1.2 g, Yield: 38%) was obtained as white solid. MS (ESI): m/z 345 [M+H]$^+$ (R)-(5-(Isoxazol-5-yl)isochroman-1-yl)methanamine hydrochloride salt (Compound 92)

To a solution of rel-(R)-tert-butyl ((5-(isoxazol-5-yl)isochroman-1-yl)methyl)(methyl)carbamate (1.2 g, 3.48 mmol) in ethyl acetate (10 mL) was added HCV/ethyl acetate (11.6 mL, 3.0 M, 34.8 mmol). The reaction was stirred at ambient temperature for 4 h. Filtered a white solid as the title compound (0.7 g, Yield 82%). MS(ESI): m/z 245 [M+H]$^+$. $^1$H NMR (400 MHz, Methanol-d4): δ 8.51 (d, J=1.9 Hz, 1H), 7.72 (d, J=7.5 Hz, 1H), 7.46 (d, J=7.7 Hz, 1H), 7.41 (t, J=8.9 Hz, 1H), 6.71 (d, J=1.9 Hz, 1H), 5.26-5.16 (m, 1H), 4.26-4.23 (m, 1H), 3.88-3.82 (m, 1H), 3.42-3.36 (m, 1H, 3.22-3.15 (m, 1H), 2.92-2.86 (m, 1H), 2.80 (s, 3H).

(S)-(Isoxazol-5-yl)isochroman-1-yl)methanamine hydrochloride salt (Compound 93)

To a solution of rel-(S)-tert-butyl ((5-(isoxazol-5-yl)isochroman-1-yl)methyl)(methyl) carbamate (1.5 g, 4.35 mmol) in ethyl acetate (10 mL) was added HCl/ethyl acetate (14.4 mL, 3.0 M, 43.4 mmol). The reaction was stirred at ambient temperature for 4 h. Filtered, the white solid was the title compound (0.9 g, Yield: 85%). MS(ESI): m/z 245 [M+H]$^+$. $^1$H NMR (400 MHz, Methanol-d4): δ 8.51 (d, J=1.9 Hz, 1H), 7.72 (d, J=7.5 Hz, 1H), 7.46 (t, J=7.7 Hz, 1H), 7.40 (d, J=7.7 Hz, 1H), 6.70 (d, J=1.9 Hz, 1H), 5.19 (d, J=6.7 Hz, 1H). 4.29-4.24 (m, 1H), 3.88-3.82 (m, 1H), 3.66 (dd, J=3.1/12.9 Hz, 1H), 3.46-3.36 (m, 1H), 3.25-3.10 (m, 1H), 2.92-2.87 (m, 1H), 2.80 (s, 3H).

(R)-1-(5-(Isoxazol-5-yl)isochroman-1-yl)-N-methyl-methanamine (Compound 94)

The title compound was prepared using the procedure shown in Scheme 21, substituting tert-butyl ((5-bromoisochroman-1-yl)methyl)(methyl)carbamate (Intermediate 4-2) for tert-butyl ((5-bromoisochroman-1-yl)methyl)carbamate. Filtered a white solid as the title compound (0.7 g, Yield 82%). MS(ESI): m/z 245 [M+H]$^+$. $^1$H NMR (400 MHz, Methanol-d4): δ 8.51 (d, J=1.9 Hz, 1H), 7.72 (d, J=7.5 Hz, 1H), 7.46 (d, J=7.7 Hz, 1H), 7.41 (t, J=8.9 Hz, 1H), 6.71 (d, J=1.9 Hz, 1H), 5.26-5.16 (m, 1H), 4.26-4.23 (m, 1H), 3.88-3.82 (m, 1H), 3.42-3.36 (m, 1H, 3.22-3.15 (m, 1H), 2.92-2.86 (m, 1H), 2.80 (s, 3H).

(S)-1-(5-(Isoxazol-1-yl)isochroman-1-yl)-N-methylmethanamine (Compound 95)

The title compound was prepared using the procedure shown in Scheme 21, substituting tert-butyl ((5-bromoisochroman-1-yl)methyl)(methyl)carbamate (Intermediate 4-2) for tert-butyl ((5-bromoisochroman-1-yl)methyl)carbamate. Filtered a white solid as the title compound (0.9 g, Yield: 85%). MS(ESI): m/z 245 [M+H]⁺. ¹H NMR (400 MHz, Methanol-d4): δ 8.51 (d, J=1.9 Hz, 1H), 7.72 (d, J=7.5 Hz, 1H), 7.46 (t, J=7.7 Hz, 1H), 7.40 (d, J=7.7 Hz, 1H), 6.70 (d, J=1.9 Hz, 1H), 5.19 (d, J=6.7 Hz, 1H), 4.29-4.24 (m, 1H), 3.88-3.82 (m, 1H), 3.66 (dd, J=3.1/12.9 Hz, 1H), 3.46-3.36 (m, 1H), 3.25-3.10 (m, 1H), 2.92-2.87 (m, 1H), 2.80 (s, 3H).

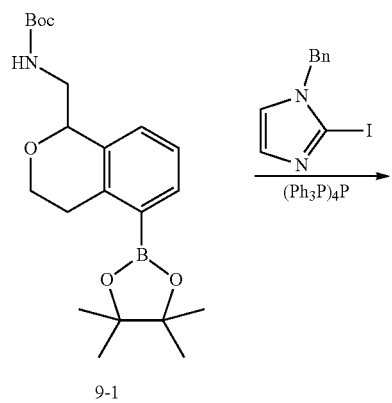

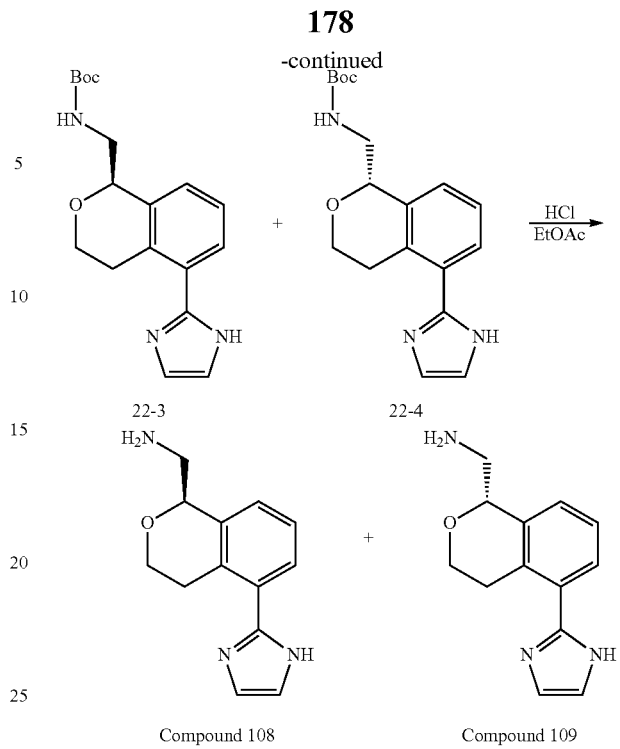

Synthesis of Compound 108 and Compound 109 tert-Butyl ((5-(1-benzyl-1H-imidazol-2-yl)isochroman-1-yl)methyl)carbamate (22-1)

To a solution of tert-butyl ((5-(4,4,5,5-tetramethyl-1,3,2-dioxaborolan-2-yl)isochroman-1-yl)methyl)carbamate (Intermediate 9-1) (12 g, 30.8 mmol) in DMF/H₂O (100/25 mL) was added K₃PO₄ (13.0 g, 61.6 mmol) and Pd(Ph₃P)₄ (3.55 g, 3.08 mmol). 1-Benzyl-2-iodo-1H-imidazole (8.74 g, 30.8 mmol) was added, and the reaction mixture was heated to 120° C. and stirred at that temperature for 16 h. Water (300 mL) was added to the reaction vessel and the resulting biphasic mixture was transferred to a separating funnel. The layers were separated and the aqueous phase was washed with ethyl acetate (3×60 mL). The combined organics were dried over anhydrous Na₂SO₄, filtered and concentrated in vacuo. The residue was purified via silica chromatography, eluting with ethyl acetate:hexane=1:1 to afford the title compound as white solid (7.0 g, Yield: 54%). MS (ESI): m/z 420 [M+H]⁺

Tert-Butyl ((5-(1H-imidazol-2-yl)isochroman-1-yl)methyl)carbamate (22-2)

To a solution of tert-butyl ((5-(1-benzyl-1H-imidazol-2-yl)isochroman-1-yl)methyl)carbamate (4.5 g, 10.7 mmol) in MeOH (120 mL) was added Pd/C (4.5 g, 45.0 mol) under H₂. The reaction mixture was stirred at ambient temperature for 16 h. LC-MS showed that the title compound was 20%, source material was 70%. Added Pd/C (500 mg), continued to stir for three days. Filtered, the filtrate was concentrated to afford the title compound as white solid (3.3 g, Yield 94%), MS (ESI): m/z 330 [M+H]⁺

(R)-tert-Butyl ((5-(1H-imidazol-2-yl)isochroman-1-yl)methyl)carbamate (22-3) and (S)-tert-butyl ((5-(1H-imidazol-2-yl)isochroman-1-yl)methyl)carbamate (22-4)

Tert-butyl ((5-(1H-imidazol-2-yl)isochroman-1-yl)methyl)carbamate (2.9 g, 8.8 mmol) was separated into its enantiomers (R)-tert-butyl ((5-(H-imidazol-2-yl)isochroman-1-yl)methyl)carbamate and (S)-tert-butyl ((5-(1H-imidazol-2-yl)isochroman-1-yl)methyl)carbamate by SFC-80 (Thar, Waters) using AD 20×250 mm, 10 μm (Daicel) and Mobile phase: $CO_2$/Methanol (0.2% Methanol Ammonia) =75/25, The flow rate was 80 g/min, back pressure was 100 Bar and cycle time of stack injections was 3.5 min. Tert-butyl ((5-(1H-imidazol-2-yl)isochroman-1-yl)methyl)carbamate (1.2 g, Yield 42%) was obtained as white solid and tert-butyl ((3R,4R)-3-ethylisochroman-4-yl)carbamate (0.9 g. Yield: 31%, retention time 0.86 min) was obtained as white solid. MS (ESI): ml 330 [M+H]$^+$

(R)-(5-(1H-Imidazol-2-yl)isochroman-1-yl)methanamine hydrochloride salt (Compound 108)

To a solution of rel-(R)-tert-butyl ((5-(H-imidazol-2-yl)isochroman-1-yl)methyl)carbamate (1.2 g, 3.64 mmol) in Ethyl acetate/MeOH (20/5 mL) was added HCl/EA (109 mg, 36.4 mmol). The reaction was stirred at ambient temperature for 16 h. Concentrated to afford the title compound as white solid (0.95 g, Yield: 100%), MS (ESI): m/z 230 [M+H]$^+$. $^1$H NMR (400 MHz, Methanol-d4): δ 7.74 (s, 2H), 7.67-7.50 (m, 3H), 5.16 (d, J=7.2 Hz, 1H), 4.31-4.16 (m, 1H), 3.97-3.75 (m, 1H), 3.64 (dd, J=3.0/13.1 Hz, 1H), 3.28-3.22 (m, 1H), 3.18-3.04 (m, 1H), 2.75-2.69 (m, 1H).

(S)-(5-(1H-Imidazol-2-yl)isochroman-1-yl)methanamine hydrochloride salt (Compound 109)

To a solution of rel-(S)-tert-butyl ((5-(1H-imidazol-2-yl)isochroman-1-yl)methyl)carbamate (1.0 g, 3.03 mmol) in Ethyl acetate/MeOH (50 mL) was added HCl/Ethyl acetate (15 mL, 3.0 M, 3.01 mmol). The reaction was stirred at ambient temperature for 16 h. concentrated to afford the title compound as white solid (0.68 g, Yield: 98%), MS (ESI): m/z 230 [M+H]$^+$.

$^1$H NMR (400 MHz, Methanol-d4): δ 7.74 (s, 2H), 7.60 (dt, J=16.8, 4.4 Hz, 3H), 5.16 (d, J=7.5 Hz, 1H), 4.30-4.17 (m, 1H), 3.96-3.80 (m, 1H), 3.64 (dd, J=13.1, 2.9 Hz, 1H), 3.28-3.22 (m, 1H), 3.18-3.07 (m, 1H), 2.75-2.69 (m, 1H).

(R)-1-(5-(1H-Imidazol-2-yl)isochroman-1-yl)-N-methylmethanamine hydrochloride salt (Compound 110)

The title compound was prepared as shown in Scheme 22, substituting tert-butyl methyl((5-(4,4,5,5-tetramethyl-1,3,2-dioxaborolan-2-yl)isochroman-1-yl)methyl)carbamate (Intermediate 8-1) for tert-butyl ((5-(4,4,5,5-tetramethyl-1,3,2-dioxaborolan-2-yl)isochroman-1-yl)methyl)carbamate.
White solid (0.624 g, Yield: 100%). MS(ESI): m/z 244 [M+H]$^+$. $^1$H NMR (400 MHz, Methanol-d4): δ 7.74 (s, 2H), 7.66-7.49 (m, 3H), 5.25 (d, J=7.6 Hz, 1H), 4.35-4.19 (m, 1H), 3.93-3.81 (m, 1H), 3.74 (d, J=3.0 Hz, 1H), 3.40-3.35 (m, 1H), 3.16-3.06 (m, 1H), 2.83 (s, 3H), 2.75-2.70 (m, 1H).

(S)-1-(5-(1H-Imidazol-2-yl)isochroman-1-yl)-N-methylmethanamine hydrochloride salt (Compound 111)

The title compound was prepared as shown in Scheme 22, substituting tert-butyl methyl((5-(4,4,5,5-tetramethyl-1,3,2-dioxaborolan-2-yl)isochroman-1-yl)methyl)carbamate (Intermediate 8-1) for tert-butyl ((5-(4,4,5,5-tetramethyl-1,3,2-dioxaborolan-2-yl)isochroman-1-yl)methyl)carbamate.
White solid (0.577 g, Yield: 100%). MS(ESI): m/z 244 [M+H]$^+$. $^1$H NMR (400 MHz, Methanol-d4): δ 7.74 (s, 2H), 7.66-7.53 (m, 3H), 5.24 (d, J=9.2 Hz, 1H), 4.32-4.21 (m, 1H), 3.93-3.81 (m, 1H), 3.72 (dd, J=2.9/12.9 Hz, 1H), 3.39-3.36 (m, 1H), 3.17-3.07 (m, 1H), 2.83 (s, 3H), 2.75-2.67 (m, 1H).

(R)-(5-(1H-pyrazol-4-yl)isochroman-1-yl)methanamine hydrochloride salt (Compound 116)

The title compound was prepared as shown in Scheme 22, substituting 1-benzyl-4-iodo-1H-pyrazole for 1-benzyl-2-iodo-1H-imidazole. (360 mg, 64%). MS (ESI): m/z 230 [M+H]$^+$. Ret. Time: 10.21, ee value 100%, $^1$H NMR (400 MHz, DMSO-d6): δ 8.23 (bs, 5H), 7.94 (s, 2H), 7.17-7.36 (m, 3H), 5.04 (d, J=8.4 Hz, 1H), 4.02-4.06 (m, 1H), 3.70-3.75 (m, 1H), 3.39 (dd, J=2.8/9.6 Hz, 1H), 3.07-3.10 (m, 1H), 2.89-2.96 (m, 1H), 2.74-2.79 (m, 1H).

(S)-(5-(1H-pyrazol-4-yl)isochroman-1-yl)methanamine hydrochloride salt (Compound 117)

The title compound was prepared as shown in Scheme 22, substituting 1-benzyl-4-iodo-1H-pyrazole for 1-benzyl-2-iodo-1H-imidazole. (358 mg, Yield: 74%). MS (ESI): m/z 230 [M+H]$^+$. Ret. Time: 13.40, e.e value 100%, H NMR (400 MHz, DMSO-d6): δ 8.20 (bs, 5H), 7.92 (s, 2H), 7.16-7.36 (m, 3H), 5.03 (d, J=8.4 Hz, 1H), 4.02-4.07 (m, 1H), 3.69-3.75 (m, 1H), 3.38-3.43 (m, 1H), 3.06-3.12 (m, 1H), 2.89-2.96 (m, 1H), 2.73-2.79 (m, 1H).

(R)-1-(5-(1H-pyrazol-4-yl)isochroman-1-yl)-N-methylmethanamine hydrochloride salt (Compound 118)

The title compound was prepared as shown in Scheme 22, substituting tert-butyl methyl((5-(4,4,5,5-tetramethyl-1,3,2-dioxaborolan-2-yl)isochroman-1-yl)methyl)carbamate (Intermediate 8-1) for tert-butyl ((5-(4,4,5,5-tetramethyl-1,3,2-dioxaborolan-2-yl)isochroman-1-yl)methyl)carbamate, and substituting 1-benzyl-4-iodo-1H-pyrazole for 1-benzyl-2-iodo-1H-imidazole. (380 mg, Yield: 59%). MS (ESI): m/z 244 [M+H]$^+$. Ret. Time: 3.47 min, ee value 100%, $^1$H NMR (400 MHz, Methanol-d4): δ 8.41 (s, 2H), 7.29-7.45 (m, 3H), 5.18 (d, J=8.0 Hz, 1H), 4.21-4.26 (m, 1H), 3.80-3.86 (m, 1H), 3.66 (dd, J=2.4/12.8 Hz, 1H), 3.33-3.38 (m, 1H), 3.06-3.14 (m, 1H), 2.76-2.80 (m, 4H).

(S)-1-(5-(1H-pyrazol-4-yl)isochroman-1-yl)-N-methylmethanamine hydrochloride salt (Compound 119)

The title compound was prepared as shown in Scheme 22, substituting tert-butyl methyl((5-(4,4,5,5-tetramethyl-1,3,2-dioxaborolan-2-yl)isochroman-1-yl)methyl)carbamate (Intermediate 8-1) for tert-butyl ((5-(4,4,5,5-tetramethyl-1,3,2-dioxaborolan-2-yl)isochroman-1-yl)methyl)carbamate, and substituting 1-benzyl-4-iodo-1H-pyrazole for 1-benzyl-2-iodo-1H-imidazole. (300 mg, Yield: 55%). MS (ESI): m z 244 [M+H]$^+$. Ret. Time: 3.99, e.e value 100%, $^1$H NMR (400 MHz, Methanol-d4) δ 8.36 (s, 2H), 7.28-7.45 (m, 3H), 5.18 (d, J=7.2 Hz, 1H), 4.21-4.26 (m, 1H), 3.79-3.85 (m, 1H), 3.65 (dd, J=2.8/12.8 Hz, 1 H), 3.33-3.38 (m, 1H), 3.06-3.13 (m, 1H), 2.76-2.80 (m, 4H).

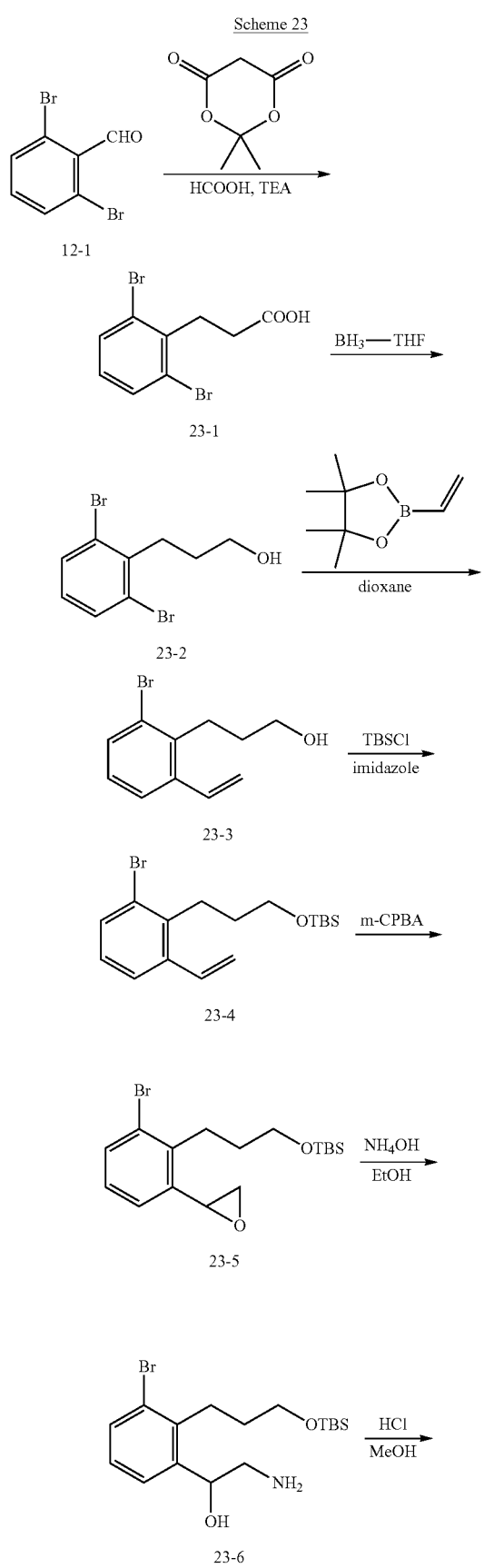
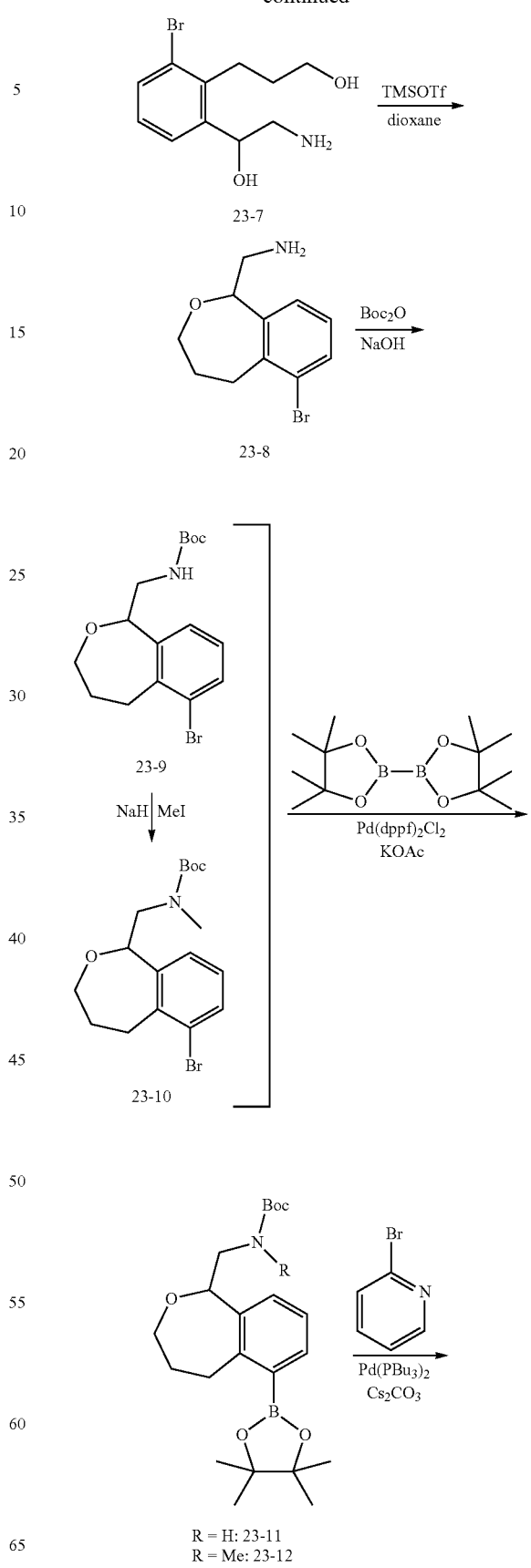

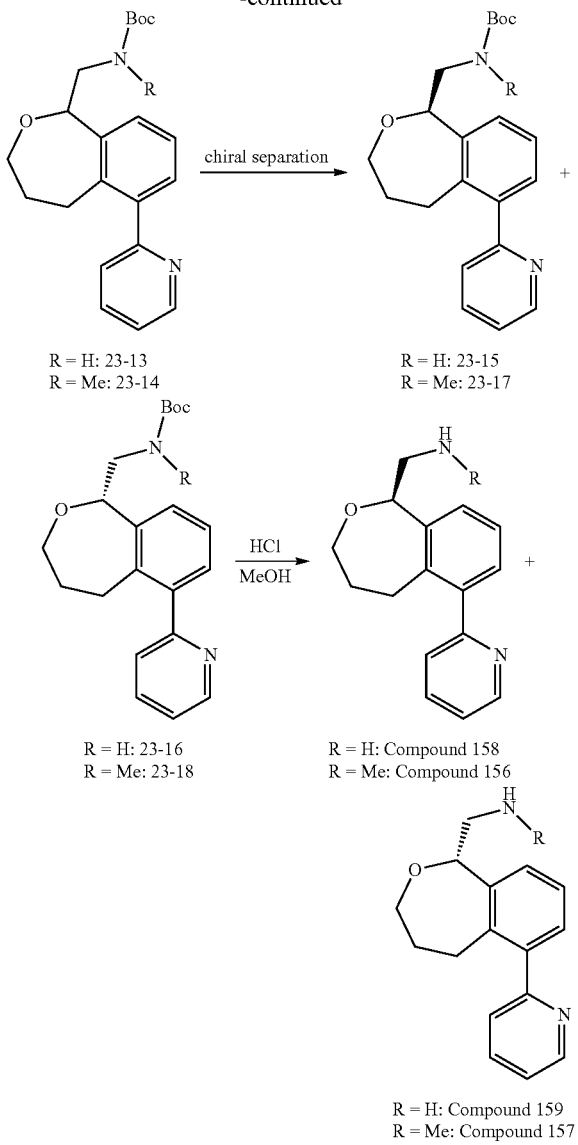

Synthesis of Compounds 156, 157, 158 and 159

3-(2,6-Dibromophenyl)propanoic acid (23-1)

To a solution of formic acid (2 mL) at 5° C. was added triethylamine (2.67 g, 26.4 mmol) drop-wise maintaining the temperature below 10° C. Subsequently. 2,6-dibromobenzaldehyde (Intermediate 12-1) (1.0 g, 3.78 mmol) 2,2-dimethyl-1,3-dioxane-4,6-dione (652 mg, 4.53 mmol) were added to the solution and the mixture was refluxed for 4 h. Afterwards the mixture was cooled to an ambient temperature and poured onto ice-cold water (8 mL). The resulting suspension was acidified by 5.5M HCl until pH 1 and stored in a refrigerator overnight. The precipitated crystals were filtered with suction, washed with water (3×4 mL) to provide 3-(2,6-dibromophenyl)propanoic acid (854 mg, 2.55 mmol) as a yellow solid. MS (ESI): m/z 309.1 [M+H]$^+$, $^1$H NMR (400 MHz, Methanol-d$_4$): δ 7.59 (d, J=8.0 Hz, 2H), 7.03 (t, J=8.0 Hz, 1H), 3.32-3.28 (m, 2H), 2.55-2.51 (m, 2H).

3-(2,6-Dibromophenyl)propan-1-ol (23-2)

To (tetrahydro-1H-furan-1-ium-1-yl)trihydroborate (19.4 g, 226 mmol) at 0° C. was added 3-(2,6-dibromophenyl) propanoic acid (35 g, 113 mmol) slowly. Then the reaction mixture was stirred at room temperature for 16 h. The reaction solution was poured into ice water. Ethyl acetate (200 mL) was added to the solution. The resulting biphasic mixture was transferred to a separating funnel. The layers were separated and the organic phase was washed with saturated aqueous NH$_4$Cl (2×60 mL) and saturated aqueous NaHCO$_3$(2×100 mL). The combined organics were dried over anhydrous Na$_2$SO$_4$, filtered and concentrated in vacuo. The resulting oil was purified by flash column chromatography with a gradient elution of petroleum ether (100%) and ethyl acetate (0%) to ethyl acetate (30%) and petroleum ether (70%° 0) to provide 3-(2,6-dibromophenyl)propan-1-ol (24.5 g, 83.3 mmol, Yield: 74%) as a white solid. MS (ESI): m/z 277.1 [M–H$_2$O+H]$^+$. 1H NMR (400 MHz, methanol-d$_4$): δ 7.57 (d, J=8.0 Hz, 2H), 6.99 (t, J=8.0 Hz, 1H), 3.68 (t, J=6.6 Hz, 2H), 3.08-3.05 (m, 2H), 1.84-1.77 (m, 2H).

3-(2-Bromo-6-vinylphenyl)propan-1-ol (23-3)

To a solution of 3-(2,6-dibromophenyl)propan-1-ol (20 g, 68.0 mmol) in dioxane (200 mL) and water (100 mL) was added potassium orthophosphate (43.3 g, 204 mmol), Tetrakis(triphenylphosphine)palladium (7.85 g, 6.80 mmol) and 4,4,5,5-tetramethyl-2-vinyl-1,3,2-dioxaborolane (10.4 g, 68.0 mmol). The reaction mixture was heated to 100° C. and stirred at that temperature for 5 h. The reaction mixture was concentrated. Water (100 mL) and ethyl acetate (200 mL) was added to the reaction vessel and the resulting biphasic mixture was transferred to a separatory funnel. The layers were separated and the organic phase was washed with water (2×50 mL) and saturated aqueous NaCl (50 mL). The combined organics were dried over anhydrous Na$_2$SO$_4$, filtered and concentrated in vacuo. The resulting oil was purified by flash column chromatography with a gradient elution of petroleum ether (100%) and ethyl acetate (00%) to ethyl acetate (30%) and petroleum ether (70%) to provide 3-(2-bromo-6-vinylphenyl)propan-1-ol (9.60 g, 39.8 mmol, Yield: 58%) as a yellow oil. MS (ESI): no mass detected by LC-MS.

(3-(2-Bromo-6-vinylphenyl)propoxy)(tert-butyl) dimethylsilane (23-4)

To a solution of 3-(2-bromo-6-vinylphenyl)propan-1-ol (15 g, 62.2 mmol) in Dichloromethane (200 mL) was added tert-Butylchlorodimethylsilane (12.1 g, 80.8 mmol), Imidazole (6.35 g, 93.3 mmol) and Triethylamine (8.80 g, 87.0 mmol). The reaction was stirred at room temperature for 2 h. Saturated aqueous NH$_4$Cl (50 mL) was added to the reaction vessel and the resulting biphasic mixture was transferred to a separatory funnel. The layers were separated and the organic phase was washed with saturated aqueous NaHCO$_3$(2×30 mL) and water (30 mL). The combined organics were dried over anhydrous Na$_2$SO$_4$, filtered and concentrated in vacuo. The resulting oil was purified by flash column chromatography with a gradient elution of petroleum ether (100%) and ethyl acetate (0%) to petroleum ether (95%) and ethyl acetate (5%) to provide (3-(2-bromo-6-vinylphenyl)propoxy)(tert-butyl)dimethylsilane (9.90 g, (3-(2-Bromo-6-(oxiran-2-yl)phenyl)propoxy)(tert-butyl)dimethylsilane (23-5)

To a solution of (3-(2-bromo-6-vinylphenyl)propoxy)(tert-butyl)dimethylsilane (40 g, 112 mmol) in Dichloromethane (400 mL) was added 3-Chloroperbenzoic acid (34.0 g, 168 mmol). The reaction was stirred at ambient temperature for 16 h. The suspension was filtered out. The filtrate was diluted with DCM and washed with $Na_2SO_3$ aqueous, saturated $NaHCO_3$ aqueous, water, and brine. The organic phase was dried over $Na_2SO_4$, filtered and concentrated. The resulting oil was purified by flash column chromatography with a gradient elution of petroleum ether (100%) and ethyl acetate (0%) to petroleum ether (85%) and ethyl acetate (15%) to provide (3-(2-bromo-6-(oxiran-2-yl)phenyl)propoxy)(tert-butyl)dimethylsilane (22.5 g, purity: 90%, Yield: 54%) as a yellow oil. MS (ESI): m/z 372.3 $[M+H]^+$, $^1H$ NMR (400 MHz, $CDCl_3$): δ 7.40 (dd, J=8.0 Hz, J=1.2 Hz, 1H), 7.11 (dd, J=8.0 Hz, J=1.2 Hz, 1H), 6.96 (t, J=8.0 Hz, 1H), 4.04-4.02 (m, 1H), 3.64 (t, J=6.0 Hz, 2H), 3.07-3.05 (m, 1H), 2.92-2.87 (m, 2H), 2.55-2.53 (m, 1H), 1.76-1.68 (m, 2H), 0.84 (s, 9H), 0.00 (s, 6H).

2-Amino-1-(3-bromo-2-(3-((tert-butyldimethylsilyl)oxy)propyl)phenyl)ethanol (23-6)

To a solution of (3-(2-bromo-6-(oxiran-2-yl)phenyl)propoxy)(tert-butyl)dimethylsilane (17 g, 45.7 mmol) in ethanol (100 mL) was added ammonia water (35 mL). The mixture was stirred at 65° C. for 16 h. The reaction solution was concentrated. The resulting oil was purified by flash column chromatography with a gradient elution of ethyl acetate (0%) and petroleum ether (100%) to ethyl acetate (50%) and petroleum ether (50%) to provide 2-amino-1-(3-bromo-2-(3-((tert-butyldimethylsilyl)oxy)propyl)phenyl)ethanol (9.78 g, Yield: 55%) as a yellow oil. MS (ESI): m/z 370 $[M-H_2O+H]^+$. 1H NMR (400 MHz, $CDCl_3$): δ 7.50-7.47 (m, 2H), 7.11-7.07 (m, 1H), 4.95 (dd, J=3.6 Hz. J=8.0 Hz, 1H), 3.74-3.69 (m, 2H), 3.02 (dd, J=3.6 Hz, J=12.8 Hz, 1H), 2.95-2.83 (m, 2H), 2.78-2.73 (m, 1H), 2.32 (s, 3H), 1.83-1.76 (m, 2H), 0.97 (s, 9H), 0.09 (s, 6H).

3-(2-(2-Amino-1-hydroxyethyl)-6-bromophenyl)propan-1-ol hydrochloride salt (23-7)

To a solution of 2-amino-1-(3-bromo-2-(3-((tert-butyldimethylsilyl)oxy)propyl)phenyl) ethanol (10.3 g, 26.5 mmol) in methanol (75 mL) was added hydrogen chloride (5.79 g, 159 mmol). The reaction was stirred at ambient temperature for 2 h. The mixture was concentrated. The residue was used for the next step without further purification.

(6-Bromo-1,3,4,5-tetrahydrobenzo[c]oxepin-1-yl)methanamine (23-8)

To a solution of 3-(2-(2-amino-1-hydroxyethyl)-6-bromophenyl)propan-1-ol hydrochloride salt (9.19 g, 26.4 mmol) in 1,4-dioxane (5 mL) was added trimethylsilyl trifluoromethanesulfonate (35 mL). The reaction mixture was heated to 65° C. and stirred at that temperature for 24 h. The cooled mixture was poured to ice water. The reaction mixture was used for the next step directly.

tert-Butyl ((6-bromo-1,3,4,5-tetrahydrobenzo[c]oxepin-1-yl)methyl)carbamate (23-9)

To the solution of the previous step was added 10N NaOH aqueous until pH~10, di-tert-butyl dicarbonate (8.62 g, 39.5 mmol) in Ethyl Acetate (100 mL) was added. The mixture was stirred at room temperature for 2 h. Ethyl acetate (75 mL) was added. Then the aqueous phase was extracted with ethyl acetate (100 mL) for 3 times. The combined organic phase was washed with brine, dried over $Na_2SO_4$, filtered, and concentrated. The resulting oil was purified by flash column chromatography with an isocratic elution of DCM (100%) and MeOH (0%) to DCM (90%) and MeOH (10%) to provide tert-butyl ((6-bromo-1,3,4,5-tetrahydrobenzo[c]oxepin-1-yl)methyl)carbamate (4.8 g, purity: 96%, Yield: 49%) as a yellow oil. MS (ESI): m/z 356.1 $[M+H]^+$, $^1H$ NMR (500 MHz, $CDCl_3$): δ 7.49 (d, J=7.5 Hz, 1H), 7.11 (d, J=7.5 Hz, 1H), 7.01 (t, J=8.0 Hz, 1H), 5.07 (s, 1H), 4.71-4.69 (m, 1H), 4.23-4.20 (m, 1H), 3.85-3.80 (m, 2H), 3.53-3.48 (m, 1H), 3.47-3.41 (m, 1H), 3.11-3.05 (m, 1H), 1.88-1.75 (m, 2H), 1.49 (s, 9H).

tert-Butyl ((6-bromo-1,3,4,5-tetrahydrobenzo[c]oxepin-1-yl)methyl)(methyl) carbamate (23-10)

To a solution of tert-butyl ((6-bromo-1,3,4,5-tetrahydrobenzo[c]oxepin-1-yl)methyl) carbamate (11 g, 30.8 mmol) in THF (150 mL) was added sodium hydride (2.76 g, 92.4 mmol). The mixture was stirred at room temperature for 30 min, and then iodomethane (8.74 g, 61.6 mmol) was added. The mixture was stirred at room temperature for 16 h. Water (50 mL) was added to the reaction vessel and the resulting biphasic mixture was transferred to a separatory funnel. The layers were separated and the aqueous phase was washed with ethyl acetate (2×100 mL). The combined organics were dried over anhydrous $Na_2SO_4$, filtered and concentrated in vacuo. The resulting oil was purified by flash column chromatography with a gradient elution of ethyl acetate (0%) and petroleum ether (100%) to ethyl acetate (10%) and petroleum ether (90%) to provide tert-butyl ((6-bromo-1,3,4,5-tetrahydrobenzo[c]oxepin-1-yl)methyl)(methyl) carbamate (10.2 g, purity: 98%, Yield: 89%) as yellow oil. MS (ESI): m/z 370 $[M+H]^+$, $^1H$ NMR (400 MHz, $CDCl_3$): δ 7.50-7.49 (m, 1H), 7.09-6.98 (m, 2H), 4.91-4.86 (m, 1H), 4.13-4.07 (m, 1H), 3.96-3.64 (m, 2H), 3.45-3.35 (m, 2H), 3.13-3.12 (m, 1H), 2.95 (s, 3H), 1.93 (s, 1H), 1.67 (s, 1H) (m, 1H), 1.41 (s, 9H).

tert-Butyl ((6-(4,4,55-tetramethyl-1,3,2-dioxaborolan-2-yl)-1,3,4,5-tetrahydrobenzo[c]oxepin-1-yl)methyl)carbamate (23-11)

To a solution of tert-butyl ((6-bromo-1,3,4,5-tetrahydrobenzo[c]oxepin-1-yl)methyl)carbamate (2.0 g, 5.61 mmol) in 1,4-dioxane (20 mL) was added 4,4,4',4',5,5,5',5'-octamethyl-2,2'-bi(1,3,2-dioxaborolane) (1.70 g, 6.73 mmol), potassium acetate (1.64 g, 16.8 mmol) and 4,4,4',4',5,5,5',5'-octamethyl-2,2'-bi(1,3,2-dioxaborolane) (1.70 g, 6.73 mmol). The reaction mixture was heated to 90° C. and stirred at that temperature for 8 h. The reaction mixture was concentrated to dry, the residue was used for the next step without further purification.

tert-Butyl methyl((6-(4,4,5,5-tetramethyl-1,3,2-dioxaborolan-2-yl)-1,3,4,5-tetrahydrobenzo[c]oxepin-1-yl)methyl)carbamate (23-12)

To a solution of 1-(6-bromo-1,3,4,5-tetrahydrobenzo[c]oxepin-1-yl)-N-methyl methanamine (2.5 g, 9.25 mmol) in 1,4-dioxane (30 mL) was added 4,4,4',4',5,55',5'-octamethyl-2,2'-bi(1,3,2-dioxaborolane) (3.50 g, 13.8 mmol), potassium acetate (2.71 g, 27.7 mmol) and lambda2-iron palladium bis(2-(diphenylphosphanyl)cyclopenta-2,4-dien-1-ide) dichloride (676 mg, 925 µmol). The reaction mixture was heated to 95° C. and stirred at that temperature for 4 h. The reaction solution was concentrated in vacuo to get the crude product which was used for the next step directly. MS (ESI): m/z 318.1 [M+H]$^+$.

tert-Butyl ((6-(pyridin-2-yl)-1,3,4,5-tetrahydrobenzo [c]oxepin-1-yl)methyl)carbamate (23-13)

To a solution of tert-butyl ((6-(4,4,5,5-tetramethyl-1,3,2-dioxaborolan-2-yl)-1,3,4,5-tetrahydrobenzo[c]oxepin-1-yl) methyl)carbamate (2.08 g, 5.16 mmol) in 1,4-dioxane (20 mL) and water (8 mL) was added cesium carbonate (5.01 g, 15.4 mmol), Bis(tri-tert-butylphosphine)palladium(0) (263 mg, 516 µmol) and 2-bromopyridine (1.05 g, 6.70 mmol). The reaction mixture was heated to and stirred at 90° C. for 16 h. The reaction mixture was concentrated. The residue was diluted with ethyl acetate (100 mL) and H$_2$O (50 mL). The water phase was extracted with ethyl acetate (50 mL) for 3 times. The combined organic phase was washed with brine, dried over Na$_2$SO$_4$, filtered and concentrated. The resulting oil was purified by flash column chromatography with a gradient elution of DCM (100%) and MeOH (0%) to MeOH (10%) and DCM (90%) to provide tert-butyl ((6-(pyridin-2-yl)-1,3,4,5-tetrahydrobenzo[c]oxepin-1-yl) methyl)carbamate (882 mg, purity: 98%, Yield: 48%) as a yellow oil. MS (ESI): m/z 355 [M+H]$^+$, $^1$H NMR (400 MHz, Methanol-d$_4$): δ 8.71 (d, J=4.4 Hz, 1H), 8.39 (td, J=2.0/8.0 Hz, 1H), 7.35-7.33 (m, 1H), 7.31-7.25 (m, 3H), 5.07 (s, 1H), 4.80-4.77 (m, 1H), 4.24-4.21 (m, 1H), 3.91-3.84 (m, 2H), 3.56-3.50 (m, 1H), 3.16-3.10 (m, 1H), 2.88-2.81 (m, 1H), 1.92-1.84 (m, 1H), 1.77-1.70 (m, 1H), 1.49 (s, 9H).

tert-Butyl methyl((6-(pyridin-2-yl)-1,3,4,5-tetrahydrobenzo[c]oxepin-1-yl)methyl)carbamate (23-14)

To a solution of tert-butyl methyl((6-(4,4,5,5-tetramethyl-1,3,2-dioxaborolan-2-yl)-1,3,4,5-tetrahydrobenzo[c]oxepin-1-yl)methyl)carbamate (2.81 g, 6.75 mmol) in 1,4-dioxane (30 mL) and water (10 mL) was added C$_{S2}$CO$_3$ (6.58 g, 20.2 mmol), 2-bromopyridine (1.59 g, 10.1 mmol) and Tetrakis (triphenylphosphine)palladium (780 mg, 675 µmol). The reaction mixture was heated to 95° C. and stirred at that temperature for 16 h. The reaction solution was concentrated. Ethyl acetate (50 mL) and water (40 mL) was added to the reaction vessel and the resulting biphasic mixture was transferred to a separating funnel. The layers were separated and the organic phase was washed with saturated aqueous NaCl (20 mL). The combined organics were dried over anhydrous Na$_2$SO$_4$, filtered and concentrated in vacuo. The resulting oil was purified by flash column chromatography with a gradient elution of ethyl acetate (00%) and petroleum ether (100%) to ethyl acetate (30%) and petroleum ether (70%) to provide tert-butyl methyl((6-(pyridin-2-yl)-1,3,4, 5-tetrahydrobenzo[c]oxepin-1-yl)methyl)carbamate (1.69 g, Yield: 68%) as a yellow oil. MS (ESI): m/z 369.2 [M+H]$^+$, $^1$H NMR (400 MHz, Methanol-d$_4$): δ 8.61 (d, J=4.4 Hz, 2H), 7.94 (td, J=1.6/7.6 Hz, 1H), 7.47-7.44 (m, 2H), 7.31-7.23 (m, 3H), 5.03 (dd, J=4.0/9.2 Hz, 1H), 4.17-4.09 (m, 1H), 3.92-3.76 (m, 2H), 3.70-3.57 (m, 1H), 3.09-3.04 (m, 1H), 2.98 (s, 3H), 2.85-2.75 (m, 1H), 1.86 (s, 1H), 1.68-1.66 (m, 1H), 1.47 (s, 9H).

rel-(R)-tert-Butyl (6-(pyridin-2-yl)-1,3,4,5-tetrahydrobenzo[c]oxepin-1-yl)methylcarbamate (23-15) and rel-(S)-tert-butyl (6-(pyridin-2-yl)-1,3,4,5-tetrahydrobenzo[c]oxepin-1-yl)methylcarbamate (23-16)

The racemic tert-butyl (6-(pyridin-2-yl)-1,3,4,5-tetrahydrobenzo[c]oxepin-1-yl)methylcarbamate (1.1 g, 3.10 mmols) was separated into its enantiomers rel-(R)-tert-butyl (6-(pyridin-2-yl)-1,3,4,5-tetrahydrobenzo[c]oxepin-1-yl) methylcarbamate and rel-(S)-tert-butyl (6-(pyridin-2-yl)-1, 3,4,5-tetrahydrobenzo[c]oxepin-1-yl)methylcarbamate by Preparative-SFC using column: OD 20×250 mm, 10 µm (Daicel) and mobile phase: CO$_2$/Methanol (0.2% Methanol Ammonia)=85/15. The flow rate was 80 g/min, back pressure was 100 bar and cycle time of stack injections was 8.0 min. rel-(R)-tert-butyl (6-(pyridin-2-yl)-1,3,4,5-tetrahydrobenzo[c]oxepin-1-yl)methylcarbamate (420 mg, Yield: 38%, retention time 1.06 min) as a yellow solid and rel-(S)-tert-butyl (6-(pyridin-4-yl)-1,3,4,5-tetrahydrobenzo[c]oxepin-1-yl)methylcarbamate (410 mg, Yield: 37%, retention time 1.42 min) as a yellow solid.

rel-(R)-tert-Butyl methyl((6-(pyridin-2-yl)-1,3,4,5-tetrahydrobenzo[c]oxepin-1-yl)methyl) carbamate (23-17) and rel-(S)-tert-butyl methyl((6-(pyridin-2-yl)-1,3,4,5-tetrahydrobenzo[c] oxepin-1-yl)methyl) carbamate (23-18)

The racemic tert-butyl methyl((6-(pyridin-2-yl)-1,3,4,5-tetrahydrobenzo[c]oxepin-1-yl)methyl)carbamate (1300 mg, 3.52 mmols) was separated into its enantiomers rel-(R)-tert-butyl methyl((6-(pyridin-2-yl)-1,3,4,5-tetrahydrobenzo [c]oxepin-1-yl)methyl) carbamate and rel-(S)-tert-butyl methyl((6-(pyridin-2-yl)-1,3,4,5-tetrahydrobenzo[c] oxepin-1-yl)methyl)carbamate by Preparative-SFC using column: OZ 20×250 mm, 10 µm (Daicel) and mobile phase: CO$_2$/IPA (0.2% Methanol Ammonia)=87/13. The flow rate was 80 g/min, back pressure was 100 bar and cycle time of stack injections was 8.0 min. rel-(R)-tert-butyl methyl((6-(pyridin-2-yl)-1,3,4,5-tetrahydrobenzo[c]oxepin-1-yl) methyl)carbamate (600 mg, Yield: 45%, retention time 2.89 min) as a light yellow oil and rel-(S)-tert-butyl methyl((6-(pyridin-2-yl)-1,3,4,5-tetrahydrobenzo[c]oxepin-1-yl) methyl)carbamate (610 mg, Yield: 47%, retention time 3.81 min) as a yellow oil.

(R)-(6-(pyridin-2-yl)-1,3,4,5-tetrahydrobenzo[c] oxepin-1-yl)methanamine hydrochloride salt (Compound 158)

To a solution of rel-(R)-tert-butyl ((6-(pyridin-2-yl)-1,3, 4,5-tetrahydrobenzo[c]oxepin-1-yl)methyl)carbamate (400 mg, 1.12 mmol) in methanol (10 mL) was added 3 M hydrogen chloride in methanol (2.24 mL, 6.72 mmol). The mixture was stirred at room temperature for 4 hs. The mixture was concentrated to obtain the title compound (330 mg, purity: 100%, Yield: 90%) as white solid. MS (ESI): m/z 255 [M+H]$^+$, $^1$H NMR (400 MHz, DMSO-d$_6$): δ 8.96 (d, J=4.8 Hz, 1H), 8.48-7.39 (m, 4H), 7.93-7.89 (m, 2H), 7.43-7.38 (m, 3H), 5.10-5.08 (m, 1H), 4.18-4.15 (m, 1H), 3.99-3.92 (m, 1H), 3.41-3.33 (m, 2H), 2.89-2.81 (m, 2H), 1.72 (s, 2H).

(S)-(6-(pyridin-2-yl)-1,3,4,5-tetrahydrobenzo[c]oxepin-1-yl)methanamine hydrochloride salt (Compound 159)

To a solution of rel-(S)-tert-butyl ((6-(pyridin-2-yl)-1,3, 4,5-tetrahydrobenzo[c]oxepin-1-yl)methyl)carbamate (410 mg, 1.17 mmol) in methanol (10 mL) was added 3 M hydrogen chloride in methanol (2.34 mL, 7.02 mmol). The mixture was stirred at room temperature for 4 h. Then the reaction mixture was concentrated to provide rel-(S)-(6-(pyridin-2-yl)-1,3,4,5-tetrahydrobenzo[c]oxepin-1-yl)methanamine hydrochloride salt (353 mg, purity: 98%, Yield: 92%) as a white solid. MS (ESI): m/z 255 [M+H], H NMR (400 MHz, DMSO-$d_6$): δ 8.89 (d, J=5.6 Hz, 1H), 8.47-7.42 (m, 4H), 7.92-7.90 (m, 2H), 7.44-7.39 (m, 3H), 5.10 (d, J=8.0 Hz, 1H), 4.17-4.15 (m, 1H), 3.99-3.93 (m, 1H), 3.41-3.32 (m, 2H), 2.89-2.80 (m, 2H), 1.72 (s, 2H).

(R)—N-Methyl-1-(6-(pyridin-2-yl)-1,3,4,5-tetrahydrobenzo[c]oxepin-1-yl)methanamine hydrochloride salt (Compound 156)

To a solution of rel-(R)-tert-butyl methyl((6-(pyridin-2-yl)-1,3,4,5-tetrahydrobenzo[c]oxepin-1-yl)methyl)carbamate (590 mg, 1.60 mmol) in methanol (8 mL) was added 3M hydrogen chloride in methanol (4.27 mL, 12.8 mmol). The reaction was stirred at ambient temperature for 16 h. The solvent was concentrated to obtain the rel-(R)—N-methyl-1-(6-(pyridin-2-yl)-1,3,4,5-tetrahydrobenzo[c]oxepin-1-yl)methanamine hydrochloride salt (506 mg, 1.48 mmol, Yield: 93%, retention time 4.29 min, ee value 100%) as a white solid. MS (ESI): m/z 269.2 [M+H]$^+$, $^1$H NMR (400 MHz, DMSO-$d_6$): δ 9.99 (s, 1H), 8.95 (d, J=5.2 Hz, 1H), 8.92 (s, 1H), 8.64 (t, J=8.0 Hz, 1H), 8.08 (t, J=6.8 Hz, 1H), 8.03 (d, J=8.4 Hz, 1H), 7.46-7.39 (m, 3H), 5.28 (dd, J=4.0/9.2 Hz, 1H), 4.13 (d, J=12 Hz, 1H), 4.03-3.97 (m, 1H), 3.53-3.52 (m, 2H), 2.95-2.89 (m, 1H), 2.77-2.73 (m, 1H), 2.65 (t, J=5.2 Hz, 3H), 1.76-1.71 (m, 2H).

(S)—N-Methyl-1-(6-(pyridin-2-yl)-1,3,4,5-tetrahydrobenzo[c]oxepin-1-yl)methanamine hydrochloride salt (Compound 157)

To a solution of rel-(S)-tert-butyl methyl((6-(pyridin-2-yl)-1,3,4,5-tetrahydrobenzo[c]oxepin-1-yl)methyl)carbamate (600 mg, 1.62 mmol) in methanol (8 mL) was added 3 M hydrogen chloride in methanol (4.3 mL, 12.9 mmol). The reaction was stirred at ambient temperature for 16 h. The reaction was stirred at ambient temperature for 16 h. The LC-MS indicated the reaction was completed. The solvent was concentrated to obtain the rel-(S)—N-methyl-1-(6-(pyridin-2-yl)-1,3,4,5-tetrahydrobenzo[c]oxepin-1-yl)methanamine hydrochloride salt (520 mg, 1.53 mmol, purity: 99%, Yield: 94%, retention time 4.89 min, ee value 100%) as a white solid. MS (ESI): m/z 269.2 [M+H]$^+$, $^1$H NMR (400 MHz, methanol-$d_4$): δ 8.97 (d, J=5.6 Hz, 1H), 8.76 (dt, J=1.2/7.6 Hz, 1H), 8.19 (t, J=6.8 Hz, 1H), 8.14 (d, J=8.0 Hz, 1H), 7.55-7.51 (m, 3H), 5.22 (dd, J=4.0/10 Hz, 1H), 4.35-4.30 (m, 1H), 4.07-4.00 (m, 1H), 3.73-3.64 (m, 2H), 3.11-3.04 (m, 1H), 2.95-2.89 (m, 4H), 1.91-1.81 (m, 2H).

Scheme 24

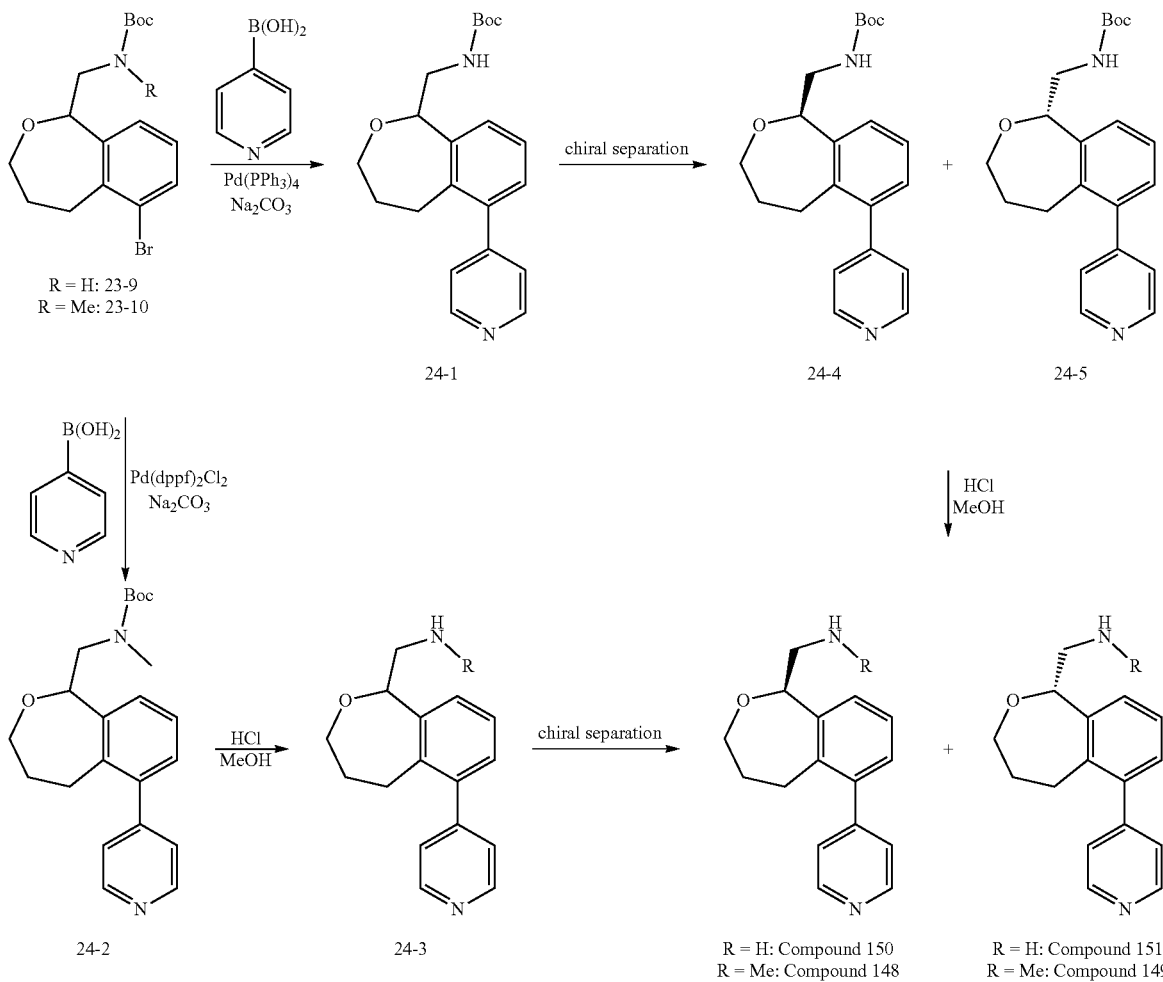

Synthesis of Compounds 148, 149, 150 and 151 tert-Butyl ((6-(pyridin-4-yl)-1,3,4,5-tetrahydrobenzo[c]oxepin-1-yl)methyl)carbamate (24-1)

To a solution of tert-butyl ((6-bromo-1,3,4,5-tetrahydrobenzo[c]oxepin-1-yl)methyl) carbamate (1.5 g, 4.21 mmol) in 1,4-Dioxane (15 mL) and water (5 mL) was added tetrakis(triphenylphosphine)palladium (486 mg, 421 µmol), sodium carbonate (1.33 g, 12.6 mmol) and pyridin-4-ylboronic acid (620 mg, 5.05 mmol). The reaction mixture was heated to 90° C. and stirred at that temperature for 12 h. The reaction solution was filtered. The filtrate was diluted with ethyl acetate (50 mL) and water (50 mL). Ethyl acetate (50 mL) was added to the reaction vessel and the resulting biphasic mixture was transferred to a separating funnel. The layers were separated and the org/aq phase was washed with water (15 mL) and saturated aqueous NaCl (15 mL). The combined organics were dried over anhydrous $Na_2SO_4$, filtered and concentrated in vacuo. The resulting oil was purified by reverse phase HPLC with a gradient elution of water (95%) and acetonitrile (5%) to water (45%) and acetonitrile (55%) to provide tert-butyl ((6-(pyridin-4-yl)-1,3,4,5-tetrahydrobenzo[c]oxepin-1-yl)methyl)carbamate (1.07 g, purity: 98%, Yield: 72%) as a yellow oil. MS (ESI): m/z 355.2 [M+H]$^+$, $^1$H NMR (500 MHz, Methanol-$d_4$): δ 8.47 (dd, J=1.5/4.5 Hz, 2H), 7.24 (dd, J=1.5/4.5 Hz, 2H), 7.2-7.14 (m, 2H), 7.05-7.03 (m, 1H), 4.71-4.68 (m, 1H), 4.09-4.06 (m, 1H), 3.78-3.73 (m, 1H), 3.61-3.57 (m, 1H), 3.39-3.35 (m, 1H), 2.91-2.87 (m, 1H), 2.77-2.72 (m, 1H), 1.68-1.66 (m, 1H), 1.60-1.55 (m, 1H), 1.29 (s, 9H).

tert-Butyl methyl((6-(pyridin-4-yl)-1,3,4,5-tetrahydrobenzo[c]oxepin-1-yl)methyl)carbamate (24-2)

To a solution of tert-butyl ((6-bromo-1,3,4,5-tetrahydrobenzo[c]oxepin-1-yl)methyl) (methyl)carbamate (2.0 g, 5.40 mmol) in dioxane (30 mL) and water (10 mL) was added pyridin-4-ylboronic acid (995 mg, 8.10 mmol), Cesium carbonate (5.27 g, 16.2 mmol) and lambda2-iron palladium bis(2-(diphenylphosphanyl)cyclopenta-2,4-dien-1-ide) dichloride (395 mg, 540 µmol). The reaction mixture was heated to 92° C. and stirred at that temperature for 6 h. The reaction mixture was concentrated. The residue was diluted with ethyl acetate (150 mL), water (40 mL) was added to the reaction vessel and the resulting biphasic mixture was transferred to a separating funnel. The layers were separated and the organic phase was washed with saturated aqueous NaCl (40 mL). The combined organics were dried over anhydrous $Na_2SO_4$, filtered and concentrated in vacuo. The resulting oil was purified by flash column chromatography with a gradient elution of petroleum ether (100%) and ethyl acetate (0%) to ethyl acetate (40%) and petroleum ether (60%) to provide tert-butyl methyl((6-(pyridin-4-yl)-1,3,4,5-tetrahydrobenzo[c]oxepin-1-yl)methyl)carbamate (1.42 g, purity: 98%. Yield: 72%) as a yellow oil. MS (ESI): m/z 369.2 [M+H]$^+$, $^1$H NMR (400 MHz, CDCl$_3$): δ 8.65 (d, J=4.8 Hz, 2H), 7.23-7.12 (m, 5H), 4.95 (s, 1H), 4.15-3.76 (m, 3H), 3.55-3.37 (m, 1H), 3.04-2.96 (m, 4H), 2.82-2.71 (m, 1H), 1.89 (s, 1H), 1.63 (s, 1H), 1.44 (s, 9H).

N-Methyl-1-(6-(pyridin-4-yl)-1,3,4,5-tetrahydrobenzo[c]oxepin-1-yl)methanamine (24-3)

To a solution of tert-butyl methyl((6-(pyridin-4-yl)-1,3,4,5-tetrahydrobenzo[c]oxepin-1-yl)methyl)carbamate (1100 mg, 2.98 mmol) in methanol (10 mL) was added 3 M hydrogen chloride in methanol (7.9 mL, 23.8 mmol). The reaction was stirred at ambient temperature for 6 h. The solution was concentrated in vacuo. The residue was dissolved in 20 mL of water based by 7N NaOH until pH ~9, and extracted by ethyl acetate (5×60 mL). The organic phase was washed with saturated aqueous NaCl (25 mL). The combined organics were dried over anhydrous $Na_2SO_4$, filtered and concentrated in vacuo to obtain the desired compound (697 mg, purity: 99%, Yield: 87%). MS (ESI): m/z 269.2 [M+H]$^+$.

rel-(R)-tert-Butyl (6-(pyridin-4-yl)-1,3,4,5-tetrahydrobenzo[c]oxepin-1-yl)methylcarbamate (24-4) and rel-(S)-tert-butyl (6-(pyridin-4-yl)-1,3,4,5-tetrahydrobenzo[c]oxepin-1-yl)methylcarbamate (24-5)

The racemic tert-butyl (6-(pyridin-4-yl)-1,3,4,5-tetrahydrobenzo[c]oxepin-1-yl)methylcarbamate (1.1 g, 3.10 mmols) was separated into its enantiomers rel-(R)-tert-butyl (6-(pyridin-4-yl)-1,3,4,5-tetrahydrobenzo[c]oxepin-1-yl) methylcarbamate and rel-(S)-tert-butyl (6-(pyridin-4-yl)-1,3,4,5-tetrahydrobenzo[c]oxepin-1-yl)methylcarbamate by Preparative-SFC using column: SC 20×250 mm, 10 µm (Daicel) and mobile phase: $CO_2$/Methanol (0.2% Methanol Ammonia)=70/30. The flow rate was 80 g/min, back pressure was 100 bar and cycle time of stack injections was 5 min. rel-(R)-tert-butyl (6-(pyridin-4-yl)-1,3,4,5-tetrahydrobenzo[c]oxepin-1-yl)methylcarbamate (401 mg, Yield: 36%, retention time 3.01 min) as a yellow solid and rel-(S)-tert-butyl (6-(pyridin-4-yl)-1,3,4,5-tetrahydrobenzo[c]oxepin-1-yl)methylcarbamate (387 mg, Yield: 35%, retention time 3.77 min) as a yellow solid.

rel-(R)—N-Methyl-1-(6-(pyridin-4-yl)-1,3,4,5-tetrahydrobenzo[c]oxepin-1-yl)methanamine (Compound 148) and rel-(S)—N-methyl-1-(6-(pyridin-4-yl)-1,3,4,5-tetrahydrobenzo[c]oxepin-1-yl)methanamine (Compound 149)

The racemic N-methyl-1-(6-(pyridin-4-yl)-1,3,4,5-tetrahydrobenzo[c]oxepin-1-yl)methanamine (697 mg, 2.59 mmols) was separated into rel-(R)—N-methyl-1-(6-(pyridin-4-yl)-1,3,4,5-tetrahydrobenzo[c]oxepin-1-yl)methanamine and rel-(S)—N-methyl-1-(6-(pyridin-4-yl)-1,3,4,5-tetrahydrobenzo[c]oxepin-1-yl)methanamine by Preparative-SFC using column: OD 20×250 mm, 10 µm (Daicel) and mobile phase: n-Hex (0.1% DEA): EtOH (0.1% DEA)=9:1. The flow rate was 80 g/min, back pressure was 100 bar and cycle time of stack injections was 14.0 min. rel-(R)—N-methyl-1-(6-(pyridin-4-yl)-1,3,4,5-tetrahydrobenzo[c]oxepin-1-yl)methanamine (300 mg, Yield: 43%, retention time 7.442 min) as a light yellow oil and rel-(S)—N-methyl-1-(6-(pyridin-4-yl)-1,3,4,5-tetrahydrobenzo[c]oxepin-1-yl)methanamine (300 mg, Yield: 43%, retention time 9.033 min) as a yellow oil.

rel-(R)-(6-(Pyridin-4-yl)-1,3,4,5-tetrahydrobenzo[c]oxepin-1-yl)methanamine (Compound 150)

To a mixture of rel-(R)-tert-butyl ((6-(pyridin-4-yl)-1,3,4,5-tetrahydrobenzo[c]oxepin-1-yl)methyl)carbamate (390 mg, 1.10 mmol) in 6 mL of methanol was added 3M HCl methanol solution 3 mL. The mixture was stirred at room temperature for 2 h. Then the mixture was concentrated to obtain the desired compound (334.4 mg, purity: 100%, Yield: 93%) as white solid. MS (ESI): m/z 255 [M+H]$^+$, $^1$H NMR (500 MHz, DMSO-d$_6$): δ 8.96 (d, J=6.5 Hz, 2H), 8.42 (s, 3H), 7.94 (d, J=6.5 Hz, 2H), 7.40-7.35 (m, 2H), 7.30 (dd, J=1.5/7.0 Hz, 1H), 5.10 (dd, J=2.5/10.5 Hz, 1H), 4.17 (dd, J=3.5/9.0 Hz, 1H), 4.00-3.95 (m, 1H), 3.40-3.33 (m, 2H), 2.88-2.87 (m, 2H), 1.73 (s, 2H).

rel-(S)-(6-(Pyridin-4-yl)-1,3,4,5-tetrahydrobenzo[c]
oxepin-1-yl)methanamine (Compound 151)

To a mixture of rel-(S)-tert-butyl ((6-(pyridin-4-yl)-1,3,4,5-tetrahydrobenzo[c]oxepin-1-yl)methyl)carbamate (377 mg, 1.06 mmol) in 6 mL of methanol was added 3M HCl methanol solution 3 mL. The mixture was stirred at room temperature for 2 h. Then the mixture was concentrated to obtain the desired compound (330.2 mg, purity: 100%, Yield: 96%) as white solid. MS (ESI): m/z 255 [M+H]$^+$, $^1$H NMR (500 MHz, DMSO-d$_6$): δ 8.95 (d, J=5.0 Hz, 2H), 8.39 (s, 3H), 7.92 (d, J=5.0 Hz, 2H), 7.40-7.35 (m, 2H), 7.30 (dd, J=1.5/7.0 Hz, 1H), 5.08 (d, J=10.0 Hz, 1H), 4.18 (dd, J=3.5/9.0 Hz, 1H), 4.00-3.94 (m, 1H), 3.41-3.34 (m, 2H), 2.88-2.87 (m, 2H), 1.73 (s, 2H).

rel-(R)-(6-(Pyrimidin-4-yl)-1,3,4,5-tetrahydrobenzo
[c]oxepin-1-yl)methanamine (Compound 166)

The title compound was prepared using the procedure shown in Scheme 23, substituting 4-bromopyrimidine for 2-bromopyridine. (400 mg, purity: 100%, Yield: 81%) as white solid. MS (ESI): m/z 256 [M+H]$^+$, $^1$H NMR (400 MHz, DMSO-d$_6$): δ 9.28 (s, 1H), 8.89 (d, J=4.8 Hz, 2H), 8.35 (s, 3H), 7.63 (d, J=4.4 Hz, 1H), 7.35-7.28 (m, 3H), 5.06 (dd, J=4.8/10.0 Hz, 1H), 4.16-4.14 (m, 1H), 3.98-3.91 (m, 1H), 3.40-3.29 (m, 2H), 3.06-3.02 (m, 1H), 2.87-2.80 (m, 1H), 1.73-1.72 (m, 2H).

rel-(S)-(6-(Pyrimidin-4-yl)-1,3,4,5-tetrahydrobenzo
[c]oxepin-1-yl)methanamine (Compound 167)

The title compound was prepared using the procedure shown in Scheme 23, substituting 4-bromopyrimidine for 2-bromopyridine. (410 mg, purity: 100%, Yield: 83%) as white solid. MS (ESI): m/z 256 [M+H]$^+$, 1H NMR (400 MHz, DMSO-d$_6$): δ 9.28 (d, J=1.6 Hz, 1H), 8.89 (d, J=5.2 Hz, 1H), 8.48 (s, 4H), 7.63 (dd, J=1.6/5.2 Hz, 1H), 7.36-7.27 (m, 3H), 5.06 (dd. J=2.4/10.4 Hz, 1H), 4.17-4.14 (m, 1H), 3.97-3.91 (m, 1H), 3.44-3.30 (m, 2H), 3.07-3.01 (m, 1H), 2.87-2.80 (m, 1H), 1.76-1.66 (m, 2H).

rel-(R)-(6-(Thiazol-5-yl)-1,3,4,5-tetrahydrobenzo[c]
oxepin-1-yl)methanamine hydrochloride salt (Compound 170)

The title compound was prepared using the procedure shown in Scheme 24, substituting 5-(4,4,5,5-tetramethyl-1,3,2-dioxaborolan-2-yl)thiazole for pyridin-4-ylboronic acid. White solid (358 mg, purity: 100%, Yield: 82%). MS (ESI): m/z 261.1 [M+H]$^+$, $^1$H NMR (400 MHz, DMSO-d$_6$): δ 9.25 (s, 1H), 8.38 (s, 3H), 7.87 (s, 1H), 7.33-7.24 (m, 3H), 6.87 (m, 3H), 5.07 (dd, J=2.4/10.0 Hz, 1H), 4.16 (dd, J=2.4/8.0 Hz, 1H), 3.95 (td, J=2.8/11.6 Hz, 1H), 3.40-3.28 (m, 2H), 3.08-3.03 (m, 1H), 2.89-2.83 (m, 1H), 1.77-1.64 (m, 2H).

rel-(S)-(6-(Thiazol-5-yl)-1,3,4,5-tetrahydrobenzo[c]
oxepin-1-yl)methanamine hydrochloride salt (Compound 171)

The title compound was prepared using the procedure shown in Scheme 24, substituting 5-(4,4,5,5-tetramethyl-1,3,2-dioxaborolan-2-yl)thiazole for pyridin-4-ylboronic acid. White solid (358 mg, purity: 100%, Yield: 84%). MS (ESI): m/z 261.1 [M+H]$^+$, $^1$H NMR (400 MHz, DMSO-d$_6$): δ 9.24 (s, 1H), 9.00 (s, 1H), 8.36 (s, 3H), 7.87 (s, 1H), 7.33-7.24 (m, 3H), 5.06 (dd, J=2.8/10.4 Hz, 1H), 4.16 (dd, J=2.4/12.0 Hz, 1H), 3.95 (td, J=2.4/11.6 Hz, 1H), 3.42-3.28 (m, 2H), 3.08-3.03 (m, 1H), 2.89-2.83 (m, 1H), 1.77-1.65 (m, 2H).

rel-(R)-(5-Phenylisochroman-1-yl)methanamine
hydrochloride salt (Compound 130)

The title compound was prepared using the procedure described in Scheme 7, substituting phenylboronic acid for pyridine-3-yl-boronic acid. White solid. MS (ESI): m/z 240.2 [M+H]$^+$, 1H NMR (400 MHz, DMSO-d6): δ 8.13 (s, 1H), 7.48-7.44 (m, 2H), 7.41-7.28 (m, 5H), 7.19-7.18 (m, 1H), 5.05 (d, J=9.6 Hz, 1H), 4.02-3.97 (m, 1H), 3.71-3.65 (m, 1H), 3.44-3.43 (m, 1H), 3.17-3.10 (m, 1H), 2.81-2.74 (m, 1H), 2.58-2.51 (m, 1H).

rel-(S)-(5-Phenylisochroman-1-yl)methanamine
hydrochloride salt (Compound 131)

The title compound was prepared using the procedure described in Scheme 7, substituting phenylboronic acid for pyridine-3-yl-boronic acid. White solid. MS (ESI): m/z 240.2 [M+H]$^+$, 1H NMR (400 MHz, DMSO-d6): δ 8.24 (s, 1H), 7.47-7.44 (m, 2H), 7.40-7.27 (m, 5H), 7.19-7.17 (m, 1H), 5.07 (d, J=8.0 Hz, 1H), 4.01-3.96 (m, 1H), 3.70-3.65 (m, 1H), 3.43-3.41 (m, 1H), 3.13 (bs, 1H), 2.80-2.73 (m, 1H), 2.58-2.51 (m, 1H).

rel-(R)—N-Methyl-1-(5-phenylisochroman-1-yl)
methanamine hydrochloride salt (Compound 128)

The title compound was prepared using the procedure shown in Scheme 18, substituting rel-(R)-tert-butyl ((5-phenylisochroman-1-yl)methyl)carbamate for rel-(R)-tert-butyl ((7-(pyridin-4-yl)isochroman-1-yl)methyl) carbamate. White solid. MS (ESI): m/z 254.2 [M+H]$^+$, $^1$H NMR (400 MHz, methanol-d4): δ 7.46-7.43 (m, 2H), 7.39-7.31 (m, 4H), 7.25-7.20 (m, 2H), 5.18 (d, J=7.2 Hz, 1H), 4.16-4.11 (m, 1H), 3.77-3.71 (m, 1H), 3.67-3.63 (m, 1H), 3.40-3.33 (m, 1H), 2.96-2.88 (m, 1H), 2.80 (s, 3H), 2.59-2.53 (m, 1H).

rel-(S)—N-Methyl-1-(5-phenylisochroman-1-yl)
methanamine hydrochloride salt (Compound 129)

The title compound was prepared using the procedure shown in Scheme 18, substituting rel-(S)-tert-butyl ((5-phenylisochroman-1-yl)methyl)carbamate for rel-(R)-tert-butyl ((7-(pyridin-4-yl)isochroman-1-yl)methyl) carbamate. White solid. MS (ESI): m/z 254.2 [M+H]$^+$, $^1$H NMR (400 MHz, DMSO-d6): δ 9.35 (bs, 1H), 8.81 (bs, 1H), 7.47-7.44 (m, 2H), 7.40-7.32 (m, 4H), 7.26 (d, J=7.2 Hz, 1H), 7.18 (d, J=6.8 Hz, 1H), 5.19 (d, J=8.4 Hz, 1H), 4.021-3.97 (m, 1H), 3.72-3.66 (m, 1H), 3.56-3.51 (m, 1H), 3.31-3.23 (m, 1H), 2.79-2.72 (m, 1H), 2.61 (t, J=5.2 Hz, 3H), 2.60-2.53 (m, 1H).

rel-(R)—N-Methyl-1-(6-(thiazol-5-yl)-1,3,4,5-tetrahydrobenzo[c]oxepin-1-yl)methanamine hydrochloride salt (Compound 168)

The title compound was prepared using the procedure shown in Scheme 24, substituting 5-(4,4,5,5-tetramethyl-1,3,2-dioxaborolan-2-yl)thiazole for pyridine-4-yl-boronic acid, and substituting cesium carbonate for sodium carbonate. Yellow solid. MS (ESI): m/z 275.1 [M+H]+, 1H NMR (400 MHz, DMSO-d6): δ 9.60 (s, 1H), 9.23 (s, 1H), 8.75 (s, 1H), 7.86 (s, 1H), 7.60 (s, 1H), 7.34-7.27 (m, 2H), 7.24-7.22 (m, 1H), 5.19 (dd, J=4.4/9.2 Hz, 1H), 4.17 (dd, J=2.4/12 Hz, 1H), 3.97 (td, J=2.8/11.6 Hz, 1H), 3.55-3.45 (m, 2H), 3.09-3.04 (m, 1H), 2.91-2.85 (m, 1H), 2.65 (t, J=5.6 Hz, 3H), 1.78-1.63 (m, 2H).

rel-(S)—N-Methyl-1-(6-(thiazol-5-yl)-1,3,4,5-tetrahydrobenzo[c]oxepin-1-yl)methanamine hydrochloride salt (Compound 169)

The title compound was prepared using the procedure shown in Scheme 24, substituting 5-(4,4,5,5-tetramethyl-1,3,2-dioxaborolan-2-yl)thiazole for pyridine-4-yl-boronic acid, and substituting cesium carbonate for sodium carbonate. Yellow solid. MS (ESI): m/z 275.11 [M+H]+, 1H NMR (400 MHz, DMSO-d6): δ 9.60 (s, 1H), 9.23 (s, 1H), 8.75 (s, 1H), 7.87 (s, 1H), 7.34-7.27 (m, 2H), 7.24-7.22 (m, 1H), 5.19 (dd, J=4.0 Hz, J=9.2 Hz, 1H), 4.17 (dd, J=2.4/12.0 Hz, 1H), 3.97 (td, J=3.2/12.0 Hz, 1H), 3.53-3.49 (m, 2H), 3.09-3.04 (m, 1H), 2.91-2.85 (m, 1H), 2.65 (t, J=5.2 Hz, 3H), 1.79-1.62 (m, 2H).

rel-(R)—N-Methyl-1-(6-(pyrimidin-4-yl)-1,3,4,5-tetrahydrobenzo[c]oxepin-1-yl)methanamine hydrochloride salt (Compound 164)

The title compound was prepared using the procedure shown in Scheme 24, substituting 4-chloropyrimidine for 4-bromopyridine. Yellow solid. MS (ESI): m/z 270.1 [M+H]+, 1H NMR (400 MHz, DMSO-d6): δ 9.77 (s, 1H), 9.31 (d, J=1.2 Hz, 1H), 8.92 (d, J=4.8 Hz, 1H), 8.80 (s, 1H), 7.66 (dd, J=1.2/5.2 Hz, 1H) 7.37-7.33 (m, 2H), 7.30-7.27 (m, 1H), 5.24 (dd, J=4.0/9.6 Hz, 1H), 4.16 (d, J=11.6 Hz, 1H), 4.02-3.95 (m, 1H), 3.55-3.47 (m, 2H), 3.08-3.04 (m, 1H), 2.90-2.84 (m, 1H), 2.65 (t, J=4.2 Hz, 3H), 1.75-1.74 (m, 2H).

rel-(S)—N-Methyl-1-(6-(pyrimidin-4-yl)-1,3,4,5-tetrahydrobenzo[c]oxepin-1-yl)methanamine hydrochloride salt (Compound 165)

The title compound was prepared using the procedure shown in Scheme 24, substituting 4-chloropyrimidine for 4-bromopyridine. Yellow solid. MS (ESI): m/z 270.1 [M+H]+, 1H NMR (400 MHz, DMSO-d6): δ 9.66 (s, 1H), 9.30 (d, J=1.2 Hz, 1H), 8.91 (d, J=4.2 Hz, 1H), 8.77 (s, 1H), 7.65 (dd J=1.2/4.6 Hz, 1H) 7.37-7.33 (m, 2H), 7.29-7.27 (m, 1H), 5.22 (dd, J=4.0/9.2 Hz, 1H), 4.18-4.15 (m, 1H), 4.01-3.95 (m, 1H), 3.55-3.47 (m, 2H), 3.08-3.04 (m, 1H), 2.91-2.84 (m, 1H), 2.65 (t, J=4.2 Hz, 3H), 1.75-1.74 (m, 2H).

rel-(R)—N-((5-(Pyridin-4-yl) isochroman-1-yl)methyl)ethanamine hydrochloride salt (Compound 66)

The title compound was prepared using the procedure shown in Scheme 19, substituting rel-(R)-tert-butyl ((5-(pyridin-4-yl)isochroman-1-yl)methyl)carbamate for (+/−)-tert-butyl ((5-(pyridin-4-yl)isochroman-1-yl)methyl)carbamate. White solid. MS (ESI): m/z 269.2 [M+H]+, H-NMR: 1H NMR (400 MHz, DMSO-d6): δ 9.49 (s, 1H), 8.98 (d, J=6.8 Hz, 2H), 8.85 (s, 1H), 8.08 (d, J=6.4 Hz, 2H), 7.50-7.46 (m, 2H), 7.39-7.37 (m, 1H), 5.28 (d, J=9.2 Hz, 1H), 4.05-4.00 (m, 1H), 3.75-3.69 (m, 1H), 3.58-3.53 (m, 1H), 3.28-3.21 (m, 1H), 3.06-3.01 (m, 2H), 2.89-2.83 (m, 1H), 2.70-2.64 (m, 1H), 1.27 (t, J=7.2 Hz, 3H).

rel-(S)—N-((5-(Pyridin-4-yl) isochroman-1-yl)methyl)ethanamine hydrochloride salt (Compound 67)

The title compound was prepared using the procedure shown in Scheme 19, substituting rel-(S)-tert-butyl ((5-(pyridin-4-yl)isochroman-1-yl)methyl)carbamate for (+/−)-tert-butyl ((5-(pyridin-4-yl)isochroman-1-yl)methyl)carbamate. White solid. MS (ESI): m/z 269.2 [M+H]+, 1H NMR (400 MHz, DMSO-d6): δ 9.56 (s, 1H), 8.99 (d, J=6.4 Hz, 2H), 8.87 (s, 1H), 8.11 (d, J=6.4 Hz, 2H), 7.51-7.46 (m, 2H), 7.40-7.37 (m, 1H), 5.29 (d, J=9.2 Hz, 1H), 4.05-3.99 (m, 1H), 3.75-3.69 (m, 1H), 3.57-3.52 (m, 1H), 3.29-3.21 (m, 1H), 3.06-3.01 (m, 2H), 2.90-2.83 (m, 1H), 2.70-2.64 (m, 1H), 1.27 (t, J=7.2 Hz, 3H).

Synthesis of Compound 105

(S)-tert-butyl methyl((5-(oxazol-2-yl)isochroman-1-yl)methyl)carbamate

To a solution of (S)-tert-butyl (5-bromoisochroman-1-yl)methyl(methyl)carbamate (1.0 g, 2.80 mmol) in toluene (4 mL) was added tetrakis(triphenylphosphane)palladium (485 mg, 420 µmol) and 2-(tributylstannyl)oxazole (748 mg, 2.09 mmol) at rt under N2 atmosphere. After stirring at room temperature for 10 min under N2 atmosphere, the sealed vial was irradiated in the microwave on a Biotage Smith Synthesis at 130° C. for 2 h. The resulting mixture was concentrated and purified by normal phase HPLC with a gradient elution of petroleum ether (100%) and EtOAc (0%) to petroleum ether (90%) and EtOAc (10%) to provide (S)-tert-butyl methyl((5-(oxazol-2-yl)isochroman-1-yl)methyl)carbamate (500 mg, Yield: 69%) as a colorless oil. MS (ESI): m/z 367 [M+Na]+.

(S)—N-methyl-1-(5-(oxazol-2-yl)isochroman-1-yl)methanamine dihydrochloride (Compound 105)

A solution of (S)-tert-butyl methyl((5-(oxazol-2-yl)isochroman-1-yl)methyl)carbamate (480 mg, 1.39 mmol) in 4M HCl in EtOAc (20 mL) was stirred at room temperature for 2 h. The reaction was monitored by LCMS. After concentration, the residue was washed with EtOAc (2×5 mL) to give (S)—N-methyl-1-(5-(oxazol-2-yl)isochroman-1-yl)methanamine dihydrochloride (330 mg, Yield: 97%) a white solid. MS (ESI): m/z 245 [M+H]+. 1H NMR (400 MHz, methanol-d4): δ 8.04 (s, 1H), 7.89 (dd, J=1.6/7.6 Hz, 1H), 7.44-7.37 (m, 3H), 5.17 (d, J=6.8 Hz, 1H), 4.25-4.20 (m, 1H), 3.85-3.79 (m, 1H), 3.64-3.60 (m, 1H), 3.37-3.26 (m, 2H), 3.20-3.15 (m, 1H), 2.76 (s, 3H).

Synthesis of Compound 126 and Compound 127

(R)-1-(5-(2,6-dimethylpyridin-4-yl)isochroman-1-yl)-N-methylmethanamine dihydrochloride (Compound 126)

To a solution of (R)-tert-butyl (5-(2,6-dimethylpyridin-4-yl)isochroman-1-yl)methyl(methyl)carbamate (500 mg, 1.3 mmol, 1.0 eq.) in HCl/EA (20 mL, 3 M) was stirred at room temperature for 2 h. The mixture was concentrated to afford (R)-1-(5-(2,6-dimethylpyridin-4-yl)isochroman-1-yl)-N-methylmethanamine dihydrochloride (300 mg, Yield: 65%), MS (ESI): m/z 269 [M+H]⁺. ¹H NMR (400 MHz, DMSO-d₆): δ 8.28 (bs, 3H), 7.75 (bs, 2H), 7.47-7.42 (m, 2H), 7.33-7.31 (m, 1H), 5.11 (d, J=8.8 Hz, 1H), 4.04-3.98 (m, 1H), 3.73-3.67 (m, 1H), 3.46-3.45 (m, 1H), 3.13-3.05 (m, 1H), 2.90-2.82 (m, 1H), 2.76 (s, 6H), 2.68-2.62 (m, 1H).

(R)-tert-butyl (5-(2,6-dimethylpyridin-4-yl)isochroman-1-yl)methyl(methyl)carbamate To a solution of (R)-tert-butyl (5-bromoisochroman-1-yl)methyl(methyl)carbamate (500 mg, 1.4 mmol, 1.0 eq.) in dioxane/H₂O (30 mL, 5:1) was added 2,6-dimethylpyridin-4-ylboronic acid (423 mg, 2.8 mmol, 2.0 eq.), K₂CO₃ (580 mg, 4.2 mmol, 3.0 eq.) and Pd(PPh₃)₄ (161 mg, 0.14 mmol, 0.1 eq.), then stirred at reflux for 10 h, monitored by LC-MS. The reaction mixture was concentrated to dry, the residue was purified by silica gel column (P.E:EA=3:1) to afforded (R)-tert-butyl (5-(2,6-dimethylpyridin-4-yl)isochroman-1-yl)methyl(methyl)carbamate (500 mg, Yield: 93%), MS (ESI): m/z 269 [M−100+H]⁺.

(S)-tert-butyl (5-(2,6-dimethylpyridin-4-yl)isochroman-1-yl)methyl(methyl)carbamate To a solution of (S)-tert-butyl (5-bromoisochroman-1-yl)methyl(methyl)carbamate (500 mg, 1.4 mmol, 1.0 eq.) in dioxane/H₂O (30 mL, 5:1) was added 2,6-dimethylpyridin-4-ylboronic acid (423 mg, 2.8 mmol, 2.0 eq.), K₂CO₃ (580 mg, 4.2 mmol, 3.0 eq.) and Pd(PPh₃)₄ (161 mg, 0.14 mmol, 0.1 eq.), then stirred at reflux for 10 h, monitored by LC-MS. The reaction mixture was concentrated to dry, the residue was purified by silica gel column (P.E:EA=3:1) to afforded (S)-tert-butyl (5-(2,6-dimethylpyridin-4-yl)isochroman-1-yl)methyl(methyl)carbamate (500 mg, Yield: 93%), MS (ESI): m/z 269 [M−100+H]⁺.

(S)-1-(5-(2,6-dimethylpyridin-4-yl)isochroman-1-yl)-N-methylmethanamine dihydrochloride (Compound 127)

To a solution of (S)-tert-butyl (5-(2,6-dimethylpyridin-4-yl)isochroman-1-yl)methyl(methyl)carbamate (500 mg, 1.3 mmol, 1.0 eq.) in HCl/EA (20 mL, 3 M) was stirred at room temperature for 2 h. The mixture was concentrated to afford (S)-1-(5-(2,6-dimethylpyridin-4-yl)isochroman-1-yl)-N-methylmethanamine dihydrochloride (300 mg, Yield: 65%), MS (ESI): m/z 269 [M+H]⁺. ¹H NMR (400 MHz, DMSO-d₆): δ 8.28 (bs, 3H), 7.75 (bs, 2H), 7.47-7.42 (m, 2H), 7.33-7.31 (m, 1H), 5.11 (d, J=8.8 Hz, 1H), 4.04-3.98 (m, 1H), 3.73-3.67 (m, 1H), 3.46-3.45 (m, 1H), 3.13-3.05 (m, 1H), 2.90-2.82 (m, 1H), 2.76 (s, 6H), 2.68-2.62 (m, 1H).

Synthesis of Compound 124 and Compound 125

(R)-tert-butyl (5-(2,6-dimethylpyridin-4-yl)isochroman-1-yl)methyl(methyl)carbamate To a solution of (R)-tert-butyl (5-bromoisochroman-1-yl)methyl(methyl)carbamate (500 mg, 1.4 mmol, 1.0 eq.) in dioxane/H₂O (30 mL, 5:1) was added 2,6-dimethylpyridin-4-ylboronic acid (423 mg, 2.8 mmol, 2.0 eq.), K₂CO₃ (580 mg, 4.2 mmol, 3.0 eq.) and Pd(PPh₃)₄ (161 mg, 0.14 mmol, 0.1 eq.), then stirred at reflux for 10 h, monitored by LC-MS. The mixture was concentrated, then purification by silica gel column (P.E:EA=3:1) to afforded (R)-tert-butyl (5-(2,6-dimethylpyridin-4-yl)isochroman-1-yl)methyl(methyl)carbamate (500 mg, Yield: 93%), MS (ESI): m/z 283 [M−100+H]⁺.

(R)-1-(5-(2,6-dimethylpyridin-4-yl)isochroman-1-yl)-N-methylmethanamine dihydrochloride (Compound 124)

To a solution of (R)-tert-butyl (5-(2,6-dimethylpyridin-4-yl)isochroman-1-yl)methyl(methyl)carbamate (500 mg, 1.3 mmol, 1.0 eq.) in HCl/EA (20 mL, 3 M) was stirred at rt for 2 h, monitored by LC-MS. The mixture was concentrated to afforded (R)-1-(5-(2,6-dimethylpyridin-4-yl)isochroman-1-yl)-N-methylmethanamine dihydrochloride (500 mg, Yield: 98%). MS (ESI): m/z 283 [M+H]⁺. ¹H NMR (400 MHz, DMSO-d₆) δ 9.43-9.30 (bs, 1H), 8.97-8.80 (bs, 1H), 7.77 (bs, 2H), 7.49-7.44 (m, 2H), 7.35-7.32 (m, 1H), 5.24 (d, J=8.8 Hz, 1H), 4.05-3.99 (m, 1H), 3.75-3.69 (m, 1H), 3.59-3.53 (m, 1H), 3.28-3.21 (m, 1H), 2.90-2.73 (m, 7H), 2.69-2.61 (m, 4H).

(S)-tert-butyl (5-(2,6-dimethylpyridin-4-yl)isochroman-1-yl)methyl(methyl)carbamate To a solution of (S)-tert-butyl (5-bromoisochroman-1-yl)methyl(methyl)carbamate (500 mg, 1.4 mmol, 1.0 eq.) in dioxane/H₂O (30 mL, 5:1) was added 2,6-dimethylpyridin-4-ylboronic acid (423 mg, 2.8 mmol, 2.0 eq.), K₂CO₃ (580 mg, 4.2 mmol, 3.0 eq.) and Pd(PPh₃)₄ (161 mg, 0.14 mmol, 0.1 eq.), then stirred at reflux for 10 h, monitored by LC-MS. The reaction mixture was concentrated to dry, the residue was purified by silica gel column (P.E:EA=3:1) to afford (S)-tert-butyl (5-(2,6-dimethylpyridin-4-yl)isochroman-1-yl)methyl(methyl)carbamate (500 mg, Yield: 93%), MS (ESI): m/z 283 [M−100+H]⁺.

(S)-1-(5-(2,6-dimethylpyridin-4-yl)isochroman-1-yl)-N-methylmethanamine dihydrochloride (Compound 125)

To a solution of (S)-tert-butyl (5-(2,6-dimethylpyridin-4-yl)isochroman-1-yl)methyl(methyl)carbamate (500 mg, 1.3 mmol, 1.0 eq.) in HCL/EA (20 mL, 3 M) was stirred at room temperature for 2 h, monitored by LC-MS. The mixture was concentrated to afford (S)-1-(5-(2,6-dimethylpyridin-4-yl)isochroman-1-yl)-N-methylmethanamine dihydrochloride (300 mg, Yield: 65%). MS (ESI): m/z 283 [M+H]⁺. ¹H NMR (400 MHz, DMSO-d₆) δ 9.32-9.17 (bs, 1H), 8.91-8.76 (bs, 1H), 7.75 (bs, 2H), 7.49-7.42 (m, 2H), 7.35-7.30 (m, 1H), 5.22 (d, J=8.8 Hz, 1H), 4.05-3.99 (m, 1H), 3.75-3.69 (m, 1H), 3.59-3.54 (m, 1H), 3.28-3.21 (m, 1H), 2.90-2.73 (m, 7H), 2.69-2.61 (n, 4H).

rel-(R)—N-((5-(Pyridin-4-yl)isochroman-1-yl)methyl)cyclopropanamine hydrochloride salt (Compound 180)

To a solution of rel-(R)-(5-(pyridin-4-yl)isochroman-1-yl)methanamine (650 mg, 2.70 mmol) in methanol (3 mL) was added (1-ethoxycyclopropoxy)trimethylsilane (705 mg, 4.05 mmol), acetic acid (162 mg) and Sodium cyanoborohydride (339 mg, 5.40 mmol), 4A molecular sieves (0.2 g) subsequently and the resulting mixture was stirred at room temperature for 3 h and 50° C. for 16 h. After cooled and concentrated under reduced pressure, the residue was partitioned between NaHCO₃ (aq, saturated) and DCM. The separated aqueous layer was extracted with DCM and the combined organic phases were dried (Na₂SO₄) and concentrated. Purification (flash column chromatography, 5% MeOH in DCM) of the crude product gave the title compound as a pale yellow solid (310 mg, 1.11 mmol, Yield 41%). MS (ESI): m/z 281.1 [M+H]⁺. To a solution of rel-(R)—N-((5-(pyridin-4-yl)isochroman-1-yl)methyl)cyclopropanamine (200 mg, 713 μmol) in methanol (3 mL) was added 3M hydrogen chloride in methanol (0.71 mL, 2.13 mmol). The reaction was stirred at ambient temperature for 30 min. The mixture was concentrated and frozen to dry to obtain rel-(R)—N-((5-(pyridin-4-yl)isochroman-1-yl)methyl)cyclopropanamine hydrochloride salt (213 mg, 603 μmol, Yield 84%) as a yellow oil.

MS (ESI): m/z 281.1 [M+H]⁺, ¹H NMR (400 MHz, methanol-d4): δ 8.95 (d, J=6.8 Hz, 2H), 8.19 (d, J=6.4 Hz, 2H), 7.54-7.51 (m, 2H), 7.47-7.44 (m, 1H), 5.28 (dd, J=2.0 Hz, J=9.6 Hz, 1H), 4.22-4.17 (m, 1H), 3.84-3.77 (m, 2H), 3.51-3.45 (m, 1H), 3.12-3.06 (m, 1H), 2.91-2.86 (m, 1H), 2.69-2.65 (m, 1H), 1.09-0.94 (m, 4H).

rel-(S)—N-((5-(Pyridin-4-yl)isochroman-1-yl)methyl)cyclopropanamine hydrochloride salt (Compound 181)

To a solution of rel-S)-(5-(pyridin-4-yl)isochroman-1-yl)methanamine (750 mg, 3.12 mmol) in methanol (2 mL) was added (1-ethoxycyclopropoxy)trimethylsilane (815 mg, 4.68 mmol), acetic acid (3 drops), Sodium cyanoborohydride (392 mg, 6.24 mmol), 4 molecule sieves (0.05 g) subsequently and the resulting mixture was stirred at room temperature for 3 h and 50° C. for 16 h. After cooled and concentrated under reduced pressure, the residue was partitioned between NaHCO₃ (aq, saturated) and DCM. The separated aqueous layer was extracted with DCM and the combined organic phases were dried (Na₂SO₄) and concentrated. Purification (flash column chromatography, 5% MeOH in DCM) of the crude product gave the title compound as a pale yellow solid (330 mg, 1.17 mmol, Yield 38%). MS (ESI): m/z 281 [M+H]⁺. To a solution of rel-(S)—N-((5-(pyridin-4-yl)isochroman-1-yl)methyl)cyclopropanamine (220 mg, 784 μmol) in methanol (3 ml) was added 3 M hydrogen chloride in methanol (0.78 mL, 2.35 mmol). The reaction was stirred at ambient temperature for 30 min. The mixture was concentrated and frozen to dry to get rel-(S)—N-((5-(pyridin-4-yl)isochroman-1-yl)methyl)cyclopropanamine hydrochloride salt (223 mg, 631 μmol, Yield 80%) as a yellow oil. MS (ESI): m/z 281.1 [M+H]⁺, ¹H NMR (400 MHz, methanol-d4): δ 8.95 (d, J=6.8 Hz, 2H), 8.19 (d, J=6.4 Hz, 2H), 7.54-7.51 (m, 2H), 7.48-7.44 (m, 1H), 5.29 (dd, J=2.0 Hz, J=9.6 Hz, 1H), 4.22-4.17 (m, 1H), 3.84-3.77 (m, 2H), 3.51-3.45 (m, 1H), 3.14-3.06 (m, 1H), 2.92-2.86 (m, 1H), 2.69-2.64 (m, 1H), 1.09-0.94 (m, 4H).

(R)-1-(5-(1H-Imidazol-1-yl)isochroman-1-yl)-N-methylmethanamine hydrochloride salt (Compound 182)

To a solution of (R)-tert-butyl ((5-bromoisochroman-1-yl)methyl)(methyl)carbamate (900 mg, 2.52 mmol) in NMP (10 mL) in a sealed tube was added cesium carbonate (821 mg, 2.52 mmol), 1,10-phenanthroline (90.8 mg, 504 μmol), 1H-imidazole (514 mg, 7.56 mmol) and copper(I) iodide (95.9 mg, 504 μmol). The reaction mixture was heated to 110° C. and stirred at that temperature for 24 h. The cooled mixture was filtered. Water (30 mL) and EtOAc (50 mL) were added to the filter and the resulting biphasic mixture was transferred to a separating funnel. The layers were separated and the organic phase was washed with water (15 mL×2) and saturated aqueous NaCl solution (15 mL). The combined organics were dried over anhydrous Na₂SO₄, filtered and concentrated in vacuo. The resulting oil was purified by flash column chromatography with a gradient elution of petroleum ether (100%) and EtOAc (0%) to EtOAc (65%) and petroleum ether (35%) to provide (R)-tert-butyl ((5-(1H-imidazol-1-yl)isochroman-1-yl)methyl)(methyl)carbamate (735 mg, 2.14 mmol, Yield: 85%) as a yellow oil. MS(ESI): m/z 344 [M+H]⁺. ¹H NMR (400 MHz, CDCl₃): δ 7.59 (s, 1H), 7.38-7.30 (m, 2H), 7.21-7.16 (m, 2H), 7.06 (s, 1H), 5.05-5.02 (m, 1H), 4.06-4.04 (m, 1H), 3.96-3.79 (m, 2H), 3.72-3.66 (m, 1H), 2.99-2.94 (m, 1H), 3.42-3.31 (m, 1H), 3.01 (s, 3H), 2.71-2.64 (m, 1H), 2.48-2.44 (m, 1H), 1.49 (s, 9H). To a solution of (R)-tert-butyl ((5-(1H-imidazol-1-yl)isochroman-1-yl)methyl)(methyl)carbamate (700 mg, 2.03 mmol) in EtOAc (5 mL) was added 3 M hydrogen chloride in acetic ether (4.03 mL, 12.1 mmol). The reaction was stirred at ambient temperature for 16 h. The mixture was concentrated to provide (R)-1-(5-(1H-imidazol-1-yl)isochroman-1-yl)-N-methylmethanamine hydrochloride salt (546 mg, 1.95 mmol, Yield: 96%) as a yellow solid. Chiral HPLC: Column AS-H (250×4.6 mm, 5 μm); Mobile Phase: n-Hexane (0.1% DEA):EtOH (0.1% DEA)=80:20: Temp=40° C.; Flow rate=1.0 mL/min; Ret Time=5.460 min; e.e value: 100%. MS(ESI): m/z 244 [M+H]⁺. ¹H NMR (400 MHz, DMSO-d6): δ 9.65 (s, 1H), 9.53 (s, 1H), 9.07 (s, 1H), 8.07 (s, 1H), 7.96 (s, 1H), 7.58-7.50 (m, 3H), 5.29 (d, J=9.2 Hz, 1H), 4.07-4.02 (m, 1H), 3.78-3.72 (m, 1H), 3.62-3.57 (m, 1H), 3.27-3.16 (m, 1H), 2.74-2.67 (m, 1H), 2.63-2.53 (m, 1H), 2.51 (s, 3H).

Scheme 25

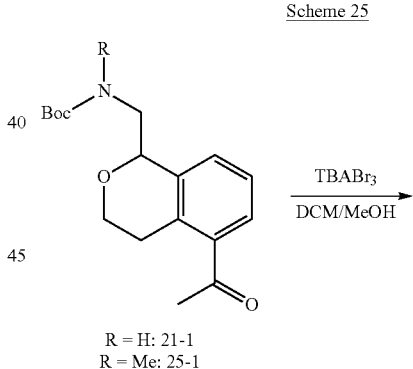

R = H: 21-1
R = Me: 25-1

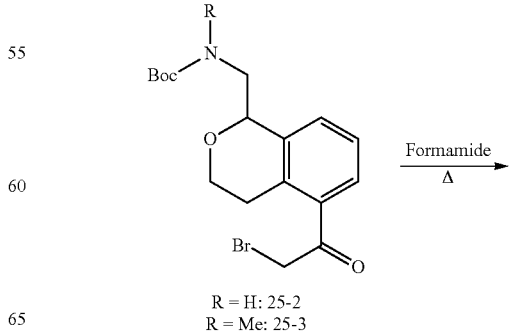

R = H: 25-2
R = Me: 25-3

201
-continued

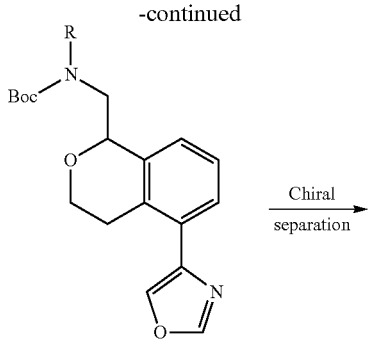

R = H: 25-4
R = Me: 25-5

Chiral separation →

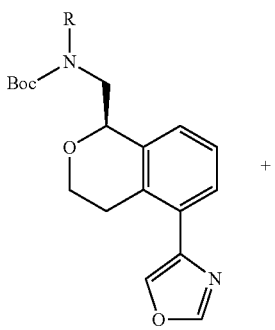

R = H: 25-6
R = Me: 25-7

+

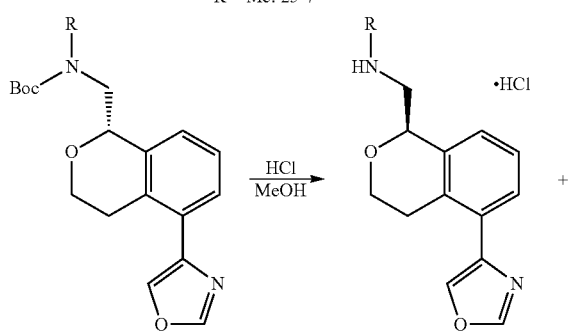

R = H: 25-8
R = Me: 25-9

HCl / MeOH →

R = H: Compound 100
R = Me: Compound 102

+

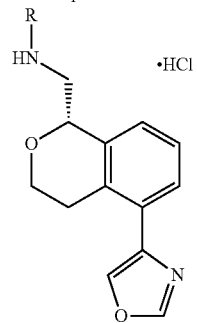

R = H: Compound 101
R = Me: Compound 103 tert-Butyl (5-(2-bromoacetyl)isochroman-1-yl)methylcarbamate (25-2)

To a solution of tert-butyl ((5-acetylisochroman-1-yl)methyl)carbamate (10.0 g, 32.6 mmol) in dichloromethane (160 mL) and methanol (80 mL) was added Tetrabutylammonium tribromide (17.2 g, 36.0 mmol) at 0° C. The mixture was stirred at room temperature overnight. The mixture was extracted with dichloromethane (1000 mL) and washed with H₂O (300 mL) and brine (300 mL). The organic layer was dried over Na₂SO₄ and concentrated in vacuo. The crude was added to a solution of di-tert-butyl dicarbonate in DCM at 0° C. Triethylamine (13.2 g, 130.4 mmol) was added and the mixture was stirred for 12 h. Water was added and the mixture was extracted with DCM. The combined organic layer was washed with water until neutrality, dried (Na₂SO₄), filtered, and concentrated in vacuo. The residue was purified by flash chromatography on silica gel (10-20 percent ethyl acetate/P.E). (5.2 g, Yield: 42%). MS (ESI): m/z 407 [M+Na]$^+$.

tert-Butyl (5-(oxazol-4-yl)isochroman-1-yl)methylcarbamate (25-4)

A solution of tert-butyl ((5-(2-bromoacetyl)isochroman-1-yl)methyl)carbamate (5.2 g, 13.5 mmol) in formamide (15 mL) was stirred at 110° C. for 2 h. The mixture was cooled to rt and diluted with water. This was extracted with ethyl acetate (120 mL×3). The combined organic layers were washed with water and brine, dried over sodium sulfate and concentrated under reduced pressure. The residue was purified by flash chromatography on silica gel (10-20 percent ethyl acetate/P.E) to give the pure one (700 mg, yield=15%). MS (ESI): m/z 353 [M+Na]$^+$.

(R)-tert-Butyl (5-(oxazol-4-yl)isochroman-1-yl) methylcarbamate (25-6) and (S)-tert-Butyl (5-(oxazol-4-yl)isochroman-1-yl)methylcarbamate (25-8)

The racemic mixture (25-4) (700 mg) was separated by chiral HPLC {Column: OJ 20*250 mm, 10 um (Daicel) and Mobile Phase: CO₂/IPA (0.2% Methanol Ammonia)=85/15} to afford (R)-tert-butyl (5-(oxazol-4-yl)isochroman-1-yl) methylcarbamate (300 mg, Yield: 43%, retention time 1.84 min, ee: 100%) as an oil, and (S)-tert-butyl (5-(oxazol-4-yl) isochroman-1-yl)methylcarbamate (300 mg, Yield: 43%, retention time 1.24 min, ee: 100%) as an oil.

(R)-(5-(oxazol-4-yl)isochroman-1-yl)methanamine HCl salt (Compound 100)

To a solution of (R)-tert-butyl (5-(oxazol-4-yl)isochroman-1-yl)methylcarbamate (300 mg, 0.91 mmol) in 1 mL of methanol was added 3 N HCl solution (3 mL, 9.1 mmol) at 0° C. The reaction was stirred at 0° C. for 3 h. After evaporation of solvent, the crude material was washed with ethyl acetate, and dried in vacuo to give the desired compound (200 mg, Yield: 73%) hydrochloride salt as a white solid. Chiral HPLC: Column IG 4.6*100 mm, 5 um; Mobile Phase: MeOH (0.2% Methanol Ammonia); Temp=40.5° C.; Flow rate=0.8 mL/min: Ret Time=2.73 min: Enantiopurity: 100% ee. MS (ESI): m/z 231 [M−HCl+H]$^+$. $^1$H NMR (400 MHz, DMSO-d6): δ 8.52 (s, 1H), 8.42 (s, 1H), 8.20 (bs, 3H), 7.73 (d, J=7.6 Hz, 1H), 7.37-7.28 (m, 2H), 5.06 (d, J=7.6 Hz, 1H), 4.13-4.08 (m, 1H), 3.81-3.75 (m, 1H), 3.45-3.40 (m, 1H), 3.17-3.10 (m, 1H), 3.00-2.96 (m, 1H), 2.94-2.80 (m, 1H).

(S)-(5-(oxazol-4-yl)isochroman-1-yl)methanamine HCl salt (Compound 101)

To a solution of (S)-tert-butyl (5-(oxazol-4-yl)isochroman-1-yl)methylcarbamate (300 mg, 0.91 mmol) in 1 mL of methanol was added 3 N HCl solution (3 mL, 9.1 mmol) at 0° C. The reaction was stirred at 0° C. for 3 h. After evaporation of solvent, the crude material was washed with ethyl acetate, and dried in vacuo to give the desired compound (200 mg, Yield: 73%) hydrochloride salt as a white solid. Chiral HPLC: Column IG 4.6*100 mm, 5 um; Mobile Phase: MeOH (0.2% Methanol Ammonia); Temp=39.3° C.; Flow rate=0.8 mL/min: Ret Time=3.44 min; Enantiopurity; 100% ee. MS (ESI): m/z 231 [M−HCl+H]$^+$. $^1$H NMR (400 MHz, DMSO-d6): δ 8.52 (s, 1H), 8.42 (s, 1H), 8.21 (bs, 3H), 7.73 (d, J=7.2 Hz, 1H), 7.37-7.28 (m, 2H), 5.06 (d, J=7.6 Hz, 1H), 4.13-4.08 (m, 1H), 3.81-3.75 (m, 1H), 3.44-3.40 (m, 1H), 3.17-3.10 (m, 1H), 3.00-2.94 (m, 1H), 2.85-2.80 (m, 1H).

tert-Butyl (5-acetylisochroman-1-yl)methyl(methyl) carbamate (25-1)

To a solution of tert-butyl ((5-bromoisochroman-1-yl)methyl)(methyl)carbamate (15.0 g, 42.0 mmol) in 1,4-dioxane (160 mL) was added dichloropalladium; bis(triphenylphosphane) (884 mg, 1.26 μmol) and tributyl(1-ethoxyvinyl)stannane (16.7 g, 46.2 mmol) was stirred at 90° C. overnight. After cooling to room temperature, the reaction was treated with ethyl acetate (400 mL) and washed with 15 percent citric acid aqueous solution (2×200 mL), H$_2$O (200 mL) and brine (200 mL). The organic layer was dried over Na$_2$SO$_4$ and concentrated in vacuo. The residue was purified by flash chromatography on silica gel (10-20 percent ethyl acetate/P.E) to give the title compound (9.6 g, Yield: 72%). MS (ESI): m/z 342 [M+Na]$^+$.

tert-Butyl (5-(2-bromoacetyl)isochroman-1-yl) methyl(methyl)carbamate (25-3)

To a solution of tert-butyl ((5-acetylisochroman-1-yl)methyl)(methyl)carbamate (6.3 g, 19.7 mmol) in dichloromethane (80 mL) and methanol (40 mL) was added Tetrabutylammonium tribromide (9.49 g, 19.7 mmol) at 0° C. The mixture was stirred at rt overnight. The mixture was extracted with dichloromethane (500 mL) and washed with H$_2$O (100 mL) and brine (100 mL). The organic layer was dried over Na$_2$SO$_4$ and concentrated in vacuo. The crude was added to a solution of Di-tert-butyl dicarbonate and DIPEA (5.09 g, 39.4 mmol) in CH$_2$Cl$_2$ at 0° C. The mixture was stirred for 12 h. Water was added and the mixture was extracted with CH$_2$Cl$_2$, the combined organic layer was washed with water until neutrality, dried (Na$_2$SO$_4$), filtered, and concentrated in vacuo. The residue was purified by flash chromatography on silica gel (10-20 percent ethyl acetate/P.E) to give the pure one (5.0 g, Yield: 64%). MS (ESI): m/z 420 [M+Na]$^+$ tert-Butyl methyl((5-(oxazol-4-yl)isochroman-1-yl) methyl)carbamate (25-5)

A solution of tert-butyl ((5-(2-bromoacetyl)isochroman-1-yl)methyl)(methyl)carbamate (4.6 g, 11.4 mmol) in formamide (10 mL) was stirred at 110° C. for 2 h. The mixture was cooled to rt and diluted with water. The mixture was extracted with ethyl acetate (120 mL×3), and the combined organic layers were washed with water and brine, dried over sodium sulfate and concentrated under reduced pressure. The residue was purified by flash chromatography on silica gel (10-20 percent ethyl acetate/P.E) to give the pure one (1.1 g, yield=27%). MS (ESI): m/z 367 [M+Na]$^+$.

(R)-tert-butyl methyl((5-(oxazol-4-yl)isochroman-1-yl)methyl)carbamate (25-7) and (S)-tert-butyl methyl((5-(oxazol-4-yl)isochroman-1-yl)methyl) carbamate (25-9)

The racemic mixture (25-5) (1.1 g) was separated by chiral HPLC {Column: IC 20*250 mm, 10 um (Daicel) and Mobile Phase: CO$_2$/IPA CO$_2$/EtOH (1% Methanol Ammonia)=80/20} to afford (R)-tert-butyl methyl((5-(oxazol-4-yl)isochroman-1-yl)methyl)carbamate (380 mg, Yield: 34%, retention time 2.21 min, ee: 100%) as an oil, and (S)-tert-butyl methyl((5-(oxazol-4-yl)isochroman-1-yl)methyl)carbamate (350 mg, Yield: 32%, retention time 3.11 min, ee: 100%) as an oil.

(R)—N-methyl-1-(5-(oxazol-4-yl)isochroman-1-yl) methanamine HCl salt (Compound 102)

To a solution of (R)-tert-butyl methyl((5-(oxazol-4-yl) isochroman-1-yl)methyl)carbamate (380 mg, 1.1 mmol) in 1 mL of methanol was added 3 N HCl solution (4 mL, 11.0 mmol) at 0° C. The reaction was stirred at 0° C. for 3 h. After evaporation of solvent, the crude was washed with ethyl acetate, dried in vacuo to give the desired compound (300 mg, Yield: 72%) hydrochloride salt as a white solid. Chiral HPLC: Column AY-H 4.6*100 mm, 5 um; Mobile Phase: EtOH (1% Methanol Ammonia); Temp=40.1° C.; Flow rate=1 mL/min: Ret Time=1.22 min; Enantiopurity: 100% ee. MS (ESI): m/z 245 [M−HCl+H]$^+$. $^1$H NMR (400 MHz, DMSO-d6): δ 9.26 (bs, 1H), 8.78 (bs, 1H), 8.52 (s, 1H), 8.42 (s, 1H), 7.73 (d, J=7.2 Hz, 1H), 7.36 (t, J=7.6 Hz, 1H), 7.26 (d, J=7.6 Hz, 1H), 5.18 (d, J=8.8 Hz, 1H), 4.08-4.12 (m, 1H), 3.77-3.83 (m, 1H), 3.51-3.55 (m, 1H), 3.23-3.28 (m, 1H), 2.94-3.01 (m, 1H), 2.81-2.86 (m, 1H), 2.61 (t, J=5.2 Hz, 3H).

(S)—N-methyl-1-(5-(oxazol-4-yl)isochroman-1-yl) methanamine HCl salt (Compound 103)

To a solution of (S)-tert-butyl methyl((5-(oxazol-4-yl) isochroman-1-yl)methyl)carbamate (350 mg, 1.0 mmol) in 1 mL of methanol was added 3 N HCl solution (3 mL, 10.0 mmol) at 0° C. The reaction was stirred at 0° C. for 3 h. After evaporation of solvent, the crude was washed with ethyl acetate, dried in vacuo to give the desired compound (300 mg, Yield: 78%) hydrochloride salt as a white solid. Chiral HPLC: Column AY-H 4.6*100 mm, 5 um; Mobile Phase: EtOH (1% Methanol Ammonia); Temp=40.1° C.: Flow rate=1 mL/min: Ret Time=2.40 min; Enantiopurity: 100% ee. MS (ESI): m/z 245 [M−HCl+H]$^+$. $^1$H NMR (400 MHz, DMSO): δ 9.46 (bs, 1H), 8.83 (bs, 1H), 8.52 (s, 1H), 8.42 (s, 1H), 7.73 (d, J=8.0 Hz, 1H), 7.33-7.37 (m, 1H), 7.26 (d, J=7.6 Hz, 1H), 5.21 (d, J=9.2 Hz, 1H), 4.07-4.12 (m, 1H), 3.76-3.82 (m, 1H), 3.50-3.55 (m, 1H), 3.21-3.29 (m, 1H), 2.93-3.00 (m, 1H), 2.80-2.86 (m, 1H), 2.61 (t. J=5.2 Hz, 3H).

Scheme 26

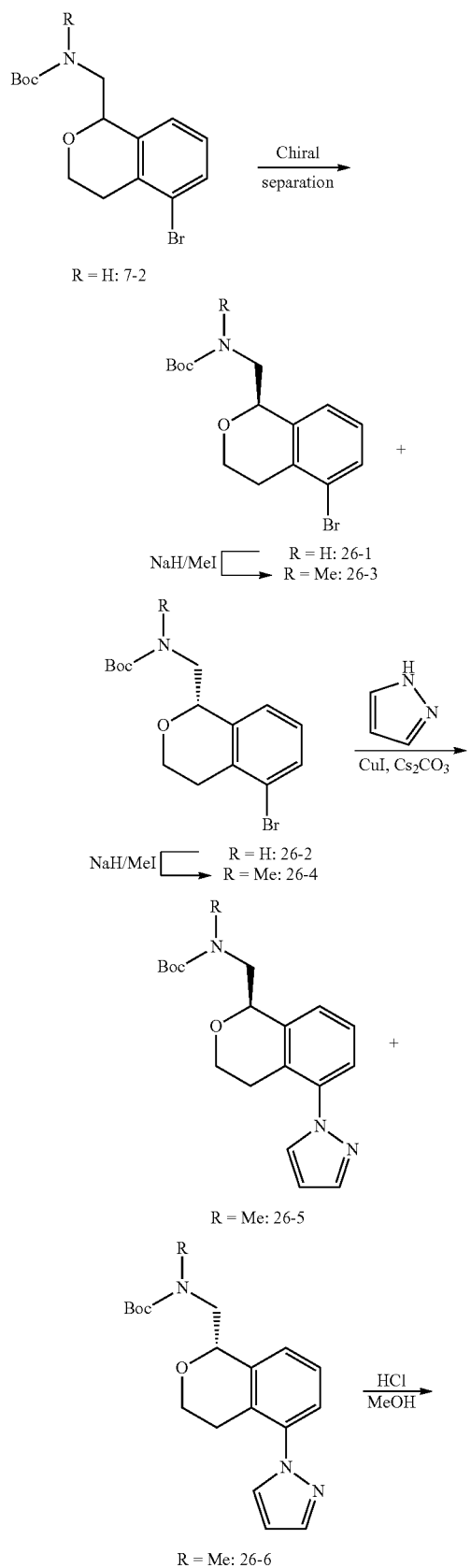

R = H: 7-2

R = H: 26-1
R = Me: 26-3

R = Me: 26-5

R = Me: 26-6

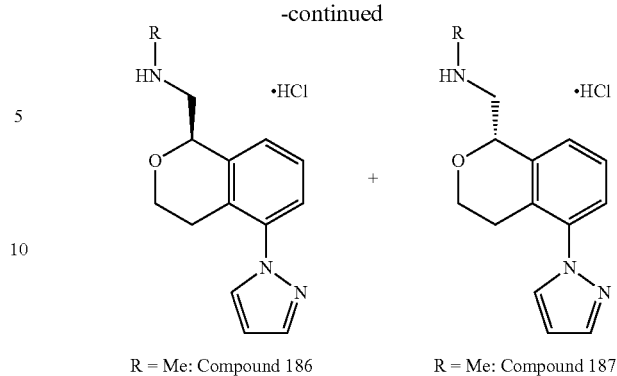

R = Me: Compound 186    R = Me: Compound 187

(R)-tert-Butyl (5-bromoisochroman-1-yl)methylcarbamate (26-1) and (S)-tert-butyl (5-bromoisochroman-1-yl)methylcarbamate (26-2)

Crude tert-butyl N-[(5-bromo-3,4-dihydro-1H-2-benzopyran-1-yl)methyl]carbamate (7-2) (6000 mg) was separated into two chiral peaks by {Instrument: SFC-80 (Thar, Waters) Column: AD 20*250 mm, 10 um (Daicel), Mobile phase: CO$_2$/EtOH (1% Methanol Ammonia)=87/13} to afford (R)-tert-butyl (5-bromoisochroman-1-yl)methylcarbamate (2700 mg. Yield 45%, ee: 1000%, retention time 1.82 min) as a white solid, and (S)-tert-butyl (5-bromoisochroman-1-yl)methylcarbamate (2200 mg, Yield 36%, ee: 100%, retention time 2.62 min) was obtained as a white solid.

(R)-tert-Butyl ((5-bromoisochroman-1-yl)methyl)(methyl)carbamate (26-3)

To a solution of (R)-tert-butyl ((5-bromoisochroman-1-yl)methyl)carbamate (900 mg, 2.62 mmol) in THF (15 mL) at 0° C. was added sodium hydride (156 mg, 5.24 mmol). The mixture was stirred at r.t for 15 min. Iodomethane (1.11 g, 7.86 mmol) was added. The reaction was stirred at ambient temperature for 16 h. Water (10 mL) and EA (20 mL) was added to the reaction vessel and the resulting biphasic mixture was transferred to a separatory funnel. The layers were separated and the organic phase was washed with saturated aqueous NaCl (15 mL). The combined organics were dried over anhydrous Na$_2$SO$_4$, filtered and concentrated in vacuo. The resulting oil was purified by flash column chromatography with a gradient elution of petroleum ether (100%) to EtOAc (35%) and petroleum ether (65%) to provide (R)-tert-butyl ((5-bromoisochroman-1-yl)methyl)(methyl)carbamate (744 mg, 2.09 mmol, 82.6% yield) as a yellow oil. MS (ESI): m/z 256 [M−100]$^+$.

(S)-tert-butyl ((5-bromoisochroman-1-yl)methyl)(methyl)carbamate (26-4)

To a solution of (S)-tert-butyl ((5-bromoisochroman-1-yl)methyl)carbamate (900 mg, 2.62 mmol) in THF (15 mL) at 0° C. was added sodium hydride (156 mg, 5.24 mmol). The mixture was stirred at r.t for 15 min. Then iodomethane (1.11 g, 7.86 mmol) was added. The reaction was stirred at ambient temperature for 16 h. Water (10 mL) and EA (20 mL) was added to the reaction vessel and the resulting biphasic mixture was transferred to a separatory funnel. The layers were separated and the organic phase was washed with saturated aqueous NaCl (15 mL). The combined organics were dried over anhydrous Na₂SO₄, filtered and concentrated in vacuo. The resulting oil was purified by flash column chromatography with a gradient elution of petroleum ether (100%) to EtOAc (35%) and petroleum ether (65%) to provide (S)-tert-butyl ((5-bromoisochroman-1-yl)methyl)(methyl)carbamate (700 mg, 1.96 mmol, 74.8% yield) as a yellow oil. MS (ESI): m/z 256 [M−100]+.

(R)-tert-butyl (5-(1H-pyrazol-1-yl)isochroman-1-yl)methyl(methyl)carbamate (26-5)

To a solution of (R)-tert-butyl ((5-bromoisochroman-1-yl)methyl)(methyl)carbamate (1.3 g, 3.66 mmol) in 1,4-dioxane (20 mL) was added 1H-pyrazole (750 mg, 11.00 mmol), CuI (350 mg, 1.84 mmol), cesium carbonate (2.39 g. 7.32 mmol) and N,N'-dimethyl-1,2-ethanediamine (323 mg, 3.67 mmol) at room temperature under N₂ atmosphere. Then the mixture was stirred at 110° C. for 2 days under N₂ atmosphere. After cooling down to rt, the residue was filtrated and the filtrate was concentrated. The resulting mixture was purified by silica gel chromatography with a gradient elution of petroleum ether (100%) and EtOAc (0%) to petroleum ether (80%) and EtOAc (20%) to provide (R)-tert-butyl ((5-(H-pyrazol-1-yl)isochroman-1-yl)methyl)(methyl)carbamate (600 mg, yield: 48%) as colorless oil. MS (ESI): m/z 244, 288, 366 [M−100+1, M−56+1, M+Na]⁺.

(S)-tert-butyl (5-(1H-pyrazol-1-yl)isochroman-1-yl)methyl(methyl)carbamate (26-6)

To a solution of (S)-tert-butyl ((5-bromoisochroman-1-yl)methyl)(methyl)carbamate (900 mg, 2.54 mmol) in 1,4-dioxane (20 mL) was added 1H-pyrazole (518 mg, 7.62 mmol), CuI (241 mg, 1.27 mmol), cesium carbonate (1.66 g, 5.08 mmol) and N,N'-dimethyl-1,2-ethanediamine (224 mg, 2.54 mmol) at rt under N₂ atmosphere. Then the mixture was stirred at 110° C. for 2 days under N atmosphere. After cooling down to rt, the residue was filtrated and the filtrate was concentrated. The resulting mixture was purified by silica gel chromatography with a gradient elution of petroleum ether (100%) and EtOAc (0%) to petroleum ether (80%) and EtOAc (20%) to provide (S)-tert-butyl ((5-(1H-pyrazol-1-yl)isochroman-1-yl)methyl)(methyl)carbamate (360 mg, yield: 40%) as colorless oil. MS (ESI): m/z 244, 288, 366 [M−100(1, M−56+1, M+Na]⁺.

(R)-1-(5-(1H-pyrazol-1-yl)isochroman-1-yl)-N-methylmethanamine (Compound 186)

To a solution of (R)-tert-butyl (5-(H-pyrazol-1-yl)isochroman-1-yl)methyl(methyl)carbamate (600 mg, 1.74 mmol) in EtOAc (20 mL) was added HCl/EA (4M, 10 mL) at 0° C. The reaction was stirred at ambient temperature for 4 h. Upon the completion, the solvent was removed and the residue was washed with EtOAc (2×10 mL) to give the desired compound (450 mg, Yield: 82%) hydrochloride salt as a white solid. Chiral HPLC: Column: AY-H (250×4.6 mm, 5 um; Mobile Phase: n-Hexane (0.1% DEA): EtOH (0.1% DEA)=80:20; Temp=40° C.; Flow rate=1.0 mL/min: Ret Time=18.67 min: Enantiopurity: 100% ee. MS (ESI): m/z 244 [M+H]⁺. ¹H NMR (400 MHz, CD₃OD): δ: 8.13 (d, J=2.0 Hz, 1H), 8.05 (d, J=2.0 Hz, 1H), 7.53-7.45 (m, 3H), 6.74 (t, J=2.0 Hz, 1H), 5.24-5.22 (m, 1H), 4.22-4.17 (m, 1H), 3.83-3.78 (m, 1H), 3.73-3.70 (m, 1H), 3.42-3.38 (m, 1H), 2.93-2.87 (m, 1H), 2.82 (s, 3H), 2.48-2.44 (m, 1H).

(S)-1-(5-(1H-pyrazol-1-yl)isochroman-1-yl)-N-methylmethanamine (Compound 187)

To a solution of (S)-tert-butyl (5-(1H-pyrazol-1-yl)isochroman-1-yl)methyl(methyl)carbamate (2) (360 mg, 1.04 mmol) in EtOAc (20 mL) was added HCl/EA (4M, 10 mL) at 0° C. The reaction was stirred at ambient temperature for 4 h. Upon the completion, the solvent was removed and the residue was washed with EtOAc (2×10 mL) to give the desired compound (2, 230 mg, yield: 70%) hydrochloride salt as a white solid. Chiral HPLC: Column: AY-H (250×4.6 mm, 5 um: Mobile Phase: n-Hexane (0.1% DEA): EtOH (0.1% DEA)=80:20; Temp=40° C.: Flow rate=1.0 mL/min; Ret Time=23.18 min; Enantiopurity: 100% ee. MS (ESI): m/z 244 [M+H]⁺. ¹H NMR (400 MHz, CD₃OD) δ: 7.95-7.94 (m, 1H), 7.86-7.85 (m, 1H), 7.45-7.35 (m, 3H), 6.59 (m, 1H), 5.16-5.15 (m, 1H), 4.15-4.11 (m, 1H), 3.76-3.71 (m, 1H), 3.65-3.62 (m, 1H), 3.36-3.32 (m, 1H), 2.89-2.82 (m, 1H), 2.75 (s, 3H), 2.43-2.38 (m, 1H).

Scheme 27

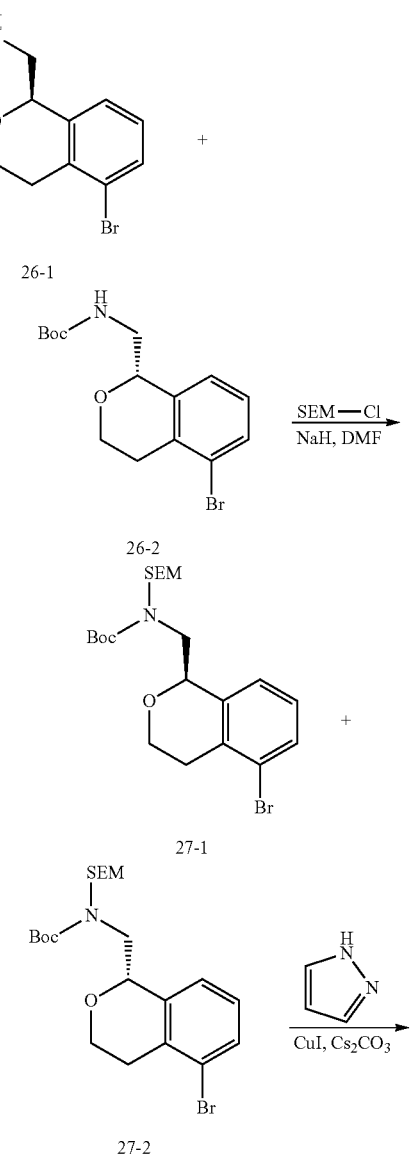

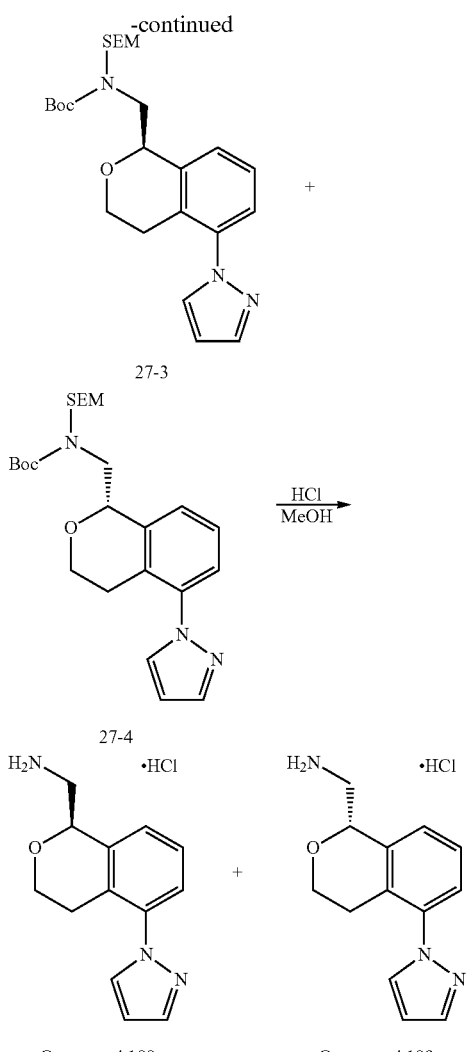

(R)-ter-butyl (5-bromoisochroman-1-yl)methyl((2-(trimethylsilyl)ethoxy)methyl)carbamate (27-1)

To a solution of (R)-tert-butyl ((5-bromoisochroman-1-yl)methyl)carbamate (2.0 g, 5.84 mol) in DMF (20 mL) was added sodium hydride (463 mg, 11.6 mmol) at 0° C. under $N_2$ atmosphere. After stirring at rt for 30 min, SEMCl (1.93 g, 11.6 mmol) was added to the mixture and stirred at rt for 2 h. The reaction was monitored by LCMS. When the reaction completed, $H_2O$ (20 mL) was added to quenched the reaction. The resulting mixture was extracted with DCM (2×20 mL). The combined organics were dried over anhydrous $Na_2SO_4$, filtered and concentrated in vacuo. The resulting mixture was purified by normal phase HPLC with a gradient elution of petroleum ether (100%) and EtOAc (0%) to petroleum ether (90%) and EtOAc (10%) to provide (R)-tert-butyl((5-bromoisochroman-1-yl)methyl)((2-(trimethylsilyl)ethoxy)methyl)carbamate (2.20 g, yield: 80%) as colorless oil. MS (ESI): m/z 494,496 [M+Na]$^+$.

(S)-tert-butyl (5-bromoisochroman-1-yl)methyl((2-(trimethylsilyl)ethoxy)methyl)carbamate (27-2)

To a solution of (S)-tert-butyl ((5-bromoisochroman-1-yl)methyl)carbamate (2.0 g, 5.84 mmol) in DMF (10 mL) was added Sodium hydride (580 mg, 14.5 mmol) at 0° C. After stirring at rt for 30 min, SEMCl (2.41 g, 14.5 mmol) was added to the mixture and stirred at rt for 2 h. Water (20 mL) was added to the reaction vessel and the resulting mixture was extracted with EtOAc (2×20 mL). The combined organics were dried over anhydrous $Na_2SO_4$, filtered and concentrated in vacuo. The resulting mixture was purified by normal phase HPLC with a gradient elution of petroleum ether (100%) and EtOAc (0%) to petroleum ether (95%) and EtOAc (5%) to provide (S)-tert-butyl ((5-bromoisochroman-1-yl)methyl)((2-(trimethylsilyl)ethoxy)methyl)carbamate (2.30 g, 4.86 mmol) as colorless oil. MS (ESI): mi/z 494,496 [M+Na]$^+$. $^1$H NMR (400 MHz, CDCl$_3$): δ 7.45-7.42 (m, 1H), 7.24-7.03 (m, 2H), 5.07-4.97 (m, 2H), 4.77-4.66 (m, 1H), 4.11-4.08 (m, 1H), 3.81-3.65 (m, 2H), 3.52-3.44 (m, 3H), 2.82-2.79 (m, 2H), 1.50 (s, 9H), 0.94-0.85 (m, 2H), 0.0 (s, 9H).

(R)-tert-butyl (5-(1H-pyrazol-1-yl)isochroman-1-yl)methyl((2-(trimethylsilyl)ethoxy)methyl)carbamate (27-3)

To a sealed tube of a solution of (R)-tert-butyl ((5-bromoisochroman-1-yl)methyl)((2-(trimethylsilyl)ethoxy)methyl)carbamate (1.0 g. 2.12 mmol) in 1,4-dioxane (30 mL) was added 1H-pyrazole (432 mg, 6.36 mmol), CuI (200 mg, 1.06 mmol), cesium carbonate (1.38 g, 4.24 mmol) and N,N'-dimethyl-1,2-ethanediamine (187 mg, 2.12 mmol) at rt under $N_2$ atmosphere. After stirring at rt for 10 min under $N_2$ atmosphere, the tube was heated to 110° C. for 3 days. The reaction was monitored by TLC. After cooling down to rt, the mixture was filtrated. The filtrate was concentrated and purified by normal phase HPLC with a gradient elution of petroleum ether (100%) and EtOAc (0%) to petroleum ether (90%) and EtOAc (10%) to provide (R)-tert-butyl((5-(1H-pyrazol-1-yl)isochroman-1-yl)methyl)((2-(trimethylsilyl)ethoxy)methyl)carbamate (560 mg, yield: 49%) as colorless oil. MS (ESI): m/z 482 [M+Na]$^+$.

(S)-tert-butyl (5-(1H-pyrazol-1-yl)isochroman-1-yl)methyl((2-(trimethylsilyl)ethoxy)methyl)carbamate (27-4)

To a sealed tube of a solution of (S)-tert-butyl ((5-bromoisochroman-1-yl)methyl)((2-(trimethylsilyl)ethoxy)methyl)carbamate 1.0 g, 2.12 mmol) in 1,4-dioxane (30 mL) was added 1H-pyrazole (432 mg, 6.36 mmol), CuI (200 mg, 1.06 mmol), Cesium carbonate (1.38 g, 4.24 mmol) and N,N'-Dimethyl-1,2-ethanediamine (187 mg, 2.12 mmol) at rt under $N_2$ atmosphere. Then the mixture was stirred at 110° C. for 3 days. After concentration, the resulting mixture was purified by normal phase HPLC with a gradient elution of petroleum ether (100%) and EtOAc (0%) to petroleum ether (90%) and EtOAc (10%) to provide (S)-tert-butyl ((5-(1H-pyrazol-1-yl)isochroman-1-yl)methyl)((2-(trimethylsilyl)ethoxy)methyl)carbamate (550 mg, yield: 56%) as colorless oil. MS (ESI): m/z 482 [M+Na]$^+$.

(R)-(5-(1H-pyrazol-1-yl)isochroman-1-yl)methanamine hydrochloride salt (Compound 188)

To a solution of (R)-tert-butyl ((5-(1H-pyrazol-1-yl)isochroman-1-yl)methyl)((2-(trimethylsilyl)ethoxy)methyl)carbamate (500 mg, 1.08 mmol) in EA (5 mL) was added 4N HCl/EA (10 mL) at rt. Then the mixture was stirred at rt for 3 h. The resulting mixture was concentrated and the residue was washed with EA (2×10 mL) to give the crude product.

Purification via chiral HPLC afforded a white solid (300 mg, Yield: 82%). Chiral HPLC: Column: AY-H (100×4.6 mm, 5 um: Mobile Phase: MeOH (0.2% Methanol Ammonia): Temp=40° C.; $CO_2$ Flow rate=3.6 mL/min: Co-solvent Flow rate=0.4 mL/min: Co-solvent % 10; Total Flow: 4; Ret Time=3.27 min; Enantiopurity: 98% ee. MS (ESI): m/z 230 [M+H]$^+$. $^1$H NMR (400 MHz, CD$_3$OD): δ 8.06-7.90 (m, 2H), 7.47-7.42 (m, 3H), 6.69-6.65 (m, 1H), 5.14 (d, J=8.8 Hz, 1H), 4.20-4.15 (m, 1H), 3.81-3.76 (m, 1H), 3.63-3.60 (m, 1H), 3.29-3.26 (m, 1H), 2.94-2.86 (m, 1H), 2.47-2.42 (m, 1H).

(S)-(5-(1H-pyrazol-1-yl)isochroman-1-yl)methanamine hydrochloride salt (Compound 189)

To a solution of (S)-tert-butyl ((5-(H-pyrazol-1-yl)isochroman-1-yl)methyl)((2-(trimethylsilyl)ethoxy)methyl)carbamate (550 mg, 1.20 mmol) in EA (5 mL) was added 4N HCl/EA (10 mL) at rt. Then the mixture was stirred at rt for 4 h. After concentration, the residue was washed with EA (2×10 mL) to give a white solid. (320 mg, yield: 90%). MS (ESI): m/z 230 [M+H]$^+$. (chiral analysis report: two peaks (1: 19)). The solid was purified by chiral-HPLC. (Instrument: SFC-80 (Thar, Waters); Column: AY 20*250 mm, 10 um (Daicel): Column temperature: 35° C.; Mobile phase: $CO_2$/MeOH (0.2% Methanol Ammonia)=80/20; Flow rate: 80 g/min; Back pressure: 100 bar: Detection wavelength: 214 nm; Cycle time: 5.0 min; Sample solution: 320 mg dissolved in 16 ml Methanol; Injection volume: 1.0 mL). 250 mg off-yellow oil was obtained. To a solution of (S)-(5-(1H-pyrazol-1-yl)isochroman-1-yl)methanamine (250 mg, 1.09 mmol) in EA (5 mL) was added 4M HCL/EA solution (5 mL). Then the mixture was stirred at rt for 10 min, the solvent was removed in vacuo and the precipitate was washed with EA (2×10 mL) to give a white solid (222 mg, yield: 67%). Chiral HPLC: Column: AY-H (100×4.6 mm, 5 um; Mobile Phase: MeOH (0.2% Methanol Ammonia); Temp=40.2° C.; $CO_2$ Flow rate=3.6 mL/min; Co-solvent Flow rate=0.4 mL/min; Co-solvent % 10; Total Flow: 4; Ret Time=3.63 min; Enantiopurity: 96% ee. MS (ESI): m/z 230 [M+H]$^+$. $^1$H NMR (400 MHz, CD$_3$OD): δ 7.97-7.80 (m, 2H), 7.48-7.37 (m, 3H), 6.62-6.58 (m, 1H), 5.12 (d, J=7.2 Hz, 1H), 4.19-4.15 (m, 1H), 3.79-3.75 (m, 1H), 3.61-3.59 (m, 1H), 3.31-3.27 (m, 1H), 2.95-2.88 (m, 1H), 2.47-2.44 (m, 1H).

(R)-tert-Butyl ((5-(1H-imidazol-1-yl)isochroman-1-yl)methyl)(methyl)carbamate To a solution of (R)-tert-butyl (5-bromoisochroman-1-yl)methylcarbamate (900 mg, 2.52 mmol) in NMP (10 mL) in a sealed tube was added cesium carbonate (821 mg, 2.52 mmol), 1,10-phenanthroline (90.8 mg, 504 μmol), 1H-imidazole (514 mg, 7.56 mmol) and copper(I) iodide (95.9 mg, 504 μmol). The reaction mixture was heated to 110° C. and stirred at that temperature for 24 h. The cooled mixture was filtered. Water (30 mL) and EA (50 mL) was added to the filter and the resulting biphasic mixture was transferred to a separatory funnel. The layers were separated and the organic phase was washed with water (2×15 mL) and saturated aqueous NaCl (15 mL). The combined organics were dried over anhydrous Na$_2$SO$_4$, filtered and concentrated in vacuo. The resulting oil was purified by flash column chromatography with a gradient elution of petroleum ether (100%) to EtOAc (65%) and petroleum ether (35%) to provide (R)-tert-butyl ((5-(1H-imidazol-1-yl)isochroman-1-yl)methyl)(methyl)carbamate (735 mg, 2.14 mmol, 85% yield) as a yellow oil. MS(ESI): m/z 344 [M+H]$^+$, H NMR (400 MHz, CDCl$_3$): δ 7.59 (s, 1H), 7.38-7.30 (m, 1H), 7.21-7.16 (m, 2H), 7.06 (s, 1H), 5.05-5.02 (m, 1H), 4.06-4.04 (m, 1H), 3.96-3.79 (m, 1H), 3.72-3.66 (m, 1H), 3.42-3.31 (m, 1H), 3.01 (s, 3H), 2.71-2.64 (m, 1H), 2.48-2.44 (m, 1H), 1.49 (s, 9H).

(R)-1-(5-(1H-Imidazol-1-yl)isochroman-1-yl)-N-methylmethanamine hydrochloride salt (Compound 182)

To a solution of (R)-tert-butyl ((5-(H-imidazol-1-yl)isochroman-1-yl)methyl)(methyl)carbamate (700 mg, 2.03 mmol) in EtOAc (5 mL) was added hydrogen chloride (441 mg, 12.1 mmol). The reaction was stirred at ambient temperature for 16 h. The mixture was concentrated to provide (R)-1-(5-(H-imidazol-1-yl)isochroman-1-yl)-N-methylmethanamine hydrochloride salt (546 mg, 1.95 mmol, 96.2% yield) as a yellow solid. Chiral HPLC: Column AS-H (250*4.6 mm 5 um); Mobile Phase: n-Hexane (0.1% DEA): EtOH (0.1% DEA)=80:20; Temp=40° C.; Flow rate=1.0 mL/min: Ret Time=5.460 min; Enantiopurity: 100% ee. MS (ESI): m/z 244 [M+H]$^+$. 1H NMR (400 MHz, DMSO-d6): δ 9.65 (s, 1H), 9.53 (s, 1H), 9.07 (s, 1H), 8.07 (s, 1H), 7.96 (s, 1H), 7.58-7.50 (m, 3H), 5.29 (d, J=9.2 Hz, 1H), 4.07-4.02 (m, 1H), 3.78-3.72 (m, 1H), 3.62-3.57 (m, 1H), 3.27-3.16 (m, 1H), 2.74-2.67 (m, 1H), 2.63-2.53 (m, 1H), 2.51 (s, 3H).

(S)-tert-Butyl ((5-(1H-imidazol-1-yl)isochroman-1-yl)methyl)(methyl)carbamate To a solution of (S)-tert-butyl ((5-bromoisochroman-1-yl)methyl)(methyl)carbamate (600 mg, 1.68 mmol) in NMP (10 mL) in a sealed tube was added 1,10-phenanthroline (302 mg, 1.68 mmol), cesium carbonate (1.09 g, 3.36 mmol) and 1H-imidazole (343 mg, 5.04 mmol) and copper(I) iodide (319 mg, 1.68 mmol). The reaction mixture was heated to 110° C. and stirred at that temperature for 2 days. The cooled mixture was filtered. Water (20 mL) and Ethyl acetate (50 mL) was added to the filter and the resulting biphasic mixture was transferred to a separatory funnel. The layers were separated and the organic phase was washed with water (2×10 mL) and saturated aqueous NaCl (15 mL). The combined organics were dried over anhydrous Na$_2$SO$_4$, filtered and concentrated in vacuo. The resulting oil was purified by flash column chromatography with a gradient elution of petroleum ether (100%) to EtOAc (65%) and petroleum ether (35%) to provide (S)-tert-butyl ((5-(H-imidazol-1-yl)isochroman-1-yl)methyl)(methyl)carbamate (200 mg, 582 μmol, 34% Yield) as a yellow oil. MS(ESI): m/z 344 [M+H]$^+$, H NMR (400 MHz, CDCl3): δ 7.59 (s, 1H), 7.38-7.30 (m, 2H), 7.21-7.14 (m, 2H), 7.06 (s, 1H), 5.06-4.99 (m, 1H), 4.06-4.04 (m, 1H), 3.96-3.78 (m, 2H), 3.72-3.66 (m, 1H), 3.42-3.31 (m, 1H), 3.01 (s, 3H), 2.71-2.64 (m, 1H), 2.48-2.44 (m, 1H), 1.49 (s, 9H).

(S)-1-(5-(1H-Imidazol-1-yl)isochroman-1-yl)-N-methylmethanamine hydrochloride salt (Compound 183)

To a solution of (S)-tert-butyl ((5-(H-imidazol-1-yl)isochroman-1-yl)methyl)(methyl)carbamate (250 mg, 727 μmol) in Ethyl acetate (3 mL) was added hydrogen chloride (132 mg, 3.63 mmol). The reaction was stirred at ambient temperature for 16 h. The LC-MS indicated the title compound was formed. The mixture was concentrated to provide (S)-1-(5-(1H-imidazol-1-yl)isochroman-1-yl)-N-methylmethanamine (153 mg, 632 μmol, 87% Yield) as an off white solid. Chiral HPLC: Column AS-H (250*4.6 mm 5 um); Mobile Phase: n-Hexane (0.1% DEA):EtOH (0.% DEA) =80:20; Temp=40° C.; Flow rate=1.0 mL/min; Ret Time=18.271 min; Enantiopurity: 100% ee. MS (ESI): m/z 244 [M+H]$^+$. 1H NMR (400 MHz, MeOD-d4): δ 9.26 (s, 1H), 7.88 (s, 1H), 7.82 (s, 1H), 7.58-7.52 (m, 3H), 5.23 (d, J=7.6 Hz, 1H), 4.25-4.21 (m, 1H), 3.87-3.82 (m, 1H), 3.75-3.71 (m, 1H), 3.42-3.36 (m, 1H), 2.94-2.82 (m, 1H), 2.53 (s, 3H), 2.51-2.49 (m, 1H).

(S)-tert-Butyl ((5-(1H-imidazol-1-yl)isochroman-1-yl)methyl)carbamate

To a solution of (S)-tert-butyl ((5-bromoisochroman-1-yl)methyl)carbamate (400 mg, 1.16 mmol) in NMP (8 mL) was added 1H-imidazole (236 mg, 3.48 mmol), copper(I) iodide (110 mg, 580 μmol), cesium carbonate (755 mg, 2.32 mmol), and (S)-1-((1-benzylpyrrolidin-2-yl)methyl)-2-methyl-1H-imidazole (148 mg, 580 μmol). The mixture was stirred in a sealed tube at 110° C. for 48. The cooled mixture was filtered. Water (20 mL) and Ethyl acetate (20 mL) was added to the filtrate and the resulting biphasic mixture was transferred to a separatory funnel. The layers were separated and the organic phase was washed with water (2×15 mL) and saturated aqueous NaCl (15 mL). The combined organics were dried over anhydrous $Na_2SO_4$, filtered and concentrated in vacuo. The resulting oil was purified by flash column chromatography with a gradient elution of petroleum ether (100%) to EtOAc (65%) and petroleum ethe (35%) to provide (S)-tert-butyl ((5-(H-imidazol-1-yl)isochroman-1-yl)methyl)carbamate (196 mg, 597 μmol) as a yellow oil. MS (ESI): m/z 330 [M+H]$^+$, 1H NMR (400 MHz, $CDCl_3$): δ 7.59 (s, 1H), 7.35-7.31 (m, 2H), 7.21 (s, 1H), 7.18-7.16 (m, 1H), 7.06 (s, 1H), 5.06 (s, 1H), 4.86 (d, J=7.2, 1H), 4.14-4.05 (m, 1H), 3.88-3.83 (m, 0.1H), 3.71-3.65 (m, 1H), 3.37-3.31 (m, 1H), 2.79-2.71 (m, 1H), 2.42-2.37 (m, 1H), 1.44 (s, 9H).

(S)-(5-(1H-Imidazol-1-yl)isochroman-1-yl)methanamine hydrochloride salt (Compound 185)

To a solution of (S)-tert-butyl ((5-(1H-imidazol-1-yl)isochroman-1-yl)methyl)carbamate (180 mg, 546 μmol) in EtOAc (6 mL) was added hydrogen chloride (119 mg, 3.27 mmol). The reaction was stirred at ambient temperature for 5 h. The mixture was concentrated to provide (S)-(5-(1H-imidazol-1-yl)isochroman-1-yl)methanamine hydrochloride salt (147 mg, 489 μmol, Yield: 90%) as a light yellow solid. Chiral HPLC: Column AD-H (100*4.6 mm 5 um); Co-Solvent: MeOH (1% Methanol Ammanial): $CO_2$ Flow Rate: 3.4: Co-Solvent Flow Rate: 0.6: Co-Solvent: 15%; Total Flow: 4: Temp=39.3° C.: Ret Time=4.23 min; Enantiopurity: 98.7% ee. MS(ESI): m/z 230 [M+H]$^+$. 1H NMR (400 MHz, MeOD-d4): δ 9.31 (s, 1H), 7.89-7.60 (m, 2H), 7.58-7.54 (m, 3H), 5.17 (d, J=8.0 Hz, 1H), 4.24-4.21 (m, 1H), 3.87-3.82 (m, 1H), 3.67-3.63 (m, 1H), 3.30-3.27 (m, 1H), 2.94-2.87 (m, 1H), 2.54-2.49 (m, 1H).

(R)-tert-Butyl ((5-(1H-imidazol-1-yl)isochroman-1-yl)methyl)carbamate

To a solution of (R)-tert-butyl ((5-bromoisochroman-1-yl)methyl)carbamate (500 mg, 1.46 mmol) in NMP (10 mL) was added 1H-imidazole (298 mg, 4.38 mmol), (S)-1-((1-benzylpyrrolidin-2-yl)methyl)-2-methyl-1H-imidazole (186 mg, 730 μmol), cesium carbonate (951 mg, 2.92 mmol) and copper(I) iodide (138 mg, 730 μmol). The mixture was stirred at 110° C. under $N_2$ protection for 48 h. The cooled mixture was diluted with Water (30 mL) and EtOAc (30 mL), and the solution was filtered. The filter was transferred to a separatory funnel. The layers were separated and the organic phase was washed with water (2×20 mL) and saturated aqueous NaCl (20 mL). The combined organics were dried over anhydrous $Na_2SO_4$, filtered and concentrated in vacuo. The resulting oil was purified by flash column chromatography with an isocratic elution of petroleum ether (100%) to EtOAc (90%) and petroleum ether (10%) to provide (R)-tert-butyl ((5-(H-imidazol-1-yl)isochroman-1-yl)methyl)carbamate (99.9 mg, 303 μmol) as a yellow suspension. MS (ESI): m/z 330 [M+H]$^+$.

(R)-(5-(1H-Imidazol-1-yl)isochroman-1-yl)methanamine hydrochloride salt (Compound 184)

To a solution of (R)-tert-butyl ((5-(H-imidazol-1-yl)isochroman-1-yl)methyl)carbamate (200 mg, 607 μmol) in EtOAc (6 mL) was added hydrogen chloride (1.21 mL, 3.64 mmol). The reaction was stirred at ambient temperature for 5 h. The mixture was concentrated to provide (R)-(5-(1H-imidazol-1-yl)isochroman-1-yl)methanamine hydrochloride salt (161 mg, 533 μmol, 87.8%) as a yellow solid. Chiral HPLC: Column AD-H (100*4.6 mm 5 um); Co-Solvent: MeOH (1% Methanol Ammanial); $CO_2$ Flow Rate: 3.4; Co-Solvent Flow Rate: 0.6; Co-Solvent: 15%; Total Flow: 4; Temp=41.6° C.; Ret Time=2.63 min; Enantiopurity: 98.6% ee. MS(ESI): m/z 230 [M+H]$^+$. 1H NMR (400 MHz, MeOD-d4): δ 9.31-9.30 (m, 1H), 7.89-7.84 (m, 2H), 7.58-7.54 (m, 3H), 5.17-5.16 (m, 1H), 4.24-4.21 (m, 1H), 3.87-3.82 (m, 1H), 3.67-3.64 (m, 1H), 3.30-3.26 (m, 1H), 2.94-2.87 (m, 1H), 2.54-2.49 (m, 1H).

(R)-tert-Butyl methyl((5-(oxazol-2-yl)isochroman-1-yl)methyl)carbamate

To a sealed tube of a solution of oxazole (203 mg, 2.94 mmol) in THF (20 mL) was added n-butyllithium (225 mg, 3.52 mmol) at −78° C. After stirring for 0.5 h at −78° C., the resulting solution was treated with zinc chloride (801 mg, 5.88 mmol) and warmed up to rt. (R)-tert-butyl ((5-bromoisochroman-1-yl)methyl)(methyl)carbamate (700 mg, 1.96 mmol) and Tetrakis(triphenylphosphine)palladium (452 mg, 392 μmol) was added to the reaction mixture. The sealed tube was irradiated in the microwave on a Biotage Smith Synthesis at 105° C. for 2 h. The reaction was monitored by LCMS. After concentration, the resulting mixture was purified by normal phase HPLC with a gradient elution of petroleum ether (100%) and EtOAc (0%) to petroleum ether (90%) and EtOAc (10%) to provide (R)-tert-butylmethyl((5-(oxazol-2-yl)isochroman-1-yl)methyl)carbamate (550 mg, 1.59 mmol) as a yellow solid. MS (ESI): m/z 245 [M−100+1]$^+$.

(R)—N-Methyl-1-(5-(oxazol-2-yl)isochroman-1-yl)methanamine hydrochloride salt (Compound 104)

A mixture of (R)-tert-butyl methyl((5-(oxazol-2-yl)isochroman-1-yl)methyl)carbamate (530 mg, 1.53 mmol) in HCl/EA (20 mL) was stirred at rt for 2 h. After concentration, the residue was washed with EA (2×10 mL) to give (R)—N-methyl-1-(5-(oxazol-2-yl)isochroman-1-yl)methanamine (370 mg, 1.51 mmol) as a yellow solid. Chiral HPLC: OZ-H (250*4.6 mm 5 um); Mobile Phase: n-Hexane (0.1% DEA):EtOH (0.1% DEA)=70:30; Temperature: 40°

C.; Ret Time=5.81 min; Enantiopurity: 100% ee. MS (ESI): m/z 245 [M+H]$^+$. $^1$H NMR (400 MHz, CD$_3$OD): δ 8.11 (s, 1H), 7.89-7.87 (m, 1H), 7.46-7.41 (m, 3H), 5.17-5.15 (m, 1H), 4.24-4.18 (m, 1H), 3.84-3.78 (m, 1H), 3.64-3.60 (m, 1H), 3.36-3.25 (m, 2H), 3.17-3.11 (m, 1H), 2.75 (s, 3H).

(R)-tert-Butyl (5-(oxazol-2-yl)isochroman-1-yl) methyl((2-(trimethylsilyl)ethoxy)methyl)carbamate To a sealed tube of a solution of oxazole (216 mg, 3.14 mmol) in THF (30 mL) was added n-butyllithium (242 mg, 3.78 mmol) at −78° C. After stirring for 0.5 h at −78° C., the resulting solution was treated with zinc chloride (858 mg, 6.30 mmol) and warmed up to rt. (R)-tert-butyl((5-bromoisochroman-1-yl)methyl)((2-(trimethylsilyl)ethoxy)methyl) carbamate (1.0 g, 2.10 mmol) and Tetrakis(triphenylphosphine)palladium (2.42 g, 2.10 mmol) was added to the reaction mixture. The sealed tube was irradiated in the microwave on a Biotage Smith Synthesis at 105° C. for 2 h. The reaction was monitored by LCMS. After concentration, the resulting mixture was purified by normal phase HPLC with a gradient elution of petroleum ether (100%) and EtOAc (0%) to petroleum ether (90%) and EtOAc (10%) to provide (R)-tert-butyl((5-(oxazol-2-yl)isochroman-1-yl) methyl)((2-(trimethylsilyl)ethoxy)methyl)carbamate (540 mg, yield: 56%) as colorless oil. MS (ESI): m/z 483 [M+Na]$^+$.

(R)-(5-(Oxazol-2-yl)isochroman-1-yl)methanamine hydrochloride salt (Compound 106)

To a solution of (R)-tert-butyl ((5-(oxazol-2-yl)isochroman-1-yl)methyl)((2-(trimethylsilyl)ethoxy)methyl)carbamate (540 mg, 1.17 mmol) in EA (5 mL) was added 4N HCl/EA (10 mL) at rt. Then the mixture was stirred at rt for 3 h. After concentration, the residue was washed with EA (2×10 mL) to give the desired product (300 mg, yield: 85%) as a white solid. MS (ESI): m/z 231 [M+H]$^+$. To a solution of (R)-(5-(oxazol-2-yl)isochroman-1-yl)methanamine (300 mg, 1.30 mmol) in DCM (20 mL) was added di-tert-butyl dicarbonate (567 mg, 2.60 mmol) and 2M NaOH solution in H$_2$O (1.3 mL) at rt. Then the mixture was stirred at rt for 16 h. Water (10 mL) was added to the reaction vessel and the resulting biphasic mixture was transferred to a separatory funnel. The layers were separated and the aqueous phase was extracted with DCM (2×15 mL). The combined organics were dried over anhydrous Na$_2$SO$_4$, filtered and concentrated in vacuo. The resulting mixture was purified by normal phase HPLC with a gradient elution of petroleum ether (100%) and EtOAc (0%) to petroleum ether (80%) and EtOAc (20%) to provide (R)-tert-butyl ((5-(oxazol-2-yl) isochroman-1-yl)methyl)carbamate (200 mg, 605 µmol) as a colorless oil. MS (ESI): m/z 353 [M+Na]$^+$. To a solution of (R)-tert-butyl ((5-(oxazol-2-yl)isochroman-1-yl)methyl)carbamate (200 mg, 605 µmol) in EtOAc (5 mL) was added HCl/EA (4M. 5 mL) at 0° C. The reaction was stirred at ambient temperature for 4 h. Upon the completion, the solvent was removed and the residue was washed with EtOAc (2×10 mL) to give the desired compound (200 mg, yield: 77%) hydrochloride salt as an off-yellow solid. Chiral HPLC: Column: Enantiopak AD (4.6×100 mm, 5 um); Co-solvent: MeOH (0.2% Methanol Ammonia): Temp=39.6° C.; CO$_2$ Flow rate=3 mL/min; Co-solvent Flow Rate: 1: Co-Solvent %: 25; Total Flow: 4: Ret Time=1.54 min; Enantiopurity: 99% ee. MS (ESI): m/z 2311 [M+H]$^+$. $^1$H NMR (400 MHz, CD$_3$OD): δ 8.18-8.15 (m, 1H), 7.94-7.92 (m, 1H), 7.54-7.47 (m, 3H), 5.15 (d, J=6.4 Hz, 1H), 4.28-4.24 (m, 1H), 3.88-3.83 (m, 1H), 3.61-3.58 (m, 1H), 3.38-3.26 (m, 2H), 3.21-3.17 (m, 1H).

(S)-tert-Butyl (5-(oxazol-2-yl)isochroman-1-yl) methyl((2-(trimethylsilyl)ethoxy)methyl)carbamate To a sealed tube of a solution of oxazole (261 mg, 3.79 mmol) in THF (20 mL) was added n-Butyllithium (291 mg, 4.55 mmol) at −78° C. After stirring for 0.5 h at −78° C., the resulting solution was treated with Zinc chloride (1.03 g, 7.58 mmol) and warmed up to rt. (S)-tert-butyl((5-bromoisochroman-1-yl)methyl)((2-(trimethylsilyl)ethoxy)methyl) carbamate (1.2 g. 2.53 mmol) and Tetrakis(triphenylphosphine)palladium (583 mg, 505 µmol) were added to the reaction mixture. The sealed tube was irradiated in the microwave on a Biotage Smith Synthesis at 105° C. for 2 h. The reaction was monitored by LCMS. After concentration, the resulting mixture was purified by normal phase HPLC with a gradient elution of petroleum ether (100%) and EtOAc (0%) to petroleum ether (90%) and EtOAc (10%) to provide (S)-tert-buty ((5-(oxazol-2-yl)isochroman-1-yl) methyl)((2-(trimethylsilyl)ethoxy)methyl)carbamate (700 mg, Yield: 58%) as colorless oil. MS (ESI): m/z 483 [M+Na]$^+$.

(S)-(5-(Oxazol-2-yl)isochroman-1-yl)methanamine hydrochloride salt (Compound 107)

To a solution of (S)-tert-butyl ((5-(oxazol-2-yl)isochroman-1-yl)methyl)((2-(trimethylsilyl)ethoxy)methyl)carbamate (680 mg, 1.47 mmol) in EA (5 mL) was added HCl/EA (10 mL) at rt. Then the mixture was stirred at rt for 2 h. After concentration, the residue was washed with EA (2×10 mL). The obtained solid was dissolved in H$_2$O (20 mL) and adjusted to pH=10 with 2N NaOH solution. The mixture was extracted with DCM (10×20 mL). The combined organic fractions were dried over Na$_2$SO$_4$, filtrated and concentrated to give the desired product as yellow oil (280 mg, Yield: 80%). MS (ESI): m/z 231 [M+H]$^+$. To a solution of (S)-(5-(oxazol-2-yl)isochroman-1-yl)methanamine (280 mg, 1.21 mmol) in DCM (20 mL) was added 2N NaOH solution (1.21 mL) and di-tert-butyl dicarbonate (528 mg, 2.42 mmol) at rt. Then the mixture was stirred at rt for 16 h. Water (10 mL) was added to the reaction vessel and the resulting biphasic mixture was transferred to a separatory funnel. The layers were separated and the aqueous phase was extracted with DCM (2×15 mL). The combined organics were dried over anhydrous Na$_2$SO$_4$, filtered and concentrated in vacuo. The resulting mixture was purified by normal phase HPLC with a gradient elution of petroleum ether (100%) and EtOAc (0%) to petroleum ether (80%) and EtOAc (20%) to provide (S)-tert-butyl ((5-(oxazol-2-yl)isochroman-1-yl)methyl)carbamate (250 mg, Yield: 63%) as colorless oil. MS (ESI): m/z 353 [M+Na]$^+$. To a solution of (S)-tert-butyl ((5-(oxazol-2-yl)isochroman-1-yl)methyl)carbamate (250 mg, 756 µmol) in EtOAc (5 mL) was added HCL/EA (4M, 5 mL) at 0° C. The reaction was stirred at ambient temperature for 4 h. Upon the completion, the solvent was removed and the residue was washed with EtOAc (2×10 mL) to give the desired compound (160 mg, yield: 70%) hydrochloride salt as an off-yellow solid. Chiral HPLC: Column: AY-H (4.6×100 mm, 5 um): Co-solvent: MeOH (0.2% Methanol Ammonia): Temp=40° C.; CO$_2$ Flow rate=3.6 mL/min: Co-solvent Flow Rate: 0.4; Co-Solvent %: 10; Total Flow: 4; Ret Time=4.24 min; Enantiopurity: 100% ee. MS (ESI): m/z 231 [M+H]$^+$. $^1$H NMR (400 MHz, CD$_3$OD): δ 8.19-8.15 (m, 1H), 7.94-

7.92 (m, 1H), 7.54-7.48 (m, 3H), 5.15 (d, J=8.4 Hz, 1H), 4.28-4.23 (m, 1H), 3.89-3.83 (m, 1H), 3.61-3.58 (m, 1H), 3.38-3.25 (m, 2H), 3.21-3.16 (m, 1H).

(R)-(6-(2-methylpyridin-4-yl)-1,3,4,5-tetrahydrobenzo[c]oxepin-1-yl)methanamine dihydrochloride salt (Compound 198)

The title compound was prepared using the procedure described in Scheme 23, substituting 4-bromo-2-methylpyridine for 2-bromopyridine. White solid (310 mg, yield=88%). (ESI): m/z 269 [M+H]$^+$. $^1$H NMR (400 MHz, CD$_3$OD): δ 8.77 (d, J=6.4 Hz, 1H), 7.92 (s, 1H), 7.84 (d, J=5.6 Hz, 1H), 7.46-7.34 (m, 3H), 5.05 (dd, J=2.8/10.4 Hz, 1H), 4.33 (d, J=9.6 Hz, 1H), 4.04-3.98 (m, 1H), 3.61-3.49 (m, 2H), 3.04-2.98 (m, 2H), 2.88 (s, 3H), 1.90-1.85 (m, 2H).

(S)-(6-(2-methylpyridin-4-yl)-1,3,4,5-tetrahydrobenzo[c]oxepin-1-yl)methanamine dihydrochloride salt (Compound 199)

The title compound was prepared using the procedure described in Scheme 23, substituting 4-bromo-2-methylpyridine for 2-bromopyridine. White solid (270 mg, Yield=94%). $^1$H NMR (400 MHz, CD$_3$OD): δ 8.77 (d, J=6.4 Hz, 1H), 7.92 (s, 1H), 7.84 (d, J=5.6 Hz, 1H), 7.46-7.34 (m, 3H), 5.05 (dd, J=2.8/10.4 Hz, 1H,), 4.33 (d, J=9.6 Hz, 1H), 4.04-3.98 (m, 1H), 3.61-3.49 (m, 2H), 3.04-2.98 (m, 2H), 2.88 (s, 3H), 1.90-1.85 (m, 2H). (ESI): m/z 269 [M+H]$^+$

(R)—N-methyl-1-(6-(2-methylpyridin-4-yl)-1,3,4,5-tetrahydrobenzo[c]oxepin-1-yl)methanamine dihydrochloride salt (Compound 196)

The title compound was prepared using the procedure described in Scheme 23, substituting 4-bromo-2-methylpyridine for 2-bromopyridine. White solid. (208 mg, yield=78%). MS(ESI): m/z 245 [M+H]$^+$. $^1$H NMR (400 MHz, CD$_3$OD): δ 8.86-8.81 (m, 1H), 7.53-7.51 (m, 2H), 7.40-7.32 (m, 2H), 5.07-5.04 (m, 1H), 4.35-4.30 (m, 1H), 4.03-3.97 (m, 1H), 3.59-3.45 (m, 2H), 3.30-3.24 (m, 1H), 3.09-3.04 (m, 1H), 1.92-1.88 (m, 2H). Chiral HPLC: column: AY-H 100×4.6 mm 5 um: Co-Solvent: EtOH (1% Methanol Ammonia); CO$_2$ Flow Rate: 3.6; Co-Solvent Flow Rate: 0.4; Co-Solvent %: 10; Column Temperature: 40° C.; Ret Time=10.43 min; Enantiopurity: 100% ee.

(S)—N-methyl-1-(6-(2-methylpyridin-4-yl)-1,3,4,5-tetrahydrobenzo[c]oxepin-1-yl)methanamine dihydrochloride salt (Compound 197)

The title compound was prepared using the procedure described in Scheme 23, substituting 4-bromo-2-methylpyridine for 2-bromopyridine. White solid (201 mg, yield=75.0%). MS(ESI): m/z 245 [M+H]$^+$. $^1$H NMR (400 MHz, CD$_3$OD): δ 8.81-8.62 (m, 1H), 7.52-7.31 (m, 4H), 5.06-5.04 (m, 1H), 4.35-4.30 (m, 1H), 4.03-3.97 (m, 1H), 3.59-3.45 (m, 2H), 3.30-3.24 (m, 1H), 3.09-3.04 (m, 1H), 1.92-1.87 (m, 2H). Chiral HPLC: column: AY-H 100×4.6 mm 5 um; Co-Solvent: EtOH (1% Methanol Ammonia): CO$_2$ Flow Rate: 3.6; Co-Solvent Flow Rate: 0.4; Co-Solvent %: 10: Column Temperature: 40° C.: Ret Time=8.14 min; Enantiopurity: 96% ee.

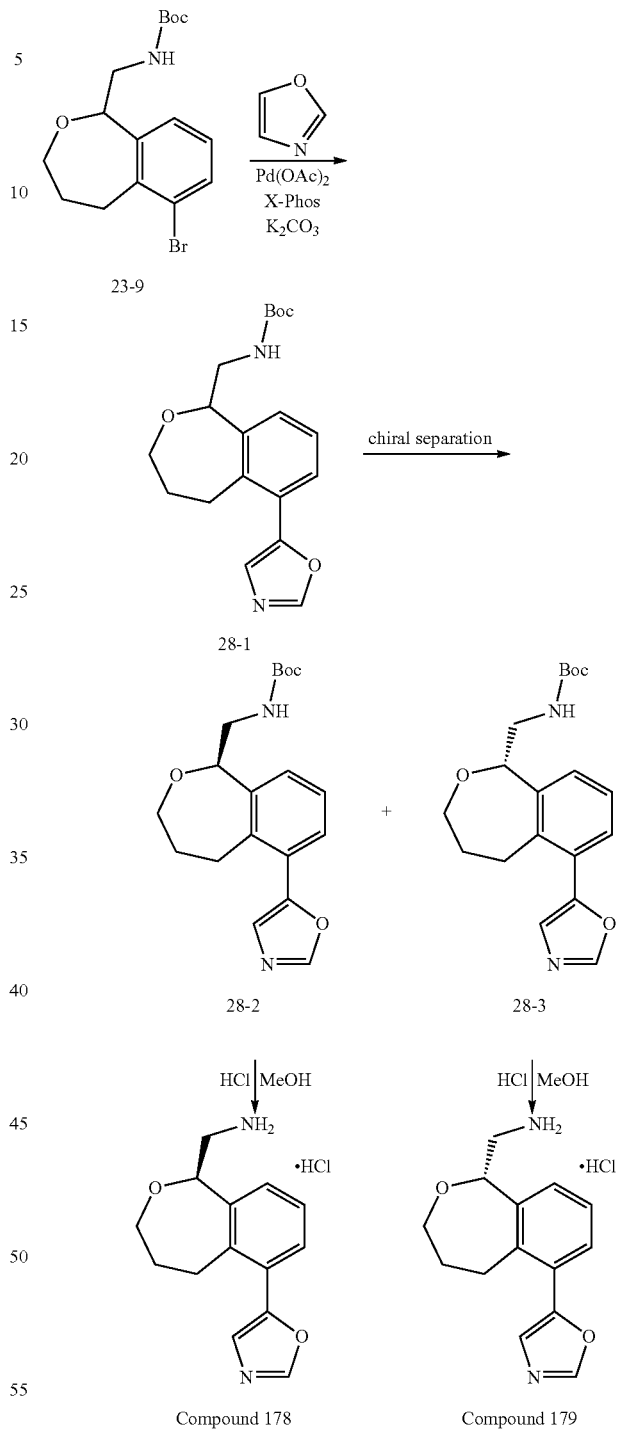

Scheme 28 tert-Butyl N-{[6-(1,3-oxazol-5-yl)-1,3,4,5-tetrahydro-2-benzoxepin-1-yl]methyl}carbamate (28-1)

To a solution of tert-butyl N-[(6-bromo-1,3,45-tetrahydro-2-benzoxepin-1-yl)methyl]carbamate (6.0 g, 16.9 mmol) in DMA (60 mL) was added 1,3-oxazole (1.75 g, 25.4 mmol), K$_2$CO$_3$ (7.0 g, 50.7 mmol) and Pd(OAc)$_2$ (759 mg, 3.38 mmol), X-Phos (3.21 g, 6.76 mmol) under N$_2$. The mixture was stirred at 120° C. for 5 h. The mixture was cooled to room temperature. Water (200 mL) was added to the reaction vessel and the resulting mixture was extracted with EtOAc (3×120 mL). The combined organics were dried over anhydrous $Na_2SO_4$, filtered and concentrated in vacuo. The resulting oil was purified by flash column chromatography (P.E/EA=3/1) to provide tert-butyl N-{[6-(1,3-oxazol-5-yl)-1,3,4,5-tetrahydro-2-benzoxepin-1-yl]methyl}carbamate (3.4 g, 9.88 mmol) as a yellow oil (Yield: 58%). MS(ESI) m/z: 245 [M−Boc]+. 1H NMR (400 MHz, $CDCl_3$): δ 7.97 (s, 1H), 7.39-7.37 (m, 1H), 7.25-7.24 (m, 2H), 7.12 (s, 1H), 5.06 (bs, 1H), 4.77-4.74 (m, 1H), 4.25-4.21 (m, 1H), 4.15-4.10 (m, 2H), 3.51-3.45 (m, 1H), 3.25-3.19 (m, 1H), 2.97-2.90 (m, 1H), 1.93-1.76 (m, 2H), 1.47 (s, 9H).

Preparation of (R)-tert-butyl (6-(oxazol-5-yl)-1,3,4,5-tetrahydrobenzo[c]oxepin-1-yl)methylcarbamate (28-2) and (S)-tert-butyl (6-(oxazol-5-yl)-1,3,4,5-tetrahydrobenzo[c]oxepin-1-yl)methylcarbamate (28-3)

tert-butyl N-([6-(1,3-Oxazol-5-yl)-1,3,4,5-tetrahydro-2-benzoxepin-1-yl]methyl)carbamate (3.2 g, 9.29 mmol) was chiral separated using column: RRWHELK 20×250 mm, 10 um (Daicel) and Mobile phase: $CO_2$/IPA (0.2% Methanol Ammonia)=70/30 to get (R)-tert-butyl (6-(oxazol-5-yl)-1,3,4,5-tetrahydrobenzo[c]oxepin-1-yl)methylcarbamate (1.3 g) as a yellow oil. Chiral HPLC: column: (RR)-Whelk-O1 4.6×100 mm 5 um; Co-Solvent: IPA (0.1% DEA); $CO_2$ Flow Rate: 2.8: Co-Solvent Flow Rate: 1.2: Co-Solvent %: 30: Column Temperature: 40° C.; Ret Time=1.2 min: Enantiopurity: 99% ee: and (S)-tert-butyl (6-(oxazol-5-yl)-1,3,4,5-tetrahydrobenzo[c]oxepin-1-yl)methylcarbamate (1.3 g) as a yellow oil. Chiral: column: (R,R)-Whelk-O1 4.6×100 mm 5 um; Co-Solvent: IPA (0.1% DEA); $CO_2$ Flow Rate: 2.8: Co-Solvent Flow Rate: 1.2: Co-Solvent %: 30: Column Temperature: 40° C.; Ret Time=1.46 min: Enantiopurity: 96% ee.

Preparation of 1-[(R)-6-(1,3-oxazol-5-yl)-1,3,4,5-tetrahydro-2-benzoxepin-1-yl]methanamine (HCl salt) (Compound 178)

A solution of tert-Butyl N-{[(1R)-6-(1,3-oxazol-5-yl)-1,3,4,5-tetrahydro-2-benzoxepin-1-yl]methyl}carbamate (330 mg, 958 μmol) in 3 M HCl/MeOH (15 mL) was stirred at rt for 3 h. The mixture was concentrated in vacuo and the residue was added EA/MeOH (5/1) (8 mL). The resulting mixture was stirred at room temperature for 10 min then filtered. The solid was collected and dried in vacuo to provide 1-[(R)-6-(1,3-oxazol-5-yl)-1,3,4,5-tetrahydro-2-benzoxepin-1-yl]methanamine (HCl salt) (208 mg, 740 μmol) as a white solid. (Yield=78%). MS(ESI): m/z 245 [M+H]+. 1H NMR (400 MHz, $CD_3OD$): δ 8.86-8.81 (m, 1H), 7.53-7.51 (m, 2H), 7.40-7.32 (m, 2H), 5.07-5.04 (m, 1H), 4.35-4.30 (m, 1H), 4.03-3.97 (m, 1H), 3.59-3.45 (m, 2H), 3.30-3.24 (m, 1H), 3.09-3.04 (m, 1H), 1.92-1.88 (m, 2H). Chiral HPLC: column: AY-H 100×4.6 mm 5 um Co-Solvent: EtOH (1% Methanol Ammonia); $CO_2$ Flow Rate: 3.6: Co-Solvent Flow Rate: 0.4; Co-Solvent %: 10; Column Temperature: 40° C.: Ret Time=10.43 min; Enantiopurity: 100% ee.

Preparation of 1-[(1S)-6-(1,3-Oxazol-5-yl)-1,3,4,5-tetrahydro-2-benzoxepin-1-yl]methanamine (HCl salt) (Compound 179)

A solution of tert-Butyl N-{[(1S)-6-(1,3-oxazol-5-yl)-1,3,4,5-tetrahydro-2-benzoxepin-1-yl]methyl}carbamate (330 mg, 958 μmol) in 3 M HCL/MeOH (15 mL) was stirred at rt for 3 h. The mixture was concentrated in vacuo and the residue was added EA/MeOH (5/1) (8 mL). The resulting mixture was stirred at rt for 10 min then filtered. The solid was collected and dried in vacuo to provide 1-[(S)-6-(1,3-oxazol-5-yl)-1,3,4,5-tetrahydro-2-benzoxepin-1-yl]methanamine (201 mg, 715 μmol) as a white solid (yield: 75.0%). MS(ESI): m/z 245 [M+H]+. 1H NMR (400 MHz, $CD_3OD$): δ 8.81-8.62 (m, 1H), 7.52-7.31 (m, 4H), 5.06-5.04 (m, 1H), 4.35-4.30 (m, 1H), 4.03-3.97 (m, 1H), 3.59-3.45 (m, 2H), 3.30-3.24 (m, 1H), 3.09-3.04 (m, 1H), 1.92-1.87 (m, 2H). Chiral HPLC: column: AY-H 100×4.6 mm 5 um: Co-Solvent: EtOH (1% Methanol Ammonia); $CO_2$ Flow Rate: 3.6; Co-Solvent Flow Rate: 0.4; Co-Solvent %: 10; Column Temperature: 40° C.; Ret Time=8.14 min; Enantiopurity: 96% ee.

Scheme 29

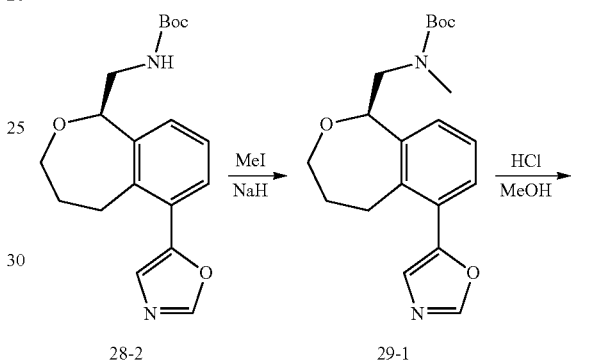

28-2    29-1

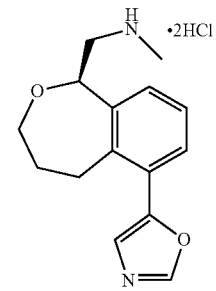

Compound 176

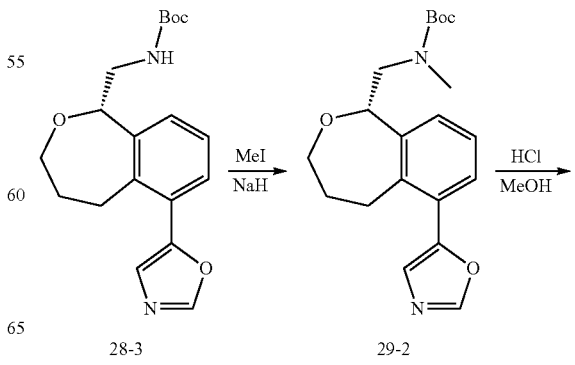

28-3    29-2

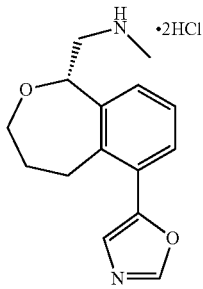

Compound 177

Preparation of tert-butyl N-methyl-N-{[(1R)-6-(1,3-oxazol-5-yl)-1,3,4,5-tetrahydro-2-benzoxepin-1-yl]methyl}carbamate (29-1)

To a solution of tert-butyl N-{[(1R)-6-(1,3-oxazol-5-yl)-1,3,4,5-tetrahydro-2-benzoxepin-1-yl]methyl}carbamate (900 mg, 2.61 mmol) in DMF (8 mL) was added sodium hydride (311 mg, 7.83 mmol) and iodomethane (1.84 g, 13.0 mmol). The reaction was stirred at ambient temperature for 2 h. Water (30 mL) was added to the reaction vessel slowly and the mixture was extracted with Et2O (3×20 mL). The combined organics were dried over anhydrous $Na_2SO_4$, filtered and concentrated in vacuo. The resulting oil was purified by flash column chromatography (P.E/EA=4/1) to provide tert-butyl N-methyl-N—{[(R)-6-(1,3-oxazol-5-yl)-1,3,4,5-tetrahydro-2-benzoxepin-1-yl]methyl}carbamate (750 mg, 2.09 mmol) as a yellow oil (Yield=80%). MS (ESI): m/z 259 [M−Boc]$^+$.

Preparation of tert-butyl N-methyl-N-{[(1S)-6-(1,3-oxazol-5-yl)-1,3,4,5-tetrahydro-2-benzoxepin-1-yl]methyl}carbamate (29-2)

To a solution of tert-butyl N—{[(S)-6-(1,3-oxazol-5-yl)-1,3,4,5-tetrahydro-2-benzoxepin-1-yl]methyl}carbamate (900 mg, 2.61 mmol) in DMF (8 mL) was added sodium hydride (311 mg, 7.83 mmol) and iodomethane (1.11 g, 7.83 mmol). The reaction was stirred at ambient temperature for 2 h. water (30 mL) was added to the reaction vessel slowly and the mixture was extracted with Et2O (3-20 mL). The combined organics were dried over anhydrous $Na_2SO_4$, filtered and concentrated in vacuo. The resulting oil was purified by flash column chromatography (P.E/EA=4/1) to provide tert-butyl N-methyl-N-{[(1S)-6-(1,3-oxazol-5-yl)-1,3,4,5-tetrahydro-2-benzoxepin-1-yl]methyl}carbamate (700 mg, 1.95 mmol) as a yellow oil (Yield: 75%). MS (ESI): m/z 259 [M−Boc]$^+$.

Preparation of methyl({[(1R)-6-(1,3-oxazol-5-yl)-1,3,4,5-tetrahydro-2-benzoxepin-1-yl]methyl})amine (HCl salt) (Compound 176)

A solution of tert-butyl N-methyl-N—{[(R)-6-(1,3-oxazol-5-yl)-1,3,4,5-tetrahydro-2-benzoxepin-1-yl]methyl}carbamate (750 mg, 2.09 mmol) in 3 M HCl/MeOH (30 mL) was stirred at room temperature for 2 h. Then the mixture was concentrated in vacuo. The residue was added EA (10 mL). The mixture was stirred at rt for 10 min then filtered. The solid was collected and dried in vacuo to provide methyl(([(1R)-6-(1,3-oxazol-5-yl)-1,3,4,5-tetrahydro-2-benzoxepin-1-yl]methyl)amine (HCl salt) (592 mg, 2.00 mmol) as a white solid (yield: 96.1%). MS(ESI): m/z 259 [M+H]$^+$. $^1$H NMR (400 MHz, $CD_3OD$): δ 8.54-8.51 (m, 1H), 7.52-7.50 (m, 1H), 7.39-7.30 (m, 3H), 5.15-5.12 (m, 1H), 4.34-4.29 (m, 1H), 4.03-3.96 (m, 1H), 3.64-3.59 (m, 2H), 3.31-3.25 (m, 1H), 3.10-3.03 (m, 1H), 2.86 (s, 3H), 1.90-1.87 (m, 2H). Chiral HPLC: column: AY-H 100×4.6 mm 5 um Co-Solvent: EtOH (1% Methanol Ammonia); $CO_2$ Flow Rate: 3.6: Co-Solvent Flow Rate: 0.4; Co-Solvent %: 10; Column Temperature: 40° C.; Ret Time=4.98 min; Enantiopurity: 99% ee.

Preparation of rel-methyl({[(1S)-6-(1,3-oxazol-5-yl)-1,3,4,5-tetrahydro-2-benzoxepin-1-yl]methyl}) amine (HCl salt) (Compound 177)

A solution of tert-butyl N-methyl-N—[(S)-6-(1,3-oxazol-5-yl)-1,3,4,5-tetrahydro-2-benzoxepin-1-yl]methylcarbamate (700 mg, 1.95 mmol) in 3 M HCl/MeOH (30 mL) was stirred at room temperature for 2 h. Then the mixture was concentrated in vacuo. The residue was added EA (10 mL). The mixture was stirred at rt for 10 min then filtered. The solid was collected and dried in vacuo to provide methyl ([(S)-6-(1,3-oxazol-5-yl)-1,3,4,5-tetrahydro-2-benzoxepin-1-yl]methyl)amine (HCl salt) (550 mg, 1.86 mmol) as a white solid (Yield=96%). MS(ESI): m/z 259 [M+H]$^+$. $^1$H NMR (400 MHz, $CD_3OD$): δ 8.58-8.56 (m, 1H), 7.52-7.32 (m, 4H), 5.15-5.13 (m, 1H), 4.34-4.31 (m, 1H), 4.01-3.99 (m, 1H), 3.66-3.62 (m, 2H), 3.30-3.27 (m, 1H), 3.09-2.87 (m, 4H), 1.90-1.89 (m, 2H). Chiral HPLC: column: AY-H 100×4.6 mm 5 um; Co-Solvent: EtOH (1% Methanol Ammonia); $CO_2$ Flow Rate: 3.6: Co-Solvent Flow Rate: 0.4; Co-Solvent %: 10; Column Temperature: 40.1° C.; Ret Time=3.48 min; Enantiopurity: 99% ee.

Scheme 30

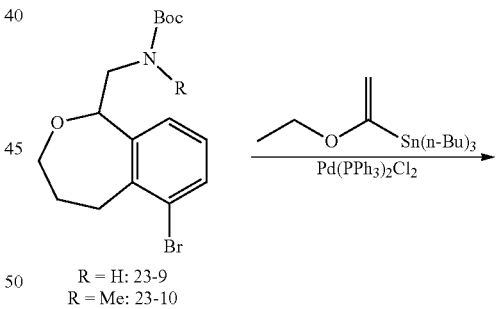

R = H: 23-9
R = Me: 23-10

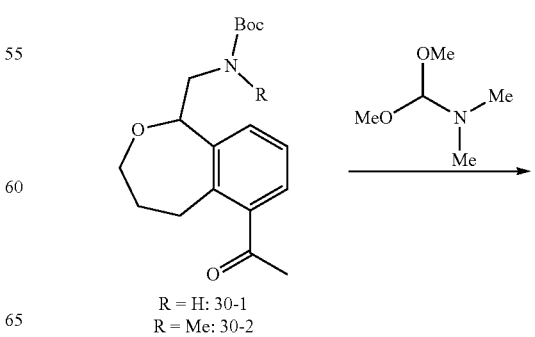

R = H: 30-1
R = Me: 30-2

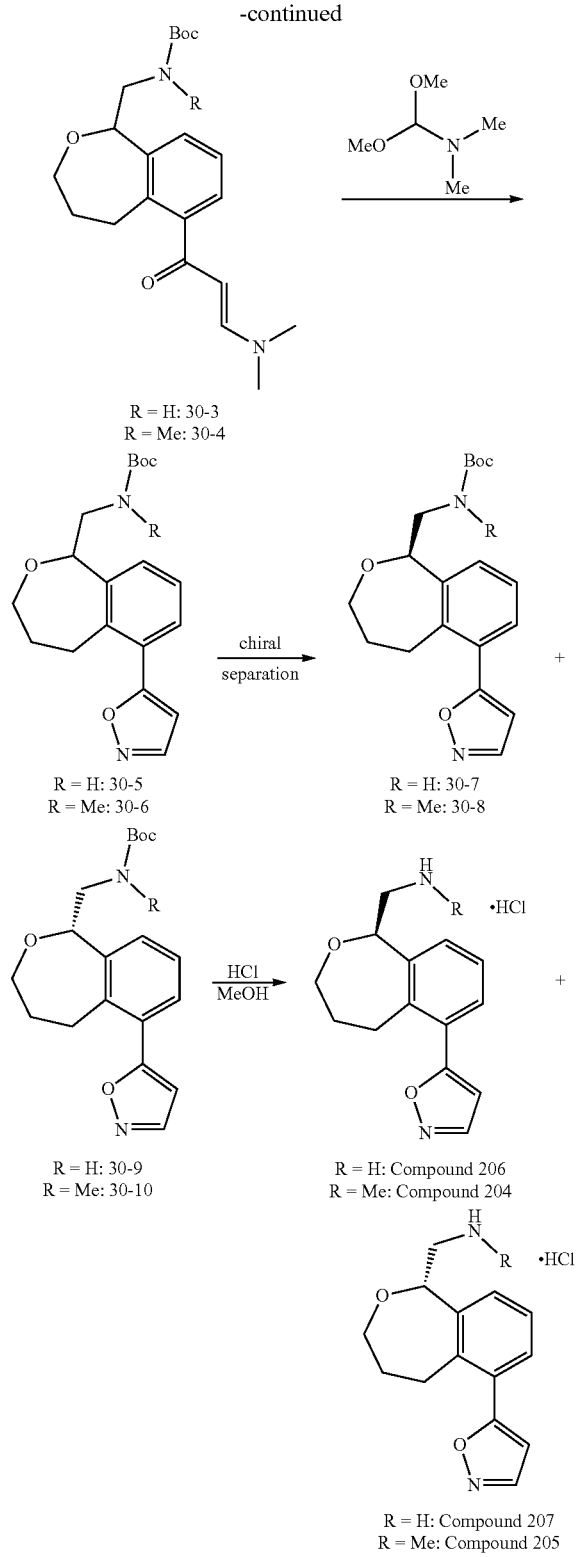

methoxyethenyl)stannane (9.10 g, 25.2 mmol) and Pd(PPh$_3$)$_2$ C$_{12}$ (2.35 g, 3.36 mmol) under N$_2$. The mixture was stirred at 90° C. for 4 h. Then the reaction mixture was cooled to rt, 1M HCl (aq) (50.0 mL, 50.0 mmol) was added. The mixture was stirred at room temperature for 1 h. Then NaHCO$_3$ (sat. aq) was added to adjust pH to 8. The mixture was extracted with EA (3×50 mL). The combined organics were dried over anhydrous Na$_2$SO$_4$, filtered and concentrated in vacuo. The resulting oil was purified by flash column chromatography (P.E/EA=4/1) to provide tert-butyl N-[(6-acetyl-1,3,4,5-tetrahydro-2-benzoxepin-1-yl)methyl] carbamate (1.80 g, 5.63 mmol) as a yellow oil (Yield=34%). MS(ESI): m/z 220 [M−Boc]$^+$.

Preparation of tert-butyl N-({6-[(2E)-3-(dimethylamino)prop-2-enoyl]-1,3,4,5-tetrahydro-2-benzoxepin-1-yl}methyl)carbamate (30-3)

A solution of tert-butyl N-[(6-acetyl-1,3,4,5-tetrahydro-2-benzoxepin-1-yl)methyl]carbamate (1.8 g, 5.63 mmol) in DMF-DMA (30 mL) was stirred at 110° C. for 24 h. The mixture was concentrated to dryness to provide crude tert-butyl N-({6-[(2E)-3-(dimethylamino)prop-2-enoyl]-1,3,4,5-tetrahydro-2-benzoxepin-1-yl}methyl)carbamate (2.5 g) as a brown oil. MS(ESI): m/z 375 [M+H]$^+$.

Preparation of tert-butyl N-{[6-(1,2-oxazol-5-yl)-1,3,4,5-tetrahydro-2-benzoxepin-1-yl] methyl}carbamate (30-5)

To a solution of crude tert-butyl N-({6-[(2E)-3-(dimethylamino)prop-2-enoyl]-1,3,4,5-tetrahydro-2-benzoxepin-1-yl}methyl)carbamate (2.5 g) in EtOH (30 mL) was added NH$_2$OH HCl (578 mg, 8.39 mmol). The reaction mixture was heated to 85° C. and stirred at that temperature for 2 h. After cooling, saturated aqueous NaHCO$_3$ (20 mL) was added to the reaction vessel and the resulting mixture was concentrated in vacuo to remove EtOH. The residue was extracted with DCM (3×20 mL). The combined organics were dried over anhydrous Na$_2$SO$_4$, filtered and concentrated in vacuo. The resulting oil was purified by flash column chromatography (P.E/EA=3/1) to provide tert-butyl N—{[6-(1,2-oxazol-5-yl)-1,3,4,5-tetrahydro-2-benzoxepin-1-yl]methyl}carbamate (1.40 g, 4.06 mmol) as a yellow oil (Yield=73%, 2 steps). MS(ESI): m/z 245 [M−Boc]$^+$. $^1$H NMR (400 MHz, CDCl$_3$): δ 8.33 (s, 1H), 7.40-7.38 (m, 1H), 7.28-7.25 (m, 2H), 6.32 (s, 1H), 5.07 (bs, 1H), 4.77-4.75 (m, 1H), 4.25-4.22 (m, 1H), 3.89-3.84 (m, 2H), 3.52-3.45 (m, 1H), 3.22-3.17 (m, 1H), 2.94-2.89 (m, 1H), 1.93-1.77 (m, 2H), 1.47 (s, 9H).

Preparation of (R)-tert-butyl (6-(isoxazol-5-yl)-1,3,4,5-tetrahydrobenzo[c]oxepin-1-yl)methylcarbamate (30-7) and (S)-tert-butyl (6-(isoxazol-5-yl)-1,3,4,5-tetrahydrobenzo[c]oxepin-1-yl)methylcarbamate (30-9)

Tert-butyl N-{[6-(1,2-oxazol-5-yl)-1,3,4,5-tetrahydro-2-benzoxepin-1-yl]methyl}carbamate (1.4 g, 4.06 mmol) was separated by chiral column: OD 20×250 mm, 10 urn (Daicel), mobile phase: CO$_2$/MEOH (0.2% Methanol Ammonia)= 80/20 to get (R)-tert-butyl (6-(isoxazol-5-yl)-1,3,4,5-tetrahydrobenzo[c]oxepin-1-yl)methylcarbamate (550 mg) as yellow oil. Chiral HPLC: column: EnantioPak OD 4.6× 100 mm 5 um Co-Solvent: MeOH (0.2% Methanol Ammonia): CO$_2$ Flow Rate: 3.6; Co-Solvent Flow Rate: 0.4; Co-Solvent %: 10: Column Temperature: 40° C.; Ret Preparation of N-[(6-acetyl-1,3,4,5-tetrahydro-2-benzoxepin-1-yl)methyl]carbamate (30-1)

To a solution of tert-butyl N-[(6-bromo-1,3,4,5-tetrahydro-2-benzoxepin-1-yl)methyl]carbamate (6.0 g, 16.8 mmol) in 1,4-dixone (70 mL) was added tributyl(1-

Time=1.51 min; Enantiopurity: 100% ee: and (S)-tert-butyl (6-(isoxazol-5-yl)-1,3,4,5-tetrahydrobenzo[c]oxepin-1-yl)methylcarbamate (550 mg) as a yellow oil. Chiral HPLC: column: EnantioPak OD 4.6–10 mm 5 um: Co-Solvent: MeOH (0.2% Methanol Ammonia); $CO_2$ Flow Rate: 3.6: Co-Solvent Flow Rate: 0.4; Co-Solvent %: 10; Column Temperature: 40.1° C.; Ret Time=2.38 min; Enantiopurity: 98% ee.

Preparation of 1-[(1R)-6-(1,2-oxazol-5-yl)-1,3,4,5-tetrahydro-2-benzoxepin-1-yl]methanamine (HCl salt) (Compound 206)

A solution of (R)-tert-butyl (6-(isoxazol-5-yl)-1,3,4,5-tetrahydrobenzo[c]oxepin-1-yl)methylcarbamate (550 mg, 1.59 mmol) in 3 M HCl/MeOH (30 mL) was stirred at room temperature for 2 h. The mixture was concentrated in vacuo. EA (8 mL) was added to the residue and the mixture was stirred at room temperature for 10 min. The mixture was filtered. The solid was collected and dried in vacuo to provide 1-[(1R)-6-(1,2-oxazol-5-yl)-1,3,4,5-tetrahydro-2-benzoxepin-1-yl]methanamine (HCl salt) (368 mg, 1.31 mmol) as a white solid (Yield=82%). MS(ESI): m z 245 [M+H]$^+$. $^1$H NMR (CD$_3$OD, 400 MHz): δ 8.50 (d, J=2.0 Hz, 1H), 7.50-7.48 (m, 1H), 7.40-7.33 (m, 2H), 6.56 (d, J=1.6 Hz, 1H), 5.05-5.02 (m, 1H), 4.35-4.30 (m, 1H), 4.02-3.95 (m, 1H), 3.59-3.55 (m, 1H), 3.52-3.46 (m, 1H), 3.26-3.20 (m, 1H), 3.06-2.99 (m, 1H), 1.92-1.86 (m, 2H). Chiral HPLC: column: AY-H 100×4.6 mm 5 um: Co-Solvent: EtOH (1% Methanol Ammonia): $CO_2$ Flow Rate: 3.2; Co-Solvent Flow Rate: 0.8; Co-Solvent %: 20; Column Temperature: 40° C.: Ret Time=4.4 min; Enantiopurity: 100% ee.

Preparation of 1-[(1S)-6-(1,2-oxazol-5-yl)-1,3,4,5-tetrahydro-2-benzoxepin-1-yl]methanamine (HCl salt) (Compound 207)

A solution of(S)-tert-butyl (6-(isoxazol-5-yl)-1,3,4,5-tetrahydrobenzo[c]oxepin-1-yl)methylcarbamate (550 mg, 1.59 mmol) in 3 M HCl/MeOH (30 mL) was stirred at rt for 2 h. The mixture was concentrated in vacuo. EA (8 mL) was added to the residue and the mixture was stirred at room temperature for 10 min. The mixture was filtered. The solid was collected and dried in vacuo to provide 1-[(1S)-6-(1,2-oxazol-5-yl)-1,3,4,5-tetrahydro-2-benzoxepin-1-yl]methanamine (HCl salt) (283 mg, 1.00 mmol) as a white solid (Yield=63%). MS(ESI): m/z 245 [M+H]$^+$. $^1$H NMR (CD$_3$OD, 400 MHz): δ 8.50 (d, J=2.0 Hz, 1H), 7.51-7.48 (m, 1H), 7.40-7.33 (m, 2H), 6.56 (d, J=1.6 Hz, 1H), 5.05-5.02 (m, 1H), 4.35-4.30 (m, 1H), 4.02-3.95 (m, 1H), 3.59-3.55 (m, 1H), 3.52-3.46 (m, 1H), 3.26-3.20 (m, 1H), 3.06-2.99 (m, 1H), 1.92-1.86 (m, 2H). Chiral HPLC: column: AY-H 100×4.6 mm 5 um: Co-Solvent: EtOH (1% Methanol Ammonia): $CO_2$ Flow Rate: 3.2; Co-Solvent Flow Rate: 0.8; Co-Solvent %: 20: Column Temperature: 40° C.; Ret Time=2.66 min: Enantiopurity: 100% ee.

Preparation of tert-butyl (6-acetyl-1,3,4,5-tetrahydrobenzo[c]oxepin-1-yl)methyl(methyl)carbamate (30-2)

To a solution of tert-butyl N-[(6-bromo-1,3,4,5-tetrahydro-2-benzoxepin-1-yl)methyl]-N-methylcarbamate (4.1 g, 11.1 mmol) in 1,4-dioxane (50 mL) was added tributyl (1-ethoxyethenyl)stannane (6.05 g. 16.7 mmol) and Pd(PPh$_3$)$_2$Cl$_2$ (1.56 g, 2.22 mmol) under N$_2$. The mixture was stirred at 90° C. for 4 h. Then the reaction mixture was cooled to rt, 1M HCl (aq) (33.3 mL, 33.3 mmol) was added. The mixture was stirred at room temperature for 1 h. Then NaHCO$_3$ (sat. aq) was added to adjust pH to 8. The mixture was extracted with EA (3×40 mL). The combined organics were dried over anhydrous Na$_2$SO$_4$, filtered and concentrated in vacuo. The resulting oil was purified by flash column chromatography (PE/EA=4/1) to provide tert-butyl (6-acetyl-1,3,4,5-tetrahydrobenzo[c]oxepin-1-yl)methyl (methyl)carbamate (2.2 g, 6.61 mmol) as a yellow oil (yield: 59.4%). MS(ESI): m/z 234 [M−Boc]$^+$.

Preparation of N-({6-[(2E)-3-(dimethylamino)prop-2-enoyl]-1,3,4,5-tetrahydro-2-benzoxepin-1-yl}methyl)-N-methylcarbamate (30-4)

A solution of tert-butyl (6-acetyl-1,3,4,5-tetrahydrobenzo [c]oxepin-1-yl)methyl(methyl)carbamate (1.97 g, 5.92 mmol) in DMF-DMA (20 mL) was stirred at 110° C. for 24 h. The mixture was concentrated to dryness to provide crude tert-butyl N-({6-[(2E)-3-(dimethylamino)prop-2-enoyl]-1,3,4,5-tetrahydro-2-benzoxepin-1-yl}methyl)-N-methylcarbamate (2.5 g) as a brown oil. MS(ESI): m/z 389 [M+H]$^+$.

Preparation of tert-butyl N-methyl-N-{[6-(1,2-oxazol-5-yl)-1,3,4,5-tetrahydro-2-benzoxepin-1-yl] methyl}carbamate (30-6)

To a solution of crude tert-butyl N-({6-[(2E)-3-(dimethylamino)prop-2-enoyl]-1,3,4,5-tetrahydro-2-benzoxepin-1-yl}methyl)-N-methylcarbamate (2.5 g) in EtOH (30 mL) was added NH$_2$OH HCl (612 mg, 8.87 mmol). The reaction mixture was heated to 85° C. and stirred at that temperature for 2 h. Then the mixture was cooled to rt, saturated aqueous NaHCO$_3$ (15 mL) was added to the reaction vessel and the resulting mixture was concentrated in vacuo. The residue was extracted with DCM (3×15 mL). The combined organics were dried over anhydrous Na$_2$SO$_4$, filtered and concentrated in vacuo. The resulting oil was purified by flash column chromatography (PE/EA=4/1) to provide tert-butyl N-methyl-N-{[6-(1,2-oxazol-5-yl)-1,3,4,5-tetrahydro-2-benzoxepin-1-yl]methyl}carbamate (1.80 g. 5.02 mmol) as a yellow oil (Yield=85%). MS(ESI): m/z 259 [M−Boc]$^+$.

Preparation of (R)-tert-butyl (6-(isoxazol-5-yl)-1,3,4,5-tetrahydrobenzo[c]oxepin-1-yl)methyl(methyl) carbamate (30-8) and (S)-tert-butyl (6-(isoxazol-5-yl)-1,3,4,5-tetrahydrobenzo[c]oxepin-1-yl)methyl (methyl)carbamate (30-10)

Tert-butyl N-methyl-N-{[6-(1,2-oxazol-5-yl)-1,3,4,5-tetrahydro-2-benzoxepin-1-yl]methyl}carbamate (1.8 g, 5.02 mmol) was separated by chiral column: OD 20×250 mm, 10 um (Daicel), mobile phase: CO$_2$/MEOH (0.2% Methanol Ammonia)=80/20 to provide (R)-tert-butyl (6-(isoxazol-5-yl)-1,3,4,5-tetrahydrobenzo[c]oxepin-1-yl)methyl(methyl) carbamate (700 mg) as a yellow oil. Chiral HPLC: column: EnantioPak OD 4.6×100 mm 5 um; Co-Solvent: MeOH (0.2% Methanol Ammonia); CO$_2$ Flow Rate: 3.6; Co-Solvent Flow Rate: 0.4: Co-Solvent %: 10; Column Temperature: 39.9° C.: Ret Time=1.12 min: Enantiopurity: 99% ee; and (S)-tert-butyl (6-(isoxazol-5-yl)-1,3,4,5-tetrahydrobenzo[c]oxepin-1-yl)methyl(methyl)carbamate (700 mg) as a yellow oil. Chiral HPLC: column: EnantioPak OD 4.6×100 mm 5 um; Co-Solvent: MeOH (0.2% Methanol Ammonia): CO$_2$ Flow Rate: 3.6; Co-Solvent Flow Rate: 0.4;

Co-Solvent %: 10: Column Temperature: 40° C.; Ret Time=1.63 min: Enantiopurity: 99% ee.

Preparation of methyl({[(1R)-6-(1,2-oxazol-5-yl)-1,3,4,5-tetrahydro-2-benzoxepin-1-yl]methyl})amine (HCl salt) (Compound 200)

A solution of (R)-tert-butyl (6-(isoxazol-5-yl)-1,3,4,5-tetrahydrobenzo[c]oxepin-1-yl)methyl(methyl)carbamate (700 mg, 1.95 mmol) in 3 M HCl/MeOH (30 mL) was stirred at room temperature for 2 h. Then the mixture was concentrated in vacuo. The residue was added EA (10 mL). The mixture was stirred at room temperature for 10 min then filtered. The solid was collected and dried in vacuo to provide methyl({[(R)-6-(1,2-oxazol-5-yl)-1,3,45-tetrahydro-2-benzoxepin-1-yl]methyl})amine (HCl salt) (443 mg, 1.50 mmol) as a white solid (Yield=77%). MS(ESI): m/z 259 [M+H]$^+$. $^1$H NMR (400 MHz, CD$_3$OD): δ 6.50 (d, J=1.6 Hz, 1H), 7.50-7.48 (m, 1H), 7.40-7.34 (m, 2H), 6.56 (d, J=2.0 Hz, 1H), 5.16-5.13 (m, 1H), 4.34-4.29 (m, 1H), 4.03-3.96 (m, 1H), 3.68-3.60 (m, 2H), 3.26-3.20 (m, 1H), 3.07-3.00 (m 1H), 2.87 (s, 3H), 1.92-1.86 (m, 2H). Chiral HPLC: column: OD-H (4.6×100×5 um); Co-Solvent: MeOH (0.2% Methanol Ammonia); CO$_2$ Flow Rate: 3.4; Co-Solvent Flow Rate: 0.6; Co-Solvent %: 15; Column Temperature: 40.3° C.; Ret Time=1.81 min; Enantiopurity: 97% ee.

Preparation of methyl({[(1S)-6-(1,2-oxazol-5-yl)-1,3,4,5-tetrahydro-2-benzoxepin-1-yl]methyl})amine (HCl salt) (Compound 201)

A solution of (S)-tert-butyl (6-(isoxazol-5-yl)-1,3,4,5-tetrahydrobenzo[c]oxepin-1-yl)methyl(methyl)carbamate (700 mg, 1.95 mmol) in 3 M HCl/MeOH (30 mL) was stirred at room temperature for 2 h. Then the mixture was concentrated in vacuo. The residue was added EA (10 mL). The mixture was stirred at room temperature for 10 min then filtered. The solid was collected and dried in vacuo to provide methyl({[(S)-6-(1,2-oxazol-5-yl)-1,3,4,5-tetrahydro-2-benzoxepin-1-yl]methyl})amine (HCl salt) (400 mg, 1.35 mmol) as a white solid. MS(ESI): m/z 259 [M+H]$^+$. $^1$H NMR (400 MHz, CD$_3$OD): δ 6.50 (d, J=1.6 Hz, 1H), 7.50-7.48 (m, 1H), 7.40-7.34 (m, 2H), 6.56 (d, J=2.0 Hz, 1H), 5.16-5.13 (m, 1H), 4.34-4.29 (m, 1H), 4.03-3.96 (m, 1H), 3.68-3.60 (m, 2H), 3.26-3.20 (m, 1H), 3.07-3.00 (m, 1H), 2.87 (s, 3H), 1.92-1.86 (m, 2H). Chiral HPLC: column: OD-H (4.6×100×5 um); Co-Solvent: MeOH (0.2% Methanol Ammonia): CO$_2$ Flow Rate: 3.4; Co-Solvent Flow Rate: 0.6: Co-Solvent %: 15; Column Temperature: 37° C.: Ret Time=3.56 min; Enantiopurity: 99% ee.

Compounds 132-147 may be prepared using the procedure described in Scheme 12, substituting the appropriate arylboronic acid for pyridine-3-boronic acid. Compounds 152-155, 160-163, 172-175 may be prepared using the procedure described in Scheme 23, substituting an appropriate heteroaryl bromide for 2-bromopyridine. Compounds 190-193 may be prepared using the procedure shown in Scheme 26, substituting 1,3,4-triazole for pyrazole. Compounds 194 and 195 may be prepared using the procedure described in Scheme 7, substituting pyridine-4-boronic acid for pyridine-3-boronic acid, and substituting N,N-dimethyl-2,2-dimethoxyethanamine for 2,2-dimethoxyethanamine.

Biological Assays

Mouse Maximum Electroshock Assay (MES)

Mouse Maximum Electroshock Assay (MES) is a model for generalized tonic-clonic seizures and provides an indication of a compound's ability to prevent seizure spread when all neuronal circuits in the brain are maximally active. These seizures are highly reproducible and are electrophysiologically consistent with human seizures. For all MES tests, 60 Hz of alternating current (50 mA in mice and 150 mA in rats) was delivered for 0.2 sec by corneal electrodes which had been primed with an electrolyte solution containing an anesthetic agent (0.5% tetracaine HCl). An animal was considered "protected" from MES-induced seizures upon abolition of the hindlimb tonic extensor component of the seizure. Initial screen for anticonvulsant activity in the MES was performed with N=4 male CF-1 mice/dose/time point. The default doses and time-points were 3 and 30 mg/kg at 0.25 and 0.5 hr following administration. Quantification of the ED$_{50}$ was conducted at the time of peak effect (TPE). To determine the TPE, groups of N=4 mice were treated with the investigational compound at 0.25, 0.5, 1.0, 2.0 and 4.0 hrs prior to MES testing, or based on time-points from prior studies. For quantification of the ED$_{50}$, groups of N=8 mice were tested with various doses of the investigational compound until at least two points can be clearly established between the limits of 100% protection or toxicity and 0% protection (i.e. at least 4 test doses). The data for each condition was presented as N/F, where N=number of animals protected and F=number of animals tested. The ED50, 95% confidence interval, the slope of the regression line, and the S.E.M. of the slope were calculated by Probit analysis. Testing in rats were initially with N=4 male Sprague-Dawley rats/dose/time point. Default dose and time points were 30 mg/kg and 0.25, 0.5, 1.0, 2.0 and 4.0 hrs. Quantitation of the ED50 was conducted the same as described for mice above.

| Number of animals protected | BIN |
|---|---|
| 4/4 | A |
| 3/4 | B |
| 2/4 | C |
| 1/4 | D |
| 0/4 | E |

| Compound No. | Seizure protection at 3 mg/kg | Seizure protection at 30 mg/kg |
|---|---|---|
| 8 | B | B |
| 12 | D | C |
| 16 | D | B |
| 17 | B | A |
| 18 | D | B |
| 19 | B | B |
| 34 | B | A |
| 36 | C | C |
| 38 | B | A |
| 39 | E | C |
| 40 | C | C |
| 44 | E | A |
| 47 | E | B |
| 67 | E | A |
| 69 | B | A |
| 71 | B | C |
| 73 | E | B |
| 77 | C | C |
| 81 | D | 3/3 animals tested |
| 85 | D | C |
| 89 | E | C |
| 91 | D | A |
| 95 | C | A |
| 96 | B | 2/2 animals tested |
| 103 | E | D |
| 119 | D | C |
| 121 | B | A |

-continued

| Compound No. | Seizure protection at 3 mg/kg | Seizure protection at 30 mg/kg |
|---|---|---|
| 123 | E | B |
| 131 | D | A |
| 149 | C | A |
| 168 | D | A |

6 Hz Psychomotor Seizure Model of Partial Epilepsy

The 6 Hz 44 mA psychomotor seizure model of partial epilepsy is described in M.E. Barton et al., Epilepsy Research, 47, (2001), pp 217-227, and provides a murine behavioral screening assay for therapy-resistant limbic seizures. In the 6 Hz model, compounds provided herein were screened for their ability to block psychomotor seizures induced by a low-frequency (6 Hz), long-duration (3 sec) stimulus delivered through corneal electrodes. These seizures are believed to model partial seizures observed in humans. The 6 Hz test employed an identical approach to that described for the MES test. Mice were challenged with a 44 mA current (2 times the CC97: convulsant current in 97% of mice tested) for 3 sec delivered through corneal electrodes to elicit a psychomotor seizure. Typically, the seizure was characterized by an initial momentary stun followed immediately by jaw clonus, forelimb clonus, twitching of the vibrissae, and Straub tail lasting for at least 1 second. Animals not displaying these behaviors were considered "protected". An initial qualitative screen for anticonvulsant activity in the 6 Hz 44 mA seizure model was performed with N=4 male CF-1 mice/dose/time point. The default doses and time points were 30, 100 and 300 mg/kg at 0.5 and 2 hour following administration. Doses and/or time points were adjusted if supported by other test data. Quantification of the ED50 was conducted at the time of peak effect (TPE). To determine the TPE, mice were treated with the investigational compound at 0.25, 0.5, 1.0, 2.0 and 4.0 hours prior to electrical stimulation, or based on time-points from prior studies. Groups of N=8 mice were tested with various doses of the investigational compound until at least two points can be clearly established between the limits of 100% protection or toxicity and 0% protection (i.e. at least 4 test doses). The data for each condition were presented as N/F, where N=number of animals protected and F=number of animals tested. The ED50, 95% confidence interval, the slope of the regression line, and the S.E.M. of the slope were calculated by Probit analysis. The data obtained from this model were consistent with MES in identifying anti-epilepsy properties of compounds provided herein.

Mesiotemporal Lobe Epilepsy (MTLE) Mouse Model

The MTLE mouse model recapitulates many of the characteristics observed in human patients with temporal lobe epilepsy (TLE) and is described in Duveau, V., et al, CNS Neuroscience & Therapeutics 2016, 22, 497-506. The MTLE mouse is characterized by an initial neurotoxic event, a unilateral intrahippocampal injection of kainic acid (KA) into the dorsal hippocampus, which induces non-convulsive status epilepticus lasting several hours. This initial event is followed by a latent phase. Four weeks after KA injection, spontaneous recurrent hippocampal paroxysmal discharges (HPD) are only recorded in the epileptic hippocampus and remain stable and stereotyped for the whole life of the animal. These HPDs occur spontaneously about 30-60 times per hour when the animals are in a state of quiet wakefulness, generally last 15-20 sec and are associated with behavioral arrest and/or mild motor automatisms.

Adult, male C57/B16 mice were stereotaxically injected with kainate (1 nmol in 50 nL) and implanted with 1 bipolar electrode in the right hippocampus, and then allowed to recover for four weeks prior to investigational compound evaluation in the screening protocol. Using a group size of 15 MTLE mice per dose of investigational compound, the compound dose-response curves were typically evaluated over a two week period using a Latin square dosing protocol. Animals were used as their own controls. Digital EEG recordings were performed on freely moving animals for 60 180 minutes pre-compound injection (reference period). A mock injection (vehicle) was administered and the EEG was recorded for 120 minutes. Following this observational period, all animals received either vehicle or test article administration, and the EEG was recorded for 4 hours post-injection. Any accompanying effect on animal behavior was noted. EEG data were presented and analyzed as the raw number and duration of hippocampal paroxysmal discharges (HPDs) during the entire 6 hour period for each MTLE mouse. Data analysis included the number and duration of HPDs and was presented in 15-minute bins.

Neuropharmacological Assay (SmartCube™)

In order to demonstrate the utility of the provided compounds to treat neurological and psychiatric diseases and disorders, exemplary compounds were evaluated using the neuropharmacological screen described in S. L. Roberds et al., Front. Neurosci. 2011 Sep. 9; 5:103 (doi: 10.3389/fnins.2011.00103) ("Roberds"). As reported in Roberds, because psychiatric diseases generally result from disorders of cell-cell communication or circuitry, intact systems are useful in detecting improvement in disease-relevant endpoints. These endpoints are typically behavioral in nature, often requiring human observation and interpretation. To facilitate testing of multiple compounds for behavioral effects relevant to psychiatric disease, PsychoGenics. Inc. (Tarrytown, N.Y., "PGI") developed SmartCube™, an automated system in which behaviors of compound-treated mice are captured by digital video and analyzed with computer algorithms. (D. Brunner et al., Drug Discov. Today 2002, 7:S107-S112). PGI Analytical Systems uses data from SmartCube™ to compare the behavioral signature of a test compound to a database of behavioral signatures obtained using a large set of diverse reference compounds. (The composition of the database as well as validation of the method is further described in Roberds). In this way, the neuropharmacological effects of a test compound can be predicted by similarity to major classes of compounds, such as antipsychotics, anxiolytics and antidepressants.

The SmartCube™ system produces an activity signature indicating the probability that the activity of the test compound at the administered dose matches a given class of neuropharmacological agents. (See. e.g., Roberds, FIGS. 2 and 3). The test compound is simultaneously compared against multiple classes of agents: thus, a separate probability is generated for each behavioral effect measured (e.g., anxiolytic activity, analgesic activity, etc.). In the table below, these probabilities are reported for each behavioral effect measured as follows:

| LOQ≤ | + | <5% |
|---|---|---|
| 5%≤ | ++ | <25% |
| 25%≤ | +++ | <50% |
| 50%≤ | ++++ | | where LOQ is the limit of quantification.

Provided compounds were dissolved in a mixture of Pharmasolve™ (N-methyl-2-pyrrolidone), polyethylene glycol and propylene glycol, and were injected i.p. 15 min. before the behavioral test. For each compound, injections were administered at 3 different doses. For each behavioral effect measured, results for the most efficacious dose(s) are presented. In the table below, DP: anti-depressant: AX: anxiolytic: SD: sedative hypnotic; PS: anti-psychotic; MS: mood stabilizer; AD: ADHD; CE: cognitive enhancer; AG: analgesic; UN: uncharacterized CNS activity.

The potency of many of the compounds in the table was also determined in the SmartCube™ system. Test compounds were routinely examined at dose levels of 0.3, 1, 3 10 and 30 mg per kg (mpk), although the dose range was increased or decreased if necessary to obtain a full dose response curve. A compound's minimal effective dose (MED) is a measure of the compounds potency. The MED was defined as the dose (in mpk) having 50% or more total activity in SmartCube. The potencies of the compounds are shown in the table below, with potency values in mpk binned in the following manner:

| MED mpk range | BIN |
|---|---|
| ≤3 mpk | A |
| >3 to 10 mpk | B |
| >10 to ≤30 mpk | C |
| >30 mpk | D |

| Compound No. | DP | AX | SD | PS | MS | AD | CE | AG | UN | MED |
|---|---|---|---|---|---|---|---|---|---|---|
| 1 | ++ | ++ | + | ++ | + | + | ++ | + | ++ | C |
| 2 | + | + | + | + | + | + | + | + | + | D |
| 3 | ++ | ++ | + | ++ | ++ | + | ++ | ++ | ++ | B |
| 4 | ++ | ++ | + | +++ | + | + | + | + | ++ | B |
| 5 | ++++ | ++ | + | ++ | + | + | + | ++ | + | B |
| 6 | +++ | ++ | + | ++ | + | + | ++ | ++ | + | C |
| 7 | +++ | ++ | + | + | + | ++ | + | + | + | C |
| 8 | ++++ | ++ | + | + | + | + | ++ | + | + | A |
| 9 | ++ | ++ | + | ++ | + | + | + | ++ | + | C |
| 10 | ++ | + | + | + | + | + | + | +++ | + | C |
| 11 | ++++ | + | + | + | + | + | + | ++ | + | C |
| 12 | ++++ | + | ++ | ++ | + | + | + | + | + | C |
| 13 | ++++ | + | +++ | ++ | + | + | ++ | ++ | + | B |
| 14 | ++++ | ++ | + | + | + | + | + | ++ | ++ | B |
| 15 | +++ | ++ | + | ++ | ++ | ++ | + | ++ | + | C |
| 16 | ++++ | ++ | + | + | + | + | ++ | + | + | A |
| 17 | ++++ | + | ++ | + | + | ++ | + | + | ++ | A |
| 18 | ++++ | + | + | + | + | + | + | + | + | C |
| 19 | ++ | ++ | + | + | + | + | ++ | ++ | + | D |
| 20 | ++++ | ++ | + | + | + | ++ | + | ++ | ++++ | A |
| 21 | ++ | ++ | + | + | + | + | ++ | ++ | + | C |
| 22 | ++ | ++ | + | + | + | + | ++ | ++ | +++ | C |
| 23 | ++++ | ++ | + | + | + | ++ | + | ++ | + | C |
| 24 | + | ++ | + | + | + | + | + | + | ++ | D |
| 25 | ++ | ++ | ++ | ++ | ++ | + | +++ | ++ | + | C |
| 26 | + | + | + | + | + | + | + | + | + | D |
| 27 | ++ | ++ | + | ++ | + | + | + | + | + | D |
| 28 | +++ | ++ | + | ++ | + | ++ | ++ | ++ | ++ | B |
| 29 | + | + | + | + | + | + | + | + | + | D |
| 30 | ++++ | ++ | + | + | + | ++ | ++ | ++ | + | B |
| 31 | ++ | ++ | + | + | + | + | + | + | + | D |
| 32 | + | + | + | + | + | + | + | + | + | D |
| 33 | ++++ | ++ | + | + | + | + | + | + | + | C |
| 34 | ++++ | ++ | + | + | ++ | + | + | + | + | A |
| 35 | ++++ | ++ | + | + | + | ++ | + | + | + | B |
| 36 | ++++ | + | + | + | + | ++ | ++ | + | + | A |
| 37 | +++ | ++ | + | + | + | ++ | + | ++ | + | C |
| 38 | ++++ | +++ | ++ | + | + | ++ | + | ++ | ++ | A |
| 39 | ++++ | ++ | ++ | + | + | ++ | + | + | + | A |
| 40 | ++++ | ++ | + | + | + | ++ | ++ | ++++ | + | A |
| 41 | ++ | ++ | ++ | + | + | + | ++ | + | ++++ | C |
| 42 | ++ | ++ | + | + | + | + | ++ | +++ | ++ | C |
| 43 | ++ | ++ | + | + | + | + | + | + | +++ | C |
| 44 | ++++ | ++ | + | + | + | + | + | ++ | + | A |
| 45 | ++ | ++ | + | + | + | + | + | ++ | +++ | C |
| 46 | ++ | ++ | + | + | + | + | + | + | ++++ | C |
| 47 | ++++ | ++ | + | ++ | + | + | + | + | + | B |
| 48 | + | ++ | +++ | ++ | + | + | ++ | + | +++ | B |
| 49 | ++ | ++ | + | ++ | + | + | ++ | ++ | ++++ | A |
| 50 | ++ | ++ | + | + | + | + | ++ | + | ++++ | B |
| 51 | ++++ | + | ++ | ++ | + | + | + | + | + | B |
| 52 | ++++ | + | + | + | + | + | + | + | ++ | B |
| 53 | ++++ | ++ | + | + | + | ++ | + | + | + | B |
| 54 | ++++ | + | + | + | + | + | ++ | + | + | B |
| 55 | +++ | ++ | + | + | + | + | ++ | ++ | + | C |
| 56 | ++++ | ++ | + | + | + | ++ | + | + | + | B |
| 57 | ++ | + | ++ | ++ | + | + | ++ | + | +++ | C |
| 58 | + | ++ | + | + | + | + | + | + | ++++ | C |

-continued

| Compound No. | DP | AX | SD | PS | MS | AD | CE | AG | UN | MED |
|---|---|---|---|---|---|---|---|---|---|---|
| 59 | ++++ | ++ | +++ | + | + | ++ | + | ++ | ++ | A |
| 60 | ++++ | ++ | + | + | + | + | + | ++ | + | B |
| 61 | ++ | ++ | + | + | + | + | + | + | ++++ | C |
| 62 | ++ | ++ | + | + | + | + | + | + | + | D |
| 63 | ++++ | ++ | + | + | + | ++ | + | + | + | B |
| 64 | ++++ | + | + | + | + | + | + | + | ++ | B |
| 65 | ++++ | + | ++ | ++ | + | ++ | ++ | + | ++ | B |
| 66 | ++ | ++ | + | + | + | + | + | + | + | C |
| 67 | ++++ | + | + | + | + | + | + | + | ++ | A |
| 68 | ++++ | ++ | + | + | + | ++ | + | + | ++ | B |
| 69 | ++++ | ++ | ++ | + | + | + | + | + | + | A |
| 70 | ++++ | ++ | + | + | + | ++ | + | + | +++ | B |
| 71 | ++ | ++ | ++ | + | + | +++ | + | + | ++++ | A |
| 72 | + | + | + | + | + | + | + | + | + | D |
| 73 | ++++ | ++ | + | + | + | + | + | + | + | B |
| 74 | ++ | + | + | + | + | + | + | + | + | D |
| 75 | ++++ | ++ | + | + | + | + | + | + | ++ | B |
| 76 | + | ++ | + | + | + | + | + | ++ | + | B |
| 77 | ++++ | ++ | + | + | + | + | + | + | + | A |
| 78 | + | ++ | + | + | + | + | + | + | + | B |
| 79 | ++ | + | + | + | + | + | + | + | + | B |
| 80 | + | ++ | + | + | + | + | + | + | + | B |
| 81 | ++++ | ++ | + | + | + | ++ | + | + | +++ | A |
| 82 | + | ++ | + | + | + | + | + | + | + | C |
| 83 | ++++ | ++ | + | + | + | ++ | + | + | + | B |
| 84 | ++ | ++ | + | + | + | ++ | ++ | + | ++ | B |
| 85 | ++++ | ++ | + | + | + | ++ | + | + | ++ | A |
| 86 | ++ | ++ | + | ++ | + | + | ++ | + | +++ | B |
| 87 | ++++ | ++++ | + | + | + | ++ | + | + | + | A |
| 88 | ++ | ++ | + | + | + | + | + | + | + | C |
| 89 | ++++ | +++ | + | ++ | + | + | + | ++ | ++ | A |
| 90 | + | ++ | + | + | + | + | + | + | + | C |
| 91 | ++++ | ++ | ++ | + | + | ++++ | + | + | +++ | A |
| 92 | ++ | ++ | ++ | + | + | ++ | + | + | +++ | A |
| 93 | + | + | + | + | + | + | + | + | + | C |
| 94 | + | + | + | + | + | + | + | + | + | C |
| 95 | ++++ | ++ | ++ | + | + | ++++ | + | + | ++ | A |
| 96 | ++++ | +++ | ++++ | + | + | ++ | + | + | + | A |
| 97 | ++ | ++ | ++++ | ++ | + | + | + | ++ | ++ | A |
| 98 | ++++ | ++ | + | + | + | ++ | + | + | + | A |
| 99 | + | ++ | ++ | + | + | + | ++ | ++ | +++ | A |
| 100 | + | ++ | + | + | + | + | + | + | ++++ | B |
| 101 | ++ | ++ | + | + | + | ++ | + | + | ++ | B |
| 102 | + | ++ | + | + | + | + | + | + | + | C |
| 103 | ++++ | ++ | + | + | + | ++ | + | + | + | A |
| 104 | ++ | ++ | + | + | + | + | + | + | + | D |
| 105 | ++++ | + | + | + | + | + | + | + | ++ | B |
| 106 | ++ | +++ | + | + | + | + | ++ | + | + | C |
| 107 | +++ | + | + | + | + | + | + | + | + | C |
| 108 | ++ | ++ | ++ | ++ | + | + | + | ++ | +++ | C |
| 109 | ++ | ++ | + | + | + | + | + | + | + | D |
| 110 | + | ++ | + | + | + | + | + | + | + | C |
| 111 | + | ++ | + | + | + | + | + | + | + | C |
| 112 | ++ | ++ | + | + | + | + | + | + | + | C |
| 113 | ++ | ++ | + | +++ | + | + | + | ++ | +++ | B |
| 114 | + | ++ | + | + | + | + | + | + | + | C |
| 115 | + | ++ | + | + | + | + | + | + | + | C |
| 116 | ++++ | ++ | + | ++ | + | + | + | + | ++ | B |
| 117 | ++ | ++ | ++ | ++ | + | + | + | + | ++ | B |
| 118 | ++ | ++ | +++ | + | + | + | + | ++ | ++ | C |
| 119 | ++++ | ++ | ++ | + | + | ++ | + | + | + | A |
| 120 | ++ | ++ | + | + | + | + | + | + | + | C |
| 121 | ++++ | ++ | ++ | + | + | ++ | + | + | + | A |
| 122 | + | ++ | + | + | + | + | + | + | + | C |
| 123 | ++++ | ++ | + | + | + | ++ | + | + | + | A |
| 124 | + | + | + | + | + | + | + | + | + | C |
| 125 | ++++ | + | + | + | + | + | + | + | ++++ | A |
| 126 | + | + | + | + | + | + | + | + | + | C |
| 127 | ++ | + | + | + | + | + | + | + | + | C |
| 128 | + | + | + | + | + | + | + | + | + | C |
| 129 | ++++ | + | ++ | + | + | + | ++ | + | + | B |
| 130 | ++ | ++ | + | + | + | + | + | + | + | C |
| 131 | ++++ | ++ | + | + | + | + | + | + | ++ | A |
| 148 | + | ++ | + | + | + | + | + | + | + | C |
| 149 | ++++ | ++ | + | + | + | ++ | + | + | ++ | A |
| 150 | ++ | ++ | + | + | + | + | + | + | + | C |

-continued

| Compound No. | DP | AX | SD | PS | MS | AD | CE | AG | UN | MED |
|---|---|---|---|---|---|---|---|---|---|---|
| 151 | ++++ | ++ | + | + | + | + | + | + | + | B |
| 156 | + | + | + | + | + | + | + | + | + | C |
| 157 | + | ++ | + | + | + | + | + | + | + | C |
| 158 | + | ++ | + | + | + | + | + | + | + | C |
| 159 | + | + | + | + | + | + | + | + | + | C |
| 164 | + | + | + | + | + | + | + | + | + | C |
| 165 | ++ | + | + | + | + | + | + | + | + | C |
| 166 | + | + | + | + | + | + | + | + | + | C |
| 167 | + | + | + | + | + | + | + | + | + | C |
| 168 | ++++ | ++ | ++ | + | + | ++ | + | + | ++ | A |
| 169 | + | + | + | + | + | + | + | + | + | C |
| 170 | ++ | ++ | ++ | + | + | + | + | + | +++ | B |
| 171 | + | + | + | + | + | + | + | + | + | C |
| 180 | ++ | ++ | + | + | + | + | + | + | ++++ | B |
| 181 | ++++ | + | + | + | + | ++ | + | + | ++ | A |
| 182 | + | ++ | + | + | + | + | + | + | + | C |
| 183 | ++++ | + | + | + | + | + | + | + | ++ | B |
| 184 | + | ++ | + | + | + | + | + | + | + | C |
| 185 | ++ | ++ | + | + | + | + | + | + | + | C |
| 186 | + | ++ | + | + | + | + | + | + | + | C |
| 187 | ++++ | + | + | + | + | ++ | + | + | + | B |
| 188 | + | ++ | + | + | + | ++ | + | + | ++++ | C |
| 189 | ++ | ++ | + | + | + | ++ | + | + | ++++ | C |

It may be found upon examination that additional species and genera not presently excluded from the claims to pharmaceutical compositions and chemical compounds are not patentable to the inventors in this application. In that case, the subsequent exclusion of species and genera in applicants' claims are to be considered artifacts of patent prosecution and not reflective of the inventors' concept or description of their invention. The invention, in a composition aspect, is all compounds of formula I except those that are in the public's possession.

The invention claimed is:

1. A method for treating a neurological or psychiatric disorder in a subject, comprising administering to said subject in need thereof an effective amount of a compound of formula

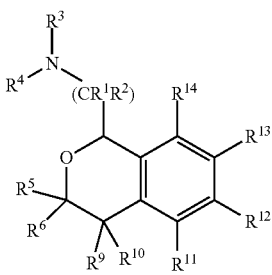

or a pharmaceutically acceptable salt thereof, wherein:
$R^1$, $R^2$, $R^3$ and $R^4$ are chosen independently from H and aliphatic $(C_1-C_8)$hydrocarbon, wherein the aliphatic $(C_1-C_8)$hydrocarbon is optionally substituted with one or more substituents selected from halogen, hydroxyl, $(C_1-C_6)$alkoxy, amino, $(C_1-C_6)$alkylamino and di$(C_1-C_6)$alkylamino;
or, taken together, $R^1$ and $R^2$ form $(C_3-C_6)$cycloalkyl;
$R^5$ and $R^6$ are chosen independently from H, halogen, $(C_1-C_6)$alkyl and $(C_1-C_6)$haloalkyl;
$R^9$ and $R^{10}$ are chosen independently from H, halogen, $(C_1-C_6)$alkyl, $(C_1-C_6)$haloalkyl and $(C_1-C_6)$alkoxy;
one of $R^{11}$, $R^{12}$, $R^{13}$, and $R^{14}$ is optionally substituted benzyl, optionally substituted aryl, or optionally substituted heteroaryl; and the remaining three are H; and
wherein said benzyl, aryl, and heteroaryl are each optionally substituted with one or more substituents selected from halogen, $(C_1-C_4)$alkyl, cyano, $(C_1-C_4)$haloalkyl, $(C_1-C_4)$alkoxy, aminocarbonyl, $(C_1-C_6)$alkylaminocarbonyl, di$(C_1-C_6)$alkylaminocarbonyl, $(C_1-C_4)$acyl, $(C_1-C_4)$haloalkoxy, hydroxy$(C_1-C_4)$alkyl, carboxy, $(C_1-C_4)$alkoxycarbonyl, acetoxy, nitro, amino, $(C_1-C_4)$alkylamino, and di$(C_1-C_4)$alkylamino,
wherein the neurological or psychiatric disorder is depression, bipolar disorder, pain, schizophrenia, obsessive compulsive disorder, social disorder, attention deficit hyperactivity disorder, an anxiety disorder, or epilepsy.

2. The method according to claim 1, wherein the neurological or psychiatric disorder is depression.

3. The method according to claim 2, wherein the depression is treatment-resistant depression (TRD), major depressive disorder (MDD), unipolar depression, bipolar depression or depression associated with another disease or disorder.

4. The method according to claim 1, wherein the neurological or psychiatric disorder is epilepsy.

5. A method for treating a neurological or psychiatric disorder in a subject, comprising administering to said subject in need thereof an effective amount of a compound which is:

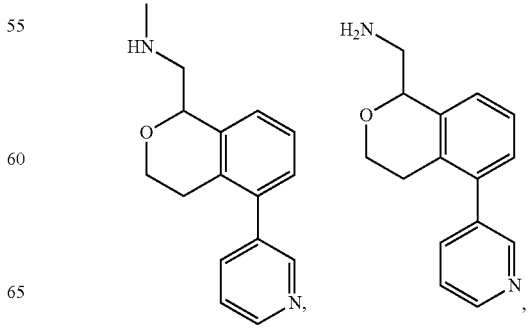

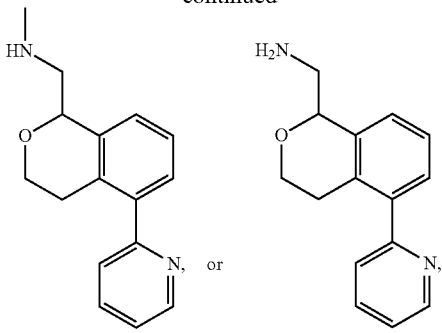

wherein the neurological or psychiatric disorder is depression, bipolar disorder, pain, schizophrenia, obsessive compulsive disorder, social disorder, attention deficit hyperactivity disorder, an anxiety disorder, or epilepsy.

6. The method according to claim 5, wherein the neurological or psychiatric disorder is epilepsy.

7. A method for treating a neurological or psychiatric disorder in a subject, comprising administering to said subject in need thereof an effective amount of a compound which is:

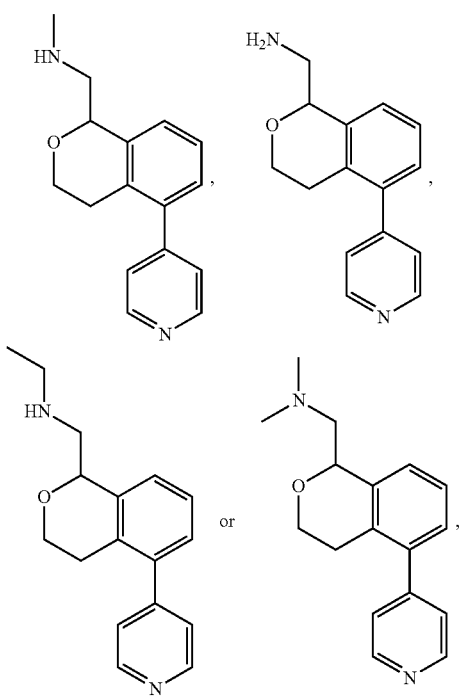

wherein the neurological or psychiatric disorder is depression, bipolar disorder, pain, schizophrenia, obsessive compulsive disorder, social disorder, attention deficit hyperactivity disorder, an anxiety disorder, or epilepsy.

8. The method according to claim 7, wherein the neurological or psychiatric disorder is epilepsy.

9. The method according to claim 1 wherein $R^1$ is hydrogen and $R^2$ is hydrogen or methyl.

10. The method according to claim 1 wherein $R^1$ and $R^2$ are both hydrogen.

11. The method according to claim 1 wherein $R^3$ is hydrogen and $R^4$ is hydrogen, methyl or ethyl.

12. The method according to claim 1 wherein $R^3$ and $R^4$ are both hydrogen.

13. The method according to claim 1 wherein $R^5$ and $R^6$ are both hydrogen.

14. The method according to claim 1 wherein $R^9$ and $R^{10}$ are chosen independently from H, fluoro, and methyl.

15. The method according to claim 1 wherein $R^9$ is chosen from H, fluoro, and methyl and $R^{10}$ is H.

16. The method according to claim 1 wherein $R^{11}$ is optionally substituted benzyl, optionally substituted aryl, or optionally substituted heteroaryl.

17. The method according to claim 1 wherein $R^{12}$ is optionally substituted benzyl, optionally substituted aryl, or optionally substituted heteroaryl.

18. The method according to claim 1 wherein $R^{13}$ is optionally substituted benzyl, optionally substituted aryl, or optionally substituted heteroaryl.

19. The method according to claim 1 wherein $R^{11}$ is optionally substituted benzyl, optionally substituted aryl, or optionally substituted heteroaryl.

20. The method according to claim 1 wherein said benzyl, aryl or heteroaryl is unsubstituted.

21. The method according to claim 1 wherein said optionally substituted aryl is phenyl, and said optionally substituted heteroaryl is nitrogen-containing heteroaryl.

22. The method according to claim 21 wherein said nitrogen-containing heteroaryl is selected from pyridinyl, pyrimidinyl, pyrazinyl, pyridazinyl, thiazolyl, isothiazolyl, oxazolyl, isoxazolyl, pyrazolyl, imidazolyl and pyrrolyl.

23. The method according to claim 21 wherein said nitrogen-containing heteroaryl is pyridinyl.

24. The method according to claim 23 wherein said pyridinyl is at the $R^{11}$, $R^{12}$ or $R^{13}$ position.

25. The method according to claim 1, wherein the compound has Formula IIa:

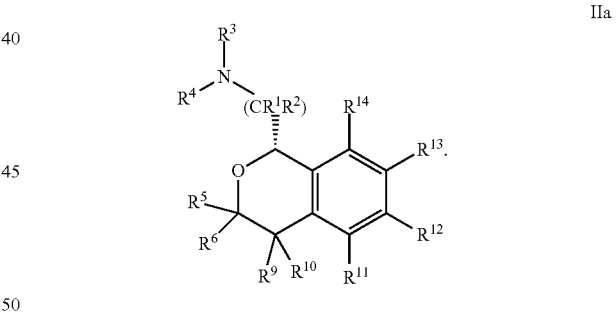

26. The method according to claim 1, wherein the compound has Formula IIb:

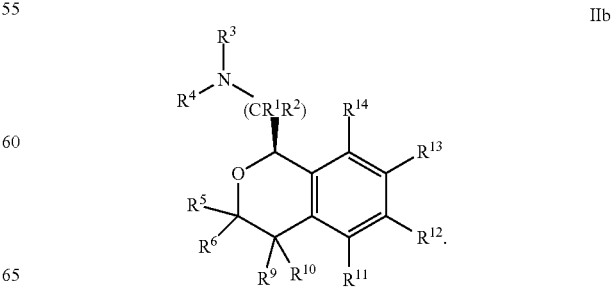

27. The method according to claim 1 wherein $R^1$ is hydrogen; $R^2$ is hydrogen or methyl; $R^3$ is hydrogen; $R^4$ is hydrogen or methyl; $R^5$ is hydrogen; and $R^6$ is hydrogen.

28. The method according to claim 27 wherein $R^9$ and $R^{10}$ are each independently hydrogen, fluoro, or methyl.

29. The method according to claim 28 wherein all of $R^1$, $R^2$, $R^3$, $R^5$, $R^6$, $R^9$ and $R^{10}$ are hydrogen, and $R^4$ is hydrogen or methyl.

30. The method according to claim 29 wherein all of $R^1$, $R^2$, $R^3$, $R^5$, $R^6$, $R^9$, $R^{10}$ and $R^{14}$ are hydrogen; $R^4$ is hydrogen or methyl; and one of $R^{11}$, $R^{12}$, or $R^{13}$ is pyridinyl, and the remaining two are H.

31. The method according to claim 30, wherein $R^{11}$ is pyridinyl.

32. The method according to claim 30, wherein $R^{12}$ is pyridinyl.

33. The method according to claim 30, wherein $R^{12}$ is 3-pyridinyl.

34. The method according to claim 30, wherein $R^{13}$ is pyridinyl.

35. The method according to claim 30, wherein $R^{13}$ is 3-pyridinyl or 4-pyridinyl.

36. The method according to claim 25 wherein all of $R^1$, $R^2$, $R^3$, $R^5$, $R^6$, $R^9$ and $R^{10}$ are hydrogen, and $R^4$ is hydrogen or methyl.

37. The method according to claim 36 wherein one of $R^{11}$, $R^{12}$, or $R^{13}$ is pyridinyl, and the remaining two are H.

38. The method according to claim 26 wherein all of $R^1$, $R^2$, $R^3$, $R^5$, $R^6$, $R^9$ and $R^{10}$ are hydrogen; and $R^4$ is hydrogen or methyl.

39. The method according to claim 38 wherein $R^4$ is hydrogen.

40. The method according to claim 1 wherein the compound is:

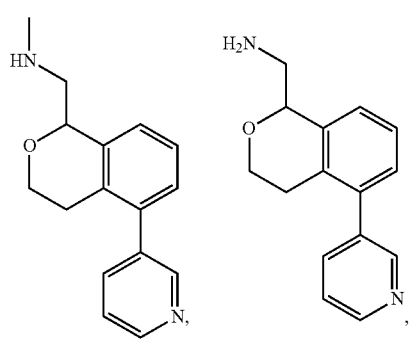

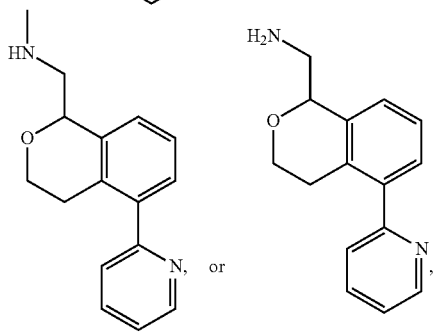

or a pharmaceutically acceptable salt thereof.

41. The method according to claim 40 wherein the compound is:

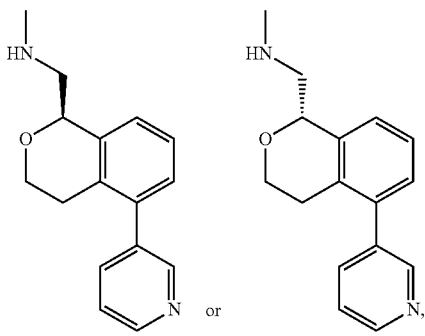 [SMILES: CNC[C@@H]1OCCc2c(-c3cccnc3)cccc21 ; CNC[C@H]1OCCc2c(-c3cccnc3)cccc21]

or a pharmaceutically acceptable salt thereof.

42. The method according to claim 40 wherein the compound is:

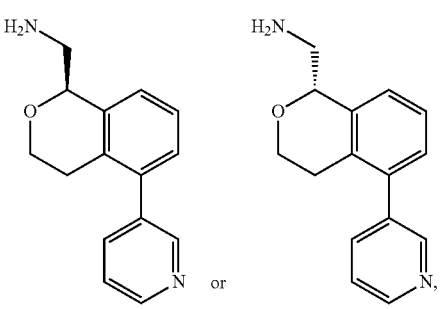 [SMILES: NC[C@@H]1OCCc2c(-c3cccnc3)cccc21 ; NC[C@H]1OCCc2c(-c3cccnc3)cccc21]

or a pharmaceutically acceptable salt thereof.

43. The method according to claim 40 wherein the compound is:

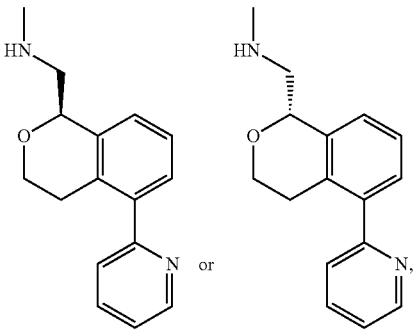

or a pharmaceutically acceptable salt thereof.

44. The method according to claim 40 wherein the compound is:

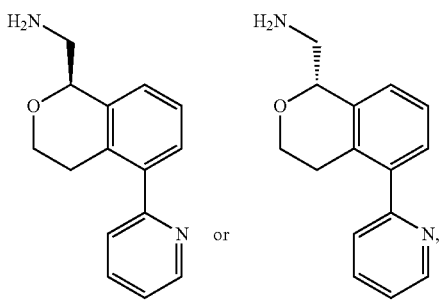 [SMILES: NC[C@@H]1OCCc2c(-c3ccccn3)cccc21 ; NC[C@H]1OCCc2c(-c3ccccn3)cccc21]

or a pharmaceutically acceptable salt thereof.

45. The method according to claim 1 wherein the compound is:

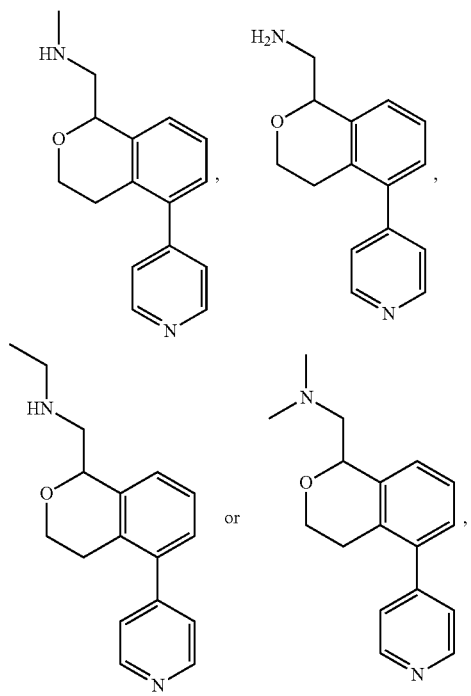

or a pharmaceutically acceptable salt thereof.

46. The method according to claim 45 wherein the compound is:

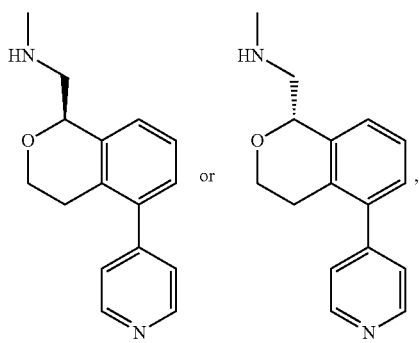 [SMILES: CNC[C@@H]1OCCc2c(-c3ccncc3)cccc21 ; CNC[C@H]1OCCc2c(-c3ccncc3)cccc21]

or a pharmaceutically acceptable salt thereof.

47. The method according to claim 45 wherein the compound is:

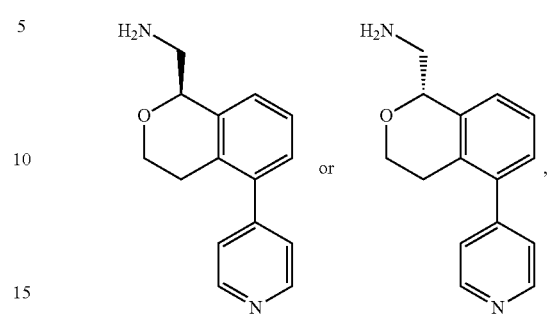

or a pharmaceutically acceptable salt thereof.

48. The method according to claim 45 wherein the compound is:

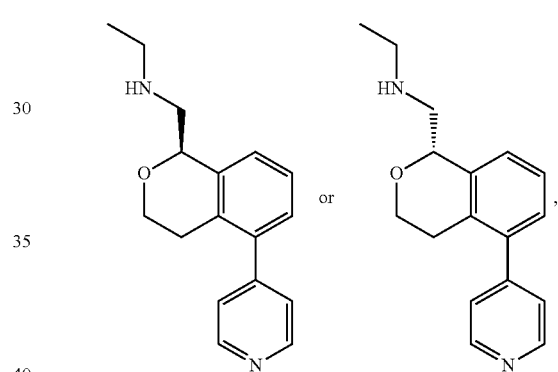

or a pharmaceutically acceptable salt thereof.

49. The method according to claim 45 wherein the compound is:

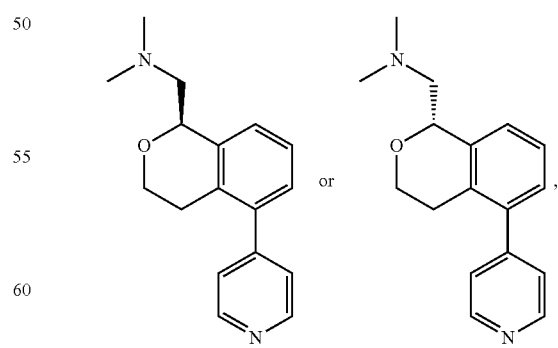

or a pharmaceutically acceptable salt thereof.

50. The method according to claim 1, wherein the compound is selected from:

| Structure | Compound No. |
|---|---|
| 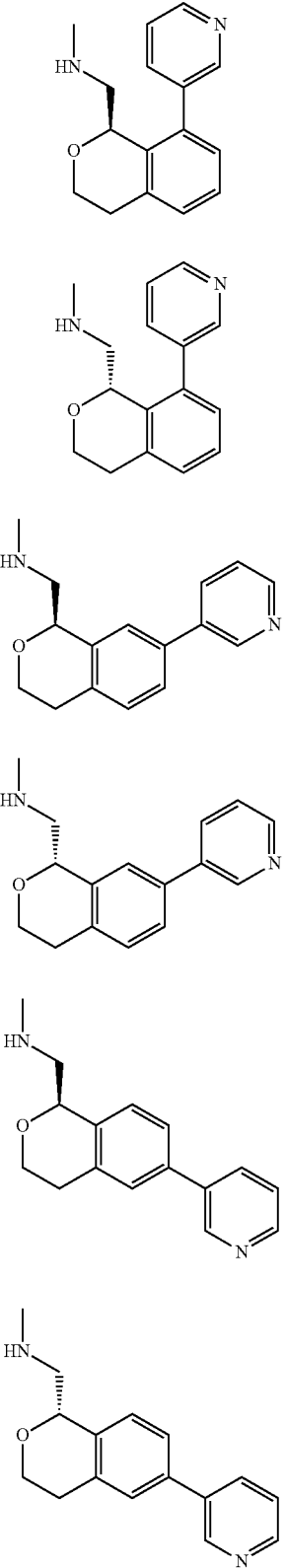 | 1 |
| 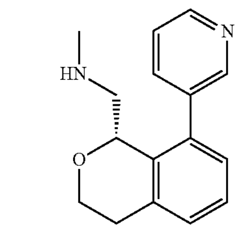 [SMILES: CNC[C@H]1OCCc2cccc(-c3cccnc3)c21] | 2 |
| 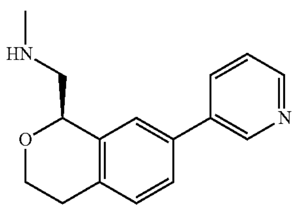 [SMILES: CNC[C@@H]1OCCc2ccc(-c3cccnc3)cc21] | 3 |
| 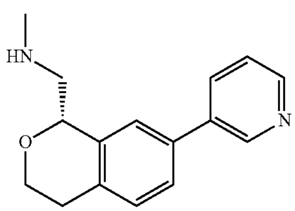 [SMILES: CNC[C@H]1OCCc2ccc(-c3cccnc3)cc21] | 4 |
| 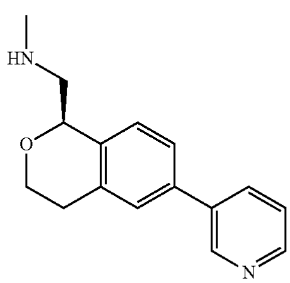 [SMILES: CNC[C@@H]1OCCc2cc(-c3cccnc3)ccc21] | 5 |
| 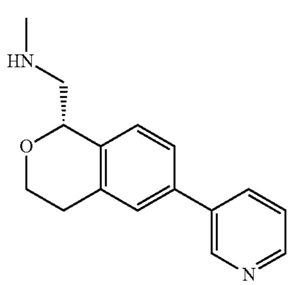 [SMILES: CNC[C@H]1OCCc2cc(-c3cccnc3)ccc21] | 6 |
-continued
| Structure | Compound No. |
|---|---|
| 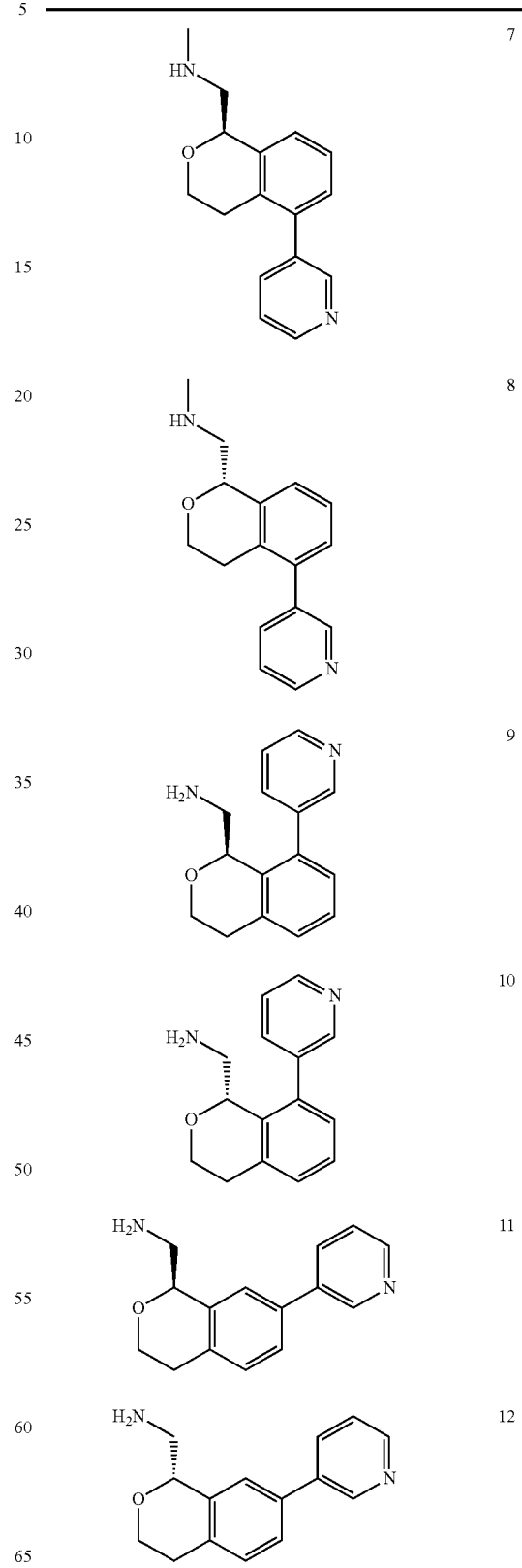 | 7 |
| 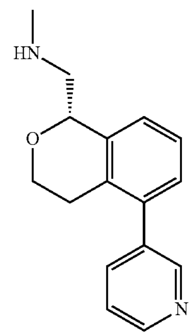 [SMILES: CNC[C@H]1OCCc2c(-c3cccnc3)cccc21] | 8 |
| 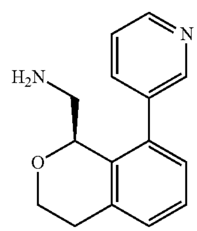 [SMILES: NC[C@@H]1OCCc2cccc(-c3cccnc3)c21] | 9 |
| 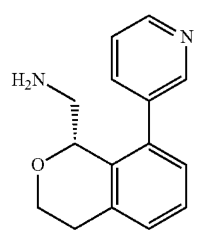 [SMILES: NC[C@H]1OCCc2cccc(-c3cccnc3)c21] | 10 |
| 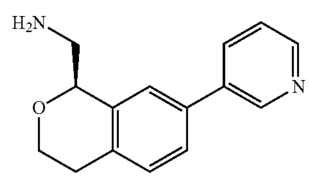 [SMILES: NC[C@@H]1OCCc2ccc(-c3cccnc3)cc21] | 11 |
| 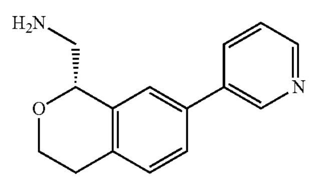 [SMILES: NC[C@H]1OCCc2ccc(-c3cccnc3)cc21] | 12 |

245
-continued
| Structure | Compound No. |
|---|---|
| 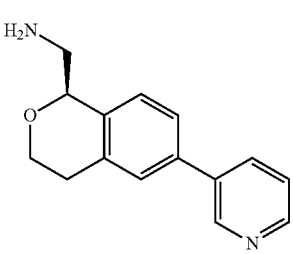 [SMILES: NC[C@@H]1OCCc2cc(-c3cccnc3)ccc21] | 13 |
| 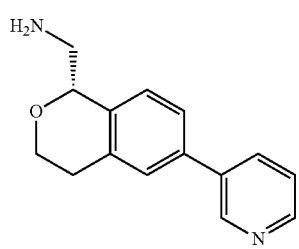 [SMILES: NC[C@H]1OCCc2cc(-c3cccnc3)ccc21] | 14 |
| 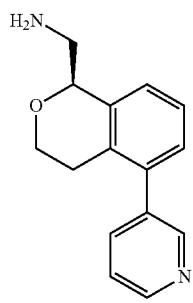 [SMILES: NC[C@@H]1OCCc2c(-c3cccnc3)cccc21] | 15 |
| 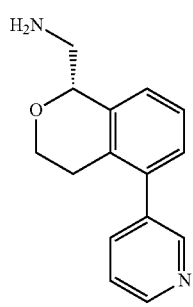 [SMILES: NC[C@H]1OCCc2c(-c3cccnc3)cccc21] | 16 |
| 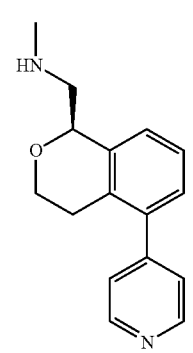 | 17 |
246
-continued
| Structure | Compound No. |
|---|---|
| 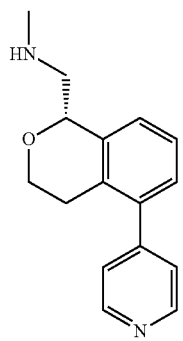 [SMILES: CNC[C@H]1OCCc2c(-c3ccncc3)cccc21] | 18 |
| 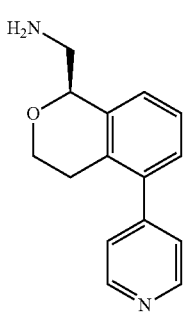 [SMILES: NC[C@@H]1OCCc2c(-c3ccncc3)cccc21] | 19 |
| 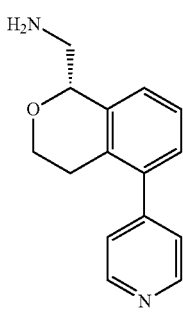 [SMILES: NC[C@H]1OCCc2c(-c3ccncc3)cccc21] | 20 |
| 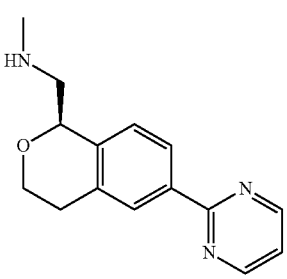 [SMILES: CNC[C@@H]1OCCc2cc(-c3ncccn3)ccc21] | 21 |
| 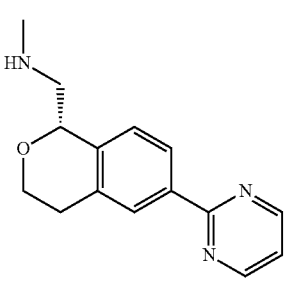 [SMILES: CNC[C@H]1OCCc2cc(-c3ncccn3)ccc21] | 22 |

| Structure | Compound No. |
|---|---|
| 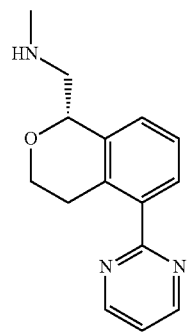 [SMILES: CNC[C@H]1OCCc2c(-c3ncccn3)cccc21] | 23 |
| 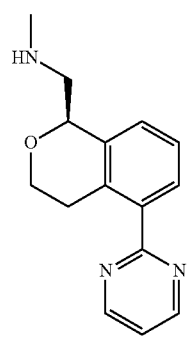 [SMILES: CNC[C@@H]1OCCc2c(-c3ncccn3)cccc21] | 24 |
| 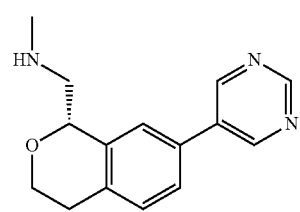 [SMILES: CNC[C@H]1OCCc2ccc(-c3cncnc3)cc21] | 25 |
| 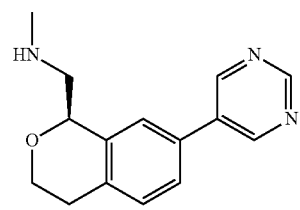 [SMILES: CNC[C@@H]1OCCc2ccc(-c3cncnc3)cc21] | 26 |
| 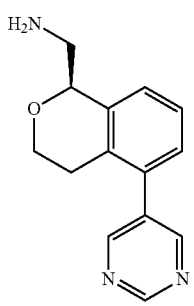 [SMILES: NC[C@@H]1OCCc2c(-c3cncnc3)cccc21] | 27 |
| Structure | Compound No. |
|---|---|
| 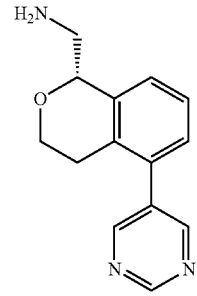 [SMILES: NC[C@H]1OCCc2c(-c3cncnc3)cccc21] | 28 |
| 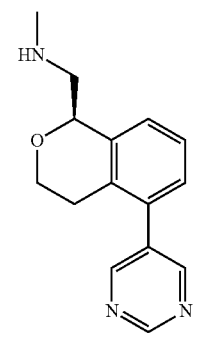 [SMILES: CNC[C@@H]1OCCc2c(-c3cncnc3)cccc21] | 29 |
| 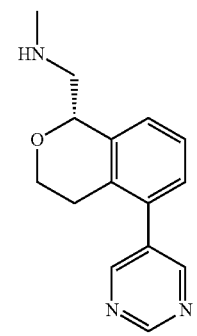 [SMILES: CNC[C@H]1OCCc2c(-c3cncnc3)cccc21] | 30 |
| 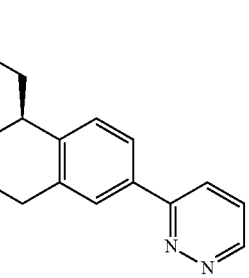 | 31 |
| 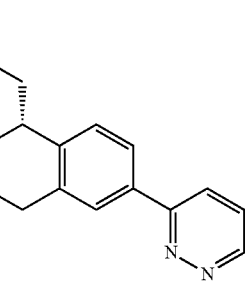 | 32 |

| Structure | Compound No. |
|---|---|
| 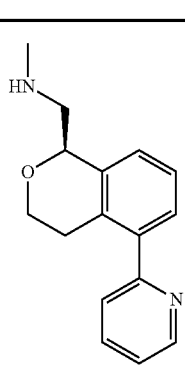 | 43 |
| 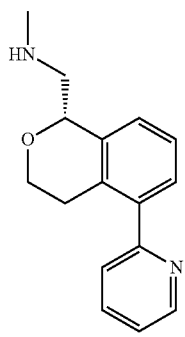 [SMILES: CNC[C@H]1OCCc2c(-c3ccccn3)cccc21] | 44 |
| 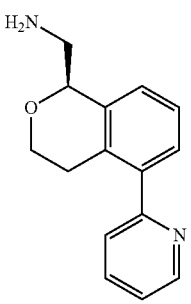 [SMILES: NC[C@@H]1OCCc2c(-c3ccccn3)cccc21] | 45 |
| 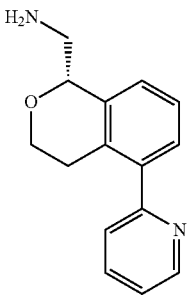 [SMILES: NC[C@H]1OCCc2c(-c3ccccn3)cccc21] | 46 |
| 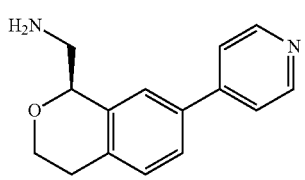 [SMILES: NC[C@@H]1OCCc2ccc(-c3ccncc3)cc21] | 47 |
| Structure | Compound No. |
|---|---|
| 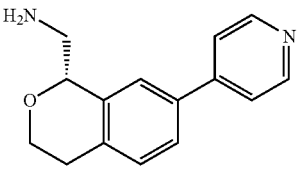 | 48 |
| 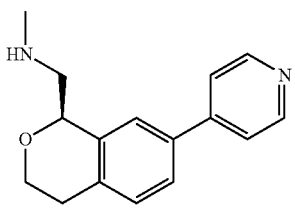 | 49 |
| 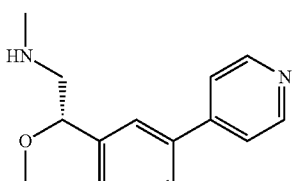 | 50 |
| 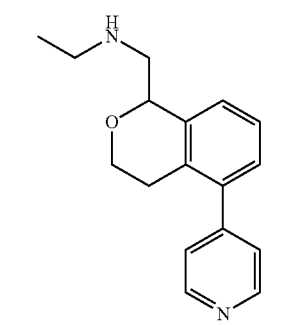 | 51 |
| 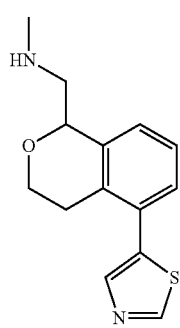 | 52 |
| 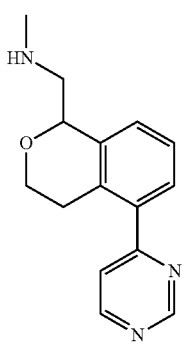 | 53 |

| Structure | Compound No. |
|---|---|
| 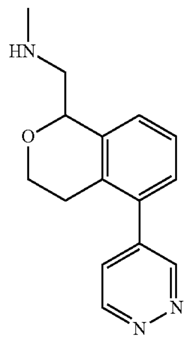 [SMILES: CNCC1OCCc2c(-c3ccnnc3)cccc21] | 54 |
| 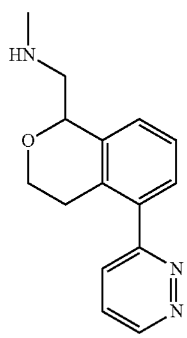 [SMILES: CNCC1OCCc2c(-c3cccnn3)cccc21] | 55 |
| 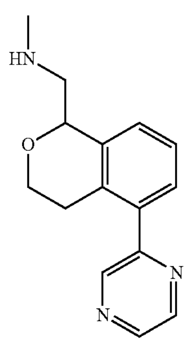 [SMILES: CNCC1OCCc2c(-c3cnccn3)cccc21] | 56 |
| 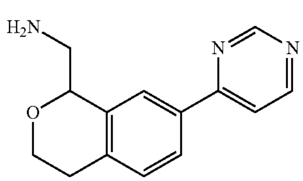 [SMILES: NCC1OCCc2ccc(-c3ccncn3)cc21] | 57 |
| 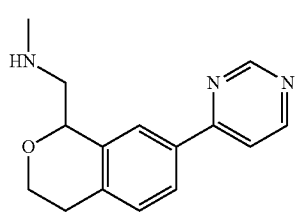 [SMILES: CNCC1OCCc2ccc(-c3ccncn3)cc21] | 58 |

| Structure | Compound No. |
|---|---|
| 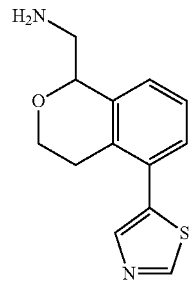 [SMILES: NCC1OCCc2c(-c3cncs3)cccc21] | 59 |
| 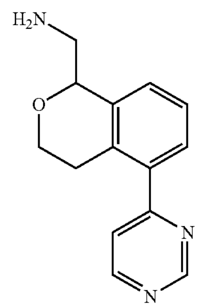 [SMILES: NCC1OCCc2c(-c3ccncn3)cccc21] | 60 |
| 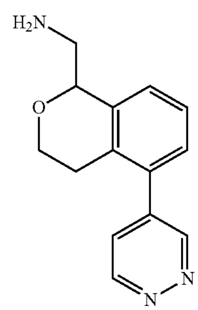 [SMILES: NCC1OCCc2c(-c3ccnnc3)cccc21] | 61 |
| 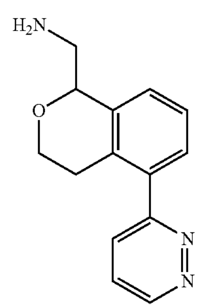 [SMILES: NCC1OCCc2c(-c3cccnn3)cccc21] | 62 |
| 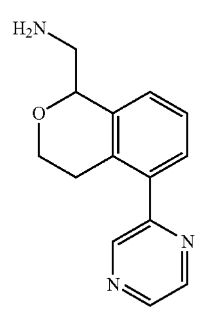 [SMILES: NCC1OCCc2c(-c3cnccn3)cccc21] | 63 |

| Structure | Compound No. |
|---|---|
| (chemical structure) | 64 |
| (chemical structure) | 65 |
| (chemical structure) | 66 |
| (chemical structure) | 67 |
| (chemical structure) | 68 |

| Structure | Compound No. |
|---|---|
| (chemical structure) | 69 |
| (chemical structure) | 70 |
| (chemical structure) | 71 |
| (chemical structure) | 72 |
| (chemical structure) | 73 |

|Structure|Compound No.|
|---|---|
| 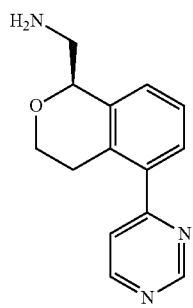 [SMILES: NC[C@@H]1OCCc2c(-c3ccncn3)cccc21] | 74 |
| 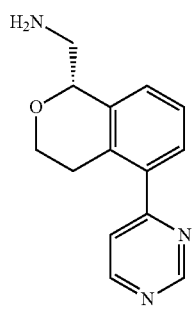 [SMILES: NC[C@H]1OCCc2c(-c3ccncn3)cccc21] | 75 |
| 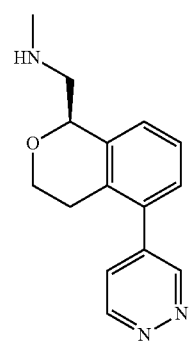 [SMILES: CNC[C@@H]1OCCc2c(-c3ccnnc3)cccc21] | 76 |
| 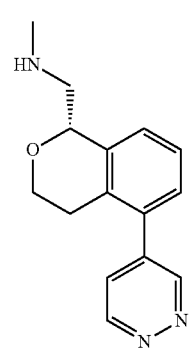 [SMILES: CNC[C@H]1OCCc2c(-c3ccnnc3)cccc21] | 77 |

257
-continued

| Structure | Compound No. |
|---|---|
| (1-aminomethyl-isochroman-5-yl linked to pyrazin-2-yl) | 83 |
| (1-(methylaminomethyl)-isochroman-5-yl linked to isoxazol-4-yl) | 84 |
| (1-(methylaminomethyl)-isochroman-5-yl linked to isoxazol-4-yl) | 85 |
| (1-aminomethyl-isochroman-5-yl linked to isoxazol-4-yl) | 86 |
| (1-aminomethyl-isochroman-5-yl linked to isoxazol-4-yl) | 87 |

258
-continued

| Structure | Compound No. |
|---|---|
| (1-aminomethyl-isochroman-5-yl linked to isoxazol-3-yl) | 88 |
| (1-aminomethyl-isochroman-5-yl linked to isoxazol-3-yl) | 89 |
| (1-(methylaminomethyl)-isochroman-5-yl linked to isoxazol-3-yl) | 90 |
| (1-(methylaminomethyl)-isochroman-5-yl linked to isoxazol-3-yl) | 91 |
| (1-aminomethyl-isochroman-5-yl linked to isoxazol-5-yl) | 92 |

| Structure | Compound No. |
|---|---|
| 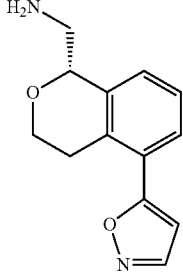 [SMILES: NC[C@H]1OCCc2c(-c3ccno3)cccc21] | 93 |
| 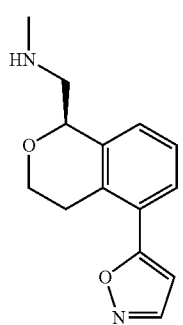 | 94 |
| 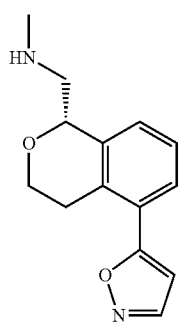 | 95 |
| 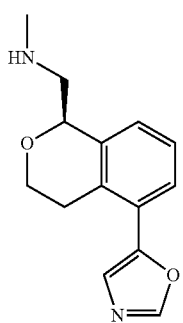 | 96 |
| 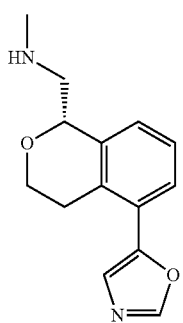 | 97 |
| Structure | Compound No. |
|---|---|
| 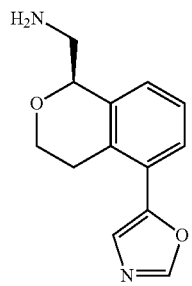 | 98 |
| 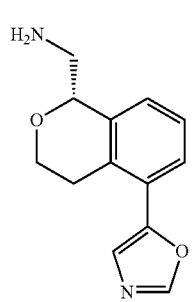 | 99 |
| 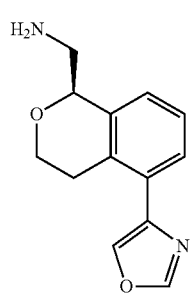 [SMILES: NC[C@@H]1OCCc2c(-c3cocn3)cccc21] | 100 |
| 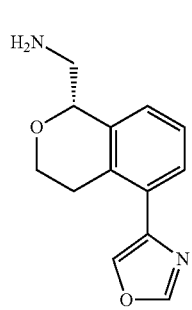 [SMILES: NC[C@H]1OCCc2c(-c3cocn3)cccc21] | 101 |
| 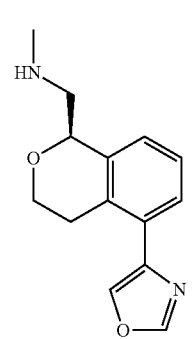 [SMILES: CNC[C@@H]1OCCc2c(-c3cocn3)cccc21] | 102 |

| Structure | Compound No. |
|---|---|
| 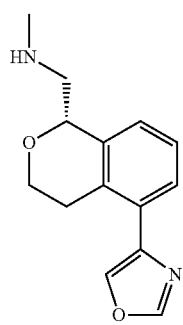 [SMILES: CNC[C@H]1OCCc2c(-c3cocn3)cccc21] | 103 |
| 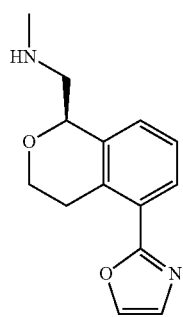 [SMILES: CNC[C@@H]1OCCc2c(-c3ncco3)cccc21] | 104 |
| 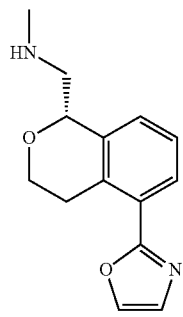 [SMILES: CNC[C@H]1OCCc2c(-c3ncco3)cccc21] | 105 |
| 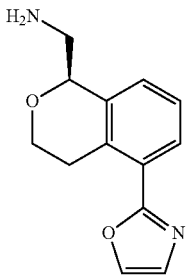 [SMILES: NC[C@@H]1OCCc2c(-c3ncco3)cccc21] | 106 |
| 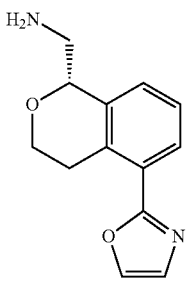 [SMILES: NC[C@H]1OCCc2c(-c3ncco3)cccc21] | 107 |
| Structure | Compound No. |
|---|---|
| 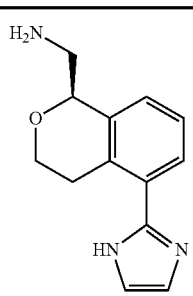 | 108 |
| 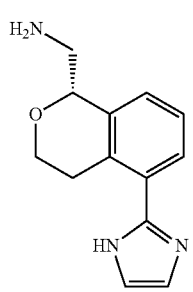 [SMILES: NC[C@H]1OCCc2c(-c3ncc[nH]3)cccc21] | 109 |
| 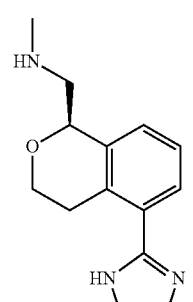 | 110 |
| 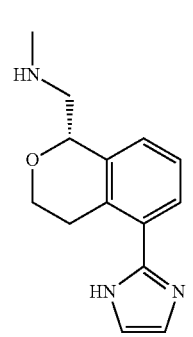 [SMILES: CNC[C@H]1OCCc2c(-c3ncc[nH]3)cccc21] | 111 |
| 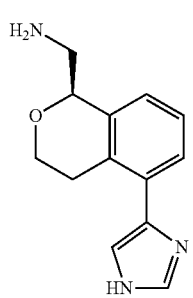 [SMILES: NC[C@@H]1OCCc2c(-c3c[nH]cn3)cccc21] | 112 |

| Structure | Compound No. |
|---|---|
| (chemical structure) | 113 |
| (chemical structure) | 114 |
| (chemical structure) | 115 |
| (chemical structure) | 116 |
| (chemical structure) | 117 |

| Structure | Compound No. |
|---|---|
| (chemical structure) | 118 |
| (chemical structure) | 119 |
| (chemical structure) | 120 |
| (chemical structure) | 121 |

| Structure | Compound No. |
|---|---|
| 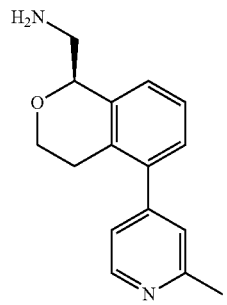 | 122 |
| 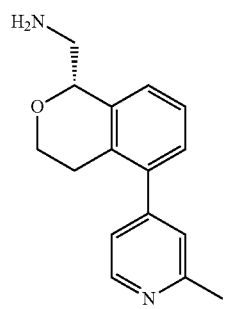 | 123 |
| 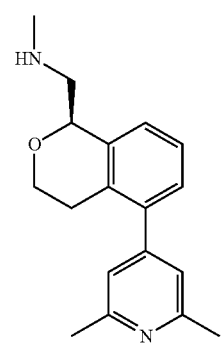 [SMILES: CNC[C@@H]1OCCc2c(-c3cc(C)nc(C)c3)cccc21] | 124 |
| 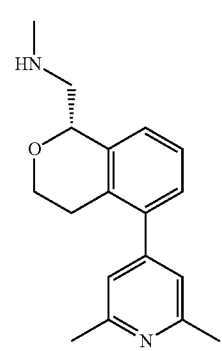 [SMILES: CNC[C@H]1OCCc2c(-c3cc(C)nc(C)c3)cccc21] | 125 |
| Structure | Compound No. |
|---|---|
| 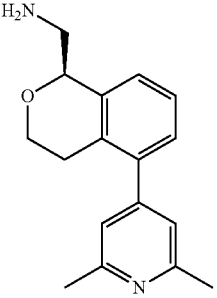 [SMILES: Cc1cc(-c2cccc3c2CCO[C@H]3CN)cc(C)n1] | 126 |
| 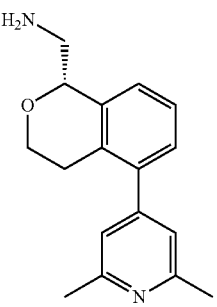 [SMILES: Cc1cc(-c2cccc3c2CCO[C@@H]3CN)cc(C)n1] | 127 |
| 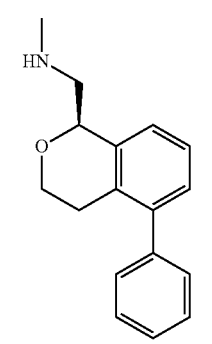 [SMILES: CNC[C@@H]1OCCc2c(-c3ccccc3)cccc21] | 128 |
| 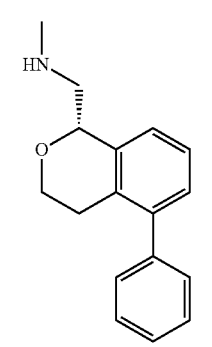 [SMILES: CNC[C@H]1OCCc2c(-c3ccccc3)cccc21] | 129 |
| 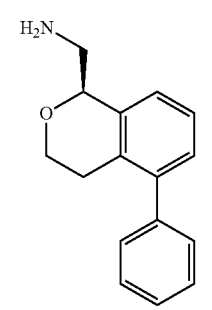 [SMILES: NC[C@@H]1OCCc2c(-c3ccccc3)cccc21] | 130 |

| Structure | Compound No. |
|---|---|
| 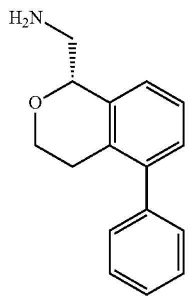 [SMILES: NC[C@H]1OCCc2c(-c3ccccc3)cccc21] | 131 |
| 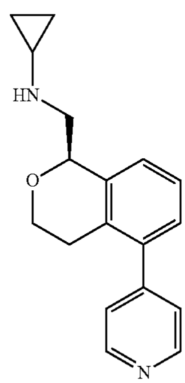 [SMILES: c1cc(-c2ccncc2)c2c(c1)[C@H](CNC1CC1)OCC2] | 180 |
| 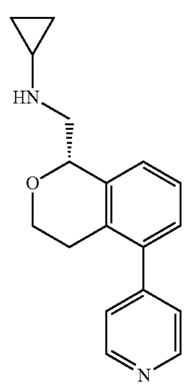 [SMILES: c1cc(-c2ccncc2)c2c(c1)[C@@H](CNC1CC1)OCC2] | 181 |
| 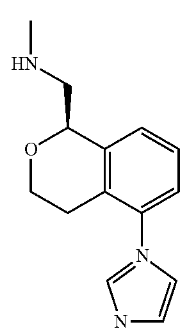 | 182 |

| Structure | Compound No. |
|---|---|
| 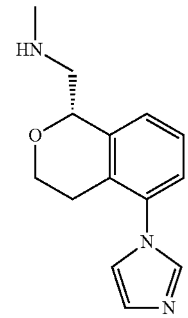 [SMILES: CNC[C@H]1OCCc2c1cccc2-n1ccnc1] | 183 |
| 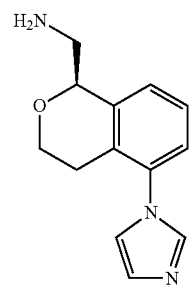 [SMILES: NC[C@@H]1OCCc2c1cccc2-n1ccnc1] | 184 |
| 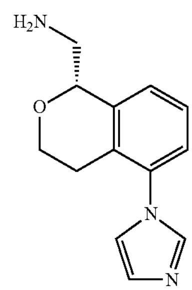 [SMILES: NC[C@H]1OCCc2c1cccc2-n1ccnc1] | 185 |
| 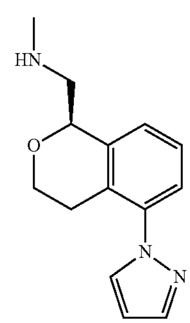 [SMILES: CNC[C@@H]1OCCc2c1cccc2-n1cccn1] | 186 |
| 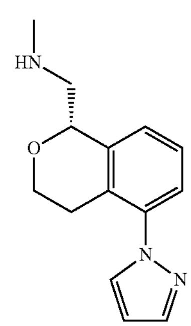 [SMILES: CNC[C@H]1OCCc2c1cccc2-n1cccn1] | 187 |

| Structure | Compound No. |
|---|---|
| (structure) | 188 |
| (structure) | 189 |
| (structure) | 190 |
| (structure) | 191 |

| Structure | Compound No. |
|---|---|
| (structure) | 192 |
| (structure) | 193 |
| (structure) | 194 |
| (structure) | 195 | or a pharmaceutically acceptable salt thereof.

51. The method according to claim 1, wherein the compound is selected from:

| Compound No | Chemical name |
|---|---|
| 1 | (R)-N-Methyl-1-(8-(pyridin-3-yl)isochroman-1-yl)methanamine bis-hydrochloride |
| 2 | (S)-N-Methyl-1-(8-(pyridin-3-yl)isochroman-1-yl)methanamine bis-hydrochloride |
| 3 | (R)-N-Methyl-1-(7-(pyridin-3-yl)isochroman-1-yl)methanamine dihydrochloride |
| 4 | (S)-N-methyl-1-(7-(pyridin-3-yl)isochroman-1-yl)methanamine dihydrochloride |
| 5 | (R)-N-Methyl(6-(pyridin-3-yl)isochroman-1-yl)methanamine bis-hydrochloride |
| 6 | (S)-N-methyl(6-(pyridin-3-yl)isochroman-1-yl)methanamine bis-hydrochloride |
| 7 | (R)-N-Methyl(5-(pyridin-3-yl)isochroman-1-yl)methanamine bis-hydrochloride |

| Compound No | Chemical name |
|---|---|
| 8 | (S)-N-Methyl(5-(pyridin-3-yl)isochroman-1-yl)methanamine bis-hydrochloride |
| 9 | (R)-(8-(Pyridin-3-yl)isochroman-1-yl)methanamine hydrochloride |
| 10 | (S)-(8-(Pyridin-3-yl)isochroman-1-yl)methanamine hydrochloride |
| 11 | (R)-(7-(pyridin-3-yl)isochroman-1-yl)methanamine hydrochloride |
| 12 | (S)-(7-(pyridin-3-yl)isochroman-1-yl)methanamine hydrochloride |
| 13 | (R)-tert-Butyl (6-(pyridin-3-yl)isochroman-1-yl)methylcarbamate hydrochloride |
| 14 | (S)-tert-Butyl (6-(pyridin-3-yl)isochroman-1-yl)methylcarbamate hydrochloride |
| 15 | (R)-(5-(Pyridin-3-yl)isochroman-1-yl)methanamine hydrochloride |
| 16 | (S)-(5-(Pyridin-3-yl)isochroman-1-yl)methanamine hydrochloride |
| 17 | (R)-N-Methyl(5-(pyridin-4-yl)isochroman-1-yl)methanamine dihydrochloride |
| 18 | (S)-N-Methyl(5-(pyridin-4-yl)isochroman-1-yl)methanamine dihydrochloride |
| 19 | (R)-(5-(Pyridin-4-yl)isochroman-1-yl)methanamine hydrochloride |
| 20 | (S)-(5-(Pyridin-4-yl)isochroman-1-yl)methanamine hydrochloride |
| 21 | (R)-N-Methyl-1-(6-(pyrimidin-2-yl)isochroman-1-yl)methanamine hydrochloride |
| 22 | (S)-N-Methyl-1-(6-(pyrimidin-2-yl)isochroman-1-yl)methanamine hydrochloride |
| 23 | (S)-N-Methyl-1-(5-(pyrimidin-2-yl)isochroman-1-yl)methanamine hydrochloride |
| 24 | (R)-N-Methyl-1-(5-(pyrimidin-2-yl)isochroman-1-yl)methanamine hydrochloride |
| 25 | (S)-N-Methyl-1-(7-(pyrimidin-5-yl)isochroman-1-yl)methanamine hydrochloride |
| 26 | (R)-N-Methyl-1-(7-(pyrimidin-5-yl)isochroman-1-yl)methanamine hydrochloride |
| 27 | (R)-(5-(Pyrimidin-5-yl)isochroman-1-yl)methanamine hydrochloride |
| 28 | (S)-(5-(Pyrimidin-5-yl)isochroman-1-yl)methanamine hydrochloride |
| 29 | (R)-N-Methyl-1-(5-(pyrimidin-5-yl)isochroman-1-yl)methanamine hydrochloride |
| 30 | (S)-N-Methyl-1-(5-(pyrimidin-5-yl)isochroman-1-yl)methanamine hydrochloride |
| 31 | (R)-N-Methyl-1-(6-(pyridazin-3-yl)isochroman-1-yl)methanamine hydrochloride |
| 32 | (S)-N-Methyl-1-(6-(pyridazin-3-yl)isochroman-1-yl)methanamine hydrochloride |
| 43 | (R)-N-Methyl-1-(5-(pyridin-2-yl)isochroman-1-yl)methanamine hydrochloride |
| 44 | (S)-N-Methyl-1-(5-(pyridin-2-yl)isochroman-1-yl)methanamine hydrochloride |
| 45 | (R)-(5-(pyridin-2-yl)isochroman-1-yl)methanamine hydrochloride |
| 46 | (S)-(5-(pyridin-2-yl)isochroman-1-yl)methanamine hydrochloride |
| 47 | (R)-(7-(pyridin-4-yl)isochroman-1-yl)methanamine hydrochloride |
| 48 | (S)-(7-(pyridin-4-yl)isochroman-1-yl)methanamine hydrochloride |
| 49 | (R)-N-Methyl-1-(7-(pyridin-4-yl)isochroman-1-yl)methanamine hydrochloride |
| 50 | (S)-N-Methyl-1-(7-(pyridin-4-yl)isochroman-1-yl)methanamine hydrochloride |
| 51 | N-((5-(pyridin-4-yl)isochroman-1-yl)methyl)ethanamine |
| 52 | N-Methyl-1-(5-(thiazol-5-yl)isochroman-1-yl)methanamine hydrochloride |
| 53 | N-Methyl-1-(5-(pyrimidin-4-yl)isochroman-1-yl)methanamine hydrochloride |
| 54 | N-Methyl-1-(5-(pyridazin-4-yl)isochroman-1-yl)methanamine hydrochloride |
| 55 | N-Methyl-1-(5-(pyridazin-4-yl)isochroman-1-yl)methanamine hydrochloride |
| 56 | N-Methyl-1-(5-(pyrazin-2-yl)isochroman-1-yl)methanamine hydrochloride |
| 57 | 7-(Pyrimidin-4-yl)isochroman-1-yl)methanamine hydrochloride |
| 58 | N-Methyl-1-(7-(pyrimidin-4-yl)isochroman-1-yl)methanamine hydrochloride |
| 59 | (5-(Thiazol-5-yl)isochroman-1-yl)methanamine hydrochloride |
| 60 | (5-(Pyrimidin-4-yl)isochroman-1-yl)methanamine hydrochloride |
| 61 | (5-(Pyridazin-4-yl)isochroman-1-yl)methanamine hydrochloride |
| 62 | (5-(Pyridazin-3-yl)isochroman-1-yl)methanaminehydrochloride |
| 63 | (5-(Pyrazin-2-yl)isochroman-1-yl)methanamine hydrochloride |
| 64 | (5-(Isoxazol-4-yl)isochroman-1-yl)methanamine hydrochloride |
| 65 | 1-(5-(Isoxazol-4-yl)isochroman-1-yl)-N-methylmethanamine hydrochloride |
| 66 | (R)-N-((5-(Pyridin-4-yl) isochroman-1-yl)methyl)ethanamine hydrochloride |
| 67 | (S)-N-((5-(Pyridin-4-yl) isochroman-1-yl)methyl)ethanamine hydrochloride |
| 68 | (R)-N-Methyl-1-(5-(thiazol-5-yl)isochroman-1-yl)methanamine hydrochloride |
| 69 | (S)-N-Methyl-1-(5-(thiazol-5-yl)isochroman-1-yl)methanamine hydrochloride |
| 70 | (R)-(5-(Thiazol-5-yl)isochroman-1-yl)methanamine hydrochloride |
| 71 | (S)-(5-(Thiazol-5-yl)isochroman-1-yl)methanamine hydrochloride |
| 72 | (R)-N-Methyl-1-(5-(pyrimidin-4-yl)isochroman-1-yl)methanamine hydrochloride |
| 73 | (S)-N-Methyl-1-(5-(pyrimidin-4-yl)isochroman-1-yl)methanamine hydrochloride |
| 74 | (R)-(5-(Pyrimidin-4-yl)isochroman-1-yl)methanamine hydrochloride |
| 75 | (S)-(5-(Pyrimidin-4-yl)isochroman-1-yl)methanamine hydrochloride |
| 76 | (R)-N-Methyl-1-(5-(pyridazin-4-yl)isochroman-1-yl)methanamine hydrochloride |
| 77 | (S)-N-Methyl-1-(5-(pyridazin-4-yl)isochroman-1-yl)methanamine hydrochloride |
| 78 | (R)-(5-(Pyridazin-4-yl)isochroman-1-yl)methanamine hydrochloride |
| 79 | (S)-(5-(Pyridazin-4-yl)isochroman-1-yl)methanamine hydrochloride |
| 80 | (R)-N-Methyl-1-(5-(pyrazine-2-yl)isochroman-1-yl)methanamine |
| 81 | (S)-N-Methyl-1-(5-(pyrazine-2-yl)isochroman-1-yl)methanamine |
| 82 | (R)-(5-(Pyrazin-2-yl)isochroman-1-yl)methanamine hydrochloride |
| 83 | (S)-(5-(Pyrazin-2-yl)isochroman-1-yl)methanamine hydrochloride |
| 84 | (R)-1-(5-(Isoxazol-4-yl)isochroman-1-yl)-N-methylmethanamine hydrochloride |
| 85 | (S)-1-(5-(Isoxazol-4-yl)isochroman-1-yl)-N-methylmethanamine hydrochloride |

-continued

| Compound No | Chemical name |
|---|---|
| 86 | (R)-(5-(Isoxazol-4-yl)isochroman-1-yl)methanamine hydrochloride |
| 87 | (S)-(5-(Isoxazol-4-yl)isochroman-1-yl)methanamine hydrochloride |
| 88 | (R)-(5-(Isoxazol-3-yl)isochroman-1-yl)methanamine hydrochloride |
| 89 | (S)-(5-(Isoxazol-3-yl)isochroman-1-yl)methanamine hydrochloride |
| 90 | (R)-1-(5-(Isoxazol-3-yl)isochroman-1-yl)-N-methylmethanamine hydrochloride |
| 91 | (S)-1-(5-(Isoxazol-3-yl)isochroman-1-yl)-N-methylmethanamine hydrochloride |
| 92 | (R)-(5-(Isoxazol-5-yl)isochroman-1-yl)methanamine hydrochloride |
| 93 | (S)-(5-(Isoxazol-5-yl)isochroman-1-yl)methanamine hydrochloride |
| 94 | (R)-1-(5-(Isoxazol-5-yl)isochroman-1-yl)-N-methylmethanamine |
| 95 | (S)-1-(5-(Isoxazol-5-yl)isochroman-1-yl)-N-methylmethanamine |
| 96 | (R)-N-Methyl-1-(5-(oxazol-5-yl)isochroman-1-yl)methanamine hydrochloride |
| 97 | (S)-N-Methyl-1-(5-(oxazol-5-yl)isochroman-1-yl)methanamine hydrochloride |
| 98 | (R)-(5-(Oxazol-5-yl)isochroman-1-yl)methanamine hydrochloride |
| 99 | (S)-(5-(Oxazol-5-yl)isochroman-1-yl)methanamine hydrochloride |
| 100 | (R)-(5-(oxazol-4-yl)isochroman-1-yl)methanamine hydrochloride |
| 101 | (S)-(5-(oxazol-4-yl)isochroman-1-yl)methanamine hydrochloride |
| 102 | (R)-N-methyl-1-(5-(oxazol-4-yl)isochroman-1-yl)methanamine hydrochloride |
| 103 | (S)-N-methyl-1-(5-(oxazol-4-yl)isochroman-1-yl)methanamine hydrochloride |
| 104 | (R)-N-Methyl-1-(5-(oxazol-2-yl)isochroman-1-yl)methanamine hydrochloride |
| 105 | (S)-N-methyl-1-(5-(oxazol-2-yl)isochroman-1-yl)methanamine dihydrochloride |
| 106 | (R)-(5-(Oxazol-2-yl)isochroman-1-yl)methanamine hydrochloride |
| 107 | (S)-(5-(Oxazol-2-yl)isochroman-1-yl)methanamine hydrochloride |
| 108 | (R)-(5-(1H-Imidazol-2-yl)isochroman-1-yl)methanamine hydrochloride |
| 109 | (S)-(5-(1H-Imidazol-2-yl)isochroman-1-yl)methanamine hydrochloride |
| 110 | (R)-1-(5-(1H-Imidazol-2-yl)isochroman-1-yl)-N-methylmethanamine hydrochloride |
| 111 | (S)-1-(5-(1H-Imidazol-2-yl)isochroman-1-yl)-N-methylmethanamine hydrochloride |
| 112 | (R)-(5-(1H-Imidazol-4-yl)isochroman-1-yl)methanamine hydrochloride |
| 113 | (S)-(5-(1H-Imidazol-4-yl)isochroman-1-yl)methanamine hydrochloride |
| 114 | (R)-1-(5-(1H-imidazol-4-yl)isochroman-1-yl)-N-methylmethanamine hydrochloride |
| 115 | (S)-1-(5-(1H-imidazol-4-yl)isochroman-1-yl)-N-methylmethanamine hydrochloride |
| 116 | (R)-(5-(1H-pyrazol-4-yl)isochroman-1-yl)methanamine hydrochloride |
| 117 | (S)-(5-(1H-pyrazol-4-yl)isochroman-1-yl)methanamine hydrochloride |
| 118 | (R)-1-(5-(1H-pyrazol-4-yl)isochroman-1-yl)-N-methylmethanamine hydrochloride |
| 119 | (S)-1-(5-(1H-pyrazol-4-yl)isochroman-1-yl)-N-methylmethanamine hydrochloride |
| 120 | (R)-N-Methyl-1-(5-(2-methylpyridin-4-yl)isochroman-1-yl)methanamine hydrochloride |
| 121 | (S)-N-Methyl-1-(5-(2-methylpyridin-4-yl)isochroman-1-yl)methanamine hydrochloride |
| 122 | (R)-(5-(2-Methylpyridin-4-yl)isochroman-1-yl)methanamine hydrochloride |
| 123 | (S)-(5-(2-Methylpyridin-4-yl)isochroman-1-yl)methanamine hydrochloride |
| 124 | (R)-1-(5-(2,6-dimethylpyridin-4-yl)isochroman-1-yl)-N-methylmethanamine dihydrochloride |
| 125 | (S)-1-(5-(2,6-dimethylpyridin-4-yl)isochroman-1-yl)-N-methylmethanamine dihydrochloride |
| 126 | (R)-1-(5-(2,6-dimethylpyridin-4-yl)isochroman-1-yl)-N-methylmethanamine dihydrochloride |
| 127 | (S)-1-(5-(2,6-dimethylpyridin-4-yl)isochroman-1-yl)-N-methylmethanamine dihydrochloride |
| 128 | (R)-N-Methyl-1-(5-phenylisochroman-1-yl)methanamine hydrochloride |
| 129 | (S)-N-Methyl-1-(5-phenylisochroman-1-yl)methanamine hydrochloride |
| 130 | (R)-(5-Phenylisochroman-1-yl)methanamine hydrochloride |
| 131 | (S)-(5-Phenylisochroman-1-yl)methanamine hydrochloride |
| 180 | (R)-N-((5-(Pyridin-4-yl)isochroman-1-yl)methyl)cyclopropanamine hydrochloride |
| 181 | (S)-N-((5-(Pyridin-4-yl)isochroman-1-yl)methyl)cyclopropanamine hydrochloride |
| 182 | (R)-1-(5-(1H-Imidazol-1-yl)isochroman-1-yl)-N-methylmethanamine hydrochloride |
| 183 | (S)-1-(5-(1H-Imidazol-1-yl)isochroman-1-yl)-N-methylmethanamine hydrochloride |
| 184 | (R)-(5-(1H-Imidazol-1-yl)isochroman-1-yl)methanamine hydrochloride |
| 185 | (S)-(5-(1H-Imidazol-1-yl)isochroman-1-yl)methanamine hydrochloride |
| 186 | (R)-1-(5-(1H-pyrazol-1-yl)isochroman-1-yL)-N-methylmethanamine |
| 187 | (S)-1-(5-(1H-pyrazol-1-yl)isochroman-1-yl)-N-methylmethanamine |
| 188 | (R)-(5-(1H-pyrazol-1-yl)isochroman-1-yl)methanamine hydrochloride |
| 189 | (S)-(5-(1H-pyrazol-1-yl)isochroman-1-yl)methanamine hydrochloride |
| 190 | (R)-1-(5-(4H-1,2,4-triazol-4-yl)isochroman-1-yl)-N-methylmethanamine |
| 191 | (S)-1-(5-(4H-1,2,4-triazol-4-yl)isochroman-1-yl)-N-methylmethanamine |
| 192 | (R)-(5-(4H-1,2,4-triazol-4-yl)isochroman-1-yl)methanamine |
| 193 | (S)-(5-(4H-1,2,4-triazol-4-yl)isochroman-1-yl)methanamine |
| 194 | (R)-N,N-dimethyl-1-(5-(pyridin-4-yl)isochroman-1-yl)methanamine, and |
| 195 | (S)-N,N-dimethyl-1-(5-(pyridin-4-yl)isochroman-1-yl)methanamine, | or a pharmaceutically acceptable salt thereof.

52. The method according to claim 46, wherein the compound is:

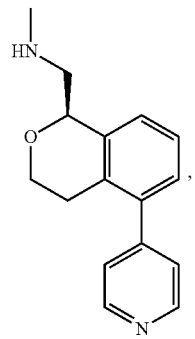

or a pharmaceutically acceptable salt thereof.

53. The method according to claim 52, wherein the compound is greater than 95% enantiomerically pure.

54. The method according to claim 52, wherein the compound is greater than 99% enantiomerically pure.

55. The method according to claim 46, wherein the compound is:

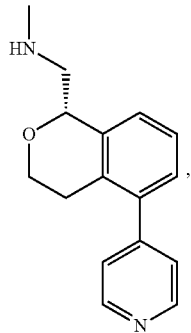

or a pharmaceutically acceptable salt thereof.

56. The method according to claim 55, wherein the compound is greater than 95% enantiomerically pure.

57. The method according to claim 55, wherein the compound is greater than 99% enantiomerically pure.

* * * * *